(12) United States Patent
Mazed et al.

(10) Patent No.: US 9,923,124 B2
(45) Date of Patent: Mar. 20, 2018

(54) DISPLAY DEVICE

(71) Applicants: Mohammad A Mazed, Chino Hills, CA (US); Sayeeda Mazed, Chino Hills, CA (US)

(72) Inventors: Mohammad A Mazed, Chino Hills, CA (US); Sayeeda Mazed, Chino Hills, CA (US)

( * ) Notice: Subject to any disclaimer, the term of this patent is extended or adjusted under 35 U.S.C. 154(b) by 0 days.

(21) Appl. No.: 14/999,601

(22) Filed: Jun. 1, 2016

(65) Prior Publication Data
US 2017/0018688 A1 Jan. 19, 2017

Related U.S. Application Data

(63) Continuation-in-part of application No. 14/120,835, filed on Jul. 1, 2014, now Pat. No. 9,823,737, and a
(Continued)

(51) Int. Cl.
| | |
|---|---|
| *H01L 33/50* | (2010.01) |
| *H01L 33/60* | (2010.01) |
| *H01L 33/06* | (2010.01) |
| *H01L 33/14* | (2010.01) |
| *H01L 33/32* | (2010.01) |
| *H01L 33/00* | (2010.01) |
| *H01L 51/50* | (2006.01) |
| *H01L 27/146* | (2006.01) |

(Continued)

(52) U.S. Cl.
CPC ............ *H01L 33/502* (2013.01); *G06F 3/011* (2013.01); *G06F 3/013* (2013.01); *G06F 3/017* (2013.01); *G06F 3/041* (2013.01); *G06F 19/70* (2013.01); *G09G 3/00* (2013.01); *G09G 3/001* (2013.01); *H01L 27/14621* (2013.01); *H01L 27/14627* (2013.01); *H01L 27/14645* (2013.01); *H01L 33/0079* (2013.01); *H01L 33/06* (2013.01); *H01L 33/145* (2013.01); *H01L 33/32* (2013.01); *H01L 33/60* (2013.01); *H01L 51/502* (2013.01); *H01S 5/187* (2013.01); *H01S 5/18375* (2013.01); *H04W 4/02* (2013.01); *G09G 3/346* (2013.01); *G09G 2380/08* (2013.01); *H01L 2224/48091* (2013.01); *H01L 2933/0083* (2013.01)

(58) Field of Classification Search
CPC ... H01L 33/502; H01L 33/0079; H01L 33/06; H01L 33/145; H01L 33/32; H01L 33/60; H01L 2224/48091; H01L 2933/0083; H01L 27/14621; H01L 27/14627; H01L 27/14645; H01S 5/18375; H01S 5/187; G06F 3/011; G06F 3/013; G06F 3/017; G06F 3/041; G06F 19/70; G09G 3/00; G09G 3/001; G09G 3/346; G09G 2380/08; H04W 4/02
See application file for complete search history.

(56) References Cited

U.S. PATENT DOCUMENTS

2017/0192129 A1* 7/2017 Cunningham ............ F21K 9/64

* cited by examiner

*Primary Examiner* — Armando Rodriguez

(57) ABSTRACT

A display device (utilizing quantum dots, photonic crystals, microlight emitting diodes/vertical cavity surface emitting lasers and electrically switchable light valves) is disclosed. Furthermore, a quantum dot(s) can be electromagnetically coupled with a three-dimensional (3-D) structure(s). Additionally, the electrically switchable light valve can include a phase change material/phase transition material.

20 Claims, 95 Drawing Sheets

Related U.S. Application Data continuation-in-part of application No. 13/448,378, filed on Apr. 16, 2012, now Pat. No. 9,697,556, and a continuation-in-part of application No. 13/663,376, filed on Oct. 29, 2012, now Pat. No. 9,557,271, application No. 14/999,601, which is a continuation-in-part of application No. 14/014,239, filed on Aug. 29, 2013, now Pat. No. 9,426,545, which is a continuation of application No. 12/931,384, filed on Jan. 31, 2011, now Pat. No. 8,548,334.

(60) Provisional application No. 62/230,249, filed on Jun. 1, 2015, provisional application No. 61/957,343, filed on Jul. 1, 2013.

(51) Int. Cl.
| | | |
|---|---|---|
| *H01S 5/183* | (2006.01) | |
| *H01S 5/187* | (2006.01) | |
| *G06F 3/01* | (2006.01) | |
| *G06F 3/041* | (2006.01) | |
| *G06F 19/00* | (2018.01) | |
| *G09G 3/00* | (2006.01) | |
| *H04W 4/02* | (2018.01) | |
| *G09G 3/34* | (2006.01) | |

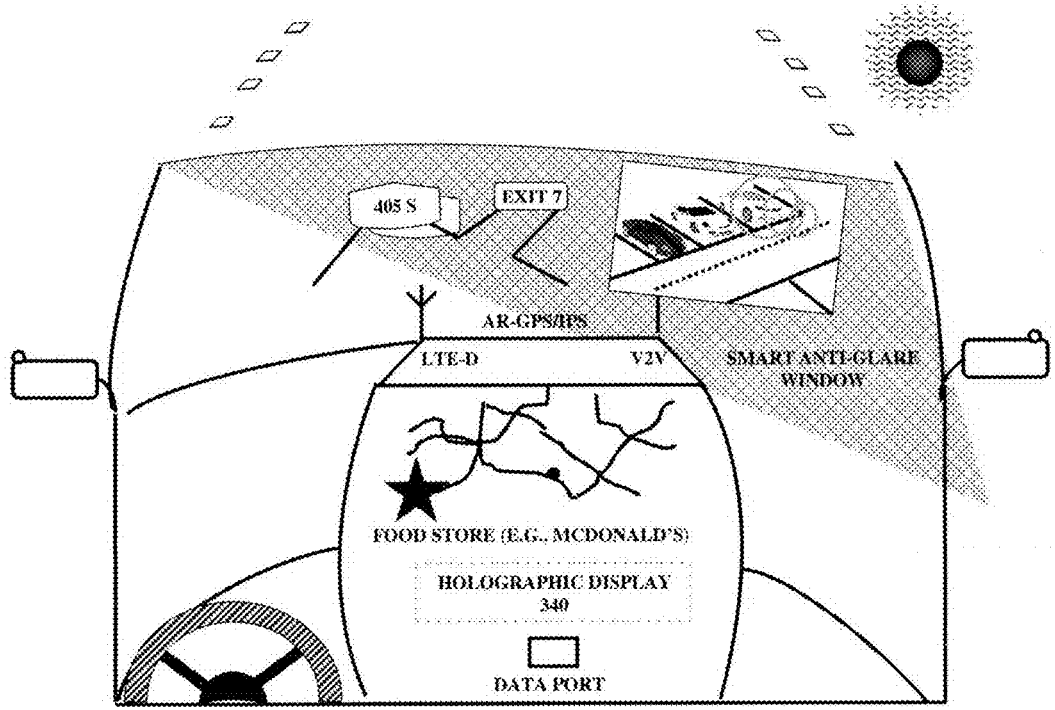
FIG. 3E
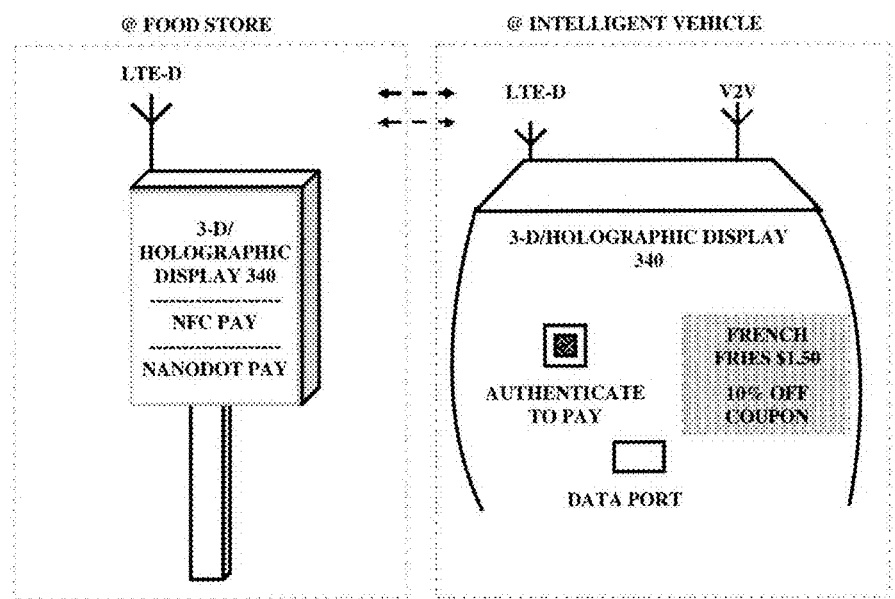
FIG. 3F
FIG. 3G

WIRED CHARGING CONFIGURATION OF CASH CARD
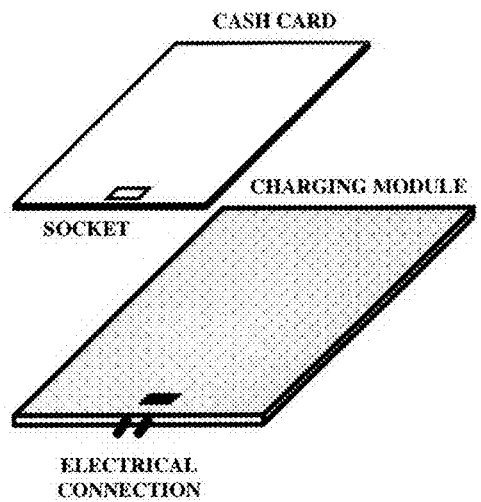
FIG. 7C
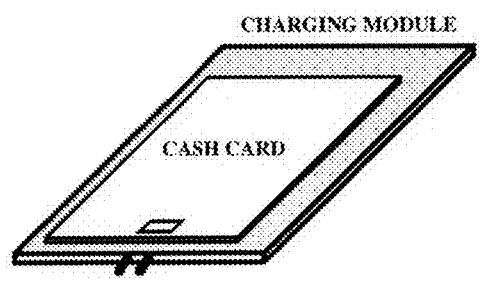
FIG. 7D
WIRELESS CHARGING CONFIGURATION OF CASH CARD
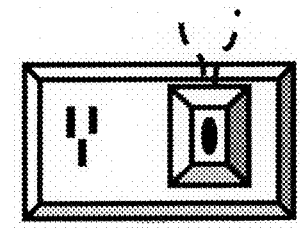
ELCTROMAGNETICALLY
CHARGING THROUGH AIR
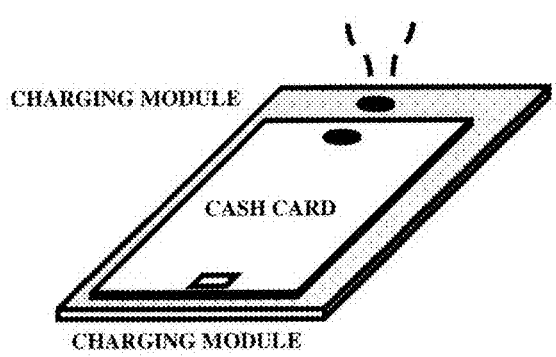
FIG. 7E STRETCHABLE DISPLAY WITH INKJET PRINTED
TRANSPARENT PROCESSOR(S) &/OR MEMRISTOR(S)

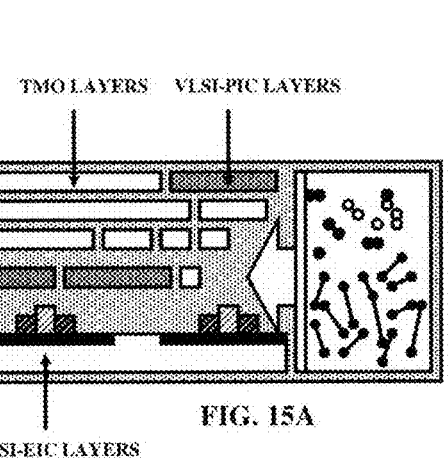
FIG. 15A
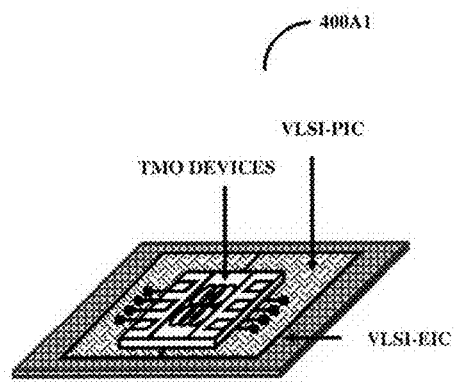
FIG. 15B
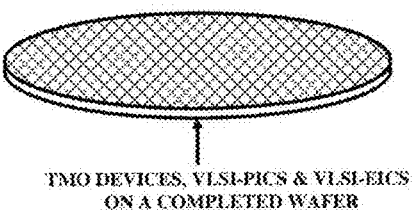
FIG. 15C
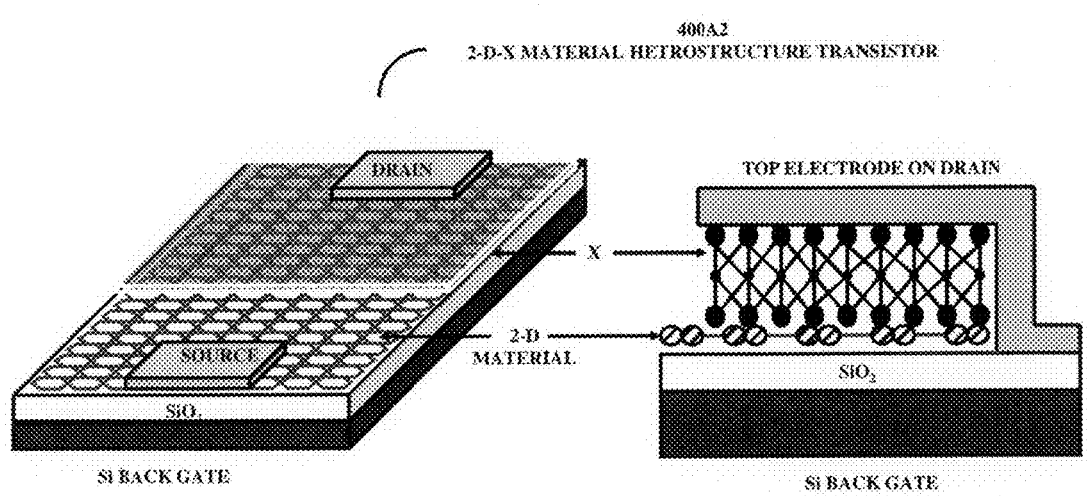
FIG. 15D
FIG. 15E

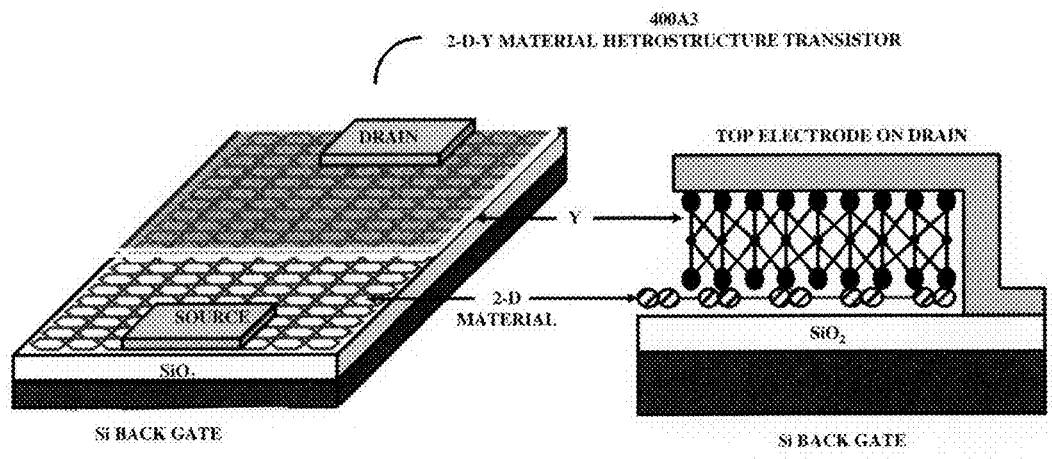
FIG. 15F
FIG. 15G
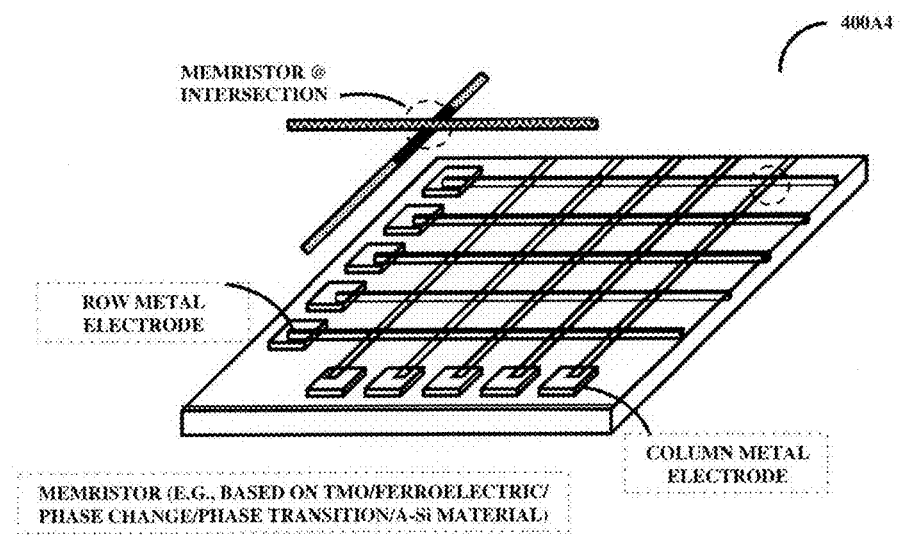
FIG. 16A

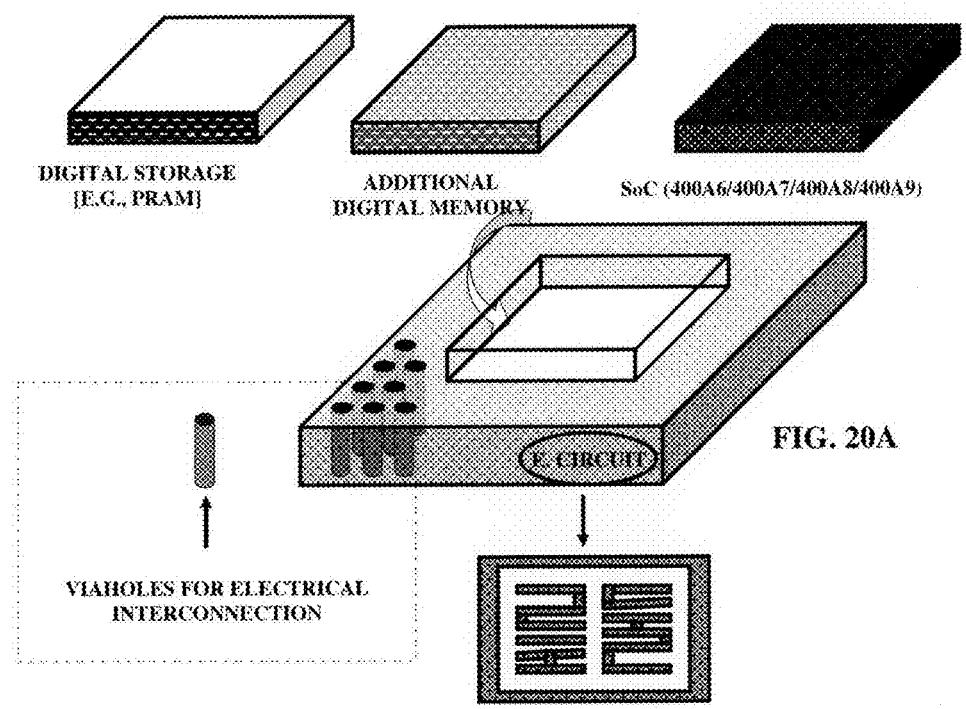
FIG. 20A
FIG. 20B
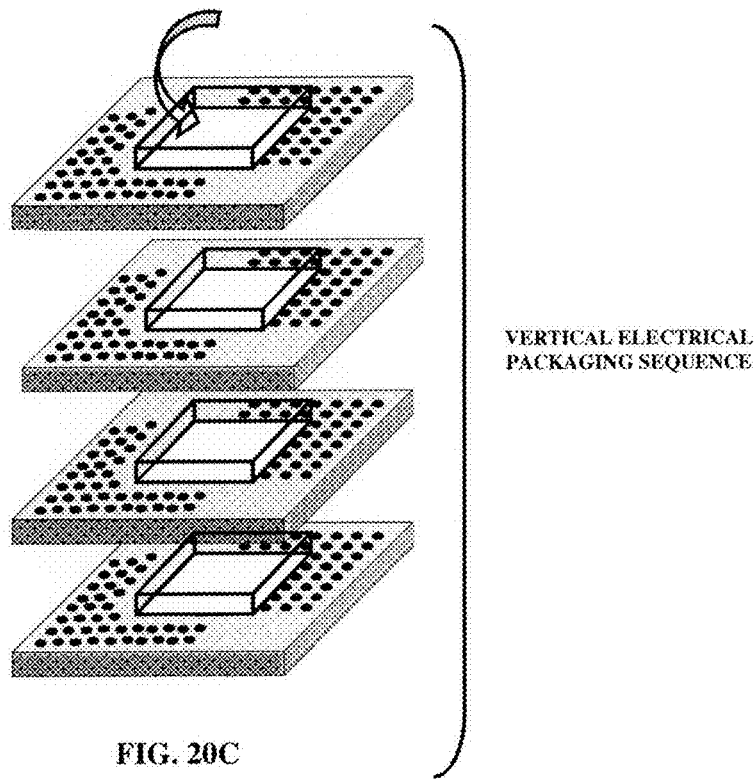
FIG. 20C

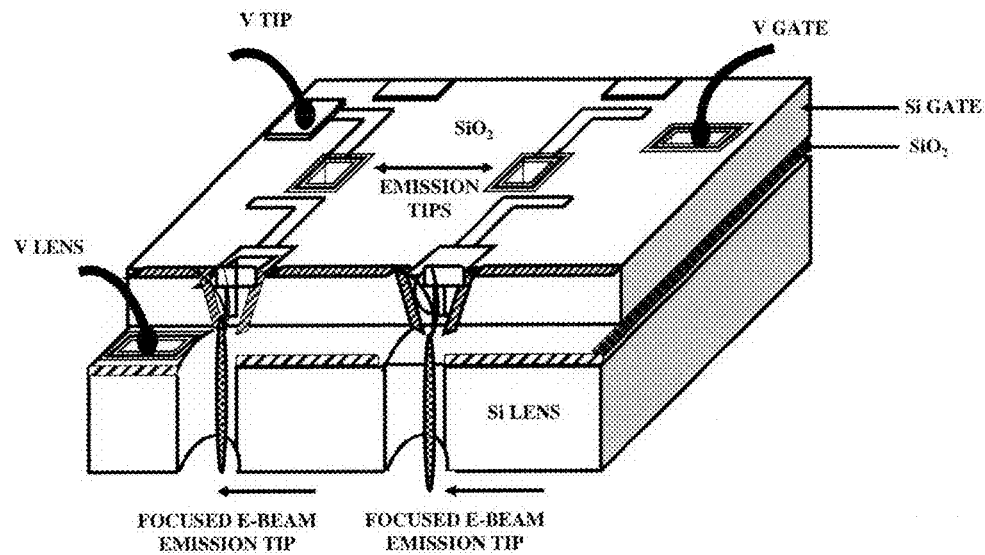
FIG. 29C
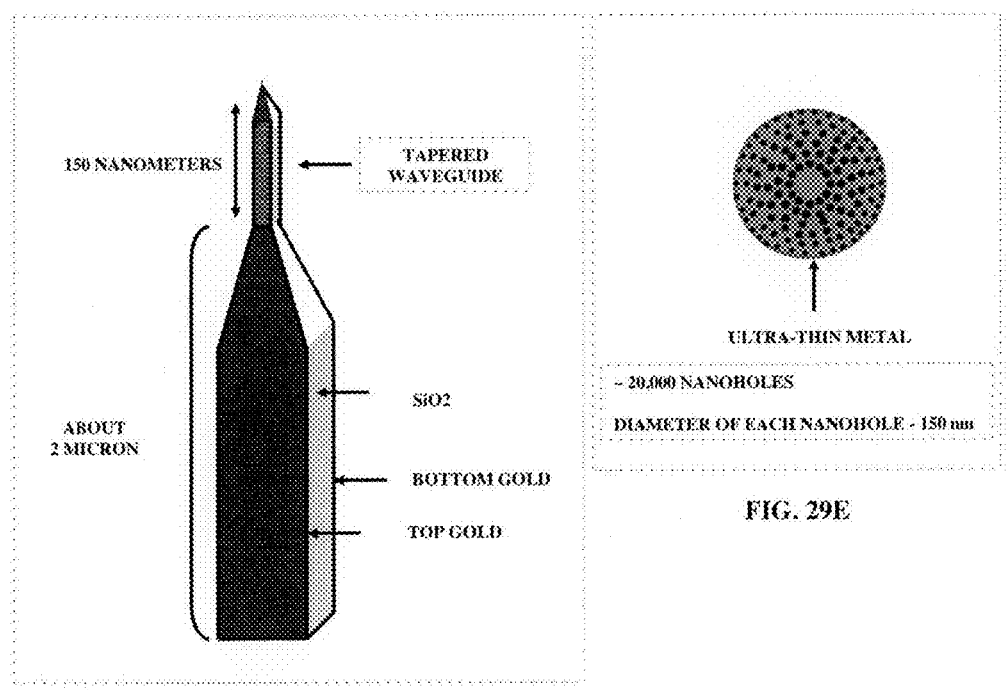
FIG. 29D
FIG. 29E

NANOSCALED OPTICAL ANTENNA (NOA)

BLUE QDS

GREEN QDS

RED QDS

BLUE QDS-NOAS

GREEN QDS-NOAS

RED QDS-NOAS

BLUE QDS IN PC

GREEN QDS IN PC

RED QDS IN PC

BLUE QDS-NOAS IN PC

GREEN QDS-NOAS IN PC

RED QDS-NOAS IN PC

ELECTRICALLY SWITCHABLE LIGHT VALVE (LV)

FIG. 34A  BLUE QDS IN LIQUID CRYSTAL GEL (LCG)
FIG. 34B  GREEN QDS IN LIQUID CRYSTAL GEL (LCG)
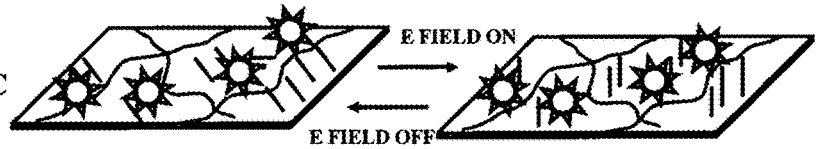
FIG. 34C  RED QDS IN LIQUID CRYSTAL GEL (LCG)
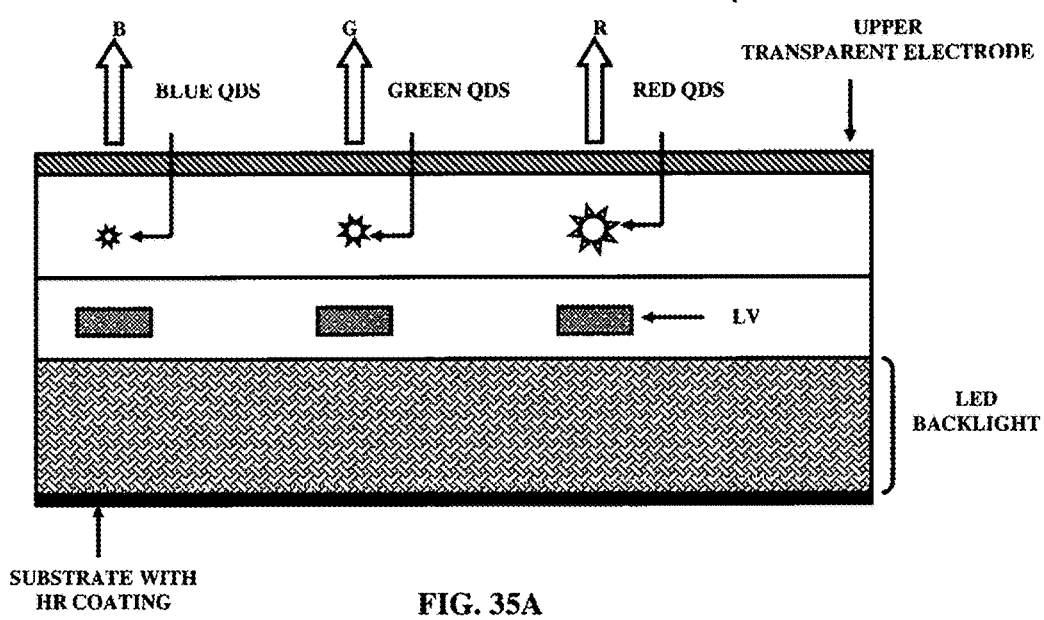
FIG. 35A

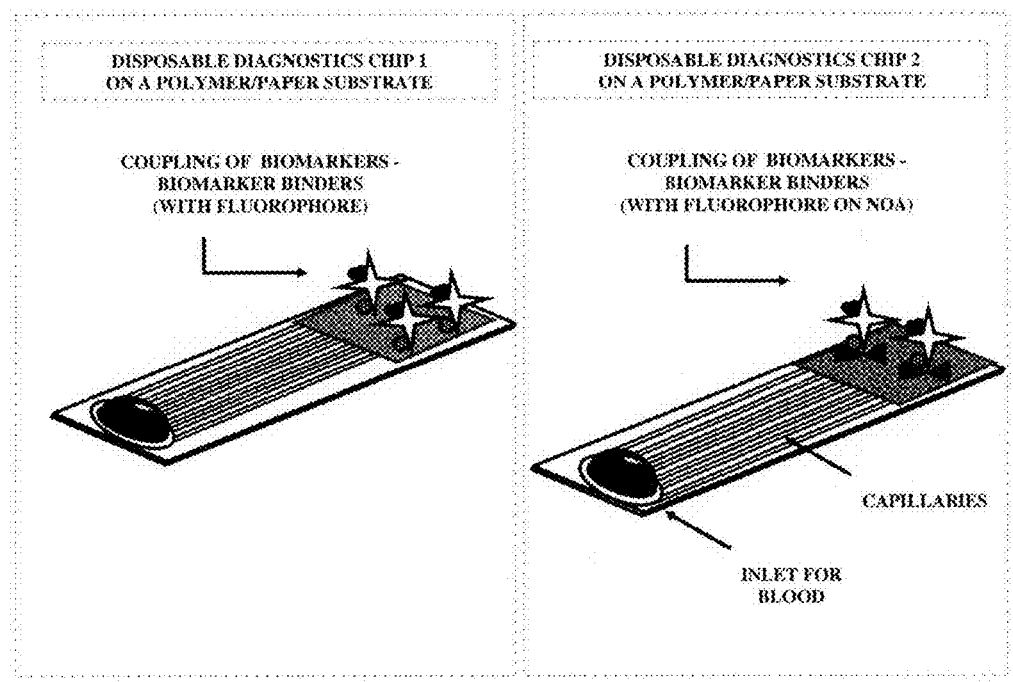
FIG. 55A
FIG. 55B
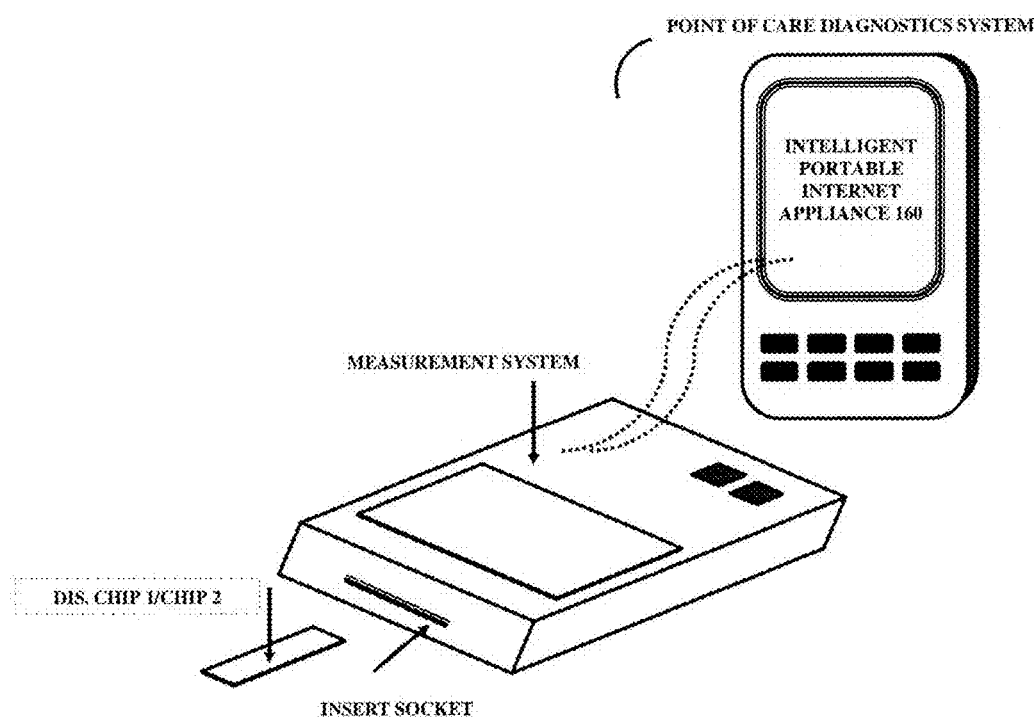
FIG. 55C

DELIVERING BIOACTIVE COMPOUND(S) IN SMART NANOSHELL

AN EXAMPLE OF A RIBOSWITCH

MITOCHONDRIA
SPECIFIC CELL RECEPTOR
MITOCHONDRIA
E. RIBOSWITCH
NUCLEUS
LIGAND TO BIND WITH CELL RECEPTOR
SMART NANOSHELL TO DELIVER E. RIBOSWITCH/NOTCH MOLECULE

DISPLAY DEVICE

RELATED PRIOR PROVISIONAL PATENT APPLICATION

U.S. Provisional Patent Application No. 62/230,249 entitled "SYSTEM AND METHOD OF AMBIENT/PERVASIVE USER/HEALTHCARE EXPERIENCE", filed on Jun. 1, 2015. The entire contents of U.S. Provisional Patent Application No. 62/230,249 are hereby incorporated by reference.

CONTINUATION-IN-PART (CIP) OF THE FOLLOWING PATENT APPLICATIONS (a) U.S. Non-Provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014, (b) U.S. Non-Provisional patent application Ser. No. 14/014,239 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Aug. 29, 2013, (c) U.S. Non-Provisional patent application Ser. No. 13/663,376 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Oct. 29, 2012, (d) U.S. Non-Provisional patent application Ser. No. 13/448,378 entitled "SYSTEM AND METHOD FOR INTELLIGENT SOCIAL COMMERCE", filed on Apr. 16, 2012, and (e) U.S. Non-Provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 (now U.S. Pat. No. 8,548,334, issued on Oct. 1, 2013). Above applications of (a), (b), (c), (d) and (e) with their benefit patent applications are all incorporated by reference, as if reproduced herein in their entirety.

FIELD OF THE INVENTION

With the dawn of the Internet of Things (IoT), the present invention is multi-disciplined and highly diverse, as it relates to objects/object nodes, bioobjects/bioobject nodes, which are connected with a personal Human OS (operating system), intelligent portable internet appliances, intelligent wearable augmented personal assistant devices, wearable personal health assistant devices and intelligent (energy efficient) vehicles.

SUMMARY OF THE INVENTION

In view of the foregoing, one objective of the present invention is to design and construct a system and method for:
  ambient/pervasive user experience in near real time or real time, and
  ambient/pervasive personal Human OS.

BRIEF DESCRIPTION OF THE DRAWINGS

Internet Connected Sensors, Devices & Systems
FIGS. 3E-3J illustrate other components/subsystems of the intelligent vehicle.
FIGS. 7A-7E illustrate an embodiment of a near field communication (NFC) based secure payment system.

Intelligent Portable Internet Appliance

Figure 14A:
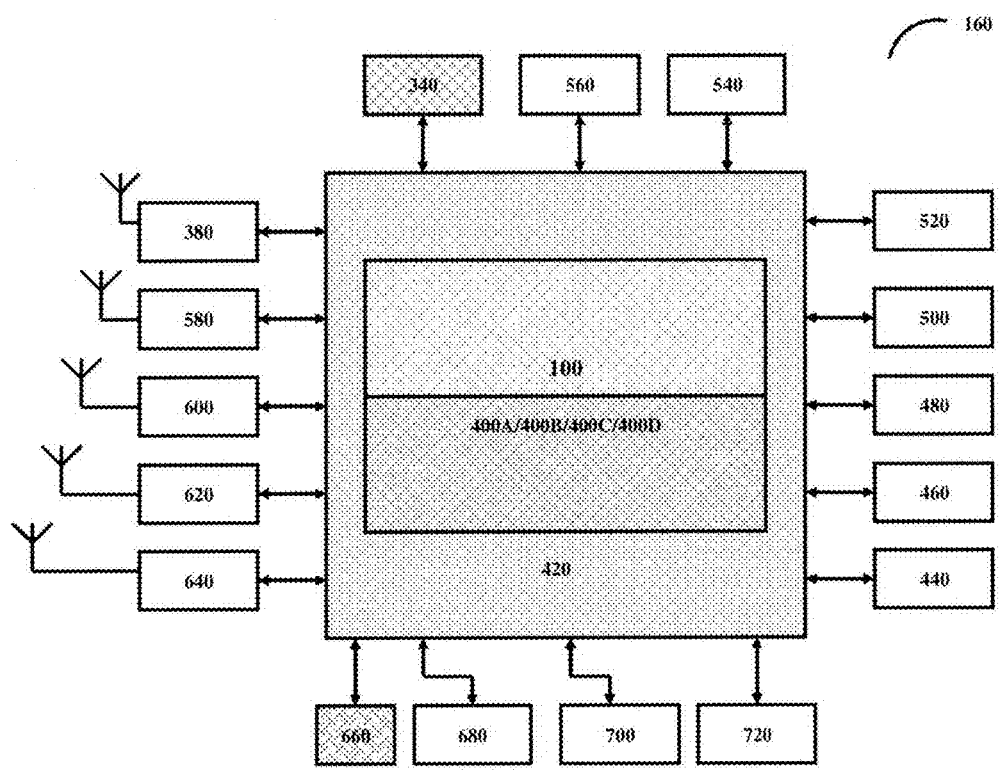
Figure 14B:
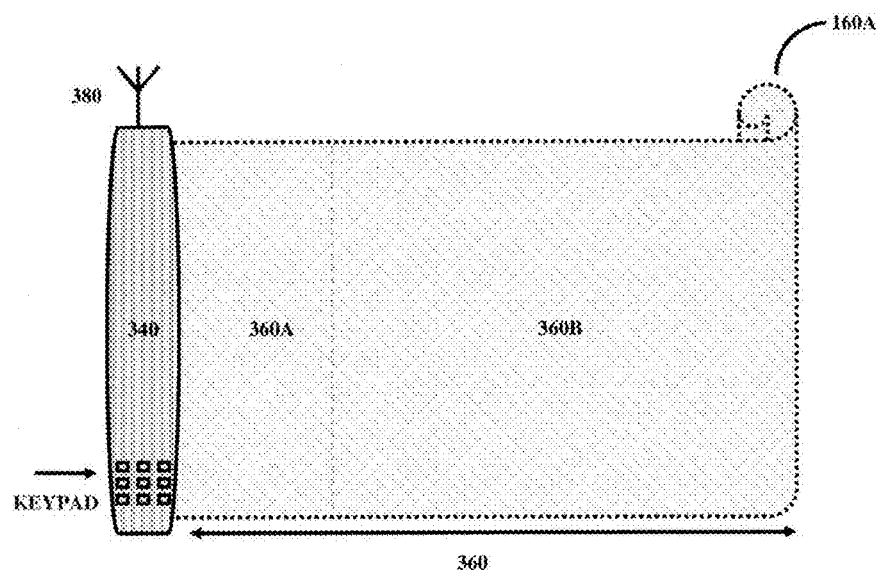

FIGS. 14A-14B illustrate two embodiments of the intelligent portable internet appliance.

Super System on Chip

FIGS. 15A-15G illustrate various embodiments of a digital processor.

FIG. 16A illustrate an embodiment of a memristor.

Figure 16B:
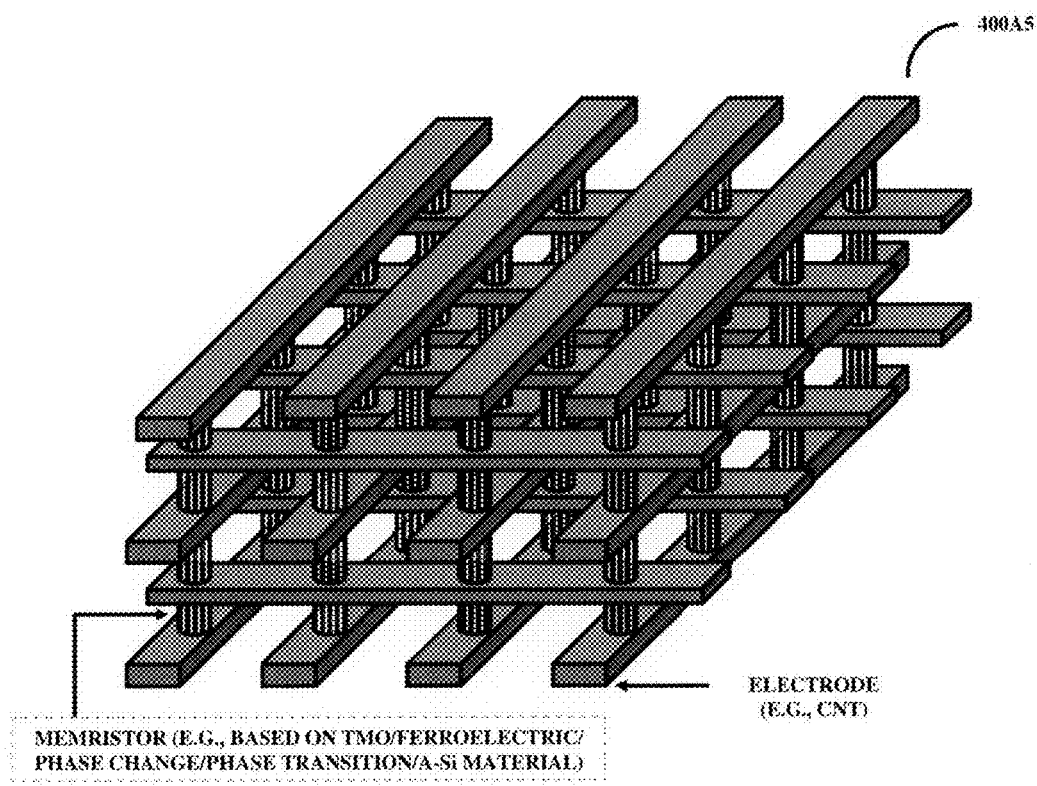

FIG. 16B illustrates an embodiment of a three-dimensional integration of a memristor.

Figure 16C:
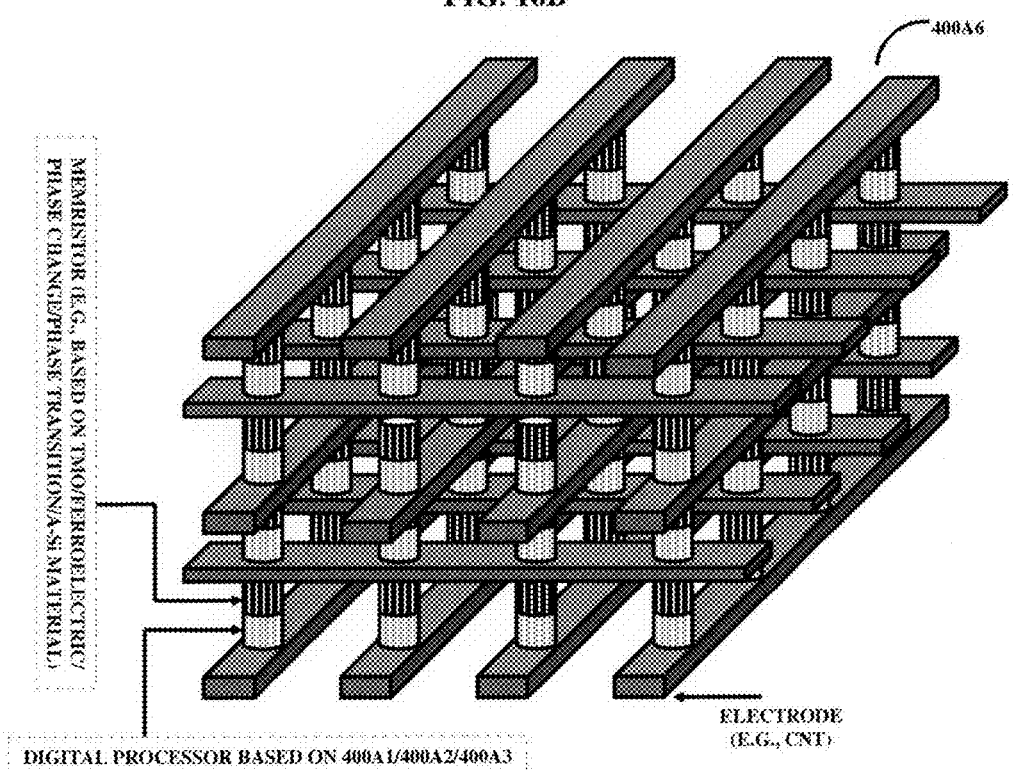

FIG. 16C illustrates an embodiment of a three-dimensional integration of a memristor with various versions of a digital processor.

Figure 16D:
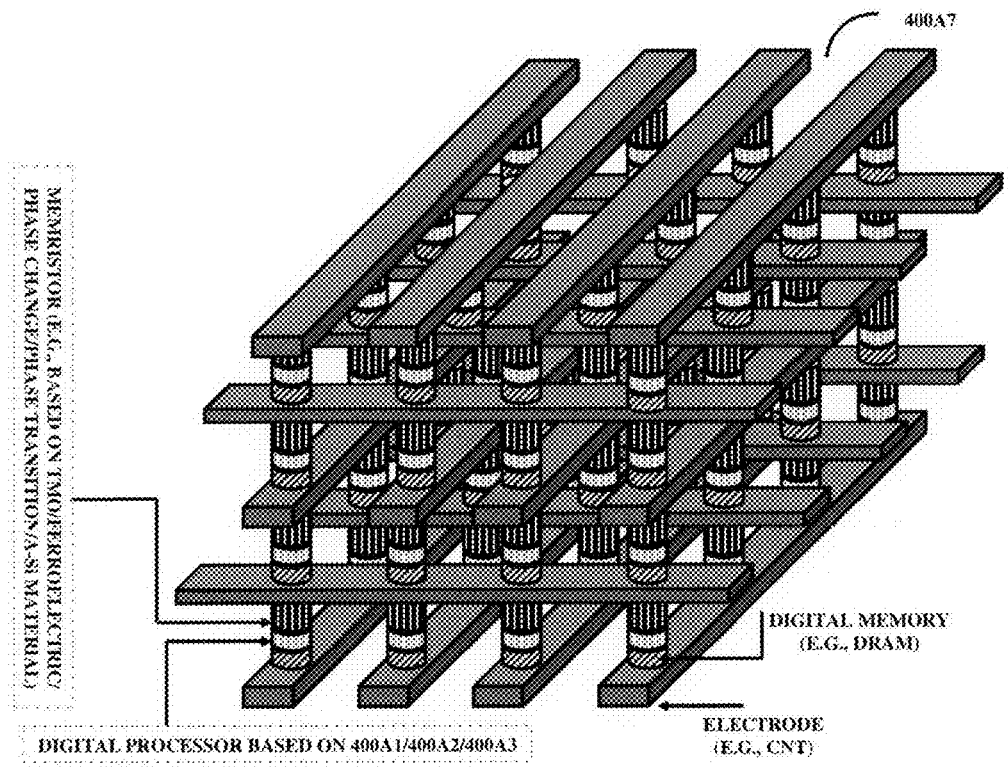

FIG. 16D illustrates an embodiment of a three-dimensional integration of a memristor and a digital memory with various versions of a digital processor.

Figure 17A:
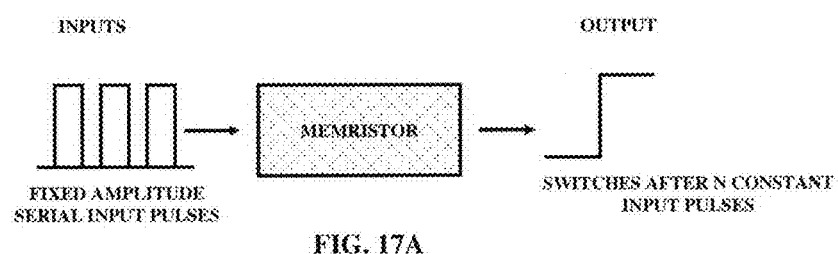
Figure 17B:
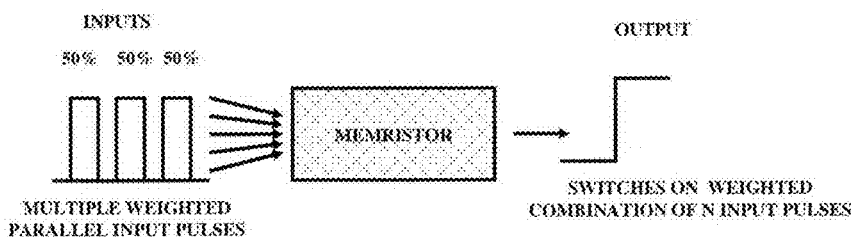

FIGS. 17A-17B illustrate an input-output relationship of a memristor.

Figure 17C:
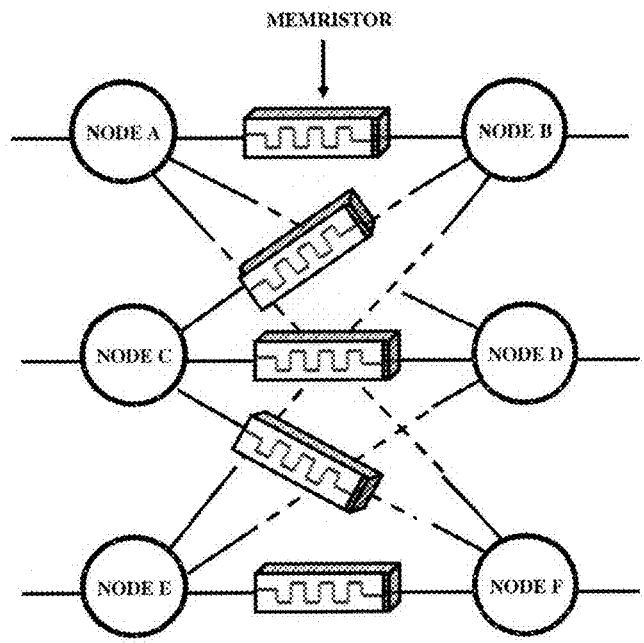

FIG. 17C illustrates interactions of memristors with nodes.

Figure 18A:
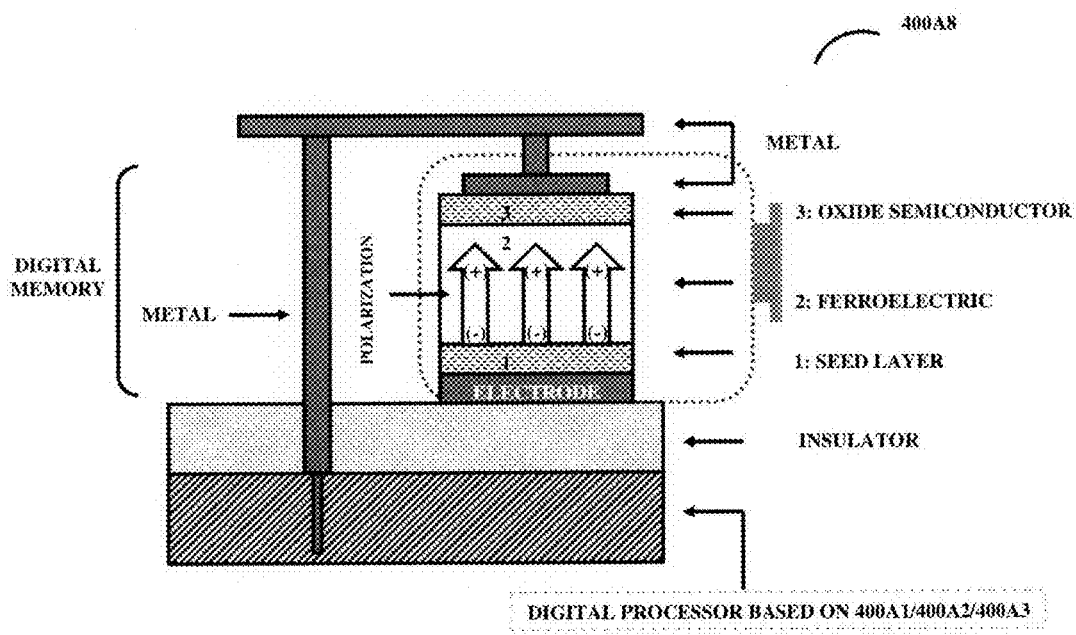
Figure 18B:
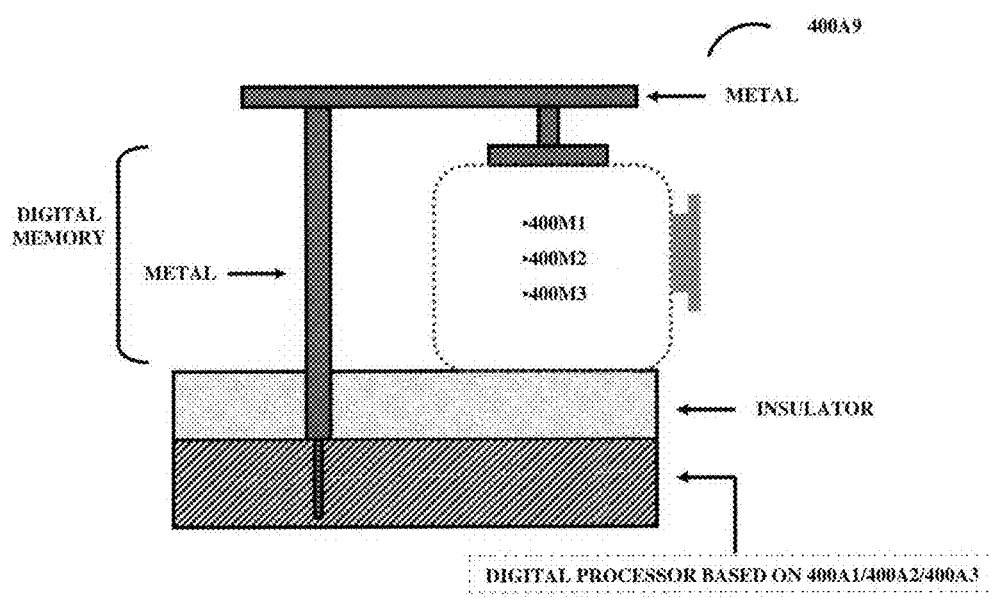

FIGS. 18A-18B illustrate various embodiments of three-dimensional integration of a digital memory with various versions of a System on Chip.

Figure 19A:
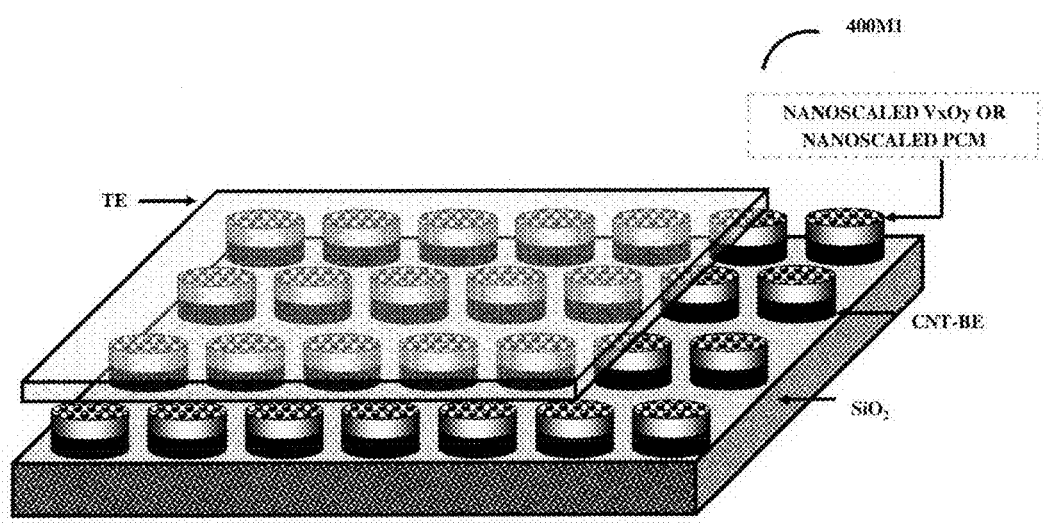
Figure 19B:
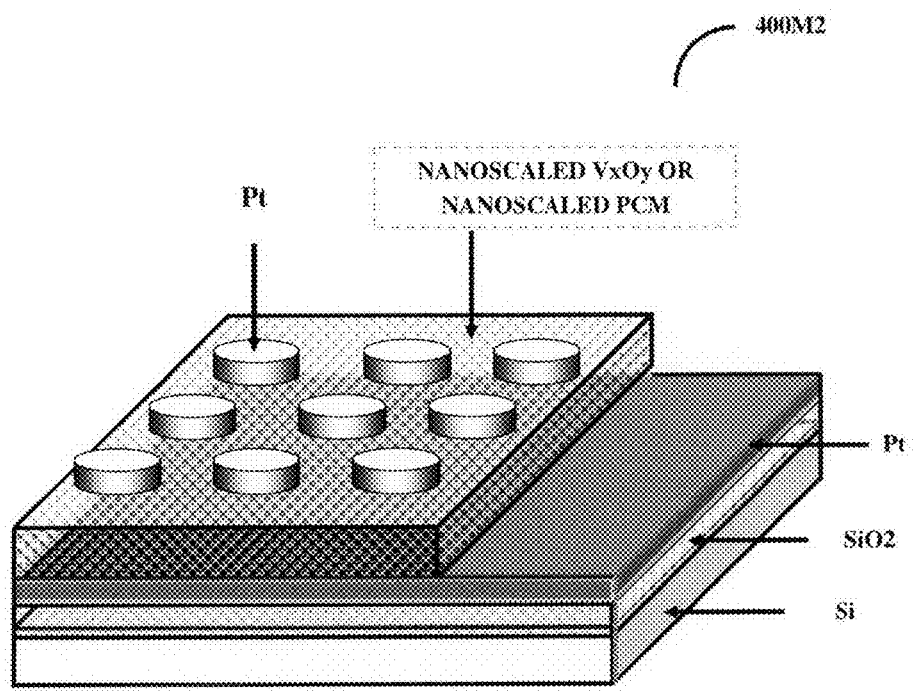
Figure 19C:
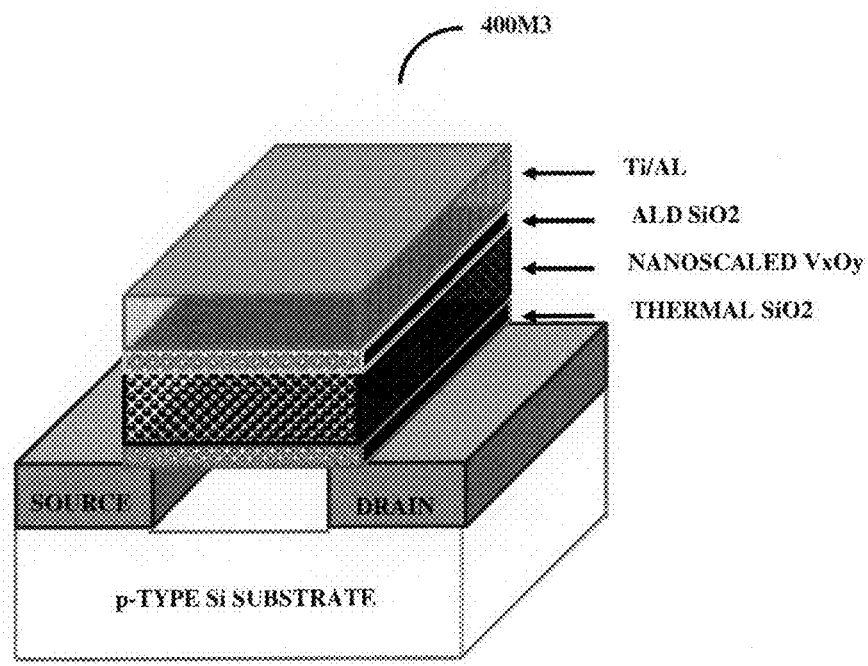

FIGS. 19A-19C illustrate three embodiments of a digital memory.

Packaging of Super System on Chip

FIGS. 20A-20G illustrate an embodiment of electrical interconnections to enable a Super System on Chip.

FIGS. 21A-21D illustrate an embodiment of optical interconnections to enable Super System on Chip.

Figure 22A:
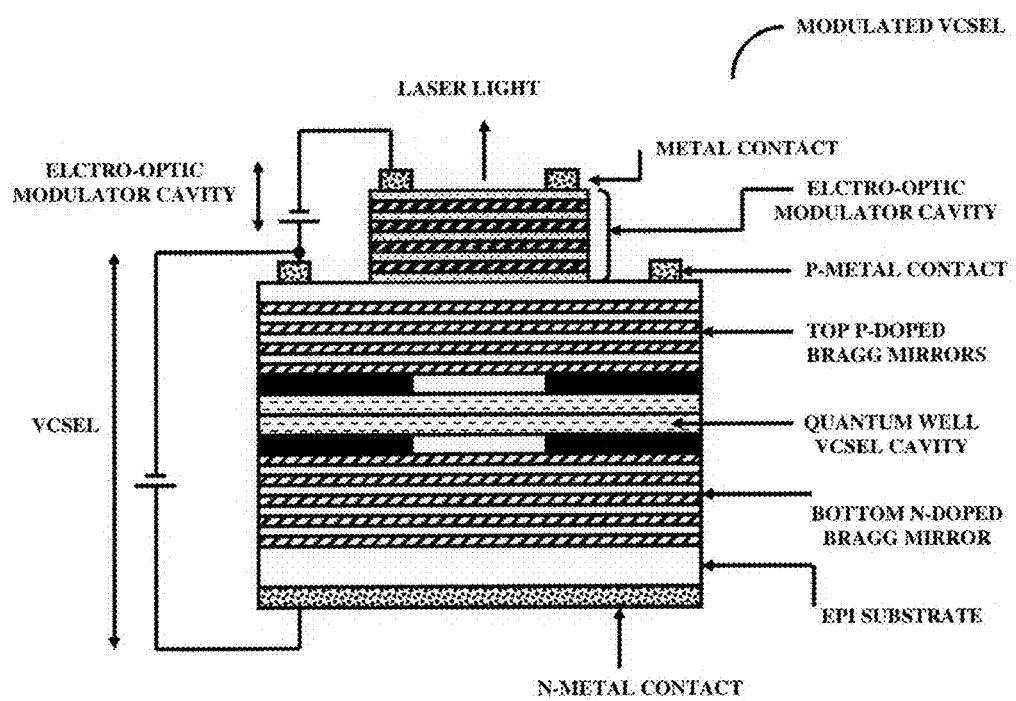
Figure 22B:
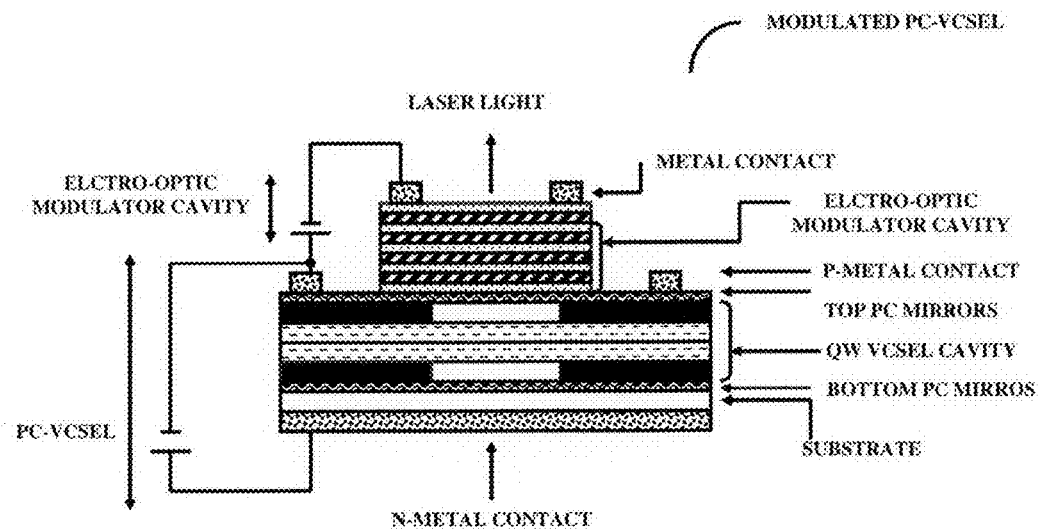

FIGS. 22A-22B illustrate two embodiments of a vertical cavity surface emitting laser for optical interconnections.

Figure 23:
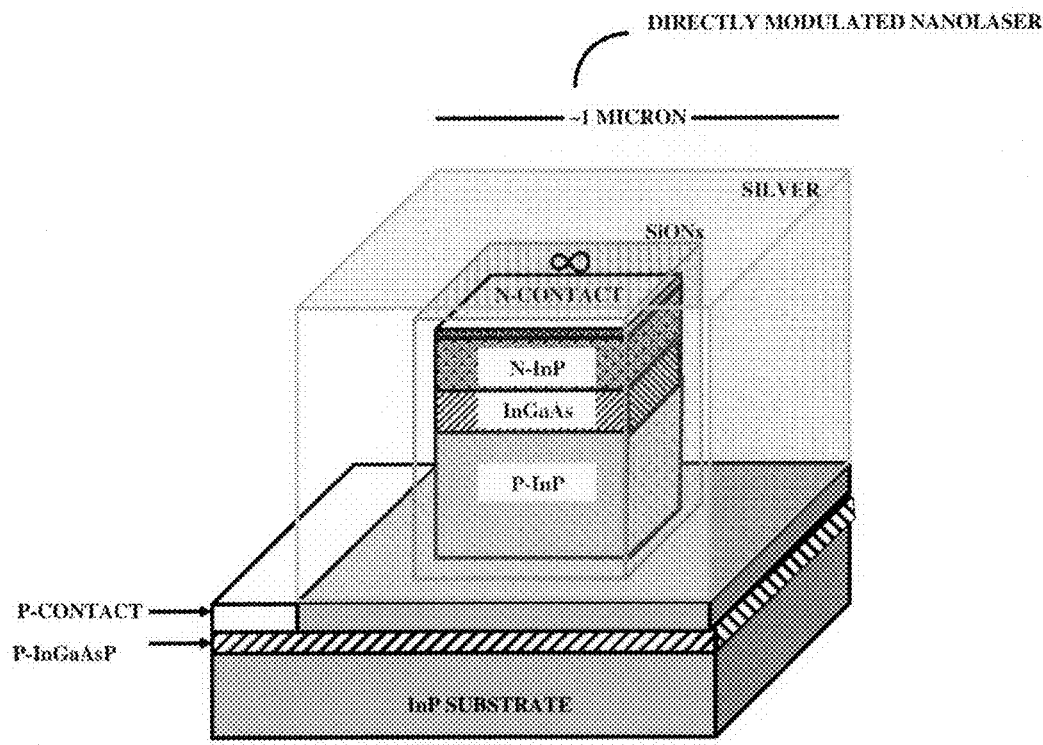

FIG. 23 illustrates an embodiment of a nanolaser for optical interconnections.

Figure 24:
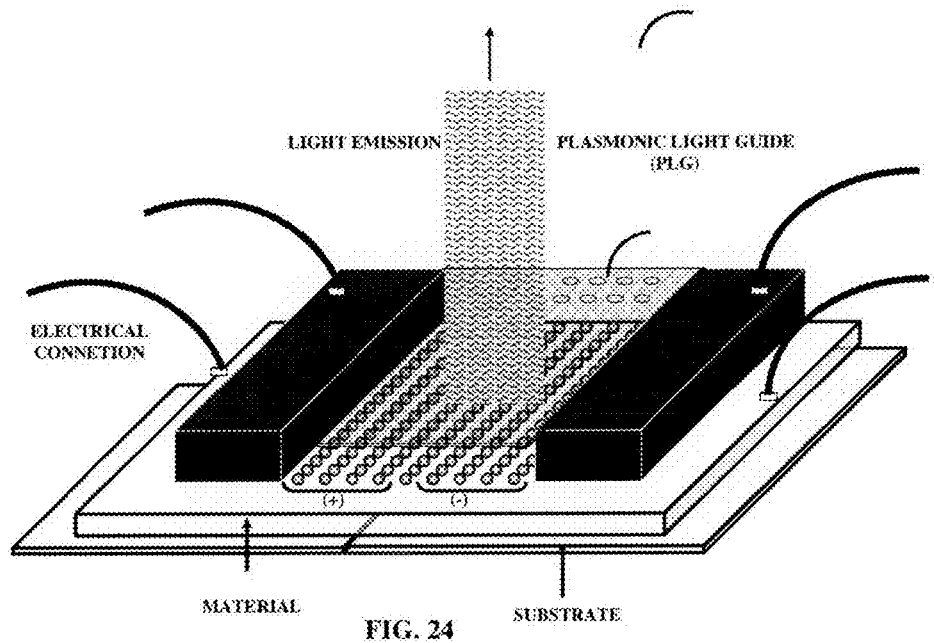

FIG. 24 illustrates an embodiment of a light emitting diode for optical interconnections.

Figure 25A:
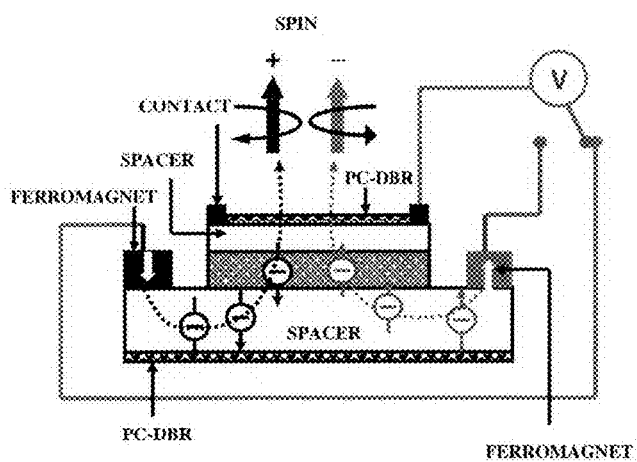
Figure 25B:
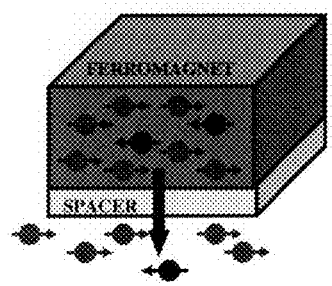

FIGS. 25A-25B illustrate an embodiment of a spin controlled laser for optical interconnections.

Optical Interconnections of Super System on Chips

FIGS. 26A-26D illustrate four embodiments of horizontally connecting a Super System on Chip on an opto-electronic printed circuit board.

Figure 27A:
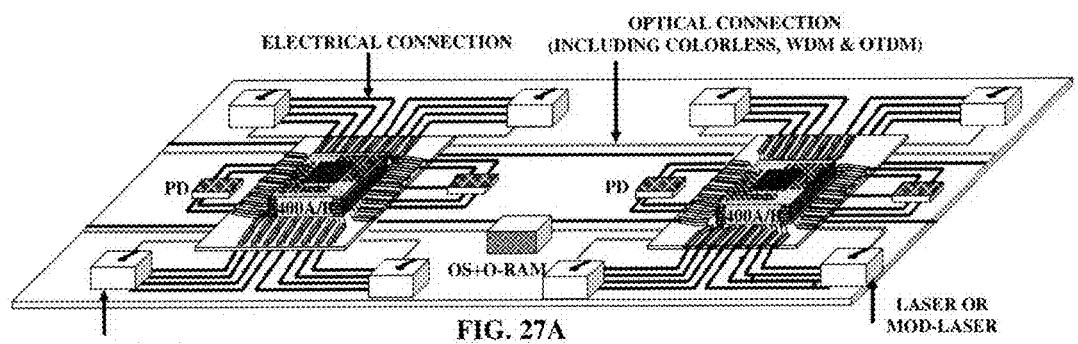
Figure 27B:
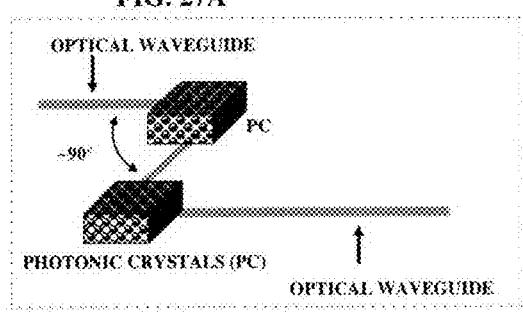

FIGS. 27A-27B illustrate an embodiment of horizontally connecting multiple Super System on Chips on an opto-electronic printed circuit board.

Figure 28A:
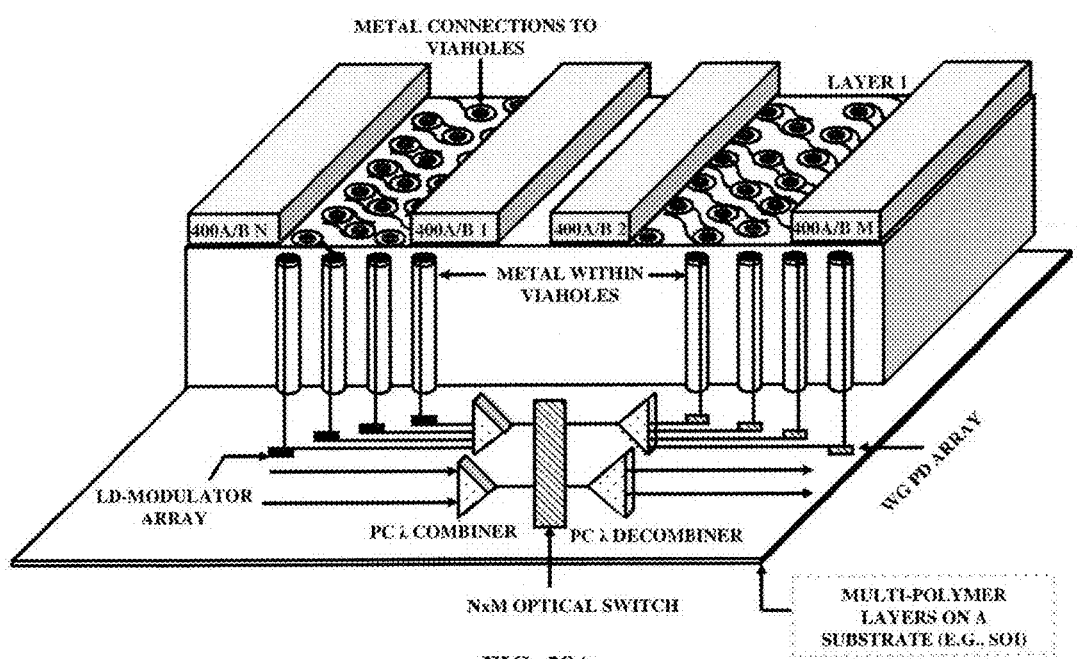
Figure 28B:
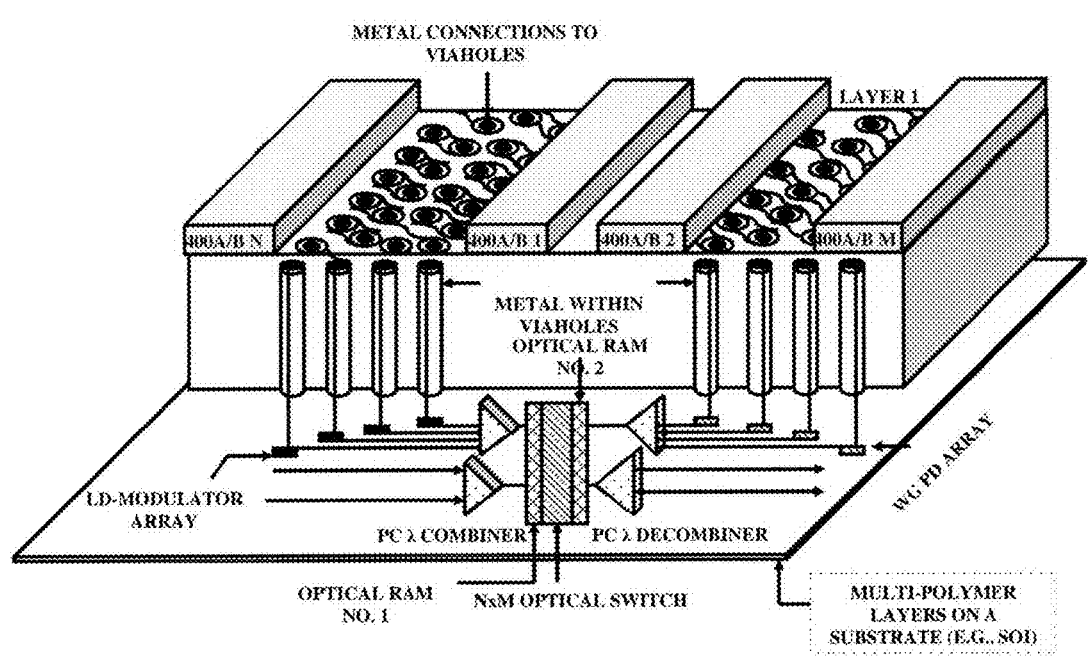

FIGS. 28A-28B illustrate two embodiments of vertically connecting multiple Super System on Chips on an opto-electronic printed circuit board.

Figure 28C:
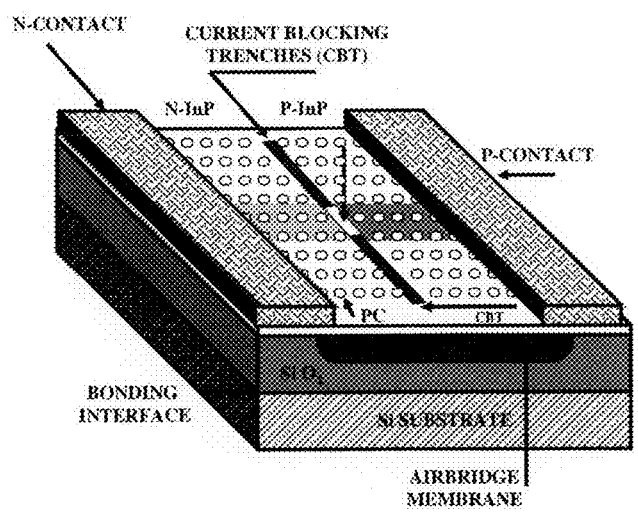
Figure 28D:
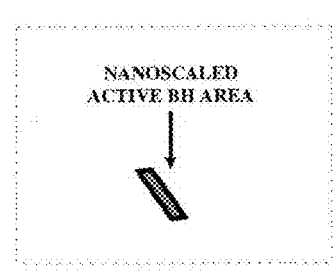

FIGS. 28C-28D illustrate an embodiment of a laser for vertically connecting multiple Super System on Chips on an opto-electronic printed circuit board.

Figure 28E:
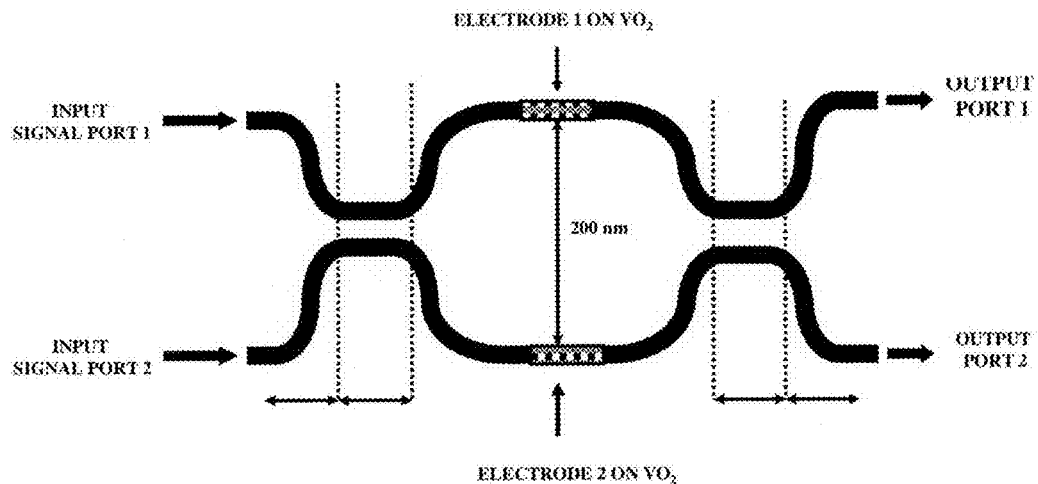
Figure 28F:
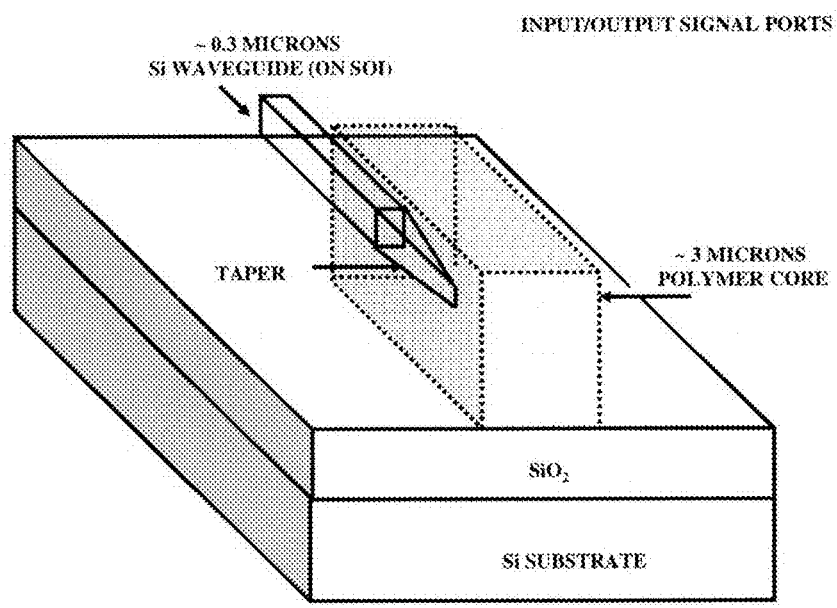

FIGS. 28E-28F illustrate an embodiment of an optical switch for vertically connecting multiple Super System on Chips on an opto-electronic printed circuit board.

Figure 28G:
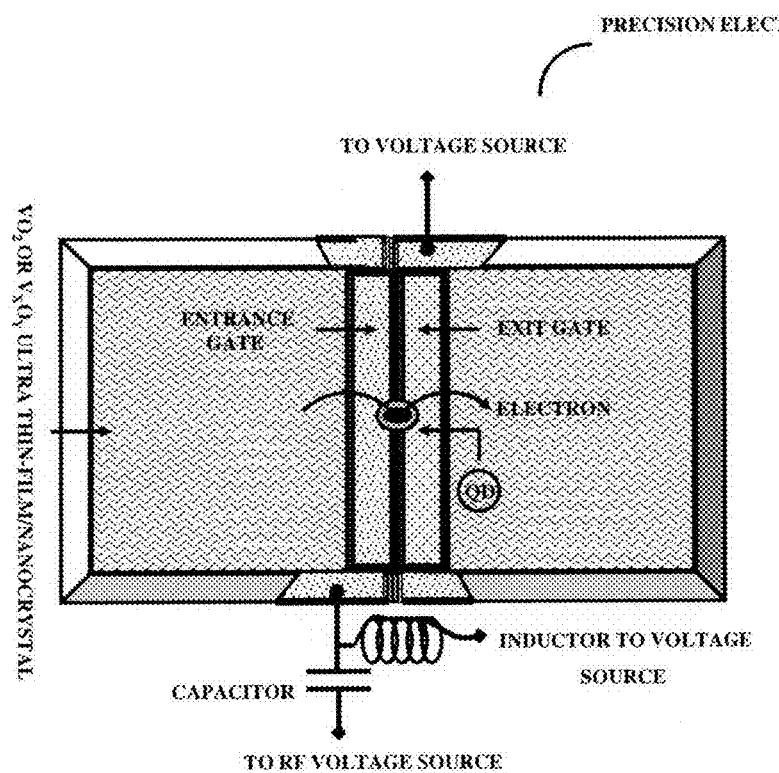

FIGS. 28G-28F1 illustrate two other components of the optical switch.

Ultrahigh Density Storage Device

Figure 29A:
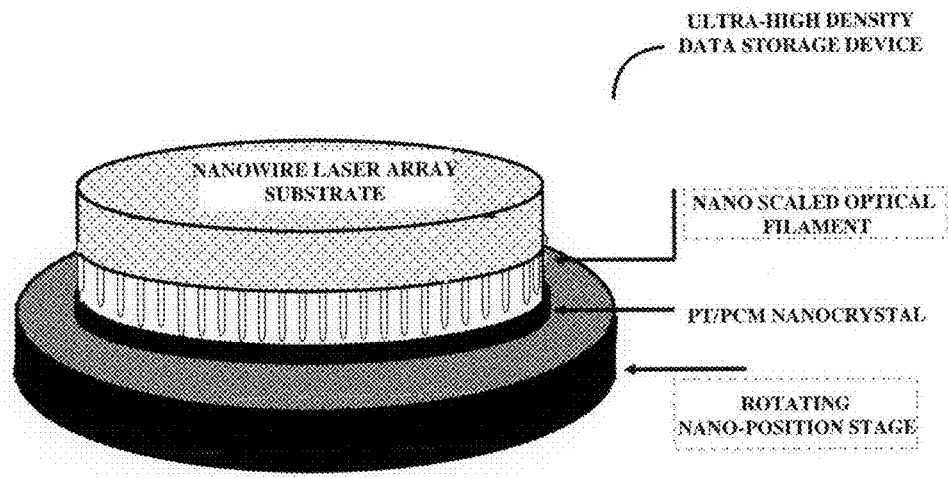

FIG. 29A illustrates an embodiment of an ultrahigh density data storage device.

FIGS. 29B-29E illustrate components for the ultrahigh density data storage device.

Three-Dimensional (3-D)/Holographic Display

FIGS. 30A-30E illustrate five embodiments of a nano optical antenna (NOA).

FIGS. 31A-31L illustrate various configurations of blue quantum dots, green quantum dots and red quantum dots and various configurations of blue quantum dots, green quantum dots and red quantum dots with nano optical antenna and photonic crystal.

FIGS. 32A-32E describe five embodiments of a light valve (LV).

Figure 32A:
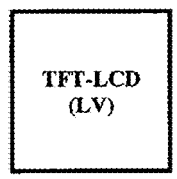
Figure 32B:
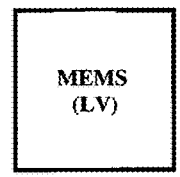
Figure 32C:
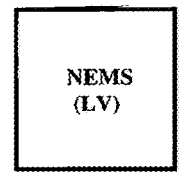
Figure 32D:
Figure 32E:
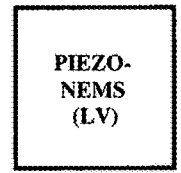
Figure 32F:
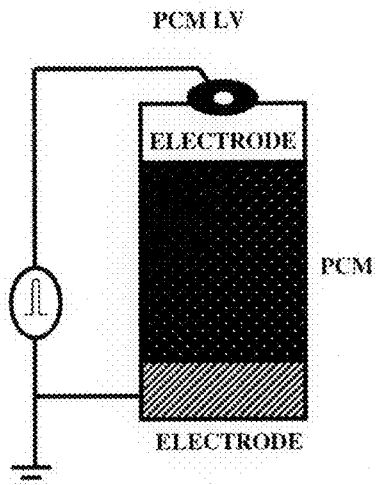
Figure 32G:
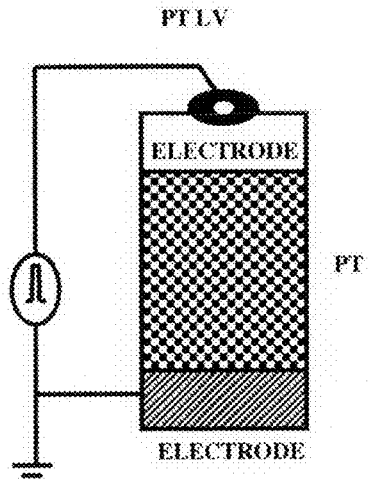

FIGS. 32F-32G illustrate two embodiments of an electrically switchable light valve.

Figure 33:
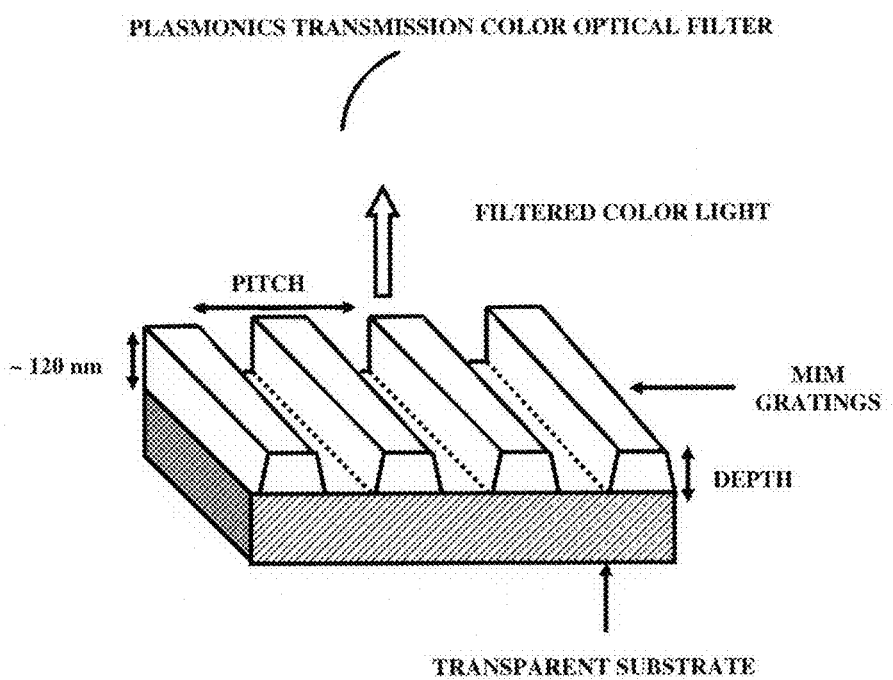

FIG. 33 illustrates an embodiment of a plasmonic optical color filter.

FIGS. 34A-34C illustrate blue quantum dots in an electrically switchable liquid crystal gel (LCG), green quantum dots in an electrically switchable liquid crystal gel and red quantum dots in an electrically switchable liquid crystal gel respectively.

FIGS. 35A-35F illustrate six embodiments of a pixel of a display, utilizing light emitting diode (LED) backlighting.

FIGS. 36A-36G illustrate materials and design/fabrication/construction for an embodiment of an ultraviolet (UV)/blue microlight emitting diode (μLED).

FIGS. 37A-37F illustrate six embodiments of a micropixel of a display, utilizing ultraviolet/blue microlight emitting diodes on each sub pixel.

Figure 38:
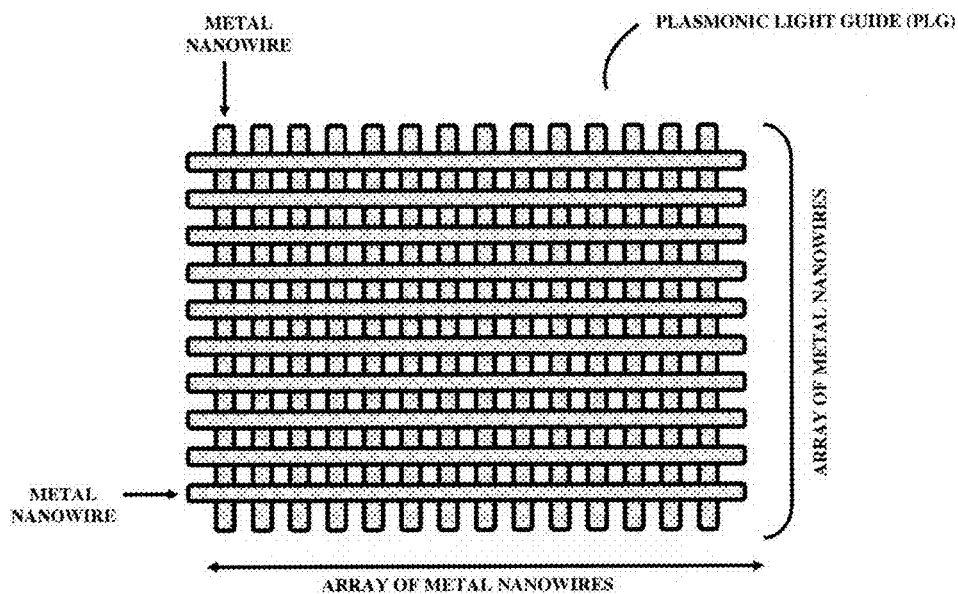
Figure 39A:
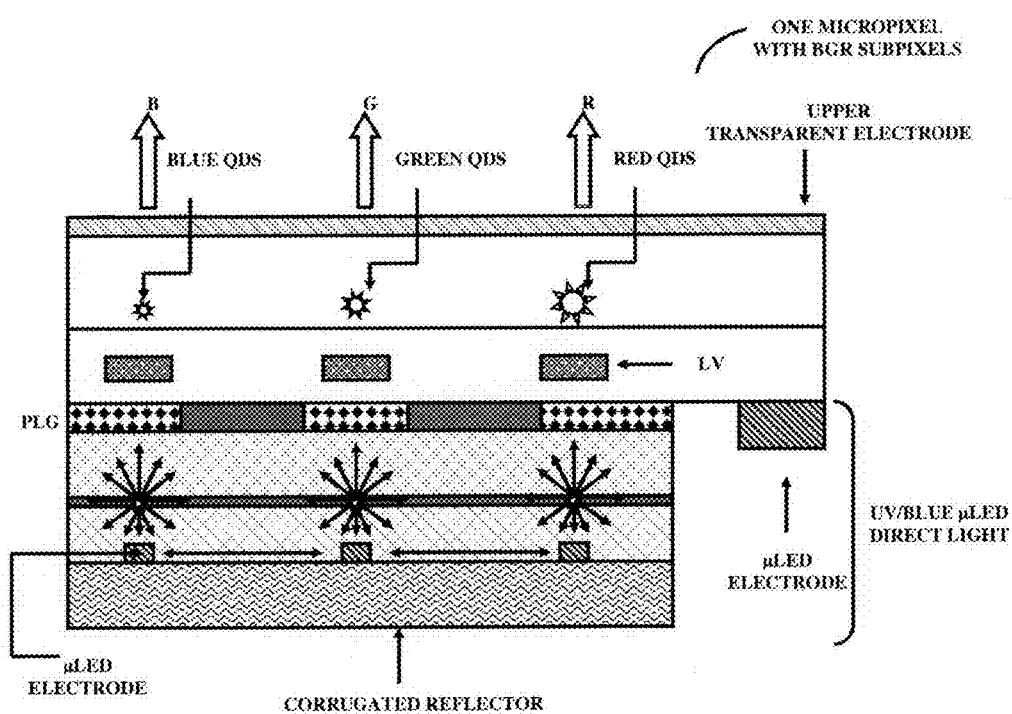
Figure 39B:
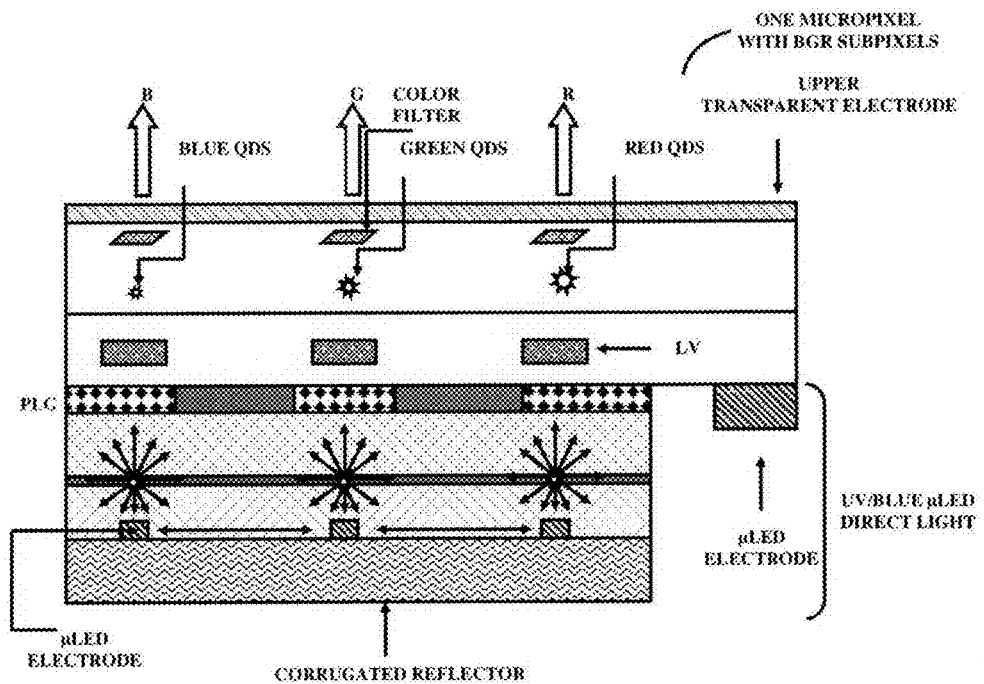
Figure 39C:
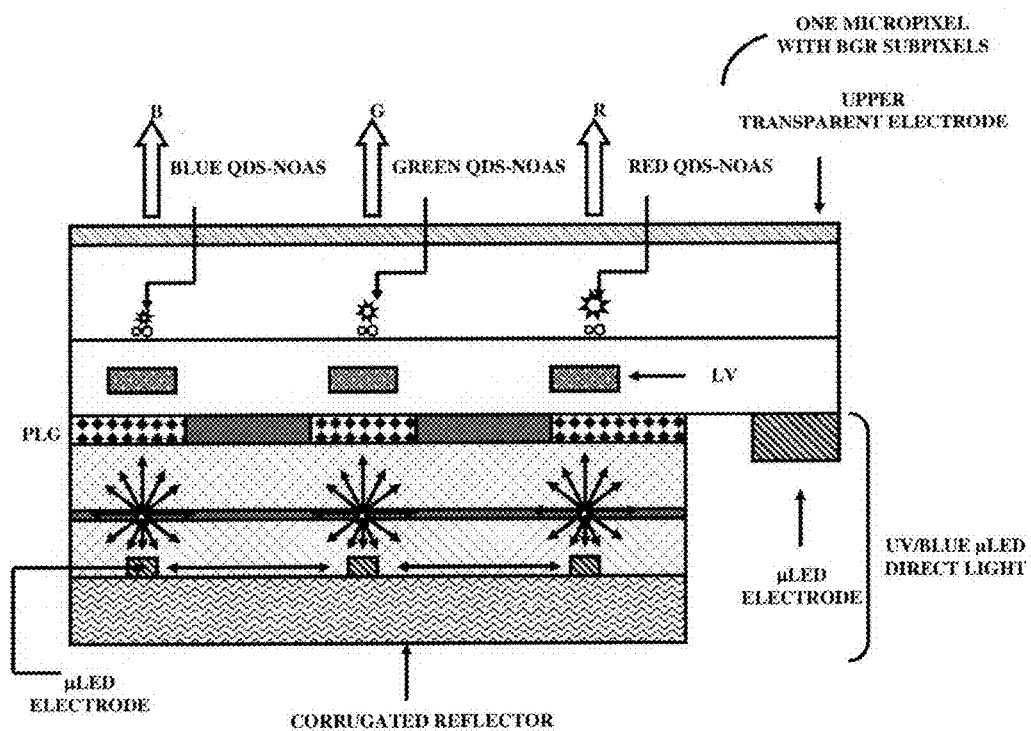
Figure 39D:
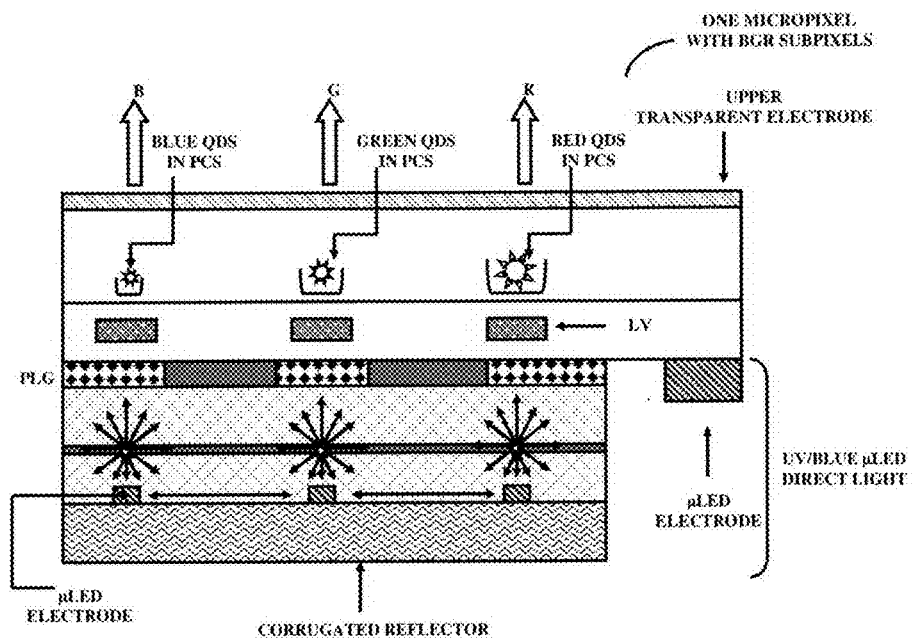
Figure 39E:
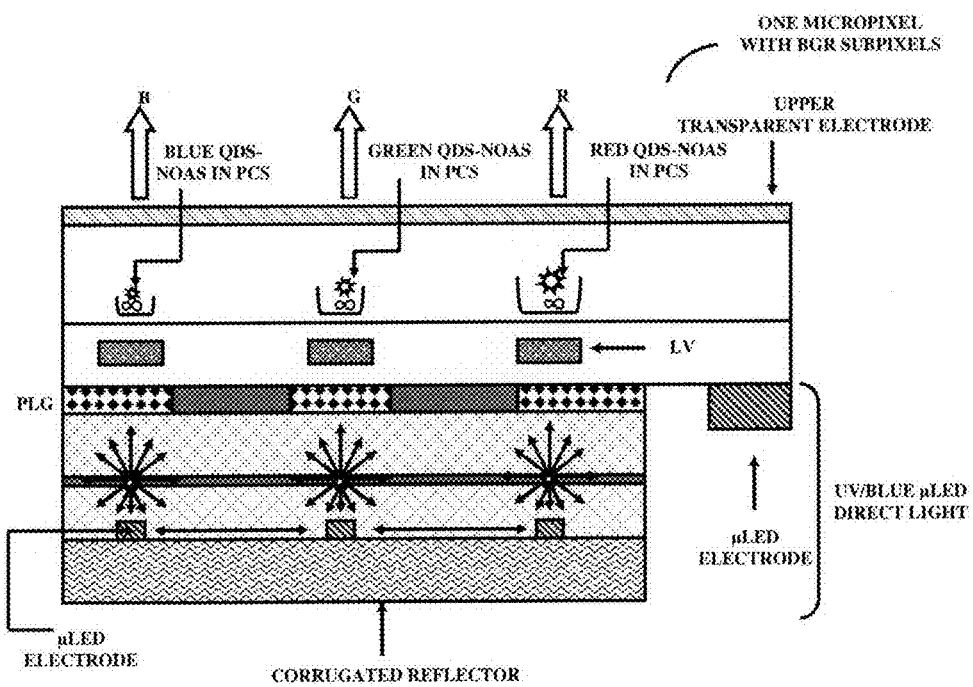
Figure 39F:
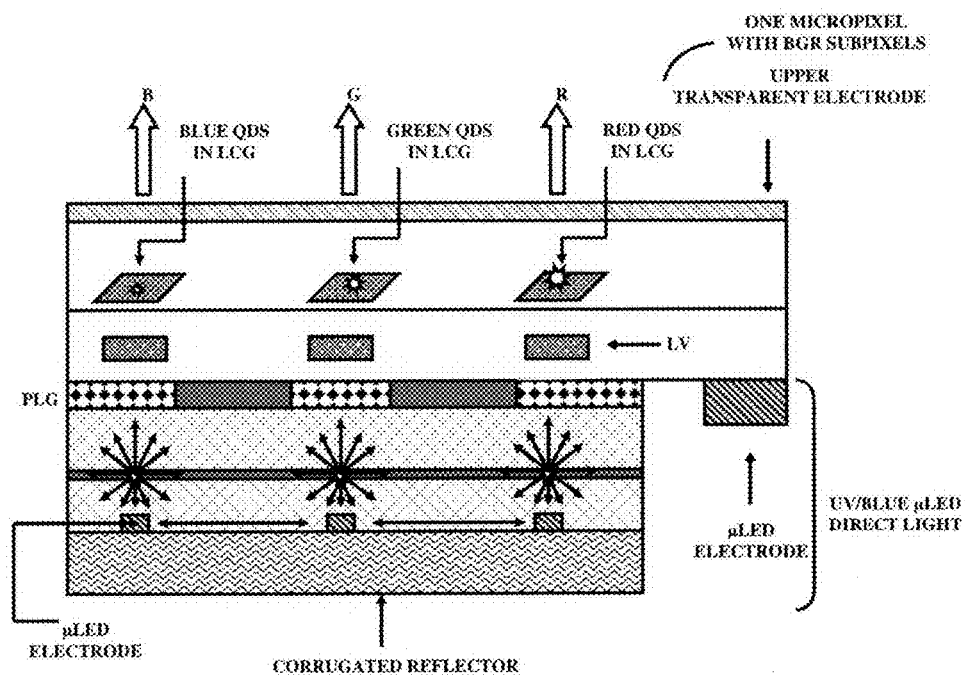

FIG. 38 illustrates a plasmonic light guide (PLG).

FIGS. 39A-39F illustrate six embodiments of a micropixel of a display, utilizing ultraviolet (UV)/blue microlight emitting diodes and plasmonic light guides on each subpixel.

Figures 40A, 40B:
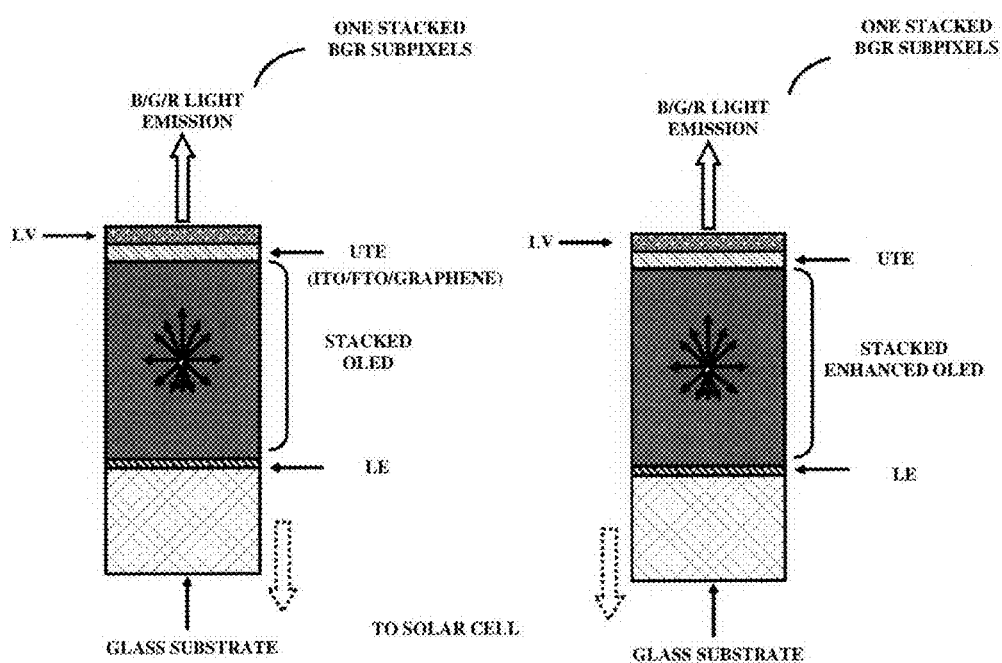
Figure 40C:
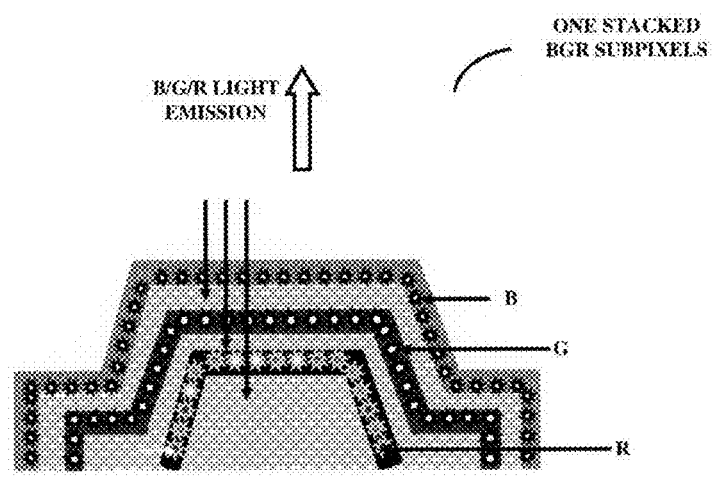

FIGS. 40A-40C illustrate two embodiments of a micropixel of a display, utilizing vertically stacked organic light emitting diodes (OLED).

Figure 41A:
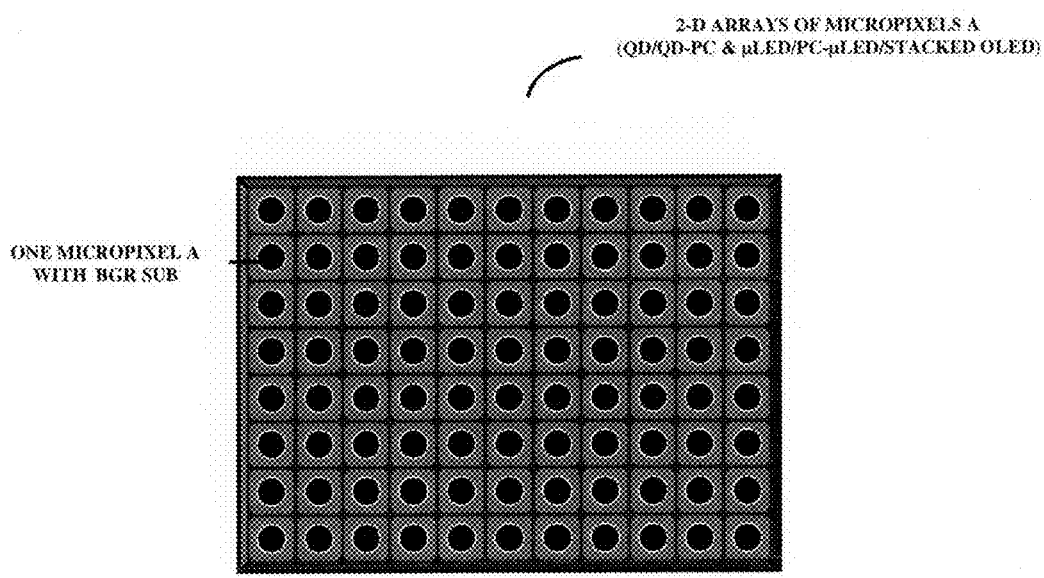

FIG. 41A illustrates an embodiment of a two-dimensional (2-D) array of micropixels of a display.

Figure 41B:
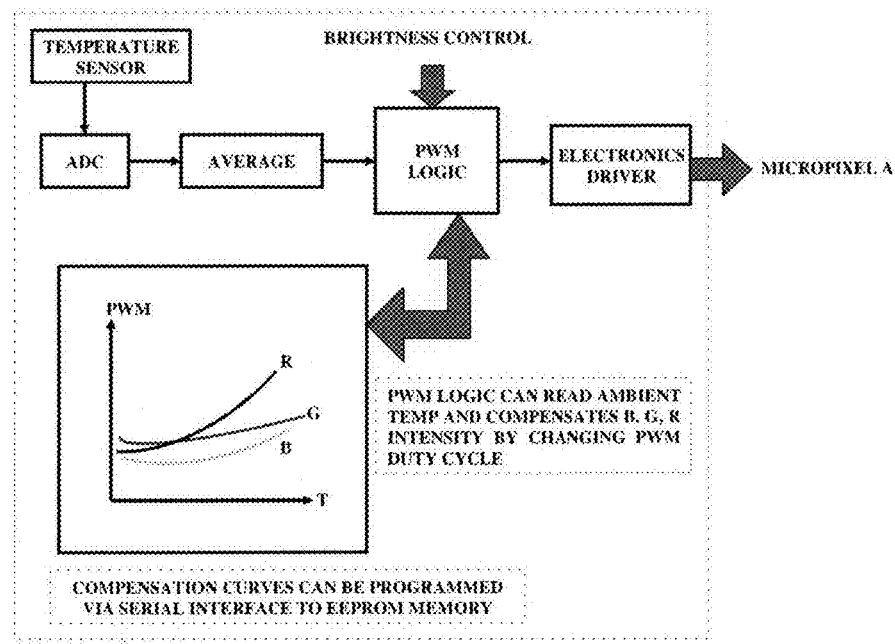

FIG. 41B illustrates an embodiment of an electronic control of the micropixel of a display.

Figure 42A:
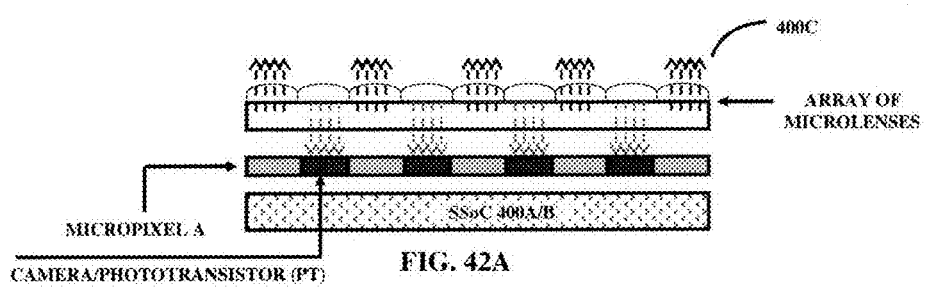
Figure 42B:
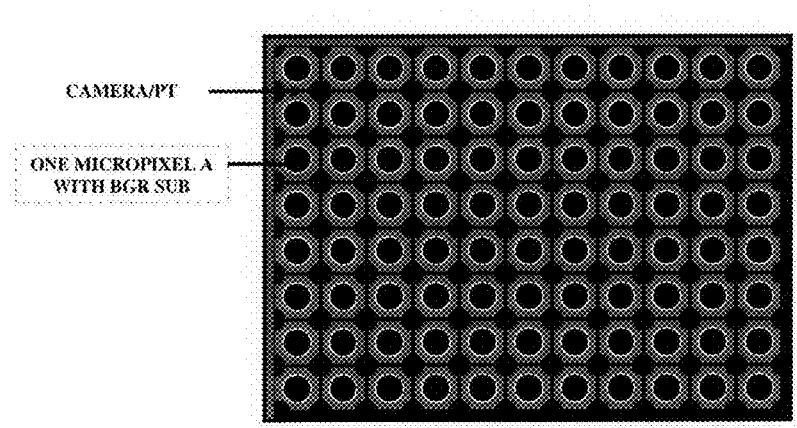

FIG. 42A-42B illustrates an embodiment of integration, micropixels, cameras/phototransistors and the Super System on Chip.

Figure 43A:
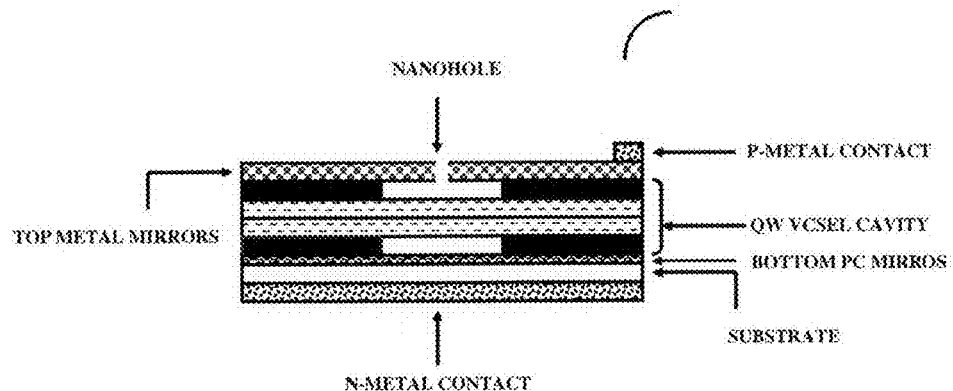
Figure 43B:
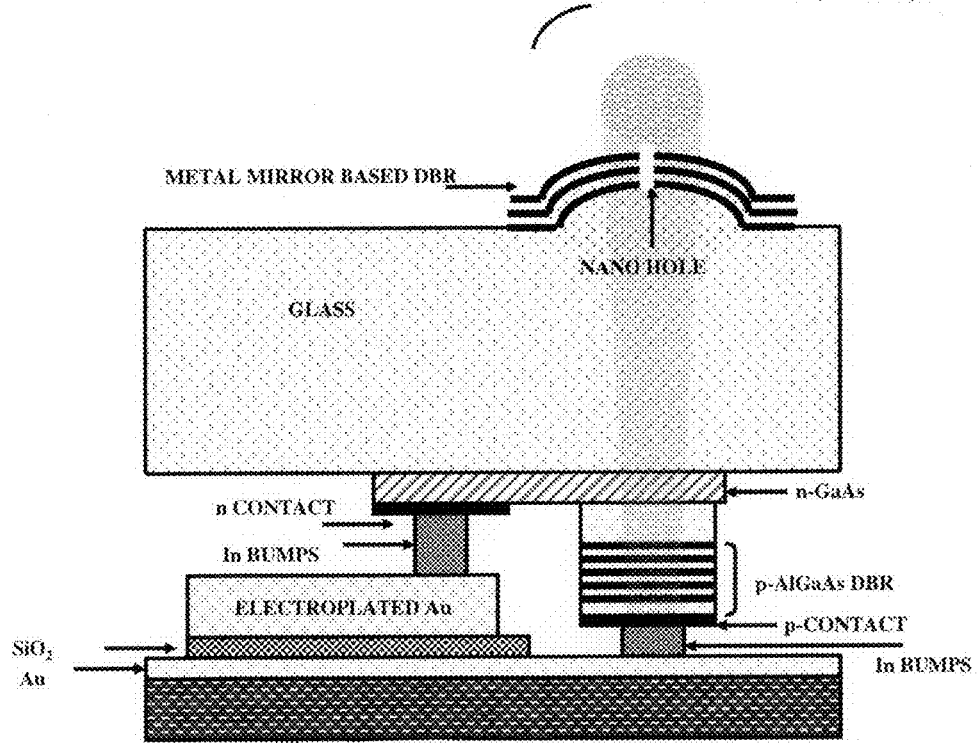

FIGS. 43A-43B illustrate an embodiment of a frustrated vertical cavity surface emitting laser (F-VCSEL).

Figure 43C:
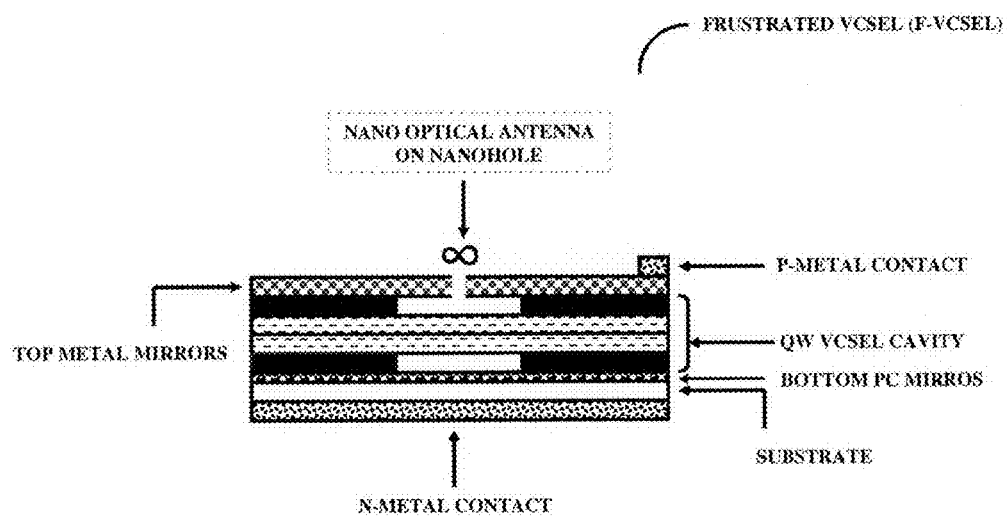
Figure 43D:
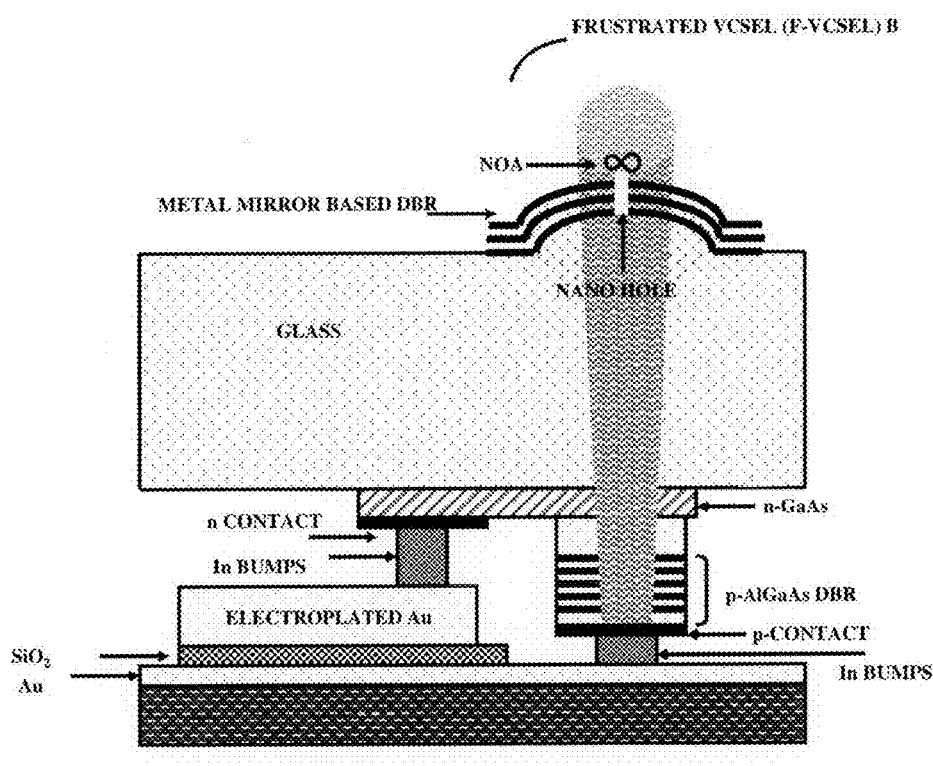

FIGS. 43C-43D illustrate an embodiment of a frustrated vertical cavity surface emitting laser integrated with a nano optical antenna.

FIGS. 44A-44F illustrate six embodiments of a micropixel of a display, utilizing a frustrated vertical cavity surface emitting laser or frustrated vertical cavity surface emitting laser integrated with a nano optical antenna on each subpixel.

Figure 45:
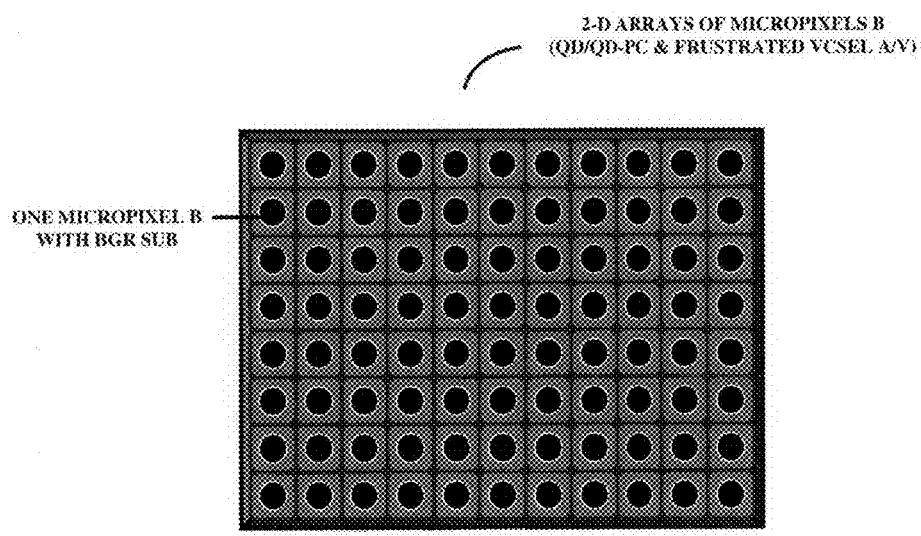

FIG. 45 illustrates another embodiment of a two-dimensional array of micropixels of a display.

Figure 46A:
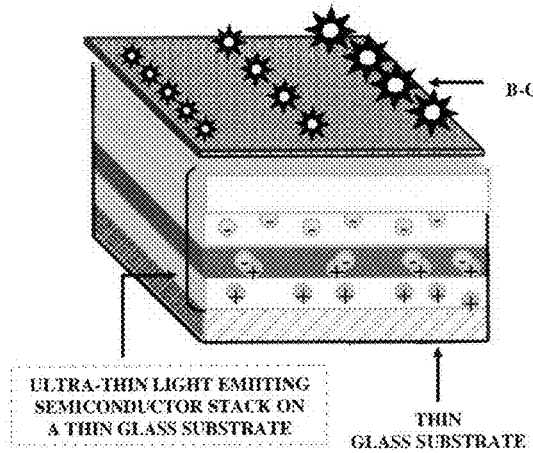
Figure 46B:
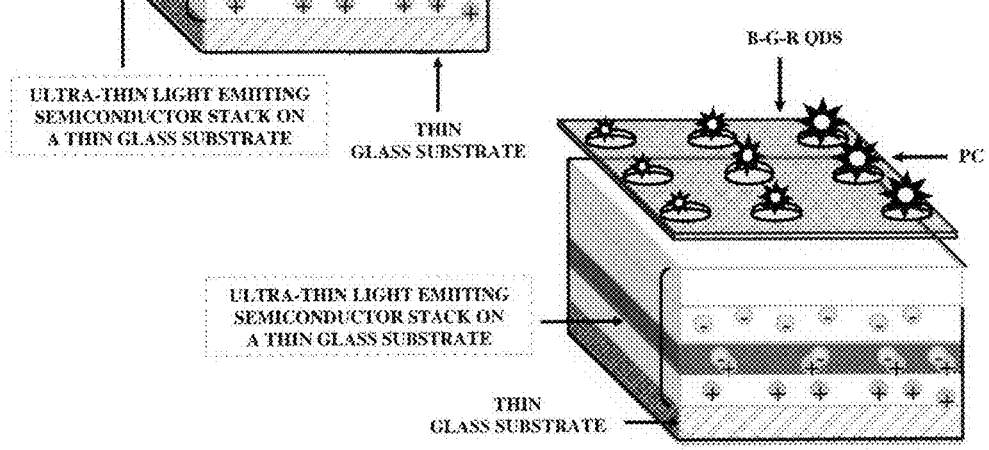

FIGS. 46A-46B illustrate two additional embodiments to enable a micropixel of a display.

Figure 47A:
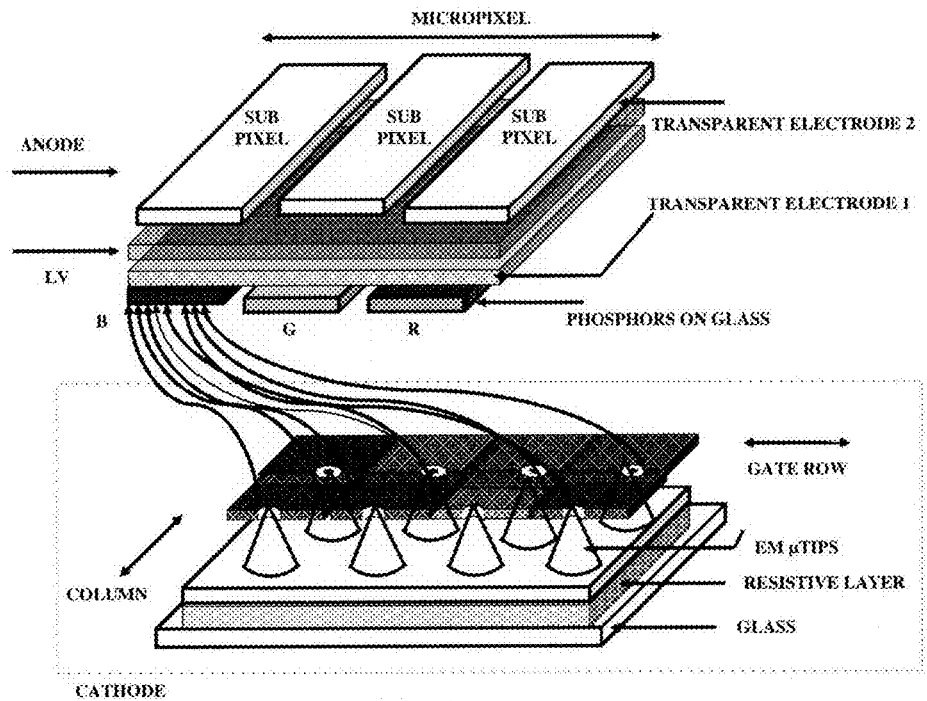
Figure 47B:
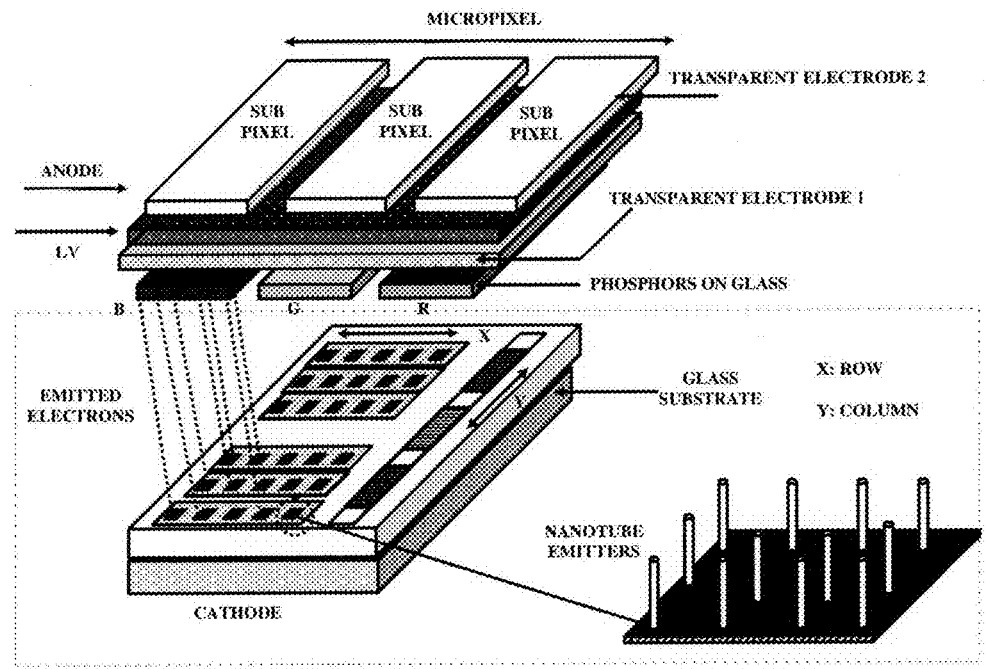

FIGS. 47A-47B illustrate two additional embodiments to enable a micropixel of a display.

Figure 48A:
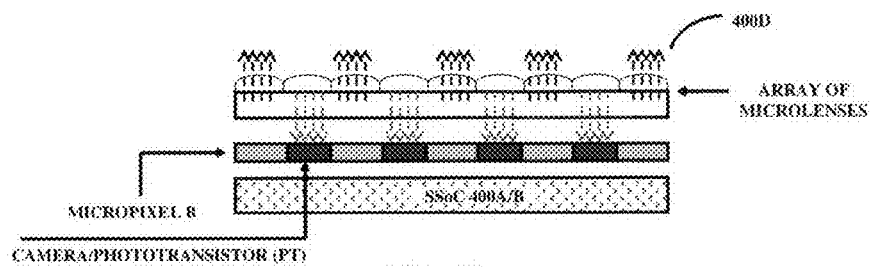
Figure 48B:
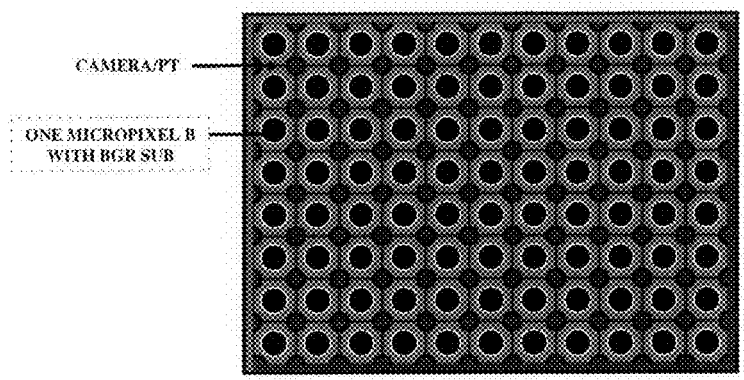

FIGS. 48A-48B illustrate an embodiment of integration, micropixels, cameras/phototransistors and the Super System on Chip.

Figure 49:
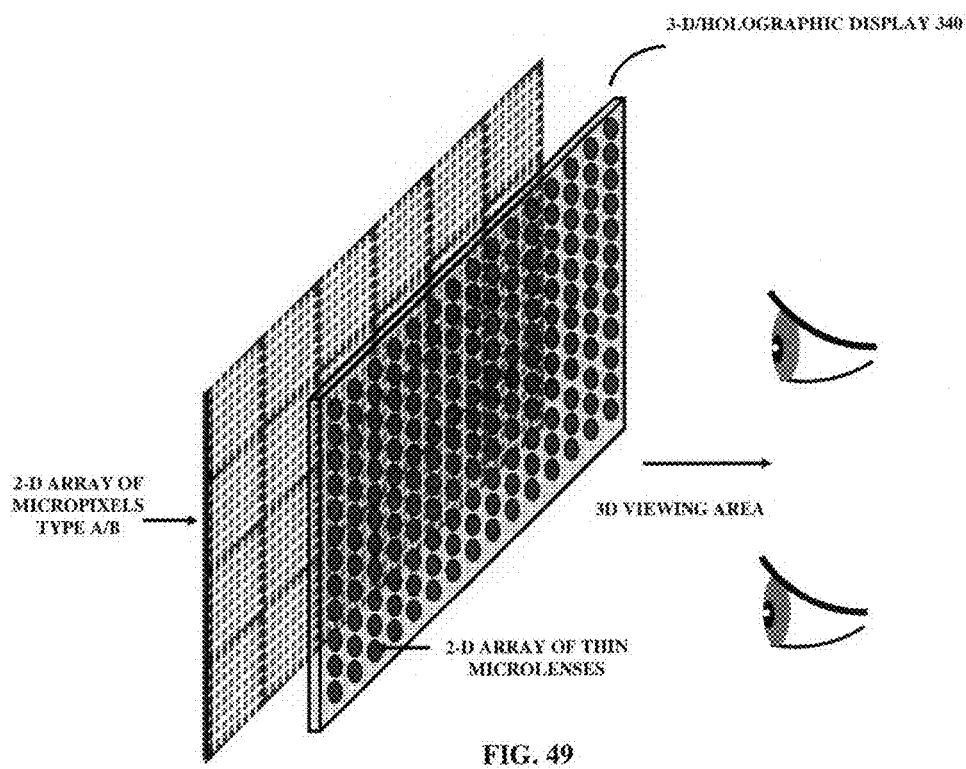

FIG. 49 illustrates an embodiment of a three-dimensional/holographic display.

Microprojector

Figure 50A:
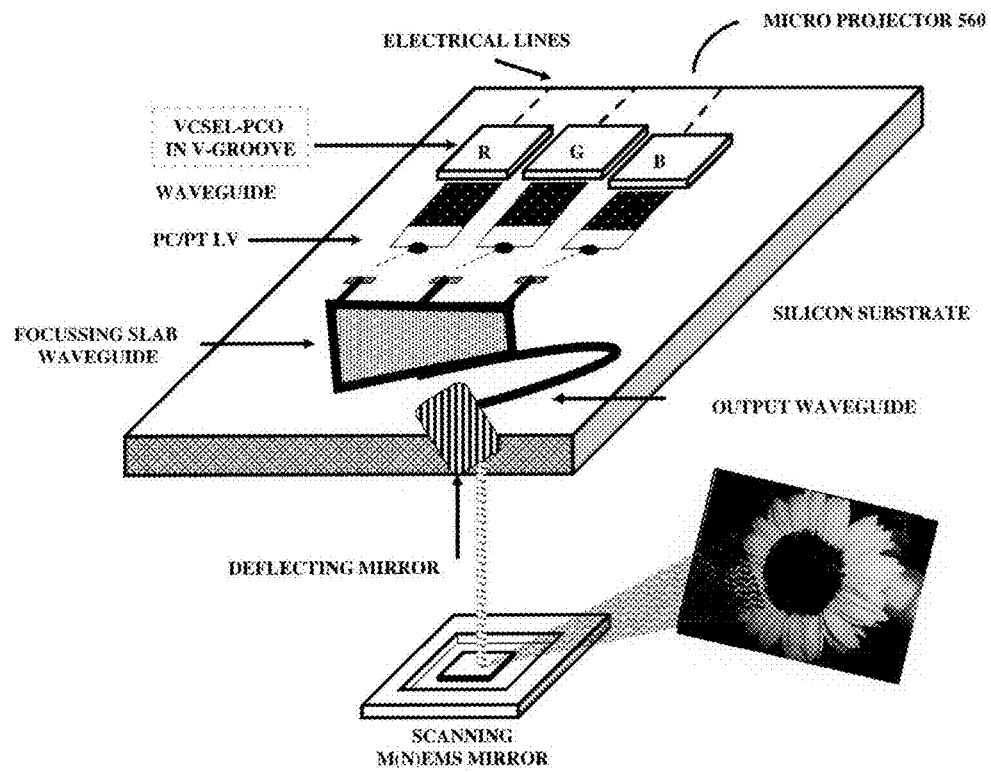
Figure 50B:
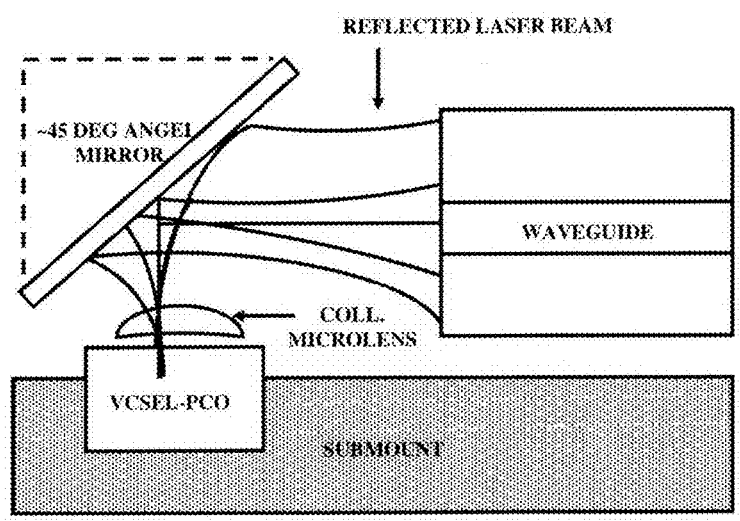
Figure 50C:
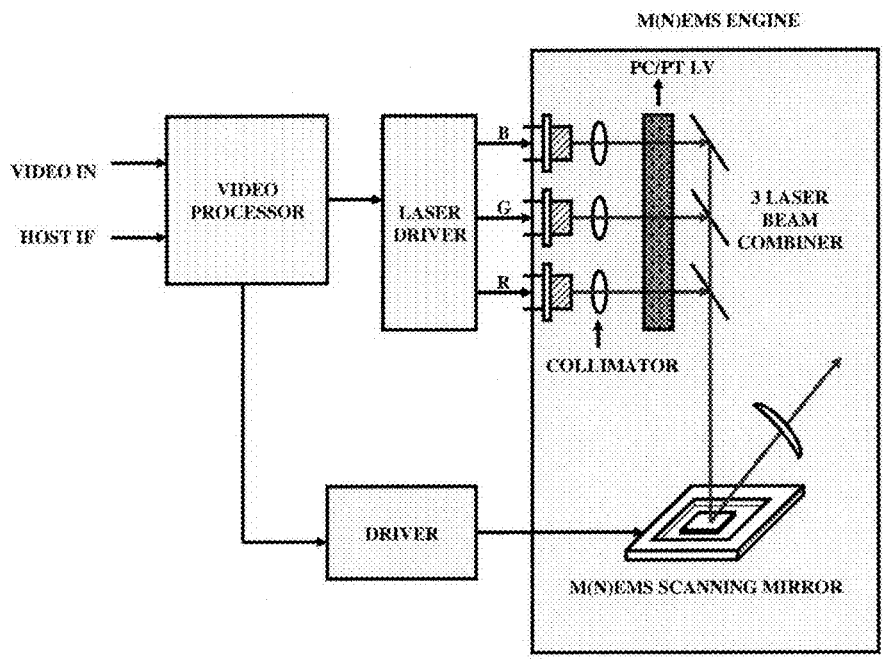

FIGS. 50A-50C illustrate an embodiment of a microprojector.

FIGS. 51A-51D illustrate four embodiments of an optical engine.

FIGS. 52A-52D illustrate two embodiments of another optical engine.

Figure 53:
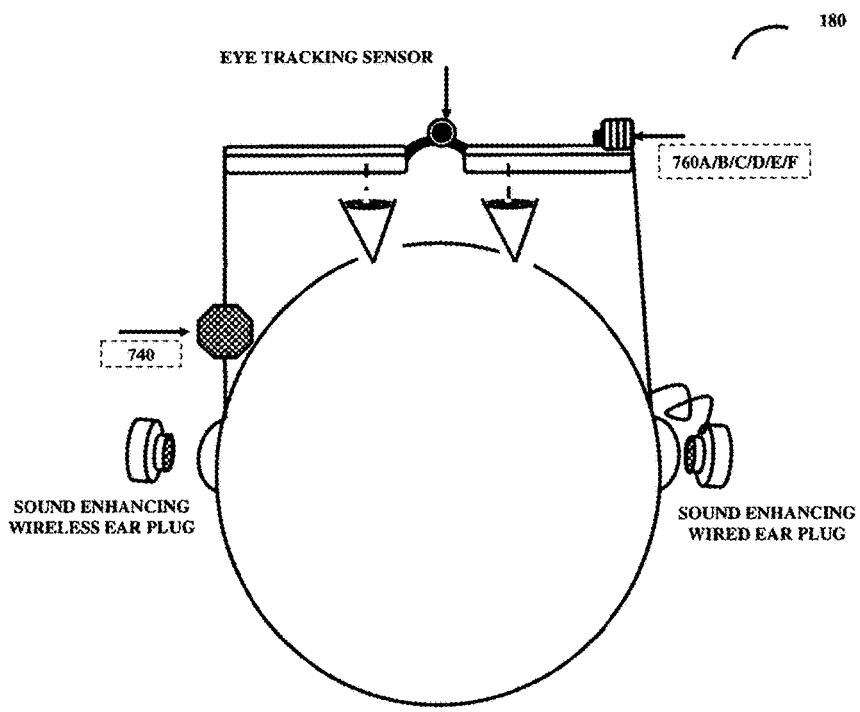

FIG. 53 illustrates an embodiment of an intelligent wearable augmented reality personal assistant device.

Point-of-Care Diagnostics

Figure 54A:
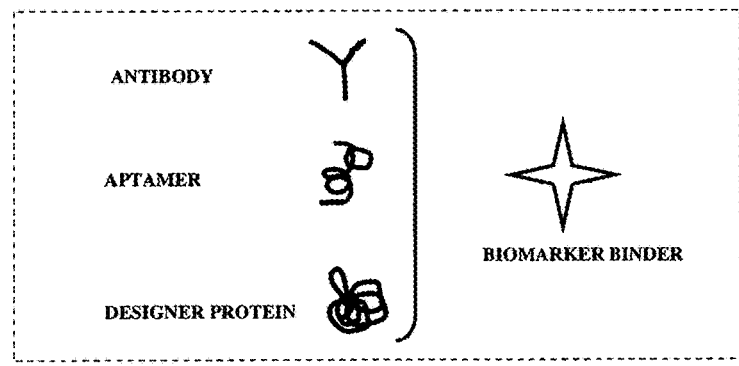
Figures 54B, 54C:
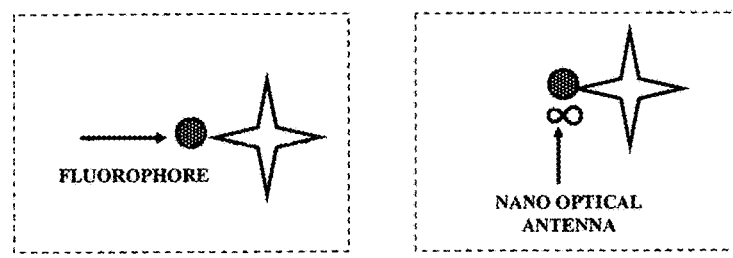

FIGS. 54A-54C represent various configurations of a generic representation of a biomarker binder.

FIGS. 55A-55C illustrate an embodiment of a point-of-care diagnostic system.

Wearable Personal Health Assistant Device

FIGS. 56A-56L illustrate an embodiment of a wearable personal health assistant device.

Figure 57A:
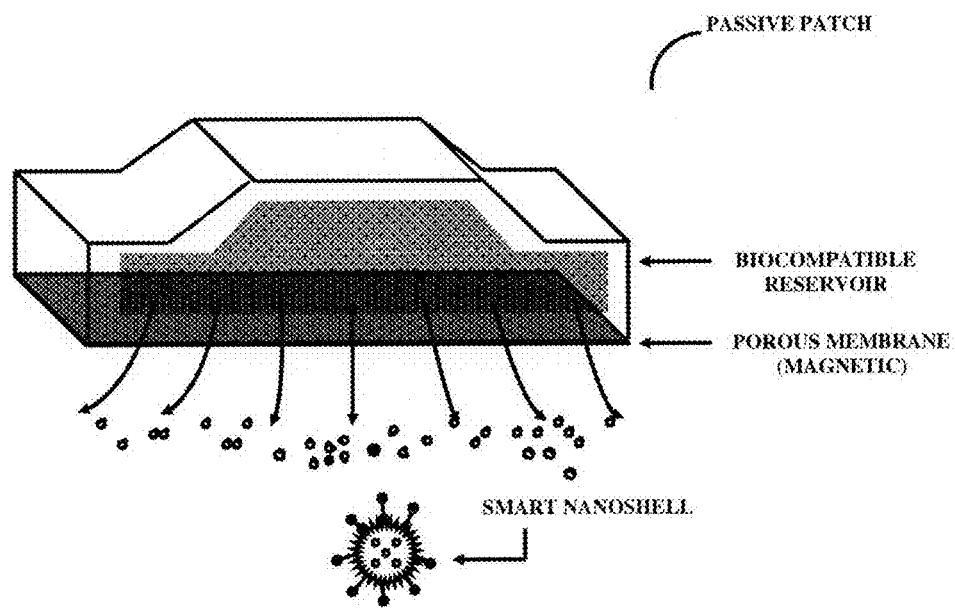

FIG. 57A illustrates an embodiment of a passive patch.

FIGS. 57B-57H illustrate an embodiment of an active patch.

Diagnostics System

Figure 58A:
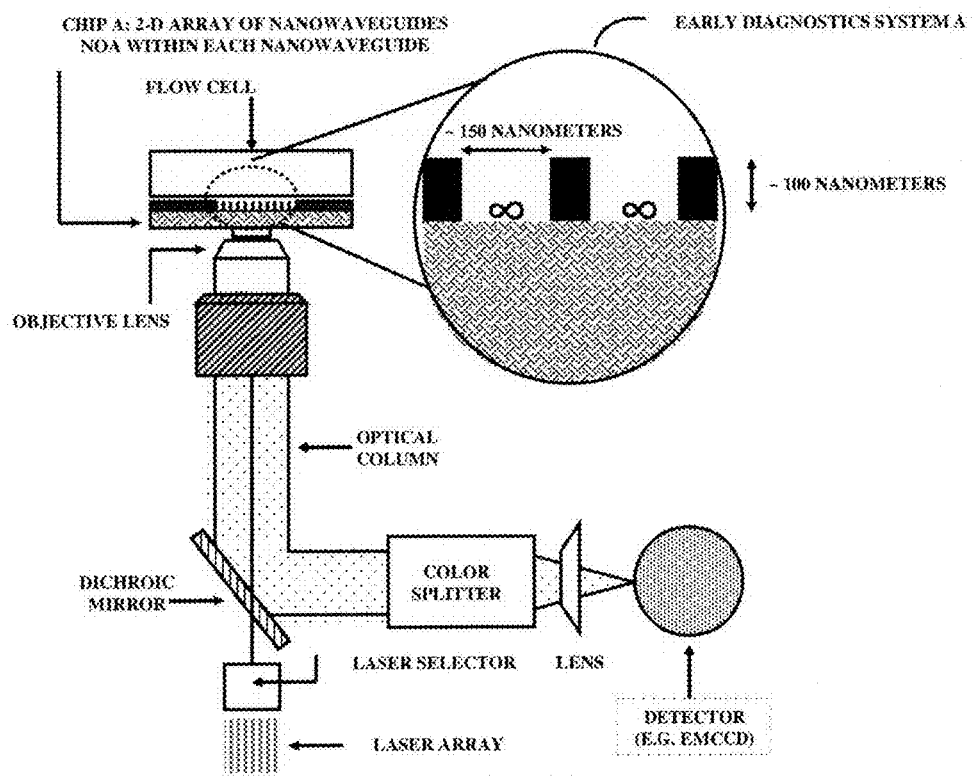
Figure 58B:
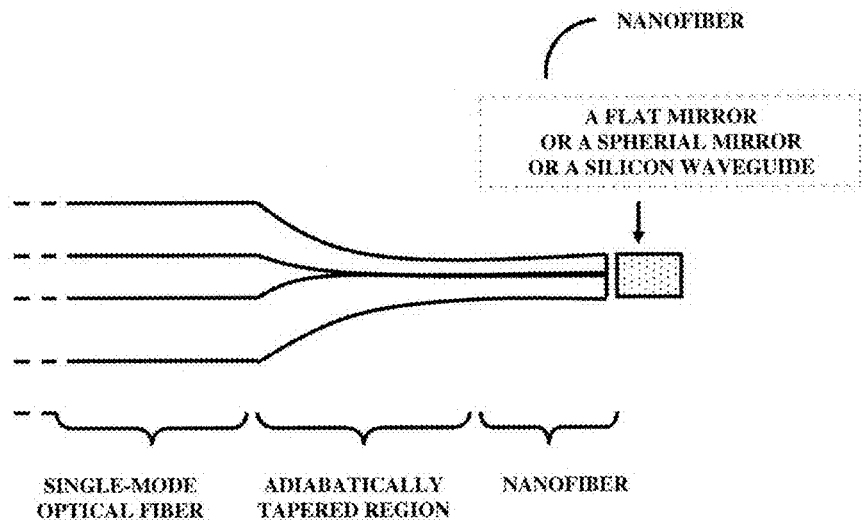

FIGS. 58A-58B illustrate an embodiment of an early diagnostic system A.

FIGS. 59A-59G illustrate an embodiment of an early diagnostic system B.

FIGS. 60A-60F illustrate an embodiment of a DNA sequencing system.

Figure 61A:
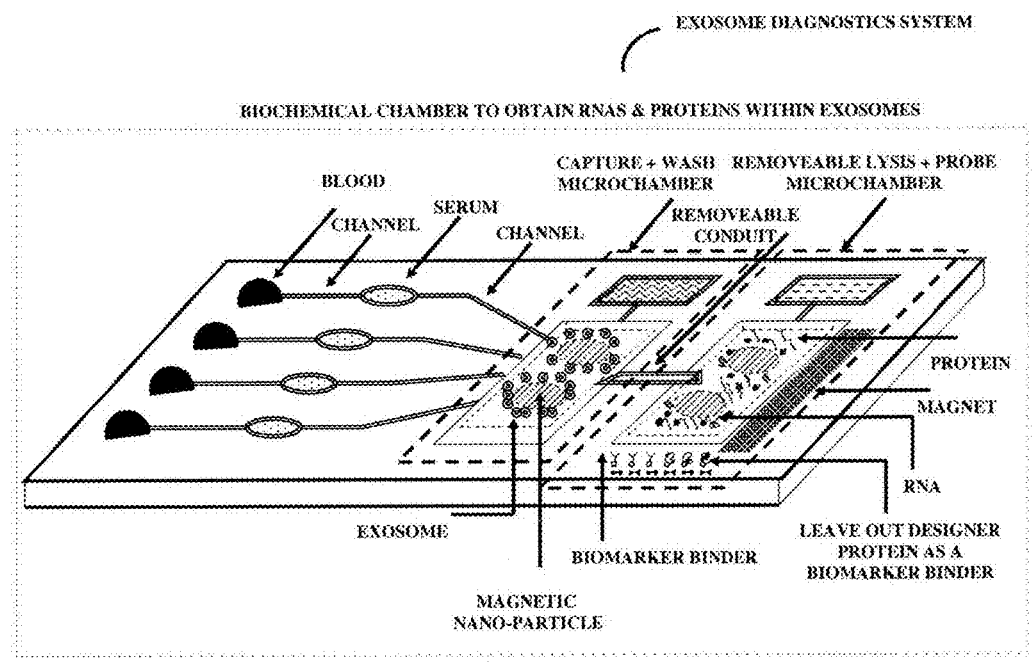
Figure 61B:
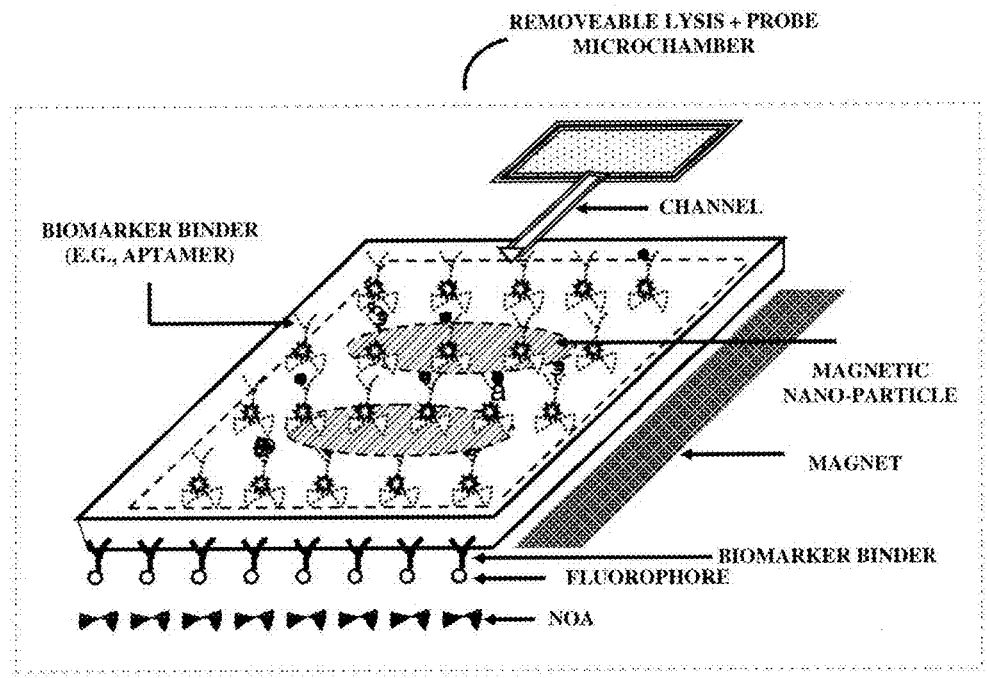
Figure 61C:
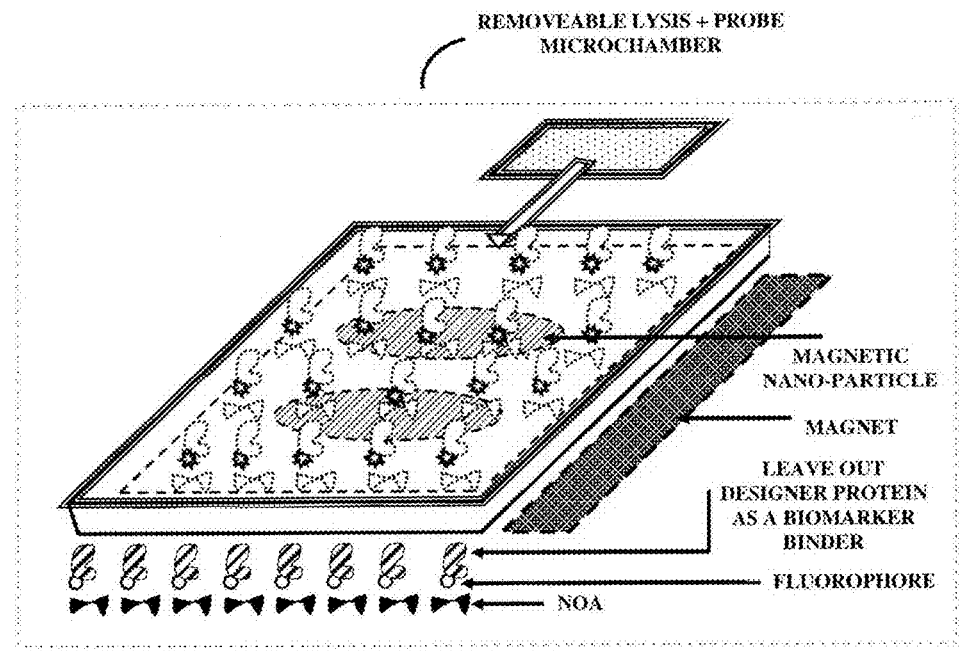

FIGS. 61A-61C illustrate an embodiment of an exosome diagnostic system.

Three-Dimensional Micro/Nano Printer

Figure 62A:
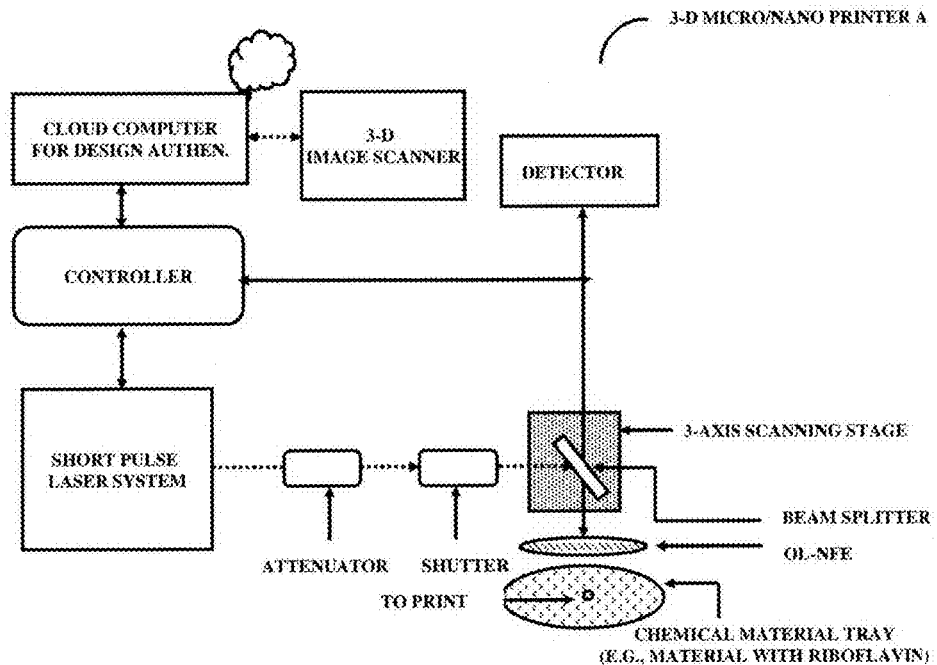
Figure 62B:
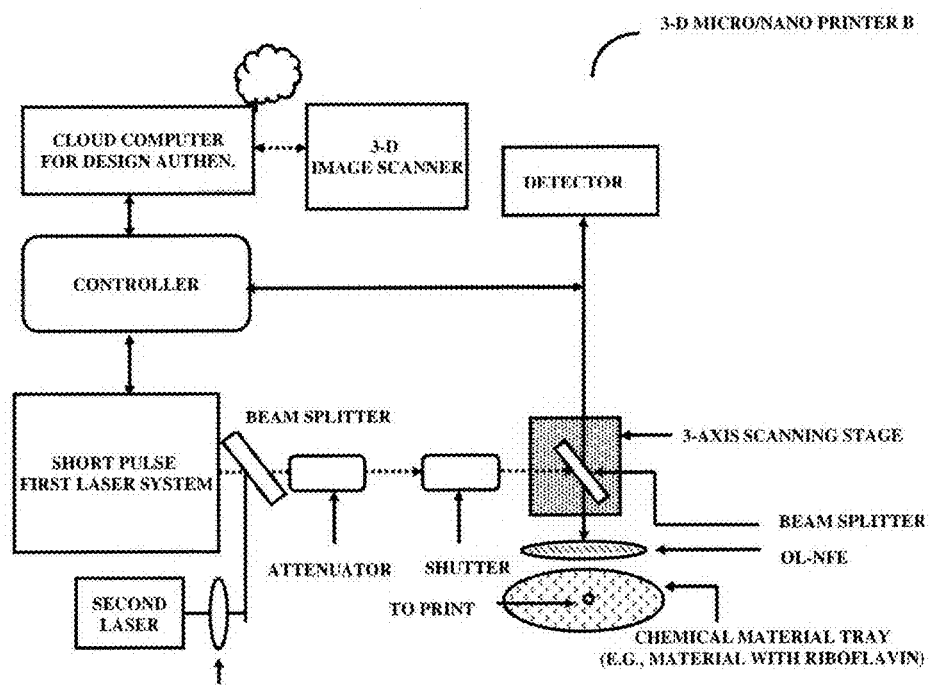

FIGS. 62A-62B illustrate two embodiments of a three-dimensional micro/nano printer.

Personal Human OS

Figure 63A:
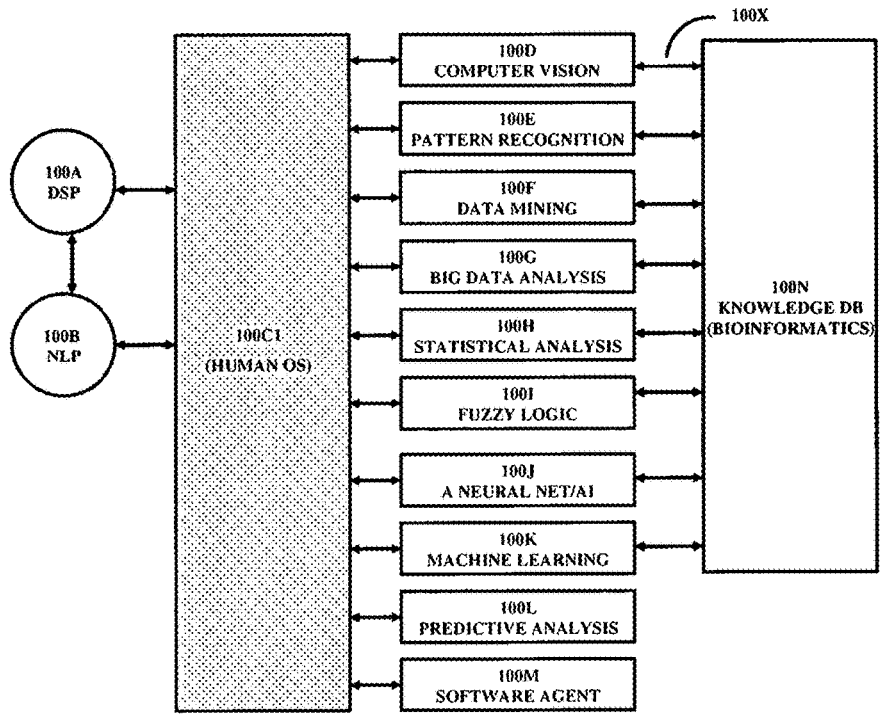
Figure 63B:
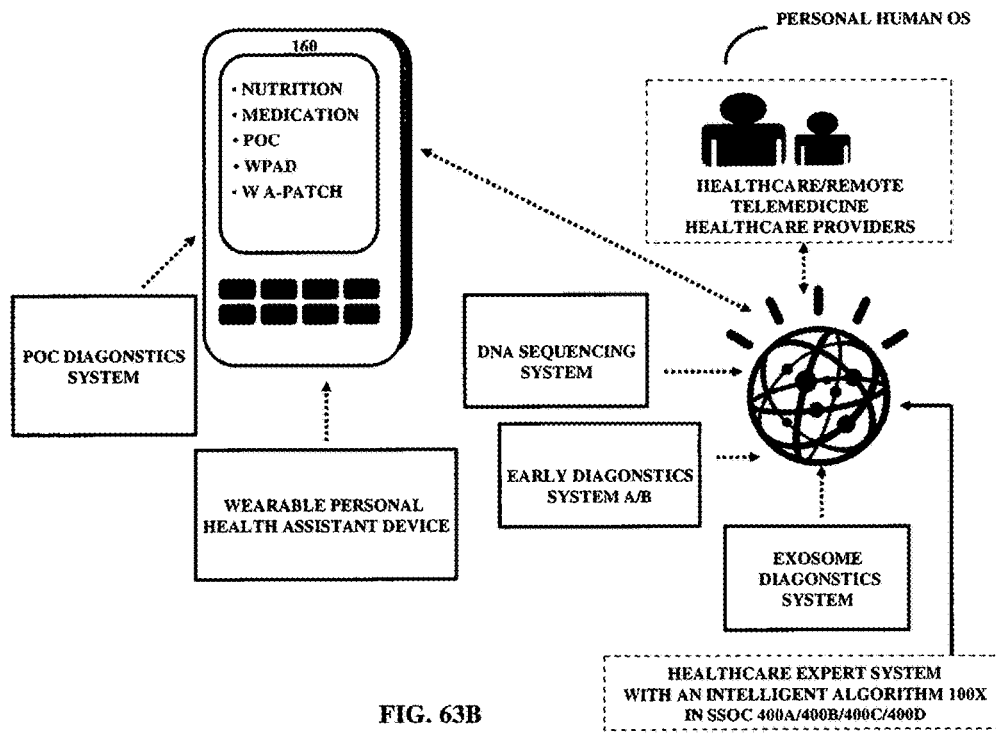

FIGS. 63A-63B illustrate an embodiment of a Personal Human OS.

DETAILED DESCRIPTION OF THE DRAWINGS

Figure 1A:
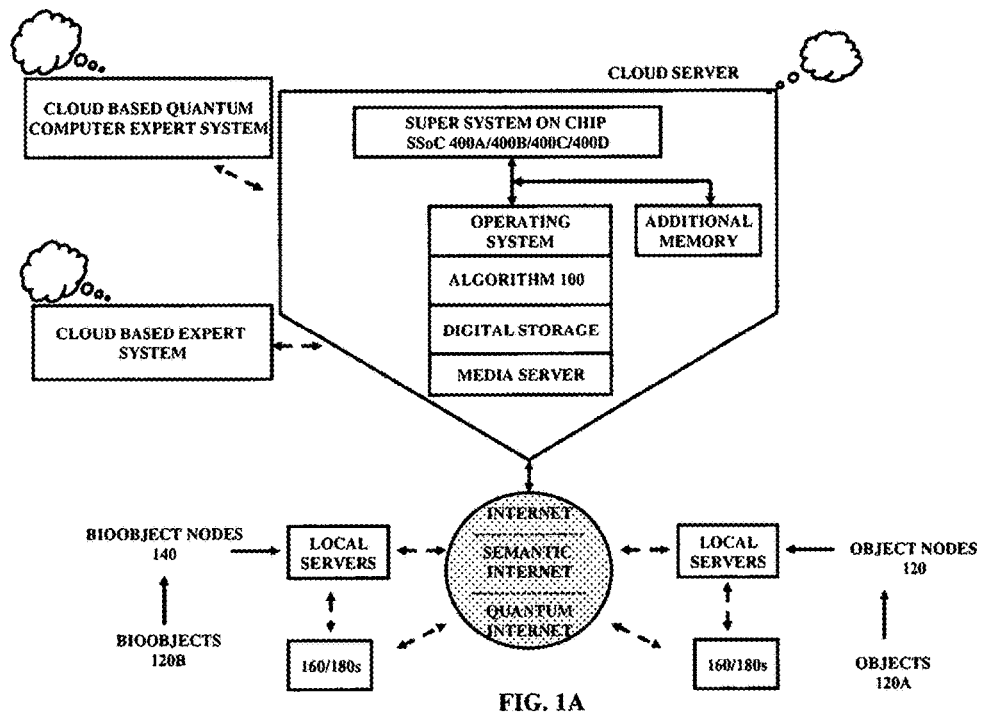
FIG. 1A illustrates an embodiment of interactions/communications among local servers (connecting with objects, object nodes, bioobjects, bioobject nodes, intelligent portable internet appliances and intelligent wearable augmented reality personal assistant devices), an intelligent algorithm in a cloud server, a cloud expert system, a cloud quantum computer expert system and the internet (including semantic/quantum internet).
Intelligent Algorithm

FIG. 1A illustrates interactions of objects 120A, bioobjects 120B, object nodes 120, bioobject nodes 140, local servers, an intelligent algorithm 100, a cloud expert system, internet (including quantum internet) and semantic web, intelligent portable internet appliance 160 and/or intelligent wearable augmented reality personal assistant device 180. An intelligent vehicle can be connected with the objects 120A via the object nodes 120.

The World Wide Web is made with computers but for people. The websites use natural language, images and page layout to present information in a way that is easy for a user to understand, but the computers themselves really can't make sense of any information and cannot read relationships or make decisions like people can. The semantic internet can help computers read and use the web. Metadata added to web pages can make the existing World Wide Web machine readable, so computers can perform more of the tedious work involved in finding, combining and acting upon information on the web.

The intelligent algorithm 100 is within a cloud server. The cloud server comprises a Super System on Chip 400A/400B/400C/400D. The Super System on Chip 400A/400B/400C/400D can comprise one or more digital processors, one or more memristors and one or more memory components. The Super System on Chip 400A/400B/400C/400D can further electrically couple with a digital storage device, additional memory components and a media server and they can be managed by an embedded operating system algorithm. The cloud server can be connected with a cloud expert system and a cloud quantum computer expert system.

Figure 1B:
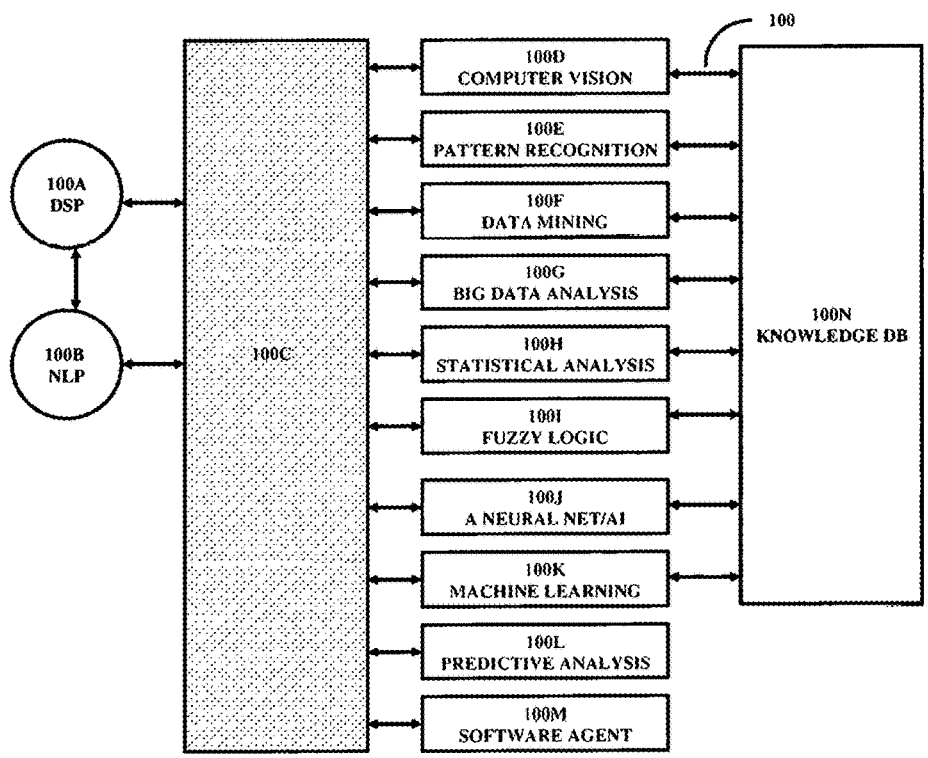
FIG. 1B illustrates an embodiment (in block diagram) of an intelligent algorithm.

FIG. 1B illustrates the intelligent algorithm 100. The intelligent algorithm 100 comprises a digital security protector (DSP) algorithm submodule 100A, a natural language processing (NLP) algorithm submodule 100B, and an application specific algorithm submodule 100C (which can vary with application). The application specific algorithm submodule 100C is coupled with a computer vision algorithm submodule 100D, a pattern recognition algorithm submodule 100E, a data mining algorithm submodule 100F, a Big Data analysis algorithm submodule 100G, a statistical analysis algorithm submodule 100H, a fuzzy logic algorithm submodule 100I, an artificial neural networks/artificial intelligence algorithm submodule 100J, a machine learning algorithm submodule 100K, a predictive analysis algorithm submodule 100L and a software agent algorithm submodule 100M.

The computer vision algorithm submodule 100D, the pattern recognition algorithm submodule 100E, the data mining algorithm submodule 100F, the Big Data analysis algorithm submodule 100G, the statistical analysis algorithm submodule 100H, the fuzzy logic algorithm submodule 100I, the artificial neural networks/artificial intelligence algorithm submodule 100J and the machine learning algorithm submodule 100K are coupled with a knowledge database 100N.

Details of the digital security protection (DSP) are described in U.S. Non-Provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and the non-provisional patent application with its benefit patent applications are incorporated in its entirety herein with this application.

The connections between various algorithm submodules can be similar to synaptic networks to enable deep learning of the intelligent algorithm 100.

Fuzzy means not clear (blurred). Fuzzy logic is a form of approximate reasoning, that can represent variation or imprecision in logic by making use of natural language (NL) in logic. The key idea of the fuzzy logic rule is that it uses a simple/easy way to secure the output(s) from the input(s), wherein the outputs can be related to the inputs by if-statements.

Fuzzy set theory is a generalization of the ordinary set theory. A fuzzy set is a set whose elements belong to the set with some degree of membership $\mu$. Let X be a collection of objects. It is called universe of discourse. A fuzzy set A$\in$X is characterized by membership function $\mu A(x)$, which represents the degree of membership. Degree of membership maps each element between 0 and 1. It is defined as: $A=\{(x, \mu_A(x)); x \in X\}$.

Figure 1C:
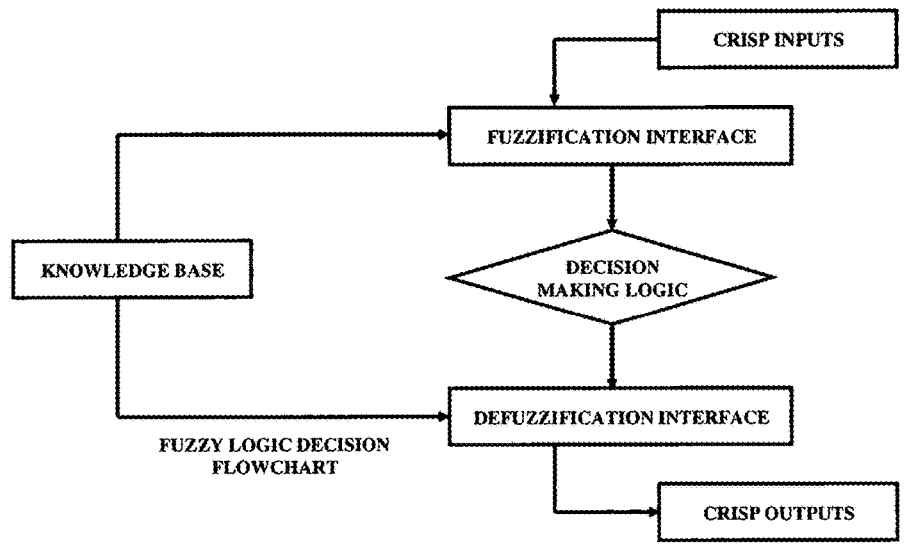
FIG. 1C illustrates an embodiment (in block diagram) of a fuzzy logic rule of the intelligent algorithm.

In FIG. 1C, crisp inputs are fed into a fuzzification interface. The fuzzification interface algorithm submodule is coupled with (a) a knowledge base and (b) a decision-making logic algorithm submodule. The decision-making logic algorithm submodule is coupled with a defuzzification interface algorithm submodule. The defuzzification interface algorithm submodule is coupled with a fuzzy logic decision flow chart. The defuzzification interface algorithm submodule creates crisp outputs.

Figure 1D:
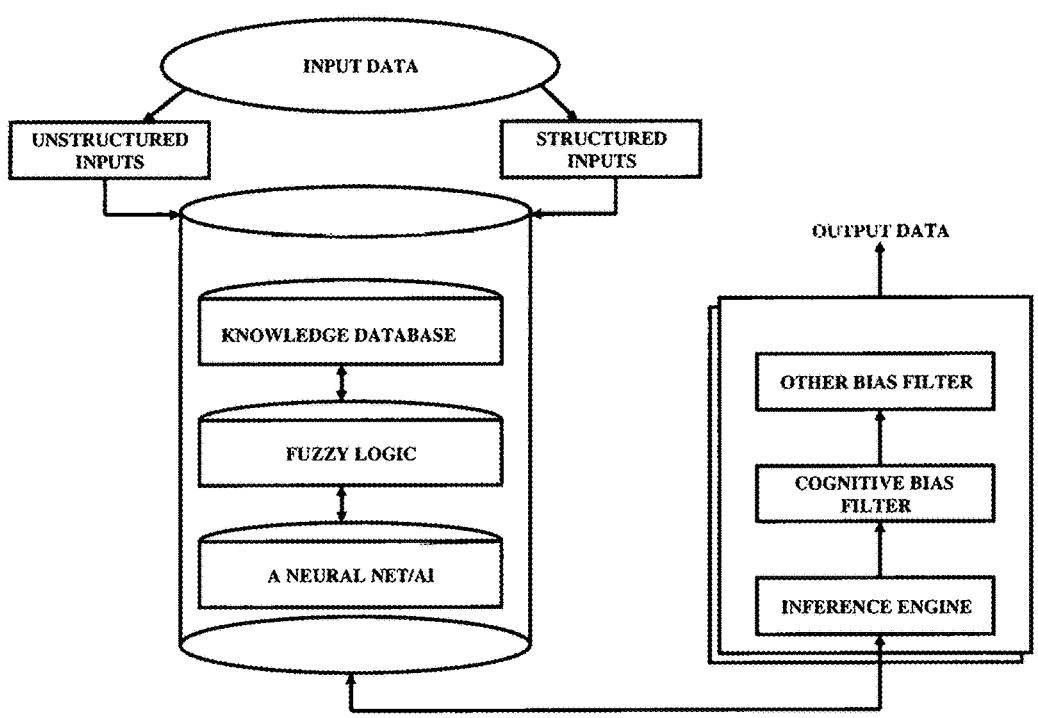
FIG. 1D illustrates an embodiment (in block diagram) of a knowledge extraction rule of the intelligent algorithm.

FIG. 1D illustrates a knowledge extraction rule within the algorithm 100. Both structured inputs and unstructured inputs are configured through (a) a knowledge database submodule, (b) a fuzzy logic algorithm submodule, (c) an artificial neural networks/artificial intelligent algorithm submodule, (d) an inference engine algorithm submodule, (e) a cognitive bias filter submodule and (f) finally other bias filter submodules to create an output data.

Figure 1E:
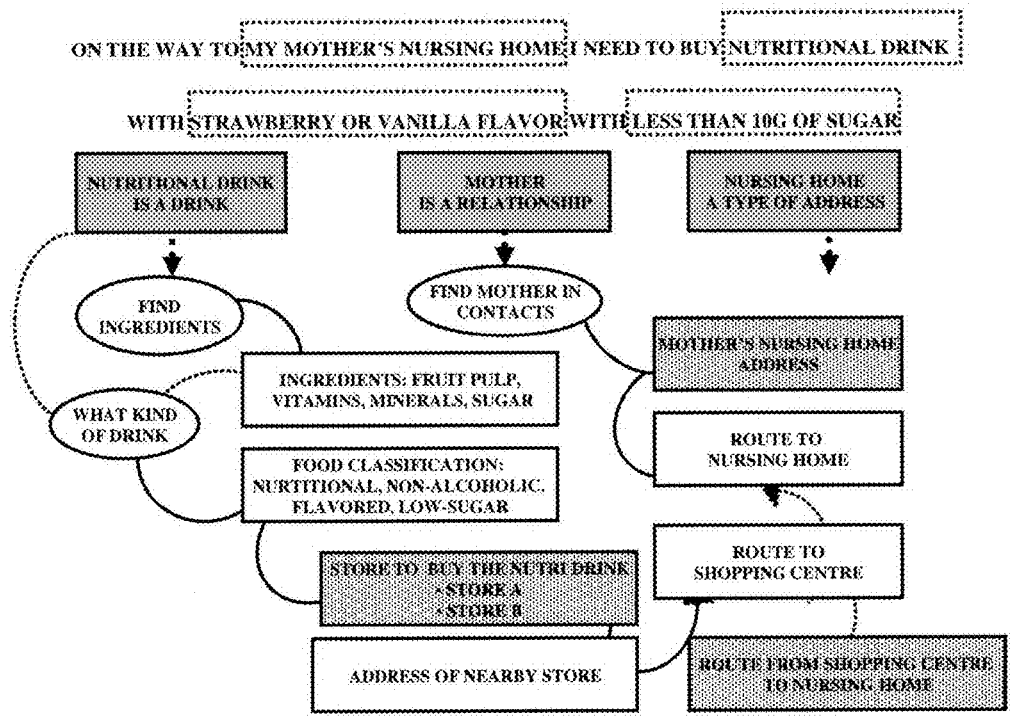
FIG. 1E illustrates an example application of the intelligent algorithm.
Sensor Enabled Social Commerce

FIG. 1E illustrates an example application of the intelligent algorithm 100. A user has to bring a low sugar nutritional drink of either strawberry or vanilla to the user mother's nursing home. The intelligent algorithm 100 understands by breaking down the natural language commands into relationship-based elements and executing each element such as (a) who is the mother of a user? (b) where is the user mother's nursing home? (c) what is a low sugar nutritional drink? (d) what is a flavor? (e) what is a strawberry flavor? (f) what is a vanilla flavor? (g) where is a suitable store to buy such a low sugar strawberry or vanilla flavored nutritional drink? (e) how to drive to the user mother's nursing home from such a suitable store, after purchasing the low sugar strawberry or vanilla flavored nutritional drink?

The intelligent algorithm 100 can then recommend an actionable solution(s) to the user.

In another application, the intelligent portable internet appliance 160 and/or intelligent wearable augmented reality personal assistant device 180 can contain rich data of the user's activities, including who the user knows (phone/social networking contact lists), who the user talks to (logs of phone calls, texts and e-mails), where the user goes (global positioning system data, Wi-Fi logs, geotagged/bokodes tagged photos) and what the user does (indoor position system, apps he/she uses, payment he/she makes and accelerometer data). Utilizing the above rich data with the intelligent algorithm 100, personal predictive analytics (social graph) of the user can be built.

Bokodes are tiny barcodes which can encode binary data, the view angle and the distance of a viewer from a thing. A camera positioned up to four meters away can capture and decode all information. Bokodes can give a robust estimate of geotagged photos.

Figure 2A:
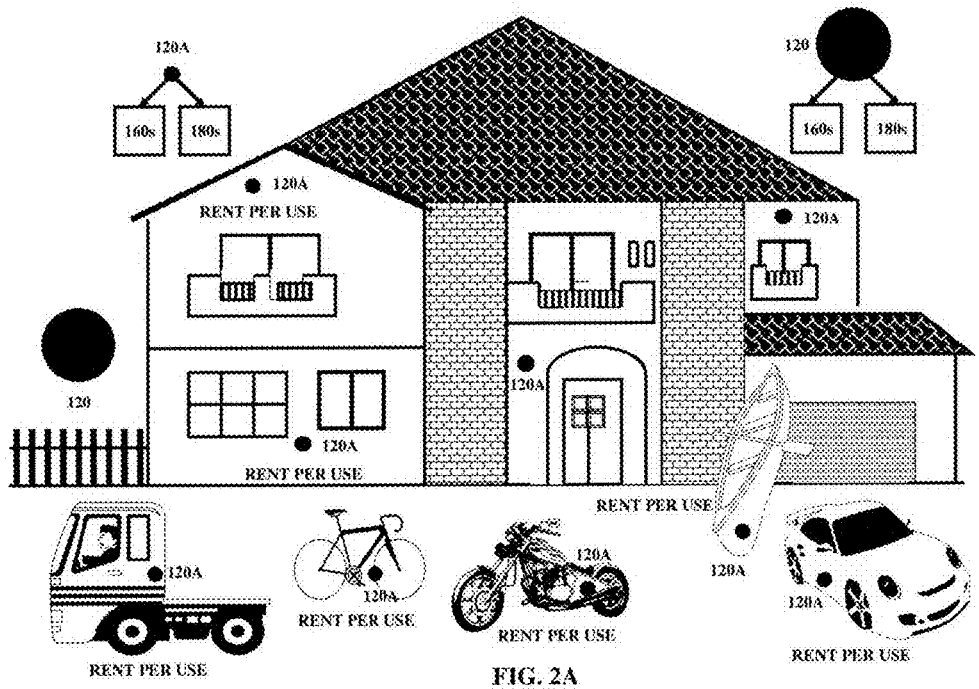
FIG. 2A illustrates an embodiment of object(s) enabled peer-to-peer social commerce.

FIG. 2A illustrates peer-to-peer social commerce, enabled by the application algorithm submodule 100C, objects 120As and object nodes 120s.

Figure 2B:
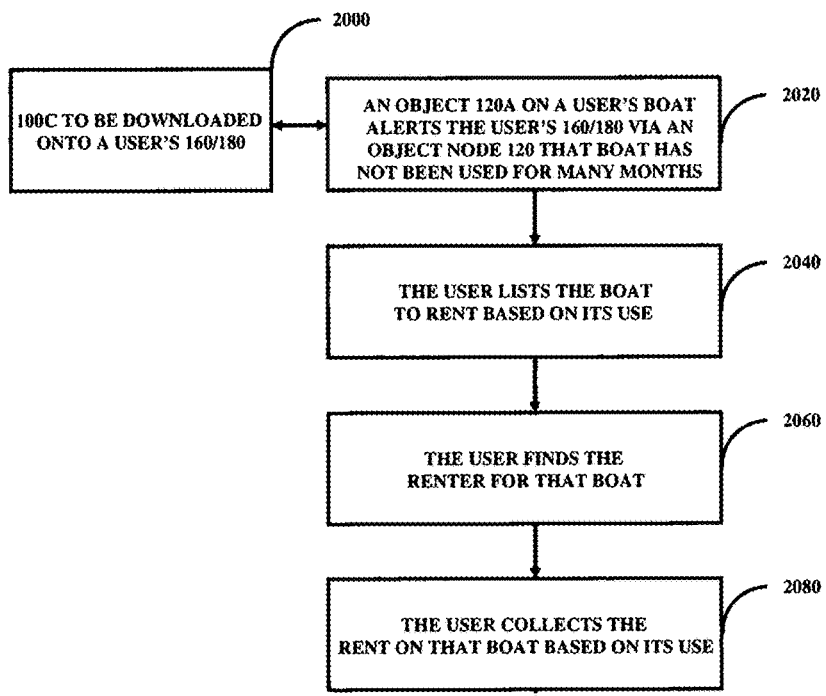
FIGS. 2B-2C illustrate an embodiment of methods of peer-to-peer social commerce, enabled by the objects, object nodes, intelligent algorithms, intelligent portable internet appliances and/or intelligent wearable augmented reality personal assistant devices.
Intelligent Vehicle

In FIG. 2B, in step 2000, the application algorithm submodule 100C can be downloaded onto the intelligent portable internet appliance 160 and/or intelligent wearable augmented reality personal assistant device 180. In step 2020, an object 120A alerts the intelligent portable internet appliance 160 and/or intelligent wearable augmented reality personal assistant device 180 of the user via the object node 120 that the user's boat has not been used for many months. In step 2040, the user lists that unused boat for rent based on its use, utilizing the application algorithm submodule 100C. In step 2060, the user finds a renter for that unused boat, utilizing the application algorithm submodule 100C. In step 2080, the user collects the rent on that unused boat based on its use.

Figure 2C:
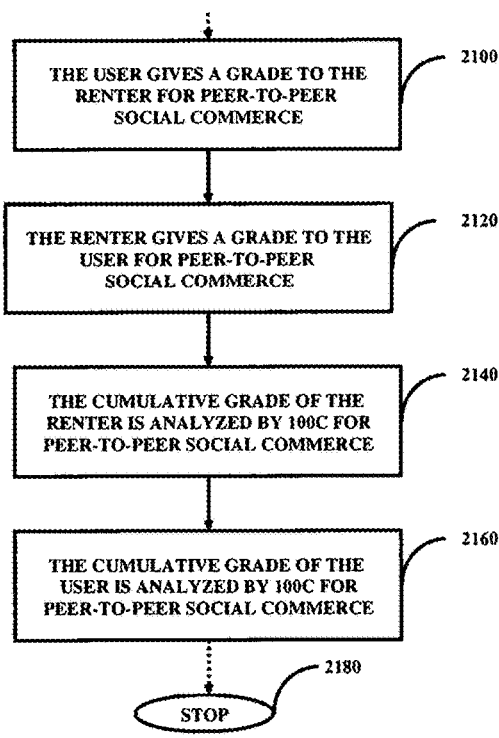

In FIG. 2C, continuing in step 2100, the user gives grades to the renter for peer-to-peer social commerce. In step 2120, the renter gives grades to the user (boat owner) for peer-to-peer social commerce. In step 2140, the cumulative grade of the renter is analyzed for future peer-to-peer social commerce. In step 2160, the cumulative grade of the user (boat owner) is analyzed for future peer-to-peer social commerce. Step 2180 denotes stop.

Figure 3A:
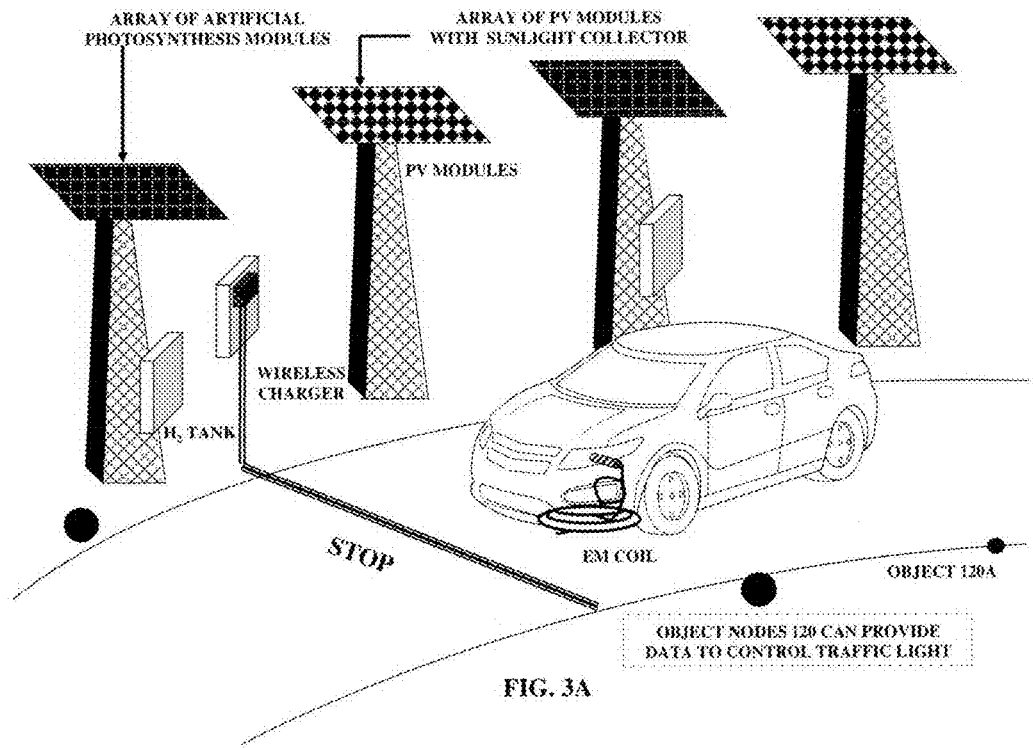
FIG. 3A illustrates an embodiment of a roadway with objects, object nodes, photovoltaic modules and artificial photosynthesis modules to enable electromagnetic (wireless) charging to an intelligent vehicle.

FIG. 3A illustrates electromagnetically (wirelessly) charging of an intelligent vehicle. The intelligent vehicle's battery/ultracapacitor can electromagnetically (wirelessly) charge from underneath the roadway. The intelligent vehicle is capable of interacting/communicating with the object nodes 120 on the roadway, wherein the object nodes 120, for example, can provide data (input) to control a traffic light. FIG. 3A also illustrates a roadway, wherein at least one side of the roadway can be fabricated/constructed with photovoltaic modules and/or artificial photosynthesis modules to provide electromagnetic (wireless) charging and hydrogen to the intelligent vehicle.

Figure 3B:
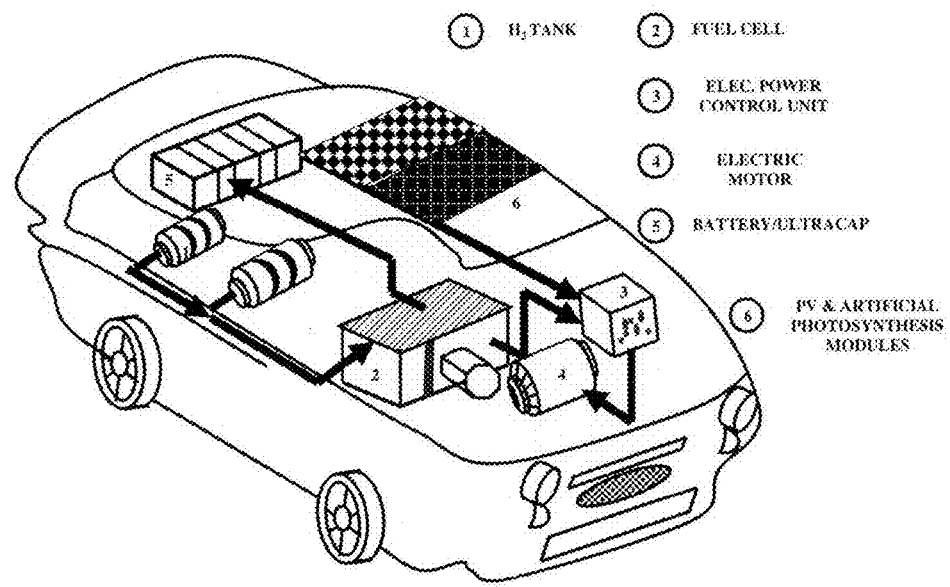
FIG. 3B illustrates an embodiment of the intelligent vehicle.

FIG. 3B illustrates the intelligent vehicle, which can comprise principal subsystems such as: high efficiency photovoltaic modules, artificial photosynthesis modules, an ultracapacitor/battery and a hydrogen fuel cell.

Figure 3C:
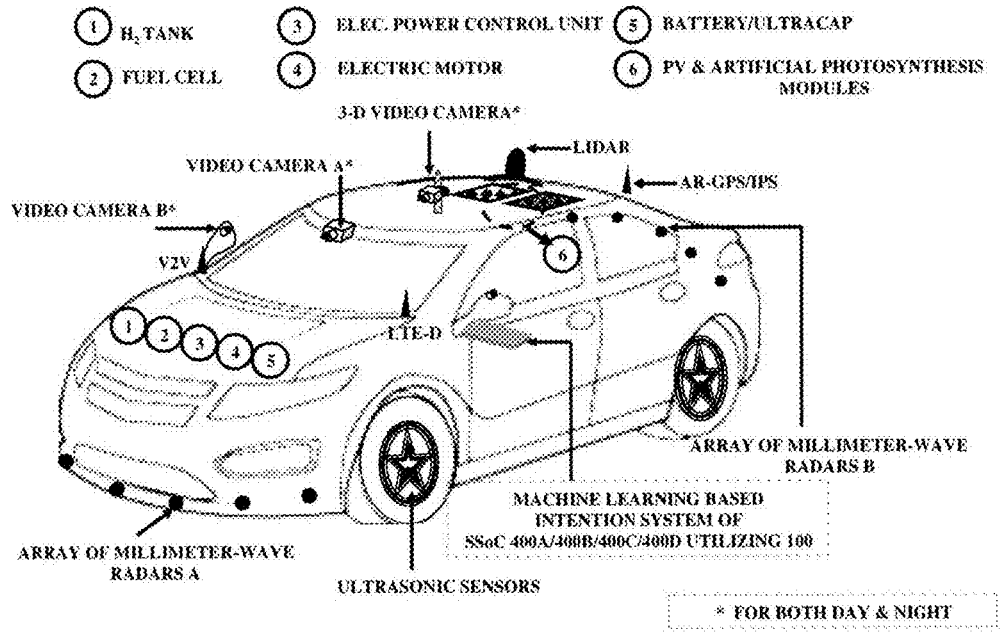
FIG. 3C illustrates an embodiment of key components/subsystems of the intelligent vehicle.

FIG. 3C illustrates the intelligent vehicle, which is configured with a machine learning based real-time intention system of the Super System on Chip 400A/400B/400C/400D. The intelligent vehicle comprises high efficiency photovoltaic modules, artificial photosynthesis modules, a battery/ultracapacitor, a hydrogen fuel cell, an array of millimeter-wave radar sensors, LiDAR, LTE-Direct radio, vehicle to vehicle (V2V) communication, an augmented reality enhanced global positioning system (AR-GPS), an augmented reality enhanced indoor positioning system (AR-IPS), video cameras (for day and night), a three-dimensional orientation video camera (for day and night), ultrasonic sensors and other sensors (e.g., anti-lock braking systems, passenger air bags and real-time fuel consumption sensor). The millimeter-wave radar is relatively unaffected by rain, fog and reflections.

Figure 3D:
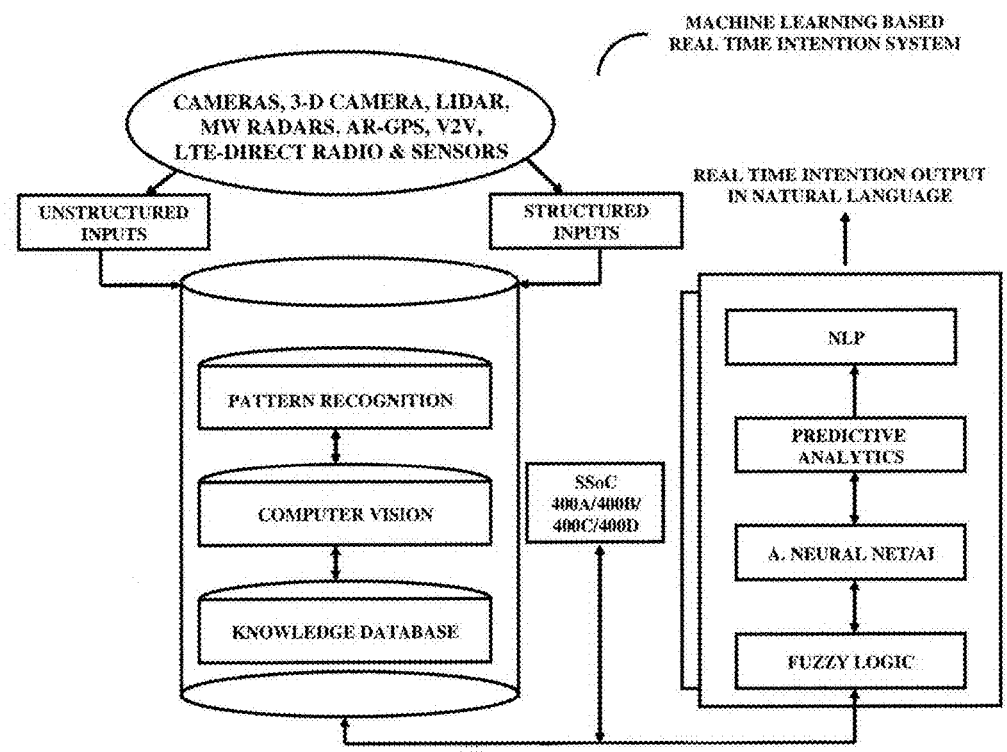
FIG. 3D illustrates an embodiment of a machine learning based intention system of the intelligent vehicle.

FIG. 3D illustrates a machine learning based real-time intention system of the Super System on Chip 400A/400B/400C/400D.

Alternatively, by creating more than 10 to 1,000 mini-circuits within a field programmable gate array (FPGA), effectively the field programmable gate array with or without traditional central processing units (CPU) can be turned into a 10 or 1,000-core processors with each core processor working on its own instructions in parallel and such a configuration can be utilized instead of the Super System on Chip 400A/400B/400C/400D.

The real-time structured and unstructured inputs from cameras, three-dimensional cameras, LiDAR, millimeter wave radars, an augmented reality enhanced global positioning system, vehicle to vehicle communication, LTE-Direct radio and sensors can be correlated through (a) a pattern recognition algorithm submodule, (b) a computer vision algorithm submodule, (c) a knowledge database, (d) a fuzzy logic algorithm submodule, (e) an artificial neural networks/artificial intelligence algorithm submodule, (e) a predictive analytics algorithm submodule and (f) a natural language processing algorithm submodule to create an intention output (in natural language) in real time.

For example, the machine learning based real-time intention system of the Super System on Chip 400A/400B/400C/400D can be sensor-aware and context-aware and it can alert the user (driver) of the intelligent vehicle about the intention of other users (drivers of other intelligent vehicles) in proximity.

The machine learning based real-time intention system can be connected with a cloud quantum computer for real time risk/scenario analysis.

The machine learning based real-time intention system of the Super System on Chip 400A/400B/400C/400D can be applied to both semi-autonomous intelligent vehicles and autonomous intelligent vehicles.

FIG. 3E illustrates an application of the intelligent algorithm submodule 100C of the intelligent vehicle for locating a nearby food store (e.g., McDonald's), utilizing an augmented reality enhanced global positioning system.

FIG. 3F illustrates a subsystem (at the food store) with an LTE-Direct radio, a three-dimensional/holographic display, and a near field communication radio based payment system/nanodots based payment system.

The LTE-Direct radio can enable (a) wireless devices to communicate directly or discover services in 500-meter proximity without any cellular reception (b) the distribution of customer-profiled advertising/coupons (e.g., vehicle/customer recognition) with instant updates. On-Demand near real time delivery of goods can be realized by utilizing an LTE-Direct radio and a global positioning system.

FIG. 3G illustrates an application of interactions of the intelligent vehicle with a food store via the three-dimensional/holographic display, LTE-Direct radio and near field communication radio based/nanodots based payment system.

FIG. 3H illustrates a smart anti-glare window (of the intelligent vehicle) integrated with a transparent processor and an array of transparent sensors (e.g., an outside light intensity/temperature/rain sensor). The transparent processor and the transparent sensors can be fabricated/constructed with indium-gallium-zinc oxide or zinc-tin oxide semiconductor material.

Figure 3I:
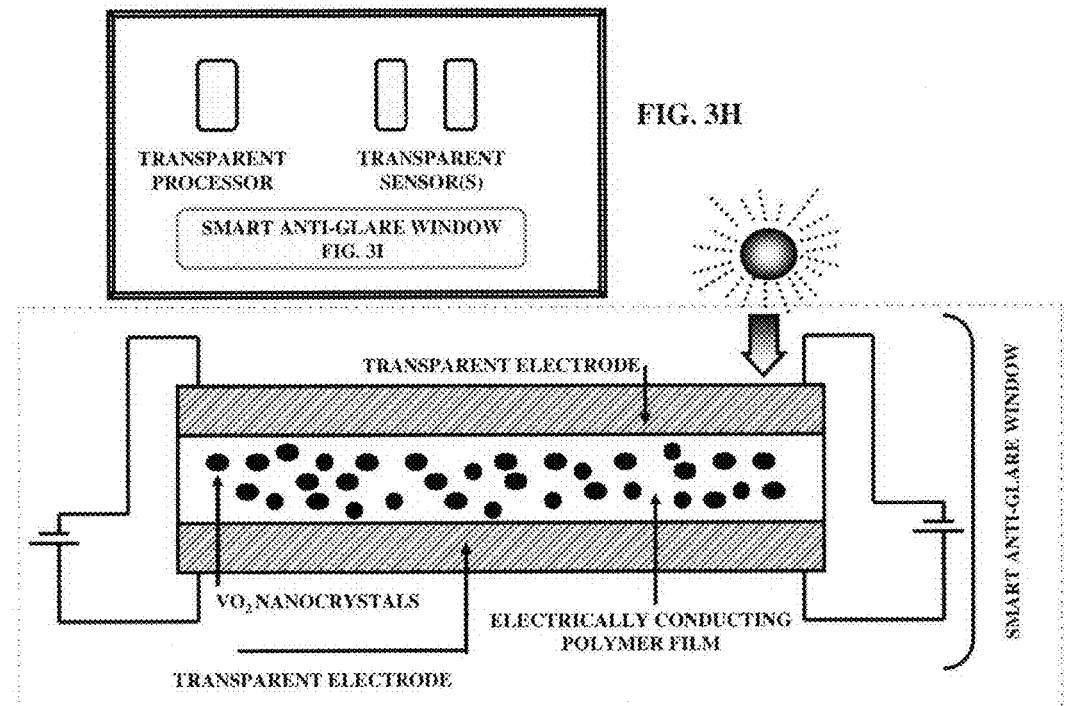

FIG. 3I illustrates an electrically switchable smart anti-glare window. Vanadium dioxide ($VO_2$) is a transparent insulator at room temperature. But after its phase transition temperature, vanadium dioxide is reflective and opaque, thus temperature determines if vanadium dioxide is an insulator or a metal. Vanadium dioxide nanoparticles embedded within transparent electrically conducting polymeric films (with transparent electrodes on the transparent electrically conducting polymeric films) can act as a smart anti-glare window, when heated electrically. Alternatively, vanadium dioxide thin-film can be utilized instead of vanadium dioxide nanoparticles. The smart anti-glare window can be coated with thin-films to protect the user (the driver of the intelligent vehicle) from harmful UV rays. A large area smart anti-glare window can be printed by a nanotransfer printing method.

Additionally, any relevant information from the internet connection of the intelligent vehicle and/or intelligent portable internet appliance 160 and/or intelligent wearable augmented reality personal assistant device 180 can be augmented and projected via a head-up display (HUD) onto the smart anti-glare window, wherein the head-up display comprises a microprojector 560, as described in FIG. 50A. The head-up display can respond/recognize voices, gestures or read an item or a person in the user's field of view, wherein a decoder is configured to convert the said reading of the item or the person into a text or an image, taking into account the context of driving.

Details of the augmented reality personal assistant device 180 are illustrated in FIG. 53.

Figure 3J:
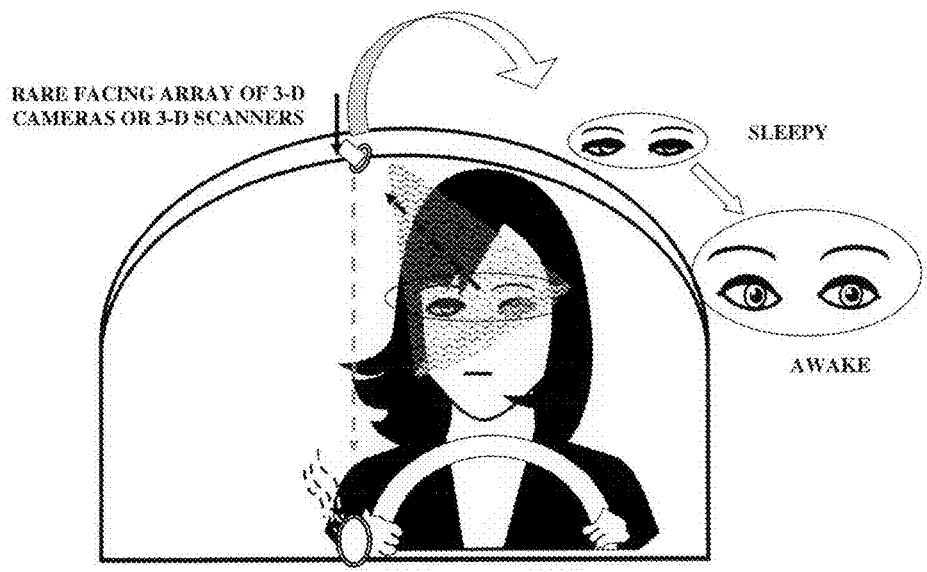

FIG. 3J illustrates an application of an array of eye-facing cameras/three-dimensional scanner to monitor the user's eye opening and closing patterns. If the user is sleepy, then an electronics system integrated with the array of eye-facing cameras/three-dimensional scanner can alert the user (the driver of the intelligent vehicle).

Figure 4A:
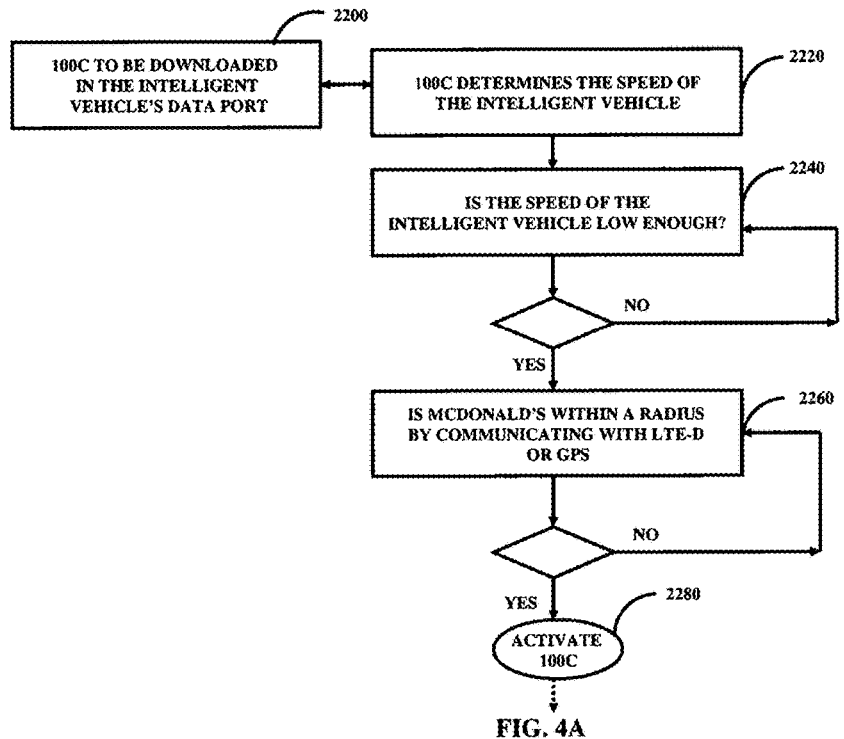
FIGS. 4A-4H illustrate an application of an intelligent algorithm of the intelligent vehicle.
Photovoltaic & Artificial Photosynthesis Module

In FIG. 4A, in step 2200, 100C can be downloaded in the intelligent vehicle's data port. In step 2220, 100C determines the speed of the intelligent vehicle. In step 2240, 100C determines if the speed of the intelligent vehicle is low enough, then 100C allows proceeding to step 2260; otherwise 100C reiterates the previous step. In step 2260, 100C determines if McDonald's is in close proximity to the intelligent vehicle by utilizing LTE-Direct radio and/or global positioning system, then 100C allows proceeding to step 2280, where the core application of 100C is activated.

Figure 4B:
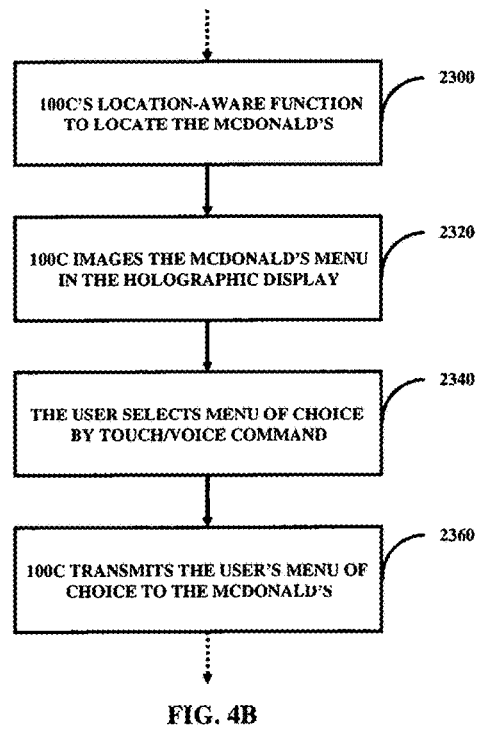

In FIG. 4B, continuing in step 2300, 100C further enables a location-aware function to locate the McDonald's. In step 2320, 100C images McDonald's menu on the intelligent vehicle's three-dimensional/holographic display. In step 2340, the user selects his/her food items from the McDonald's menu by touch/voice command. In step 2360, 100C transmits his/her choice of the McDonald's menu to the McDonald's.

Figure 4C:
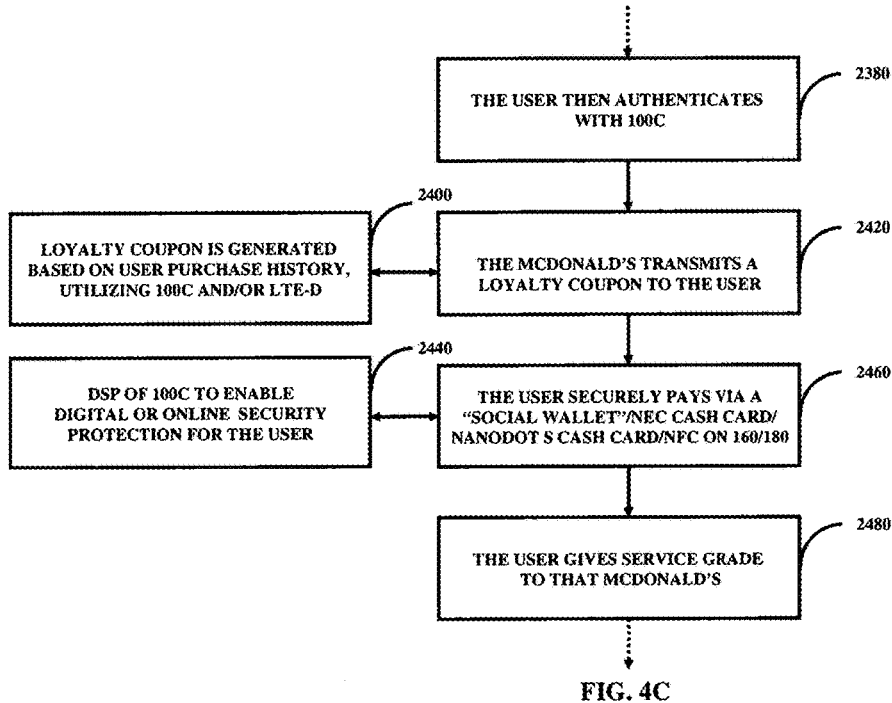

In FIG. 4C, continuing in step 2380, the user authenticates (via biometric confirmation) himself/herself with 100C. In step 2400, a loyalty coupon for the user is generated by McDonald's, utilizing 100C and/or an LTE-Direct radio. In step 2420, McDonald's transmits a loyalty coupon to the user. In step 2440, the digital security protection (DSP) of 100C provides digital or online security protection for the user. In step 2460, the user securely pays for his/her food items using a social wallet/near field communication radio cash card/nanodots cash card or near field communication radio of intelligent portable internet appliance 160/intelligent wearable augmented reality personal assistant device 180. In step 2480, the user gives a service grade (feedback) to the McDonald's for the service rendered.

Details of the social wallet are described in U.S. Non-Provisional patent application Ser. No. 13/448,378 entitled "SYSTEM AND METHOD FOR INTELLIGENT SOCIAL COMMERCE", filed on Apr. 16, 2012 and the non-provisional patent application with its benefit patent applications are incorporated in its entirety herein with this application.

Figure 4D:
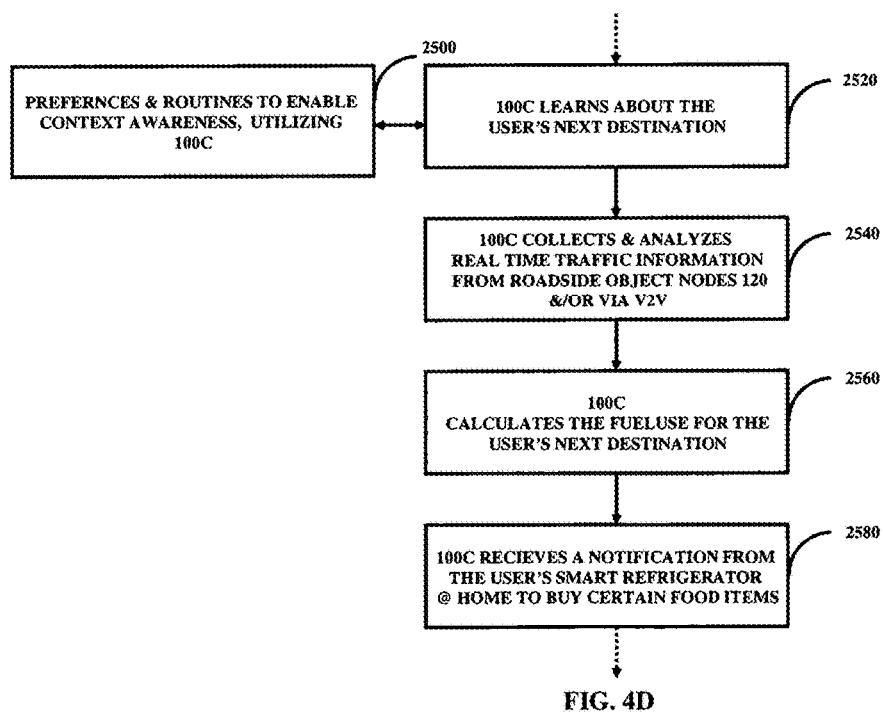

In FIG. 4D, continuing in step 2500, the user's preference and routines are utilized by 100C to enable context awareness. In step 2520, 100C contextually learns the user's next destination. In step 2540, 100C collects and/or analyzes near real-time or real-time traffic information from object nodes 120 at the roadside and/or via vehicle-to-vehicle communication. In step 2560, 100C calculates the fuel consumption for the user's next destination. In step 2580, 100C receives a notification from the user's smart refrigerator at his/her home to buy certain food items.

Figure 4E:
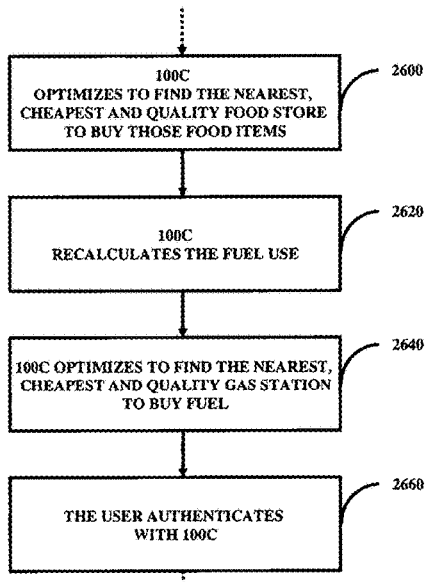

In FIG. 4E, continuing in step 2600, 100C optimizes to find the nearest cheapest and quality food store to buy those food items. In step 2620, 100C recalculates the fuel consumption. In step 2640, 100C optimizes to find the nearest cheapest and quality gasoline station store to buy fuel. In step 2660, the user authenticates (via biometric confirmation) himself/herself with 100C.

Figure 4F:
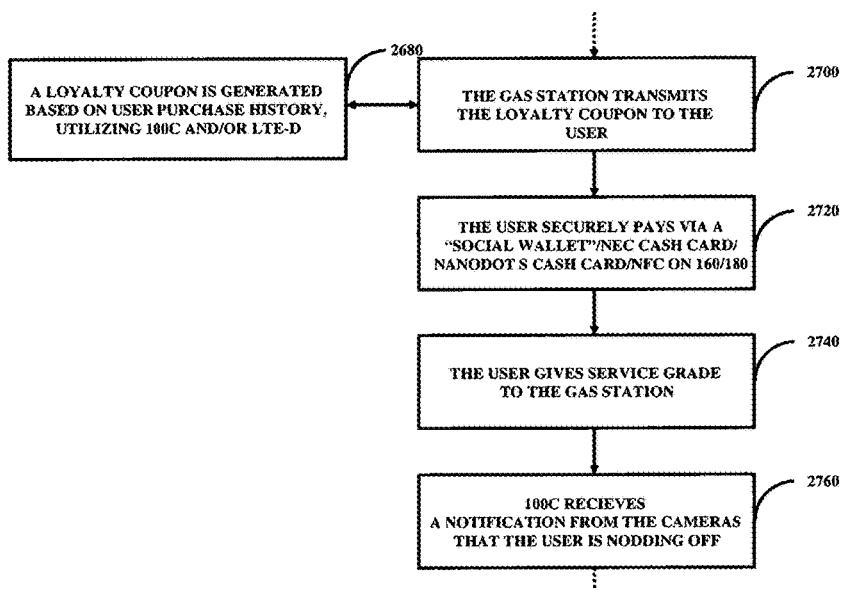

In FIG. 4F, continuing in step 2680, a loyalty coupon for the user is generated by the gasoline station, utilizing 100C and/or the LTE-Direct radio. In step 2700, the gasoline station transmits the loyalty coupon to the user. In step 2720, the user securely pays for gas using a social wallet/near field communication radio cash card/nanodots cash card or near field communication radio of intelligent portable internet appliance 160/intelligent wearable augmented reality personal assistant device 180.

In step 2740, the user gives a service grade to the gasoline station for the service rendered. In step 2760, 100C receives a notification from an array of eye-facing cameras that the user is nodding off.

Figure 4G:
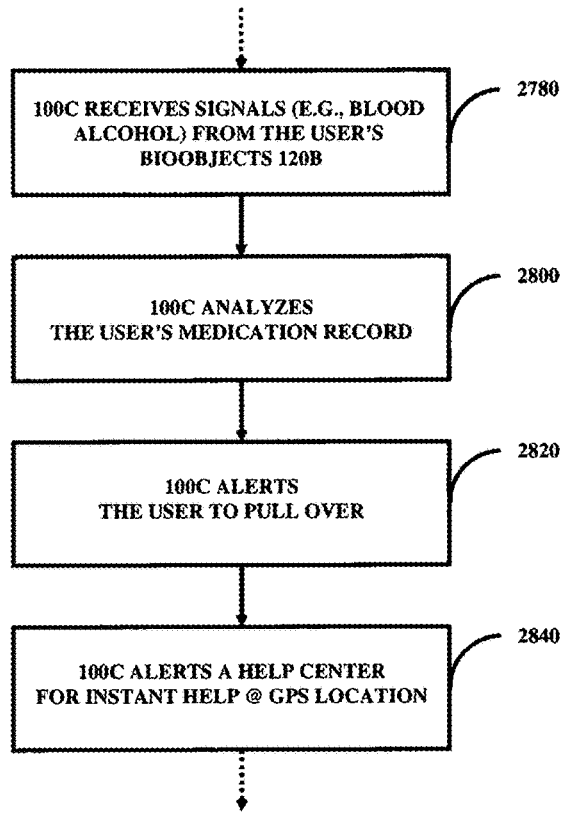
Figure 56A:
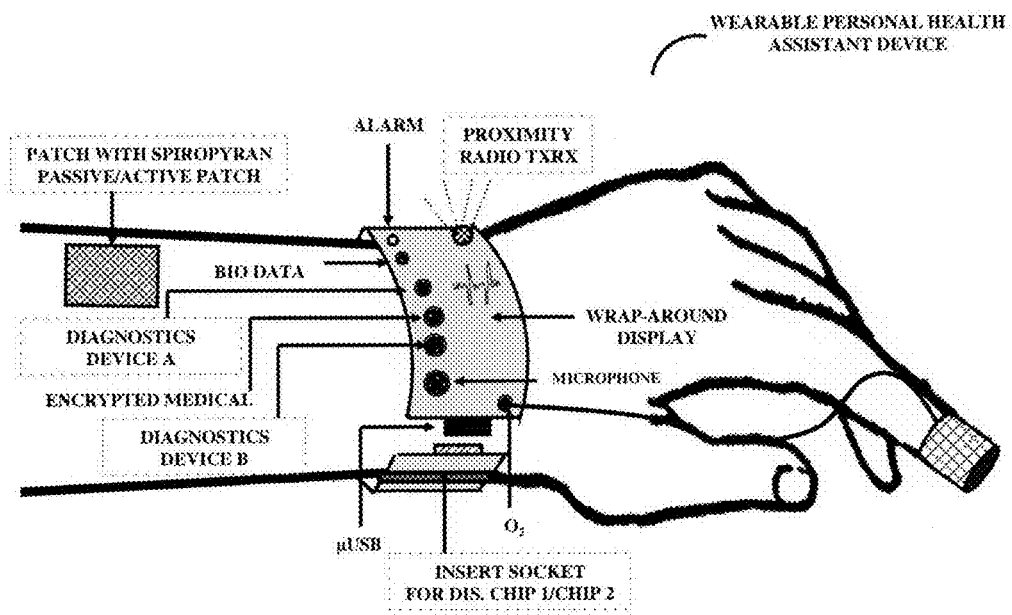

In FIG. 4G, continuing in step 2780, 100C receives vital signals (e.g., alcohol level in blood or blood pressure or sudden dizziness) from the user's bioobjects 120B. In step 2800, 100C analyzes the user's medication record, as recorded by the wearable personal health assistant device (FIG. 56A). In step 2820, 100C alerts the user to pull over from the road. In step 2840, 100C alerts a help center, identifying the user's vehicle's location (by global positioning system).

Figure 4H:
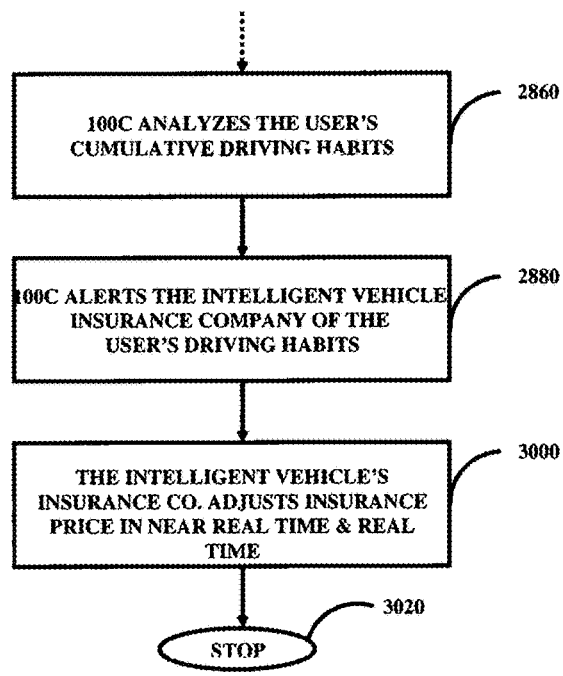

In FIG. 4H, in step 2860, 100C analyzes the user's cumulative driving habits by securing data from the intelligent vehicle. In step 2880, 100C notifies the intelligent vehicle's insurance company regarding the user's driving habits. In step 3000, the intelligent vehicle's insurance company adjusts the insurance price in near real time or real time. Step 3020 denotes a conclusion of this application.

The intelligent algorithm 100 comprises an application specific algorithm submodule 100C. There are other applications of the intelligent algorithm 100, for example (a) by converting detailed photo images of real properties using a computer vision based application specific algorithm submodule 100C, the value of the real property may be estimated and (b) by converting Monte Carlo enhanced discounted free cash flow (MC-DCF) to an application specific algorithm submodule 100C, the intrinsic value of a stock may be estimated.

Figure 5A:
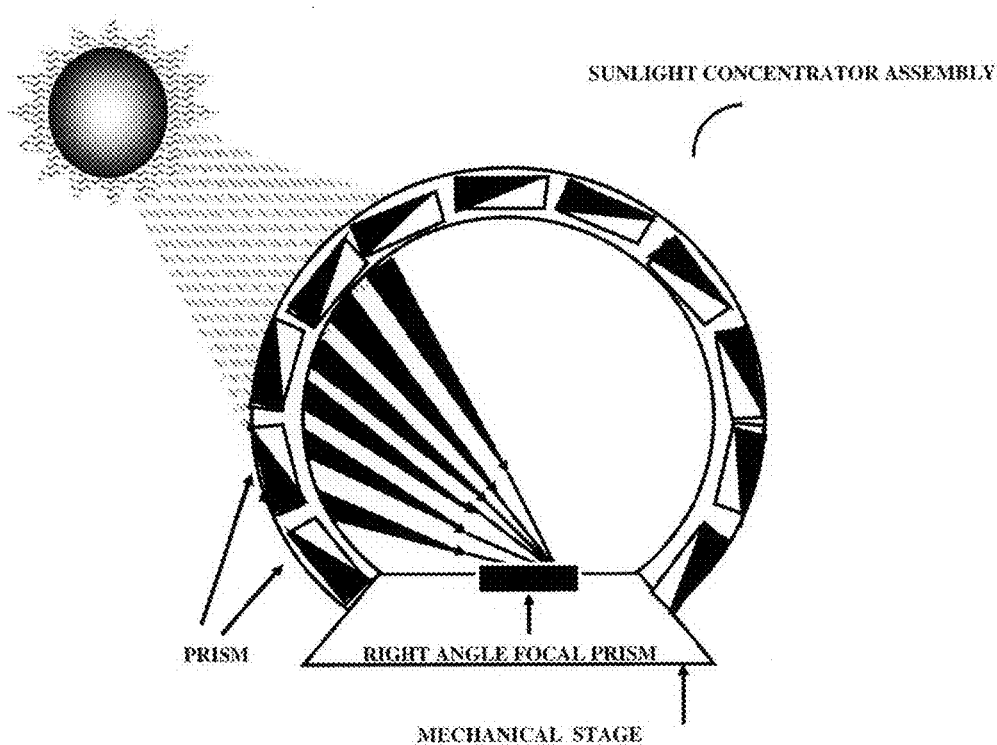
FIG. 5A illustrates an embodiment of an opto-mechanical assembly to collect sunlight.

FIG. 5A illustrates a sunlight concentrator assembly utilizing an array of prisms-further focusing onto a right-angle prism and a mechanically moveable stage.

Figure 5B:
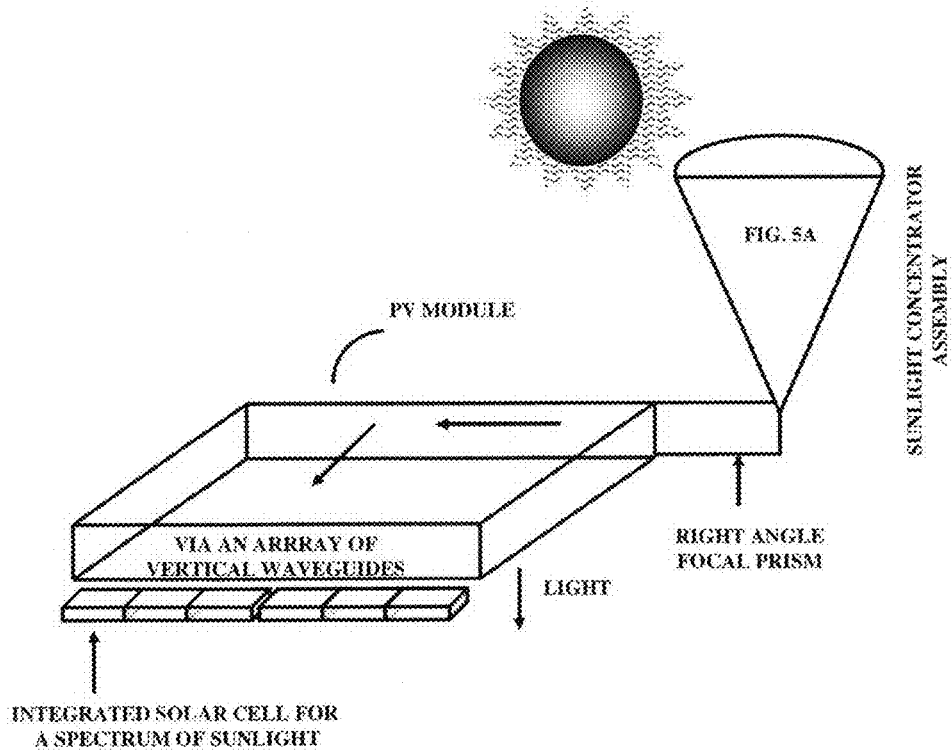
FIGS. 5B-5C illustrate an embodiment of a photovoltaic module.

FIG. 5B illustrates a sunlight concentrator assembly, which is optically coupled with a photovoltaic module via a right angle focal prism. The photovoltaic module has an array of vertical waveguides (fabricated/constructed by femtosecond laser) connecting with an array of integrated solar cells, wherein each integrated solar cell is wavelength matched for a specific (slice of) spectrum of sunlight.

Figure 5C:
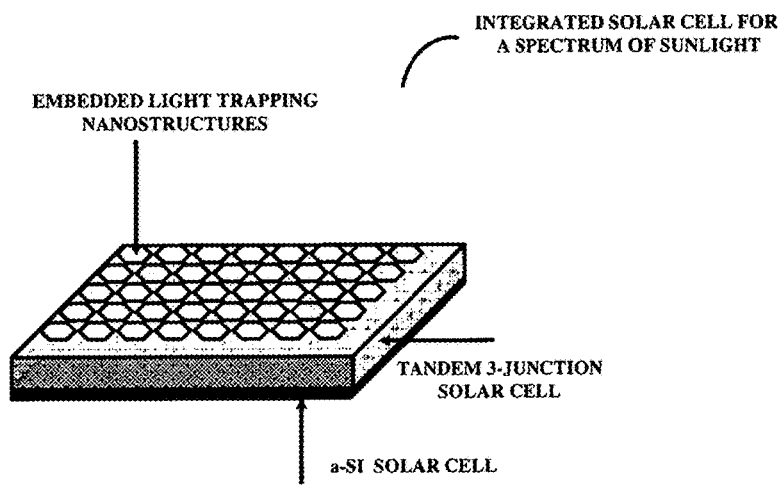

FIG. 5C illustrates an integrated solar cell, which is wavelength matched for a specific spectrum of sunlight. The integrated solar cell has embedded light trapping nanostructures and comprises a tandem 3-junction solar cell plus an amorphous silicon solar cell at the bottom.

Additionally, a tandem 3-junction solar cell can comprise silicon quantum dots and/or germanium quantum dots for carrier multiplication in order to enable a higher efficiency solar cell. Alternatively, perovskite-copper indium gallium diselenide (CIGS) tandem or perovskite-multicrystalline silicon (Si) tandem can be utilized instead of tandem 3-junction solar cell. Solar cells for both blue spectrum and green spectrum can be coated with pentacene organic thin-film to increase the conversion efficiency by about 5%.

Figure 5D:
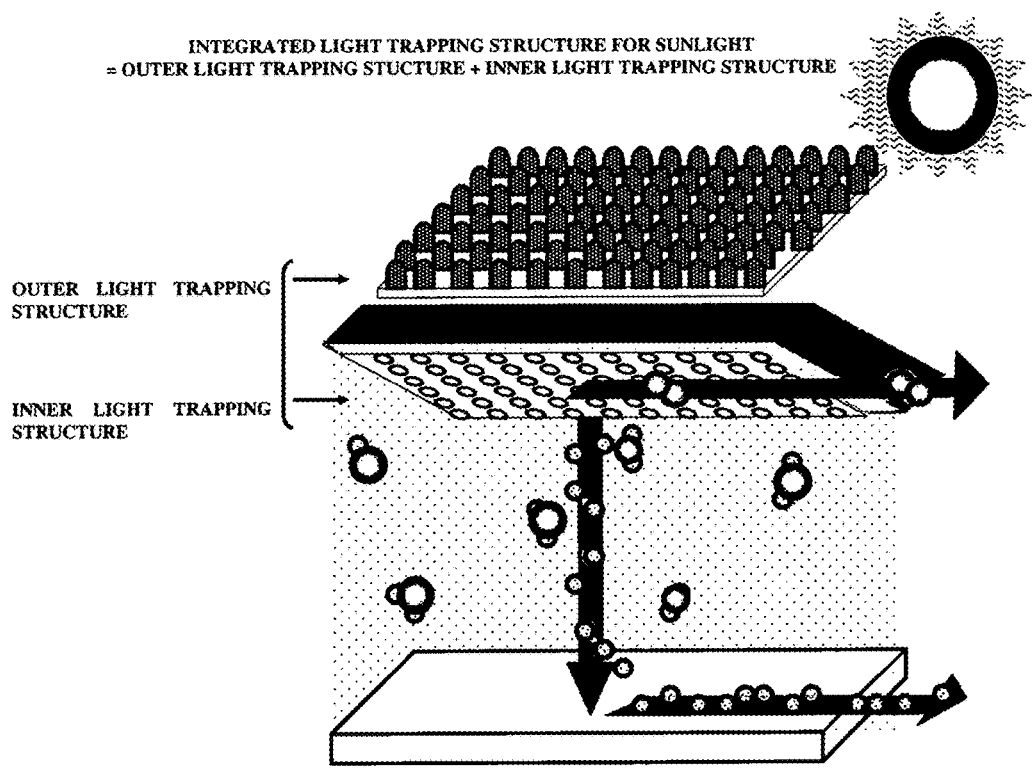
FIGS. 5D-5E illustrate an embodiment of an integrated artificial photosynthesis-solar cell module.

FIG. 5D illustrates embedded light trapping nanostructures on the outside and inside of an integrated artificial photosynthesis-photovoltaic module based energy generation system.

Figure 5E:
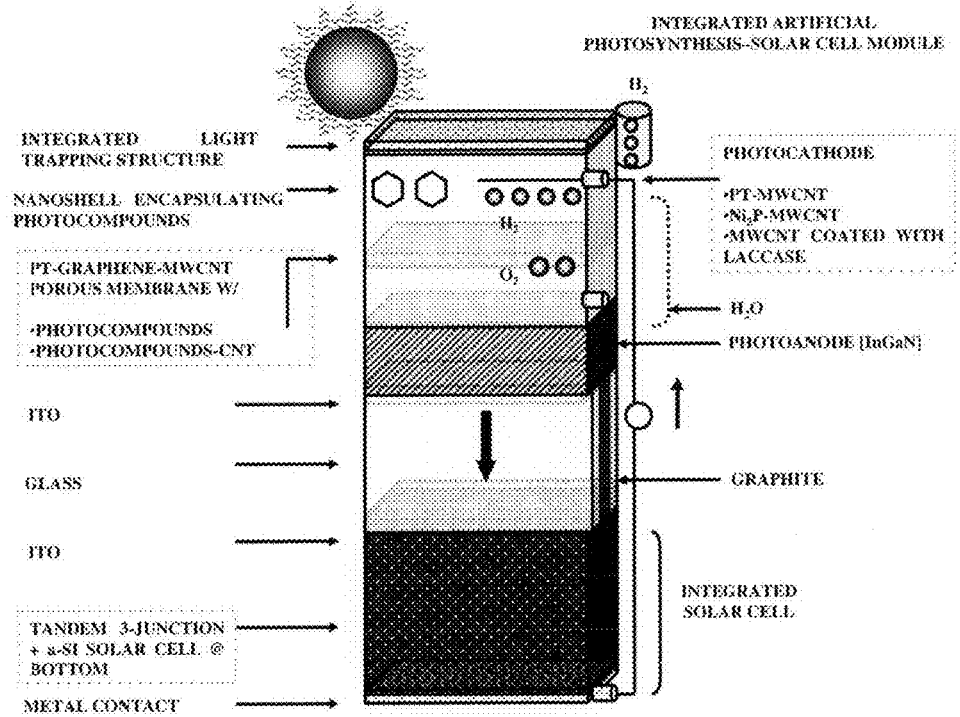

FIG. 5E illustrates an integrated artificial photosynthesis-solar cell module, wherein the artificial photosynthesis module comprises embedded light trapping nanostructures on the outside and inside, nanoshells with photocompounds inside, a porous platinum-graphene-multiwall carbon nanotube (MW-CNT) membrane with embedded photocompounds (e.g., LHC-II) or photocompounds in a carbon nanotube. A photoanode can be based on InGaN material. A photocathode for water splitting can be based on platinum-multiwall carbon nanotube/$N_2P$-multiwall carbon nanotube/multiwall carbon nanotube coated with Laccase enzyme. Below the artificial photosynthesis module is the tandem 3-junction solar cells (plus an amorphous silicon solar cell at the bottom).

Figure 6:
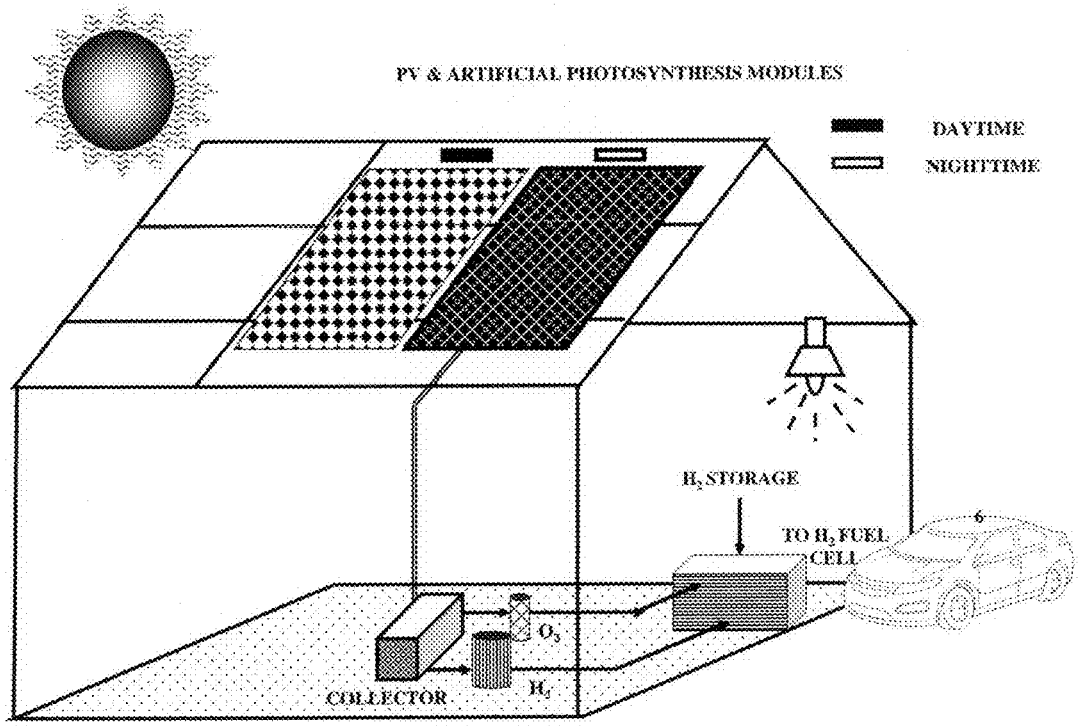
FIG. 6 illustrates an application of photovoltaic and artificial photosynthesis modules at a home.
Secure Payment System

FIG. 6 illustrates an application of photovoltaic and artificial photosynthesis modules at home.

Figure 7A:
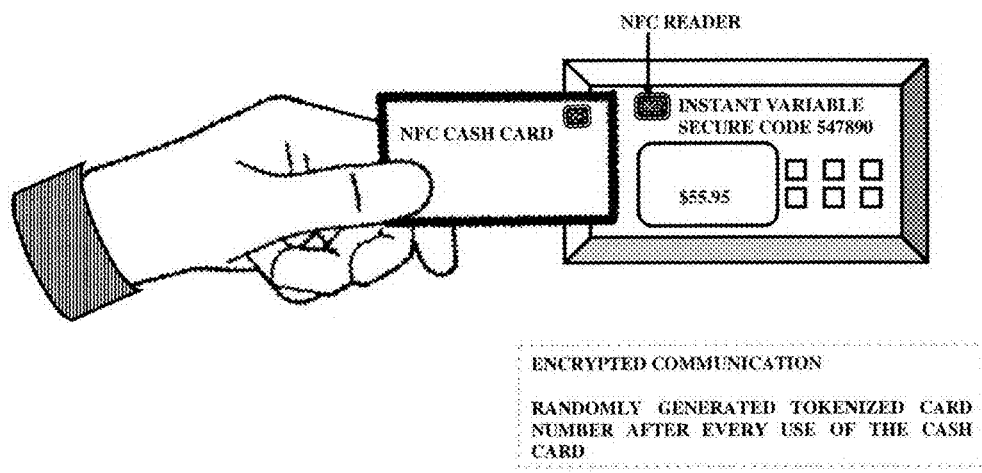

FIG. 7A illustrates a near field communication based cash card, where the cash card is integrated with at least (a) a near field communication chip and (b) a first biometric sensor (e.g., a finger vein sensor). The actual number of the cash card is tokenized, never revealed at all. When the first biometric sensor clearly identifies the user and the cash card securely communicates with a near field communication radio reader at a point of sale payment system via 256-bit strong encryption, then the display (device) at the point of sale payment system displays an instant unique variable code. The user has to input the instant unique variable code and his/her own unique password(s) into the point of sale payment system. The cash card transmits a 16-digit token and unique cryptogram to the point of sale payment system, then to a MasterCard/Visa network. The MasterCard/Visa network swaps the 16-digit token and unique cryptogram and further analyzes other identifications on the cash and information from digital security protector algorithm submodule 100B (FIG. 1B) before authorizing or rejecting the purchase within milliseconds.

The point of sale payment system can be provisioned or enabled by a second biometric sensor, in case of any malfunction of the first biometric sensor. The instant variable code for the user varies at each point of sale transaction.

Figure 7B:
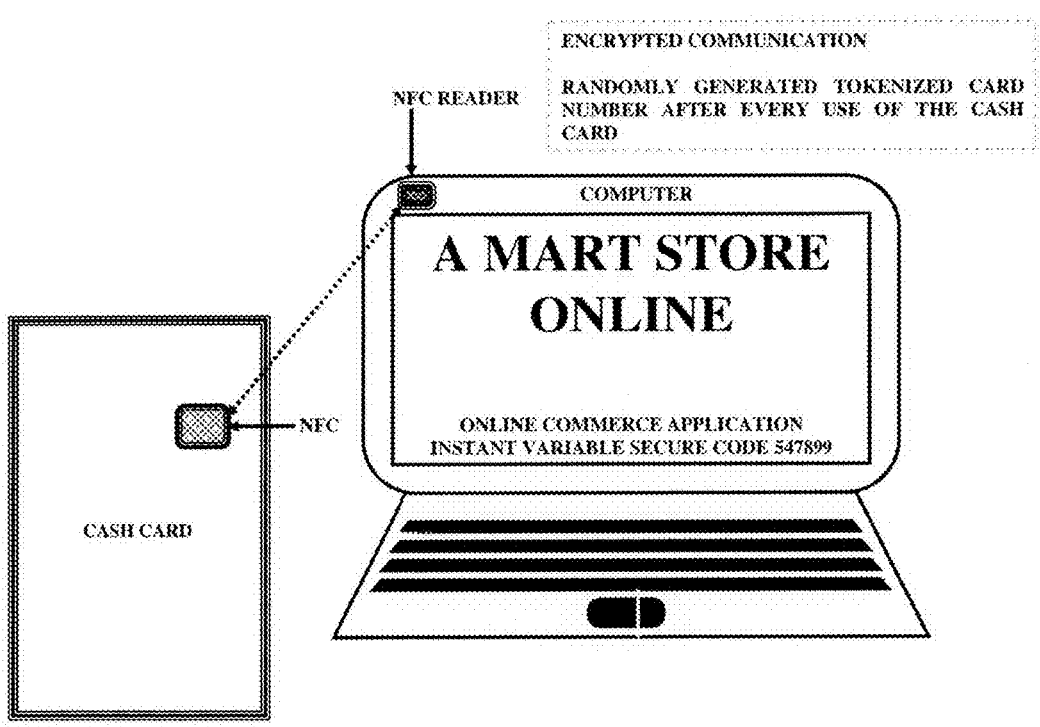

Similar to FIG. 7A, FIG. 7B illustrates the near field communication based cash card for online/internet purchases utilizing a computer, which comprises a near field communication reader.

FIG. 7C and FIG. 7D illustrate a wired charging configuration of the cash card.

FIG. 7E illustrates a wireless charging through air configuration of the cash card.

Figure 8A:
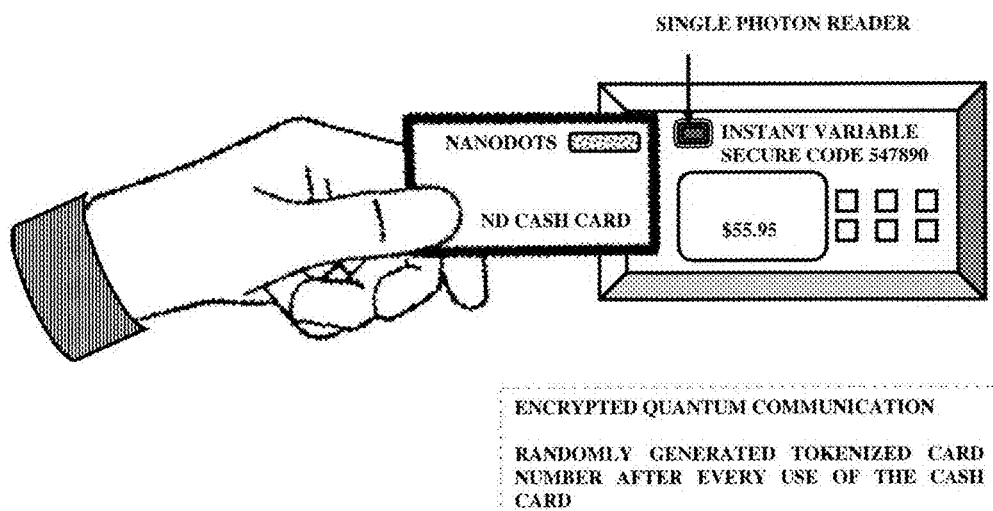
FIGS. 8A-8C illustrate an embodiment of a nanodots/quantum communication based secure payment system.

FIG. 8A illustrates a cash card, where the cash card is integrated with at least (a) millions of nanodots (e.g., ceramic nanodots) and (b) a first biometric sensor (e.g., finger vein sensor). The cash card can communicate with a single photon reader at the point of sale via unbreakable quantum physics based encryption. The actual number of the cash card is tokenized, never revealed at all. When the first biometric sensor clearly identifies the user and the cash card securely communicates with the nanodots communication reader at a point of sale payment system via unbreakable quantum physics based encryption, then the display (device) at the point of sale payment system displays an instant unique variable code. The user has to input the instant unique variable code and his/her own unique password(s) at the point of sale payment system. The cash card transmits a 16-digit token and unique cryptogram to the point of sale payment system, then to a MasterCardNisa network. The MasterCard/Visa network swaps the 16-digit token and unique cryptogram and further analyzes other identifications on the cash card and information from digital security protector algorithm submodule 100B (FIG. 1B) before authorizing or rejecting the purchase within milliseconds.

The point of sale payment system can be provisioned or enabled by a second biometric sensor, in case of any malfunction of the first biometric sensor. The instant variable code for the user varies at each point of sale transaction.

Figure 8B:
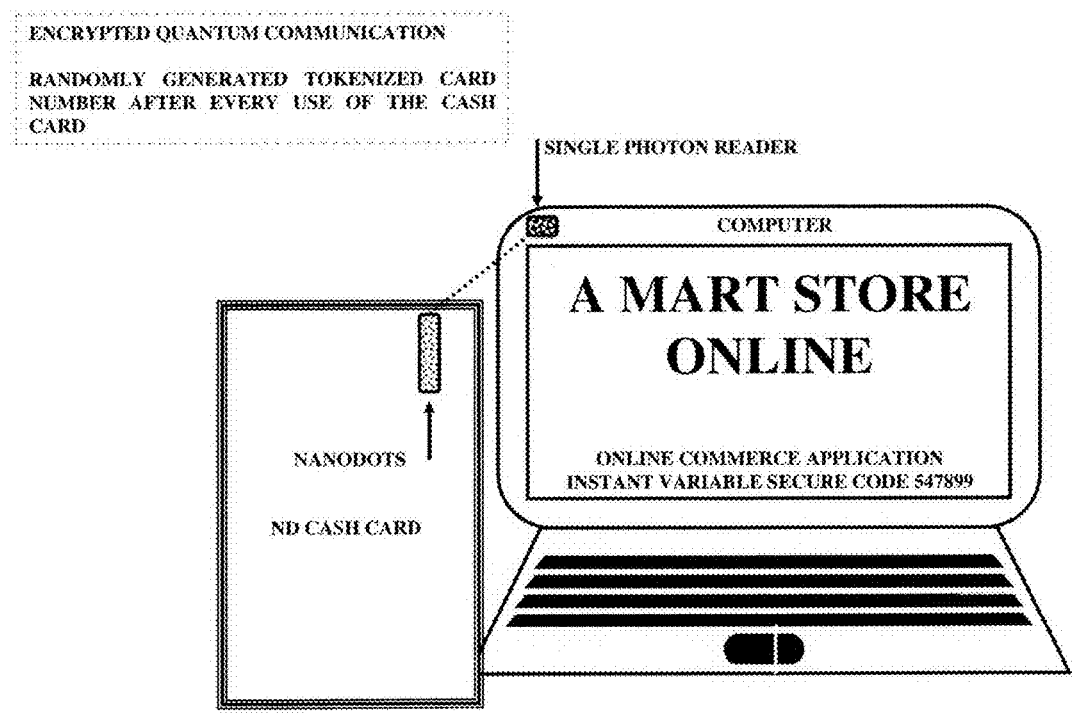

Similar to FIG. 8A, FIG. 8B illustrates the nanodots based cash card for online/internet purchases utilizing a computer, which comprises a single photon reader.

Figure 8C:
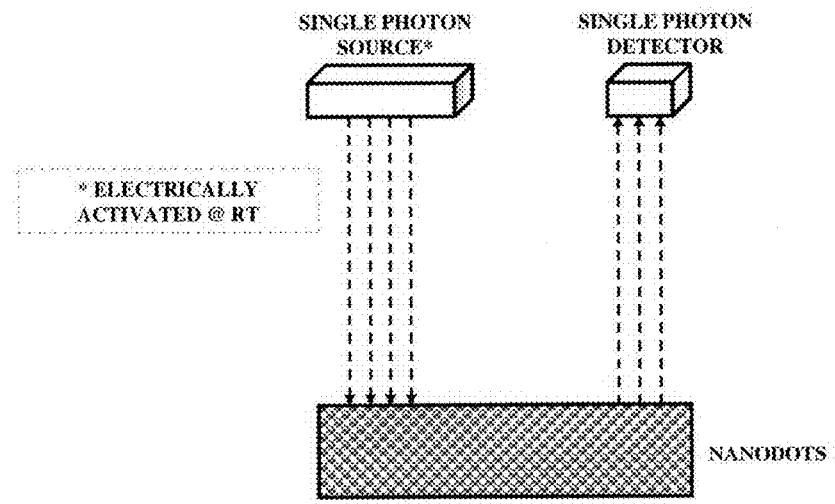

FIG. 8C illustrates the scattering of single photons from a single photon source at room temperature (e.g., diamond semiconductor with defect centers) by millions of nanodots and the scattered photons are detected by a single photon detector (e.g., a Geiger mode avalanche photodiode (APD)).

Figure 9A:
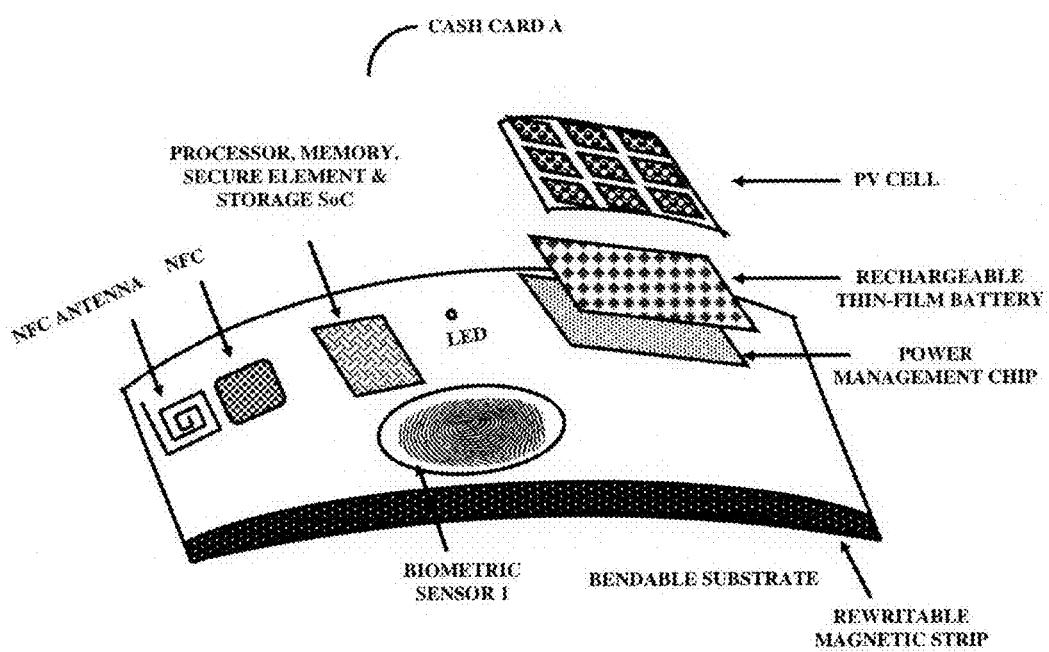
FIGS. 9A-9D illustrate four embodiments of a near field communication based physical cash card.

FIG. 9A illustrates a cash card on a bendable-flexible substrate (e.g., a plastic/polymer substrate), which can integrate a photovoltaic cell, a rechargeable thin-film battery, a power management chip, a light emitting diode (LED), a first biometric (e.g., a finger print/vein sensor) sensor, a cash card specific System on Chip (integrated with a processor, a memory component, a secure element, a storage component) (SoC) and a near field communication radio (with its antenna). The cash card as in FIG. 9A can integrate a rewritable magnetic strip.

A fingerprint sensor can be fabricated/constructed by combining colloidal crystals with a rubbery material, wherein colloidal crystals can be dissolved in a suitable chemical leaving air voids in the rubbery material, thus to create an elastic photonic crystal. The fingerprint sensor emits an intrinsic color, displaying three-dimensional ridges, valleys and pores of the user's fingerprint, when pressed. The cash card specific System on Chip with a specific algorithm and camera can be utilized to compare the user's previously captured/stored fingerprint. A non-matching fingerprint would render the cash card instantly unusable.

Details of the optical fingerprint sensor are described in U.S. Non-Provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 and the non-provisional patent application with its benefit patent applications are incorporated in its entirety herein with this application.

Figure 9B:
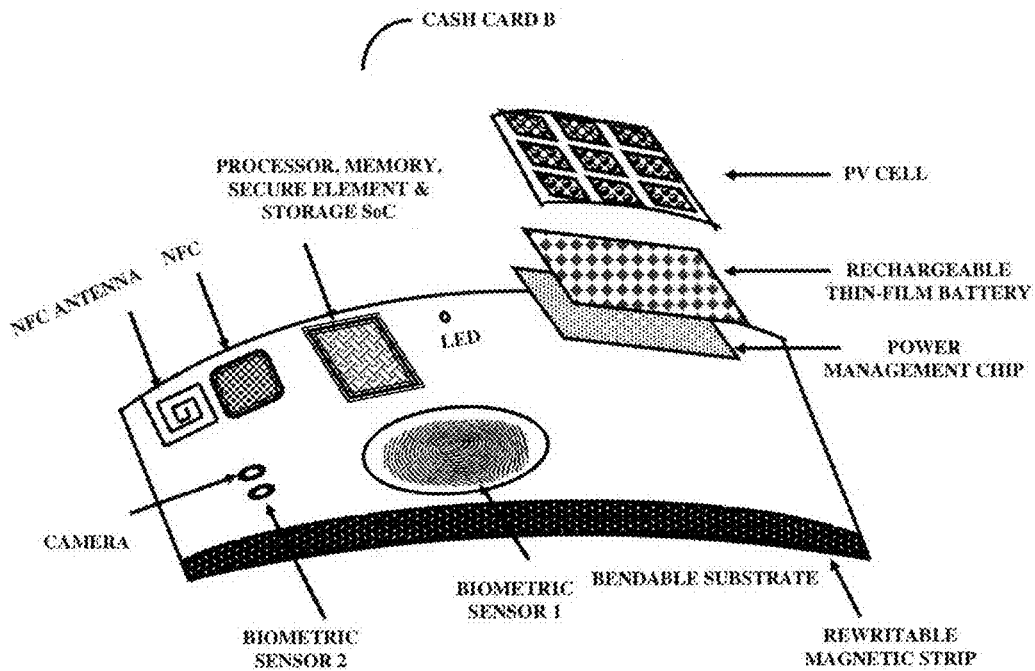

FIG. 9B illustrates the cash card B, which is the cash card A with the addition of a surface mountable low-profile camera or copper indium selenide (CIS) based flexible camera and a second biometric sensor (e.g., a sensor to recognize voice).

Figure 9C:
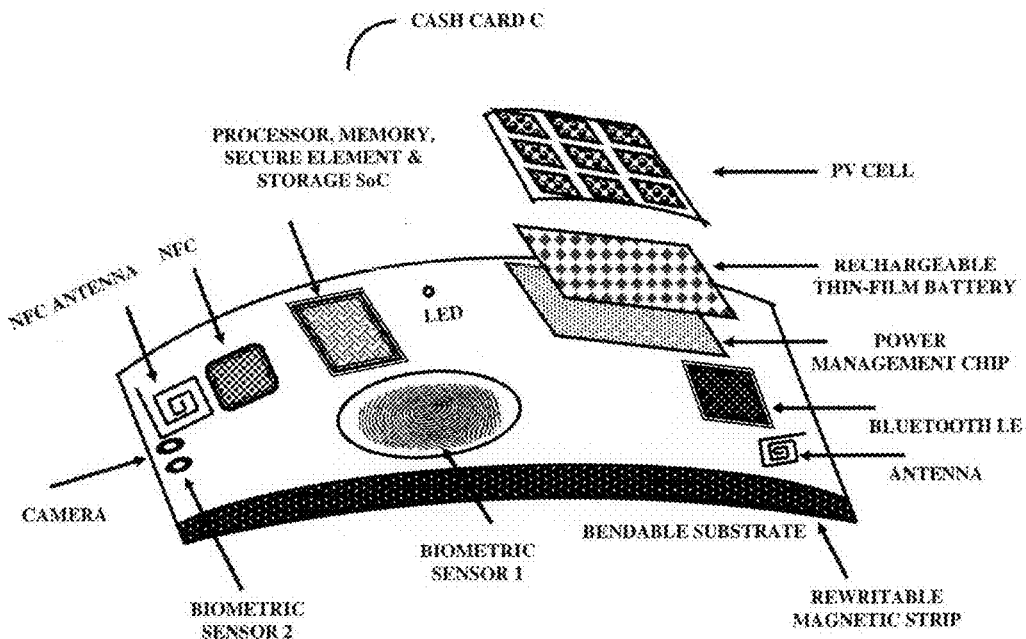

FIG. 9C illustrates the cash card C, which is the cash card B with the addition of a Bluetooth LE communication radio (with its antenna).

Figure 9D:
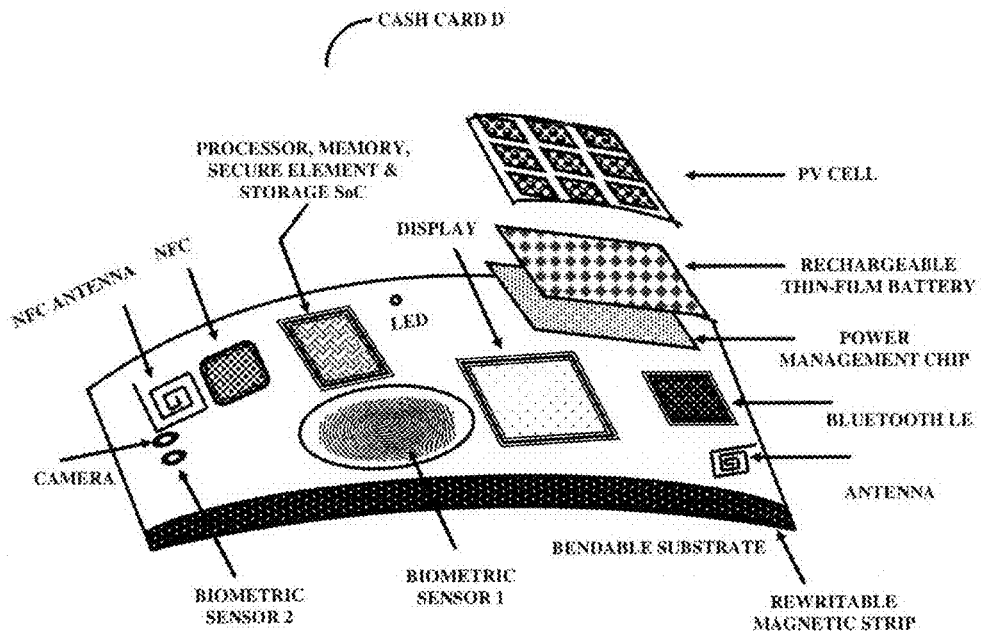

FIG. 9D illustrates the cash card D, which is the cash card C with the addition of a display (e.g., an E-Ink display).

Figure 9E:
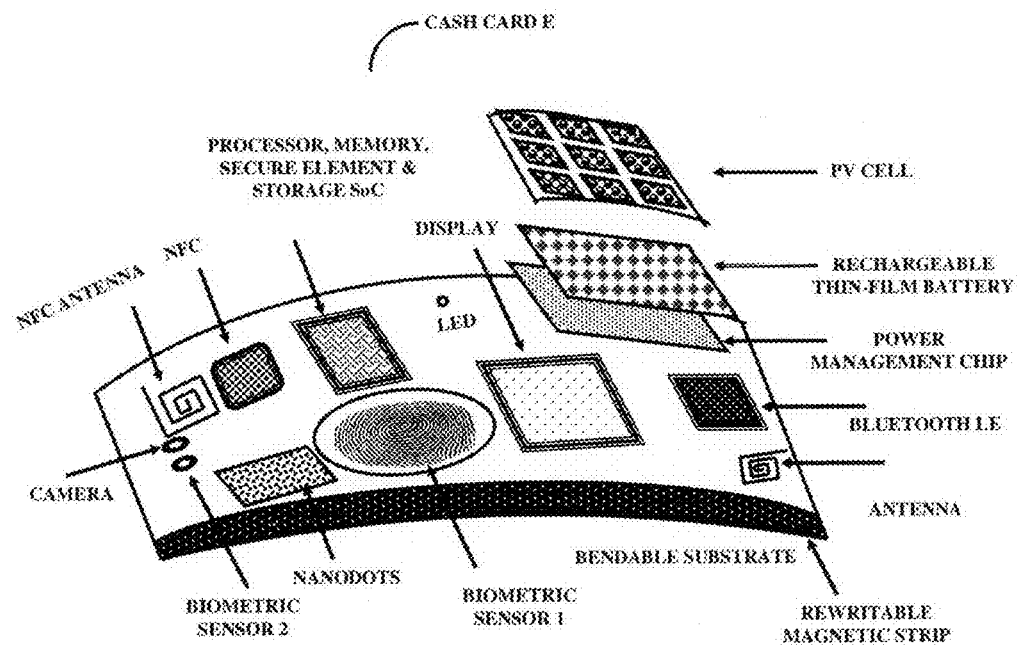
FIG. 9E illustrates an embodiment of a near field communication and nanodots based physical cash card.

FIG. 9E illustrates the cash card E, which is the cash card D with the addition of a large number of nanodots (e.g., ceramic nanodots).

Figure 10:
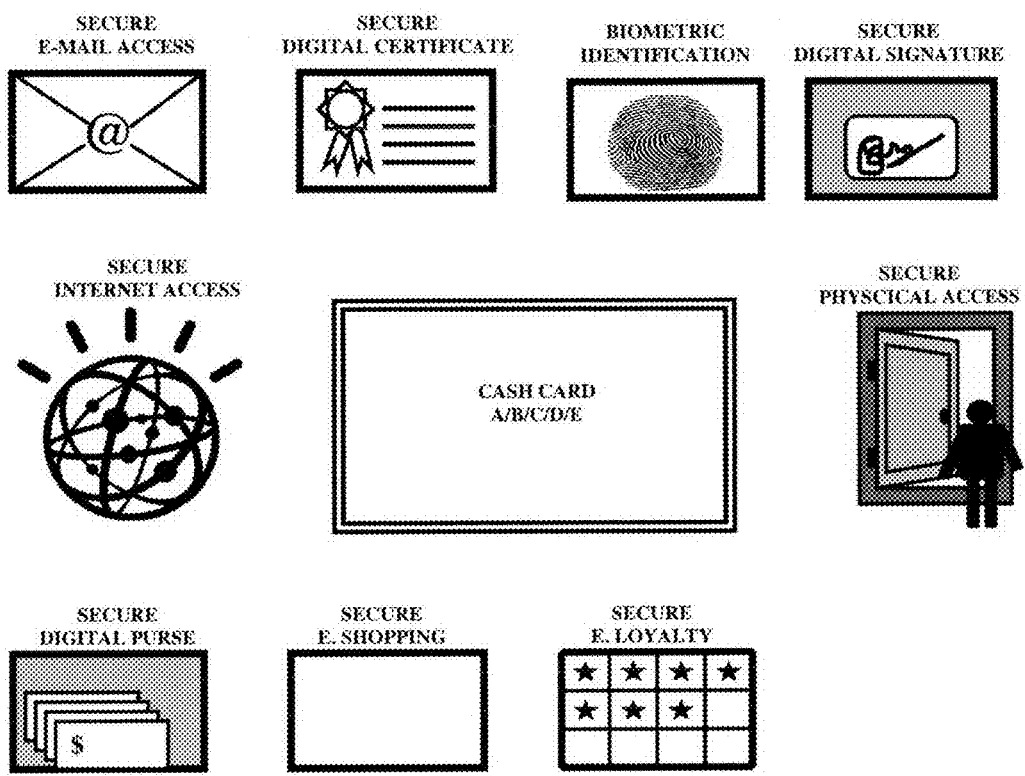
FIG. 10 illustrates a universal application of the physical cash card.
Object

FIG. 10 illustrates a universal and secure application of the cash card A/B/C/D/E, for example, with respect to digital signature, biometric identification, digital certificate, e-mail access, internet access, digital purse, electronic shopping, electronic loyalty program and physical access.

The cash card can have electromagnetic coils in its interior for receiving electrical power wirelessly at a close proximity to the intelligent portable internet appliance 160 or the intelligent wearable augmented reality personal assistant device 180.

The cash card can be integrated with the intelligent portable internet appliance 160 or the intelligent wearable augmented reality personal assistant device 180 or the social wallet.

Utilizing the cash card, the user can securely purchase/rent a product/service.

Figure 11:
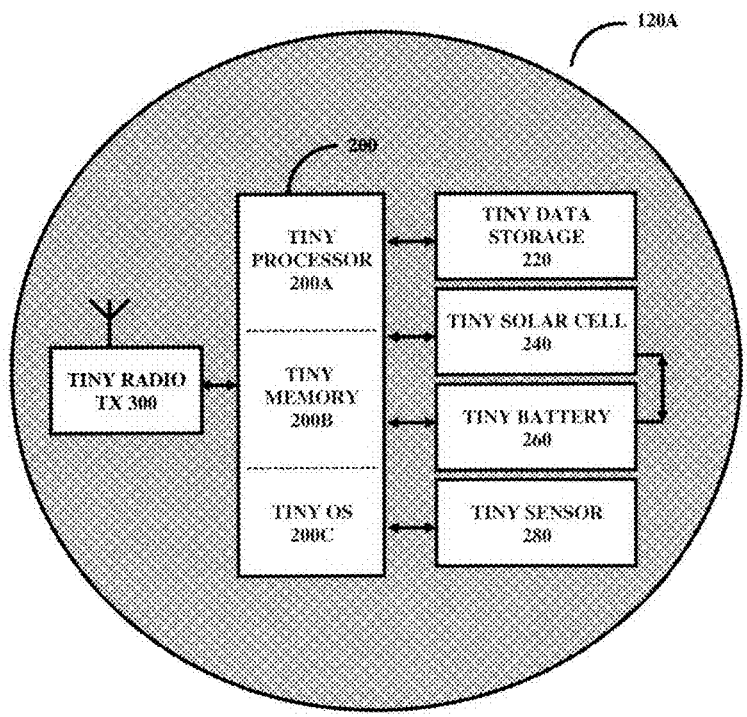
FIG. 11 illustrates an embodiment of an object.
Bioobject

FIG. 11 illustrates the object 120A. The object 120A integrates various tiny components in a System on Chip or System on Package. Tiny components are fabricated/constructed for extremely low power consumption. A tiny component 200 comprises a tiny processor 200A, a tiny memory 200B and a tiny operating system (Tiny OS) 200C. The tiny component 200 is electrically coupled with a tiny data storage component 220, a tiny solar cell 240, a tiny battery 260, a tiny sensor 280 and an extremely low power tiny wireless component 300. The tiny sensor 280 can be fabricated/constructed for a specific purpose. The tiny solar cell 240 can be fabricated/constructed on top of the tiny battery 260. The extremely low power tiny wireless transmitter component 300 can be a tiny antenna. The object 120A can be electromagnetically powered from an ambient Wi-Fi network. Various versions of the object 120A are also possible within the spirit of this invention.

Figure 12A:
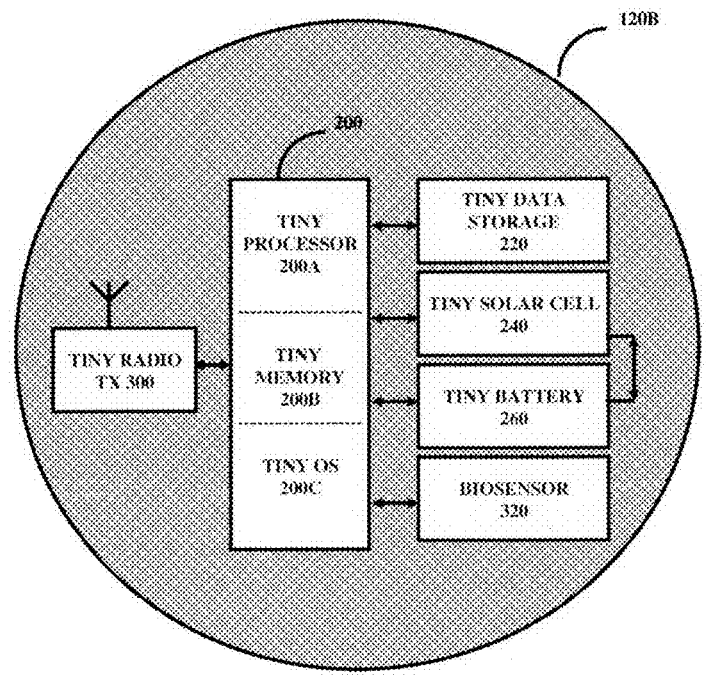
FIGS. 12A-12C illustrate three embodiments of a bioobject.

FIG. 12A illustrates the bioobject 120B. FIG. 12A is similar to FIG. 11, except the tiny sensor 280 is replaced by a tiny biosensor 320. The tiny biosensor 320 can be fabricated/constructed for a specific (e.g., glucose) purpose. The tiny solar cell 240 can be fabricated/constructed on top of the tiny battery 260. The extremely low power tiny wireless transmitter component 300 can be a tiny antenna.

Figure 12B:
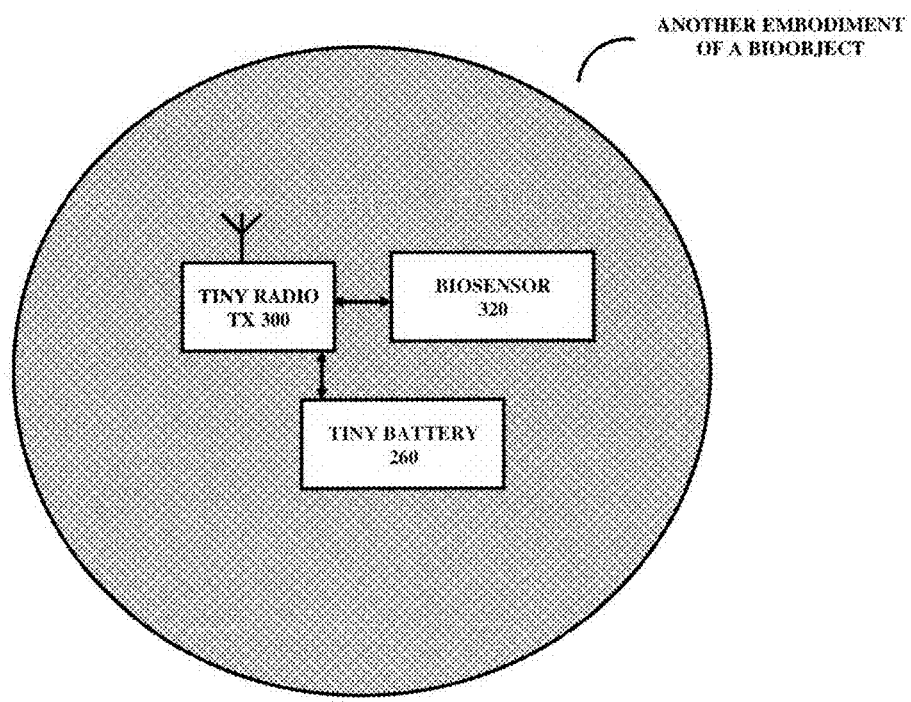

FIG. 12B illustrates another embodiment of the bioobject, which integrates the tiny battery 260, the extremely low power tiny wireless transmitter component 300 and the tiny biosensor 320. The tiny biosensor 320 can be fabricated/constructed for a specific sensing purpose. The tiny solar cell 240 can be fabricated/constructed on top of the tiny battery 260. The extremely low power tiny wireless transmitter component 300 can be a tiny antenna.

Figure 12C:
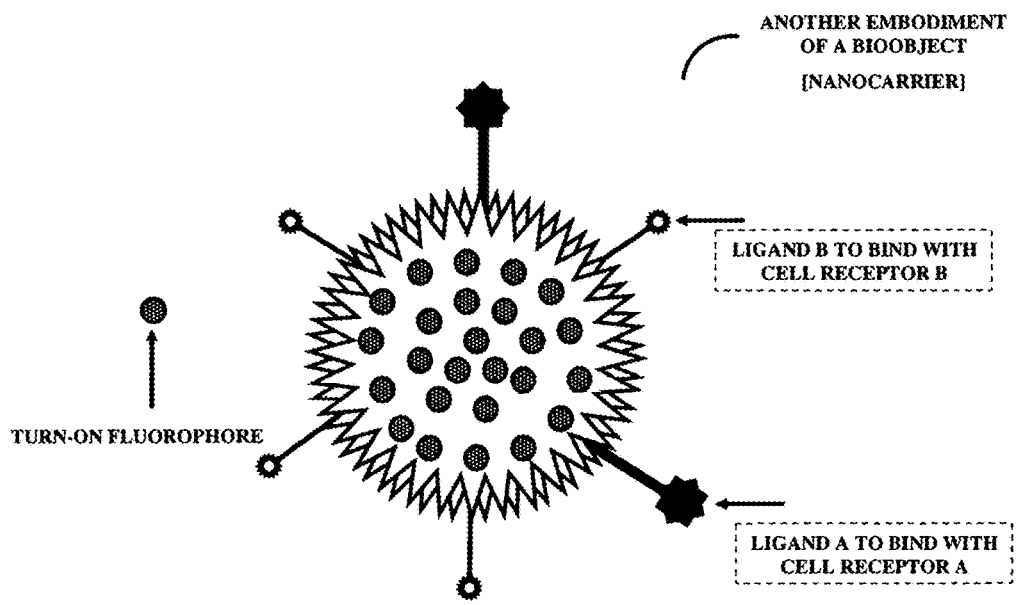

FIG. 12C illustrates another embodiment of the bioobject, which can be a biodegradable nanocarrier (encapsulating turn-on fluorophores) decorated with ligand A and ligand B to bind two specific receptors of a specific biological cell. Polymer groups shy away from water, which can cause them to aggregate and quench their fluorescence, but when polymer groups are far apart, they shine. Turn-on fluorophores are based on such polymers. Upon binding with the specific biological cell, the nanocarrier releases encapsulated turn-on fluorophores. When optically excited by a light source (e.g., light emitting diode/laser) and when turn-on fluorophores are within the specific biological cell, fluorescence can be detected by an ultrasensitive detector (e.g., indium gallium arsenide avalanche photodiode/electron-multiplying charge coupled device/charge coupled device/complementary metal oxide semiconductor). This embodiment can be suitable for in-vivo diagnostics, if the bioobject is in a biocompatible package. For in-vivo diagnostics, the light source can be coupled with an optical fiber. The end of the optical fiber can be fabricated/constructed with a nano optical antenna (FIG. 30A-30E) to enhance light intensity and/or a nano optical focusing device to focus below the Abbey's diffraction limit (FIG. 29D-29E).

Figure 13:
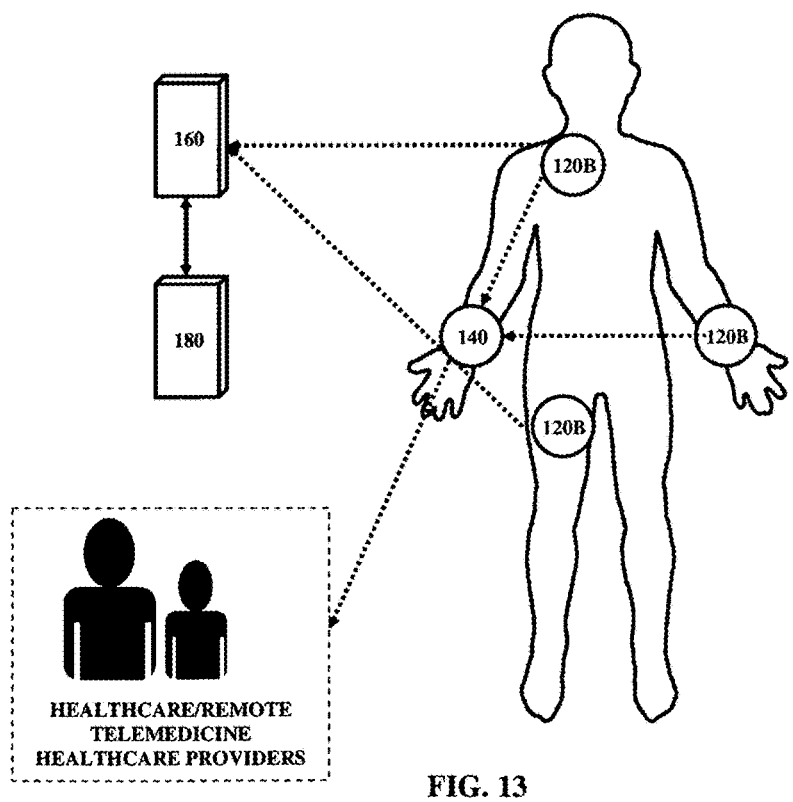
FIG. 13 illustrates an embodiment of interactions/communications among bioobject node(s), bioobject(s) with an intelligent portable internet appliance and an intelligent wearable augmented reality personal assistant device.

FIG. 13 illustrates interactions/communications among the bioobjects 120B, the bioobject node 140 with the intelligent portable internet appliance 160, intelligent wearable augmented reality personal assistant device 180 and healthcare/remote/telemedicine healthcare providers. The bioobject 120B can be implanted within a human body.

For example, the bioobject 120B can measure and transmit the user's heart rhythm periodically. If the user's heart rhythm is perceived to be abnormal (compared with the user's normal heart rhythm) then the intelligent portable internet appliance 160/intelligent wearable augmented reality personal assistant device 180 can communicate automatically for emergency 911 (indicating the user's location by a global/indoor positioning system) help without any human input.

FIG. 14A illustrates the intelligent portable internet appliance 160 and the key components of 160 (in block diagram) are listed below:

| Component | Description |
|---|---|
| 100 | Algorithm |
| 340 | Three-Dimensional/Holographic Display |
| 380 | Communication Radio* (WiMax/LTE) |
| 400A/B/C/D | Super System On Chip |
| 420 | Operating System Algorithm |
| 440 | Security & Authentication Algorithm |
| 460 | Time Shift & Place Shift Device |
| 480 | Surround Sound Microphone |
| 500 | Front Facing High Resolution Camera |
| 520 | Back Facing High Resolution Camera |
| 540 | High Resolution Camcorder |

-continued

| Component | Description |
|---|---|
| 560 | Microprojector |
| 580 | Proximity Radio* (Near Field Communication/Bluetooth LE) TxRx |
| 600 | Personal Area Networking Radio 1* (Bluetooth/Wi-Fi) TxRx |
| 620 | Personal Area Networking Radio 2* (Ultrawide Band/Millimeter-Wave) TxRx |
| 640 | Positioning System (Global Positioning System* & Indoor Positioning System) |
| 660 | Universal Communication Interface (UCI) |
| 680 | Electronic Personal Assistant |
| 700 | Electrical Powering Device (Solar Cell + Battery + Ultracapcitor) |
| 720 | Stylus |

[*With Radio Specific Antenna] [TxRx Means Transceiver]

Details of the electronic personal assistant and stylus to write on a display are described in U.S. Non-Provisional patent application Ser. No. 13/448,378 entitled "SYSTEM AND METHOD FOR INTELLIGENT SOCIAL COMMERCE", filed on Apr. 16, 2012 and the non-provisional patent application with its benefit patent applications are incorporated in its entirety herein with this application.

A universal communication interface can integrate animation, animated GIF, drawings, emotions, gestures (hand/eye), location data, text, voices, voice snippets and videos.

Solar cells can be fabricated/constructed on top of the battery, integrated with an ultracapacitor.

The intelligent portable internet appliance 160 is sensor aware and context aware, as it is wirelessly connected/sensor connected with objects 120As, object nodes 120s, bioobjects 120Bs and bioobject nodes 140s.

FIG. 14B illustrates another version of the intelligent portable internet appliance (denoted as 160A), which comprises the three-dimensional/holographic display 340, a stretchable display 360 (embedded with inkjet printed transparent processor(s) and memristors) and a communication radio 380. The stretchable display 360 can be split into two viewing windows, denoted as 360A and 360B. The two viewing windows can display different images.

FIG. 15A illustrates transition metal oxide (TMO) layers, very large-scale integration (VLSI) of photonic integrated circuits (PIC) layers and very large-scale integration of electronic integrated circuits (EIC) layers within a digital processor 400A.

FIG. 15B illustrates a top view of FIG. 15A.

FIG. 15C illustrates a completed wafer with (a) electronic integrated circuits, (b) photonic integrated circuits, utilizing III-V semiconductor epitaxial layers on silicon and (c) transition metal oxide devices.

Gradually tapered silicon waveguides (on silicon) connecting with polymer waveguides (on silicon) can enable large-scale integration of photonic integrated circuits and electronic integrated circuits. Various photonic components can be integrated utilizing an asymmetric twin-waveguide (ATG) structure.

Details of the large-scale integration of photonic integrated circuits and electronic integrated circuits are described in U.S. Non-Provisional patent application Ser. No. 13/448,378 entitled "SYSTEM AND METHOD FOR INTELLIGENT SOCIAL COMMERCE", filed on Apr. 16, 2012 and the non-provisional patent application with its benefit patent applications are incorporated in its entirety herein with this application.

FIG. 15D illustrates a top view of two-dimensional material (e.g., molybdenum disulphide/graphene)-transition metal oxide material (X) heterostructure based transistor devices.

FIG. 15E illustrates a cross-section view of FIG. 15D.

FIG. 15F illustrates a top view of two-dimensional material-phase transition material (Y) heterostructure based transistor devices. A phase change material can be utilized instead of a phase transition material.

FIG. 15G illustrates a cross-section view of FIG. 15F.

FIG. 16A illustrates 400A4, a two-dimensional integration of memristors. Memristors (e.g., based on transition metal oxide material/ferroelectric material/phase change material/phase transition/amorphous silicon material) are formed at the intersections of row metal electrodes and column metal electrodes.

Memristor is a non-linear resistive and switching device with an inherent memory similar to a synapse. Both are two-terminal devices whose conductance can be modulated by an external stimulus with the ability to store (memorize) new information. Memristor can bring data closer to a processor, without a lot of electrical power consumption, as a biological neural system does.

Details of the memristor are described in U.S. Non-Provisional patent application Ser. No. 13/448,378 entitled "SYSTEM AND METHOD FOR INTELLIGENT SOCIAL COMMERCE", filed on Apr. 16, 2012 and the non-provisional patent application with its benefit patent applications are incorporated in its entirety herein with this application.

FIG. 16B illustrates 400A5, a three-dimensional integration of memristors.

FIG. 16C illustrates 400A6, which is a three-dimensional integration of a memristor with various versions of a digital processor (based on 400A1/400A2/400A3).

FIG. 16D illustrates 400A7, which is a three-dimensional integration of a memristor and a digital memory with various versions of a digital processor (based on 400A1/400A2/400A3).

Furthermore, the digital processor can also be based on ferroelectric or carbon nanotube material. A carbon nanotube can be utilized as an electrode in 400A4/400A5/400A6/400A7 and as an interconnecting material in 400A5/400A6/400A7.

Details of the three-dimensional interconnecting material, as carbon nanotube are described in U.S. Non-Provisional Patent Application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and the non-provisional patent application with its benefit patent applications are incorporated in its entirety herein with this application.

FIG. 17A illustrates how a memristor would respond/switch with fixed amplitude serial input pulses.

FIG. 17B illustrates how a memristor would respond/switch with multiple weighted amplitude parallel input pulses.

FIG. 17C illustrates interactions of memristors with various nodes A, B, C, D, E and F. The node can be a processing node.

FIG. 18A illustrates a ferroelectric digital memory fabricated/constructed on a digital processor (based on 400A1/400A3/400A3) in a vertical stacking configuration. This configuration is denoted as 400A8.

FIG. 18B illustrates a digital memory (as illustrated in FIGS. 19A-19C) fabricated/constructed on a digital processor (based on 400A1/400A3/400A3) in a vertical stacking configuration. This configuration is denoted as 400A9.

FIG. 19A illustrates a nanoscaled vanadium oxide/phase change material based digital memory. The nanoscaled vanadium oxide/phase change material is sandwiched between a carbon nanotube bottom electrode (carbon nanotube is fabricated/constructed on silicon dioxide on silicon) and a top electrode. This digital memory embodiment is denoted as 400M1.

FIG. 19B illustrates nanoscaled vanadium oxide/phase change material based digital memory, wherein the bottom electrode and top electrode are platinum. This digital memory embodiment is denoted as 400M2.

FIG. 19C illustrates another nanoscaled vanadium oxide based digital (ferroelectric) memory, wherein the nanoscaled vanadium oxide is sandwiched between a thermal silicon dioxide ($SiO_2$) and atomic layer deposited (ALD) silicon dioxide. This digital memory embodiment is denoted as 400M3. Vanadium oxide can be vanadium dioxide ($VO_2$) or vanadium sesquioxide ($V2O3$) or other vanadium oxide composition.

FIGS. 20A-20F illustrate step by step electrical interconnections of 400A6/400A7/400A8/400A9, additional digital memories (e.g., DRAM), if needed for performance and digital storage. They are electrically connected by metalized via holes.

Figure 20D:
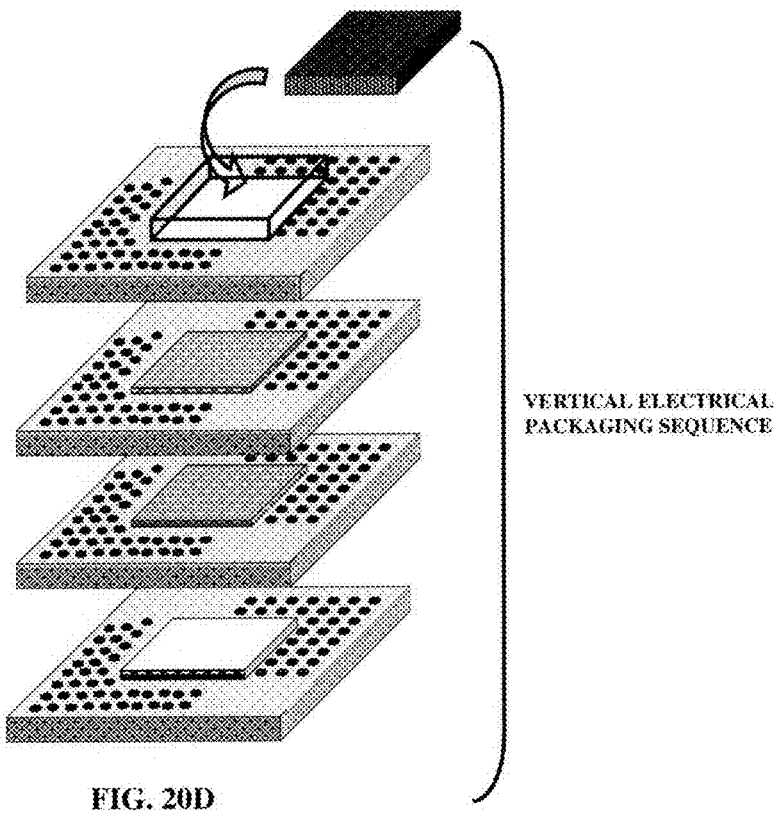
Figure 20E:
Figure 20F:
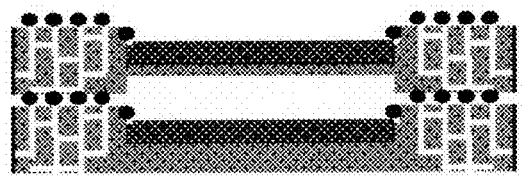
Figure 20G:
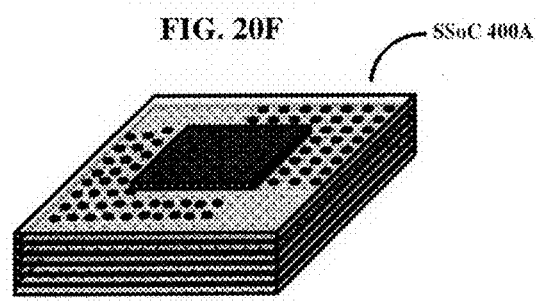

FIG. 20G illustrates a Super System on Chip 400A, utilizing electrical interconnections.

Figure 21A:
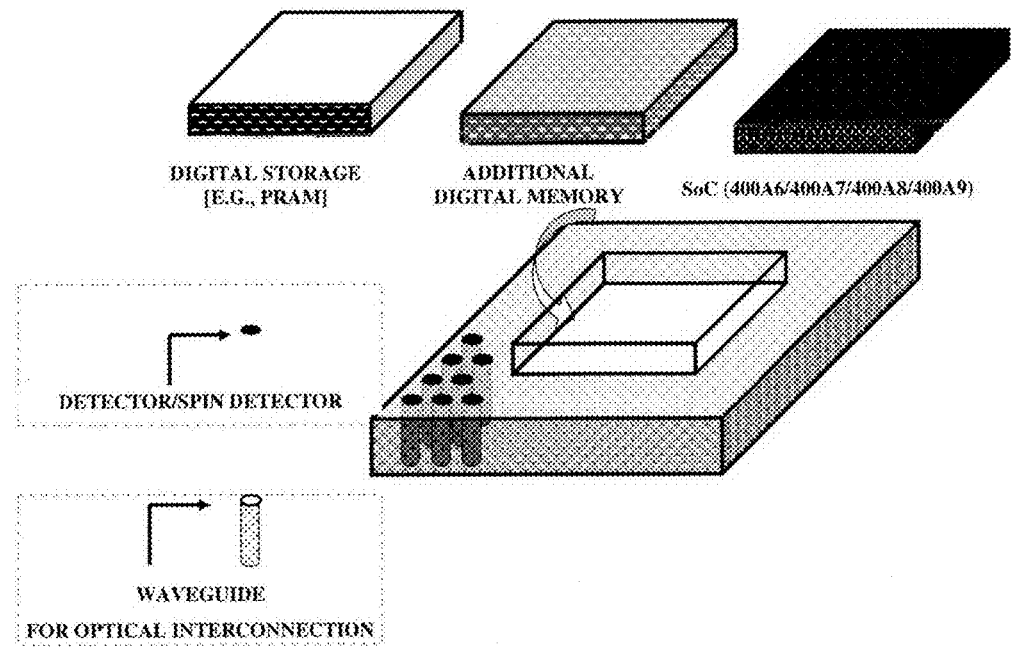
Figure 21B:
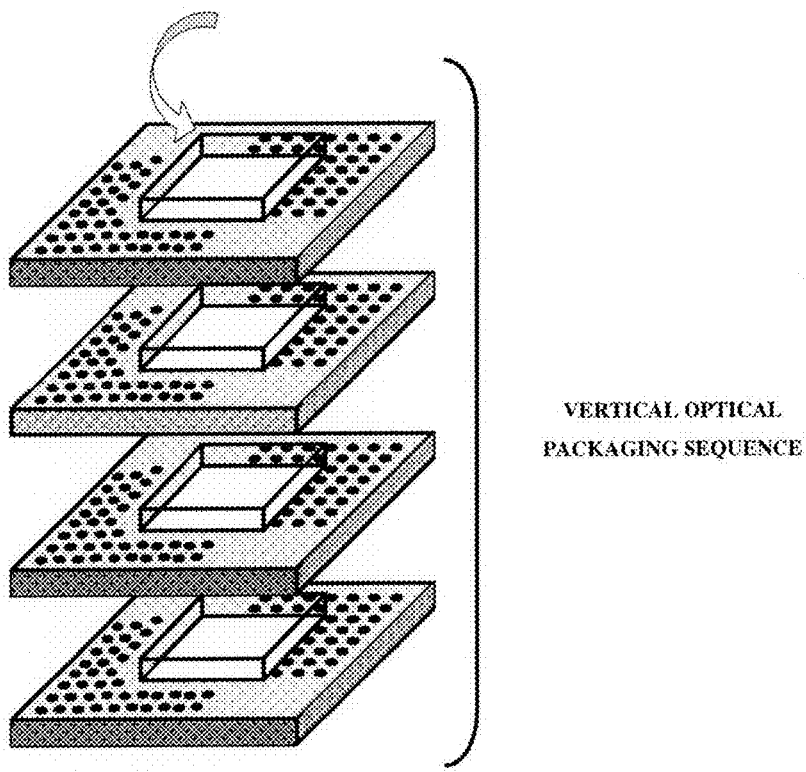
Figures 21C, 21D:
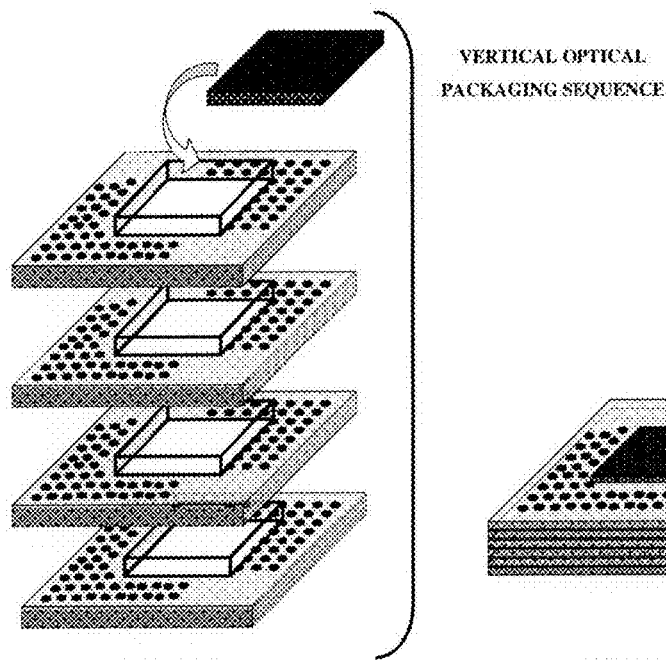

FIGS. 21A-21C illustrate step by step optical interconnections of 400A6/400A7/400A8/400A9, additional digital memories, if needed for performance and digital storage. They are optically connected by light sources, waveguides and detectors. The light source can be a modulated vertical cavity surface emitting laser (VCSEL)/modulated photonic crystal (PC) reflector vertical cavity surface emitting laser (PC-VCSEL)/directly modulated nanolaser/directly modulated light emitting diode/directly modulated spin laser. The detector can be a photodetector/spin detector.

FIG. 21D illustrates a Super System on Chip 400B, utilizing optical interconnections.

The Super System on Chip 400A/400B can enable the storage and processing of information simultaneously and it is capable of learning/relearning for self-intelligence, context-awareness and autonomous actions, remembering the patterns and movements.

FIG. 22A illustrates a cross-sectional view of a modulated vertical cavity surface emitting laser, which is monolithically integrated with an electro-optic modulator to enable 40 Gbits/s or higher bit rate optical signals.

Details of the vertical cavity surface emitting laser integrated with an electro-optic modulator are described in U.S. Non-Provisional patent application Ser. No. 13/448,378 entitled "SYSTEM AND METHOD FOR INTELLIGENT SOCIAL COMMERCE", filed on Apr. 16, 2012 and the non-provisional patent application with its benefit patent applications are incorporated in its entirety herein with this application.

FIG. 22B illustrates a cross-sectional view of a modulated photonic crystal (PC) reflector vertical cavity surface emitting laser, which is monolithically integrated with an electro-optic modulator to enable 40 Gbits/s or higher bit rate optical signals. Here, reflectors of a vertical cavity surface emitting lasers are substituted by two photonic crystal reflectors.

FIG. 23 illustrates a cross-sectional view of a directly modulated nanolaser, which is integrated with a nano optical antenna at the exit facet. Details of the nano optical antenna are described in FIGS. 30A-30D

FIG. 24 illustrates a directly modulated two-dimensional material (e.g., tungsten diselenide or molybdenum disulphide) based wavelength tunable light emitting diode, integrated with a plasmonic light guide (PLG). The plasmonic light guide can enable efficient light output from the light emitting diode. The plasmonic light guide is illustrated in FIG. 38.

FIGS. 25A-25B illustrate a spin controlled vertical cavity surface emitting laser, wherein the vertical cavity comprises photonic crystal distributed Bragg reflectors (PC-DBR).

Figure 26A:
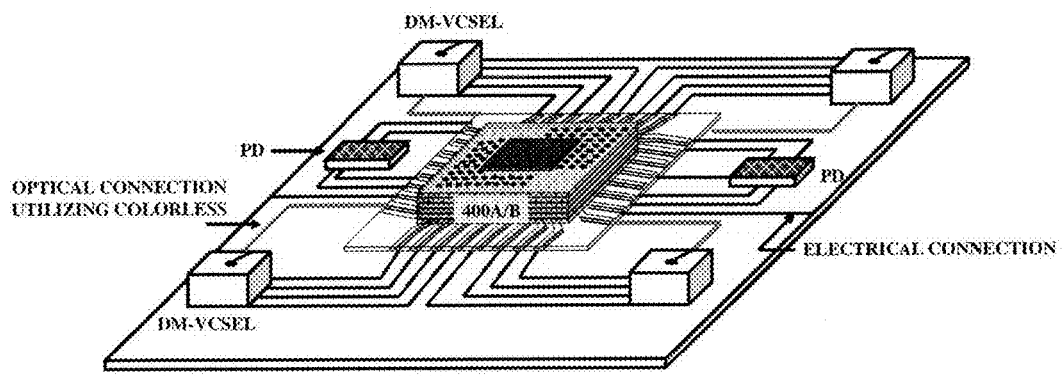

FIG. 26A illustrates wavelength non-specific (colorless) optical connections of 400A/400B, utilizing directly modulated lasers (e.g., directly modulated vertical cavity surface emitting lasers) and photodiodes.

Figure 26B:
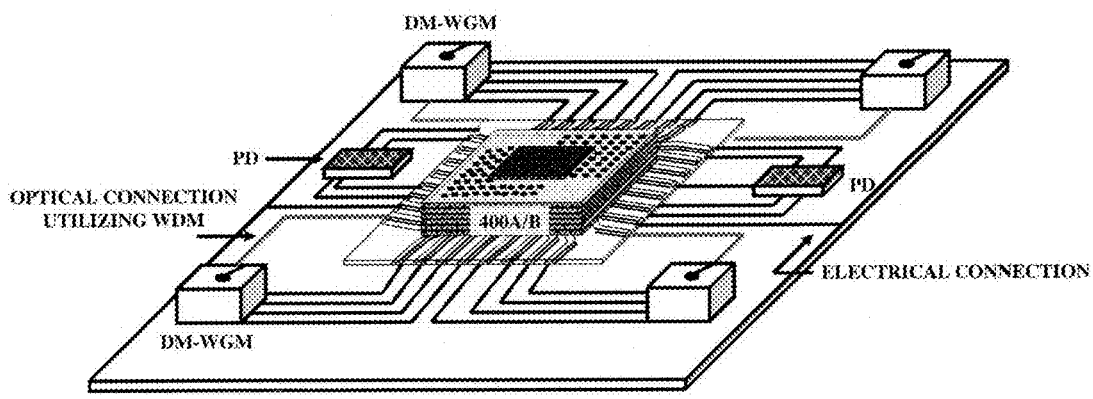

FIG. 26B illustrates a wave division multiplexed (WDM) optical connection of 400A/400B, utilizing directly modulated lasers (e.g., directly modulated wavelength specific whispering gallery mode lasers) and photodiodes.

Figure 26C:
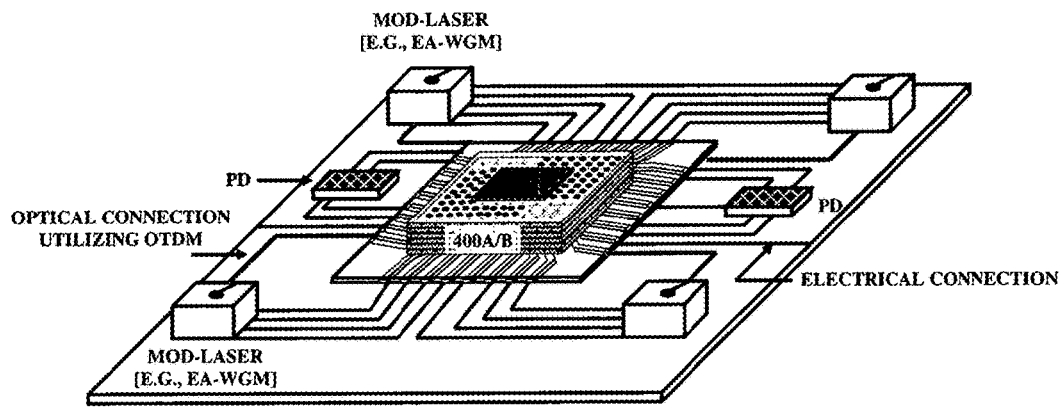

FIG. 26C illustrates an optical time division multiplexed optical connection (OTDM) of 400A/400B, utilizing modulated lasers (e.g., electro-absorption modulated whispering gallery mode lasers) and photodiodes.

Figure 26D:
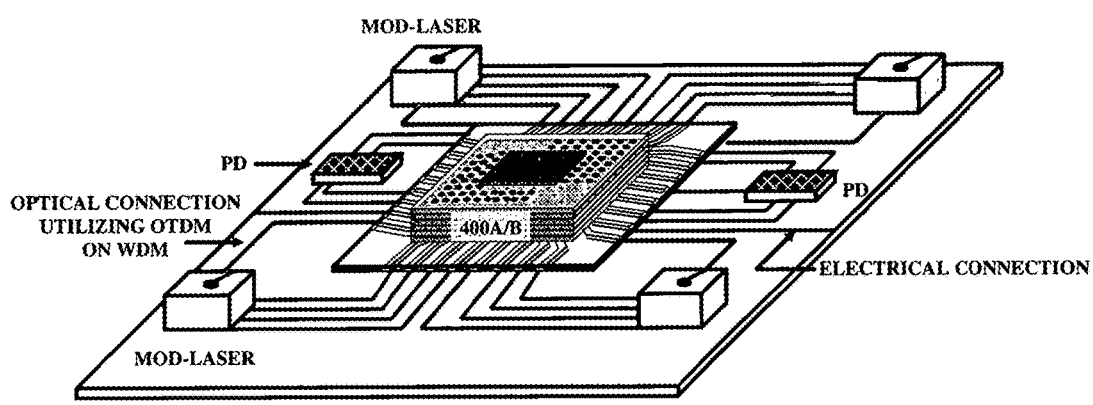

FIG. 26D illustrates an optical time division multiplexed optical connection on wave division multiplexing of 400A/400B, utilizing lasers (e.g., electro-absorption modulated wavelength specific whispering gallery mode lasers) and photodiodes.

FIG. 27A illustrates optical interconnections (in planar configuration) of multiple 400As/400Bs on an opto-electronic circuit board, wherein an optical switch (with nanoseconds switching time) and/or all-optical random-access memory (O-RAM) can be utilized.

An all-optical random-access memory utilizes optical cavities in an indium-gallium arsenide strip buried in gallium arsenide that represent a 1 or 0 by either passing or blocking light. It acts as an optical memory for about a microsecond because the indium-gallium arsenide strip changes its refractive index when exposed to a laser. The optical signal that all-optical random-access memory is trying to remember, will be blocked or passed, depending on the state of the strip. A second pulse of laser on a control section of the indium-gallium arsenide strip reverses its state.

FIG. 27B illustrates that in case of a very sharp (e.g., ~90° angle) optical waveguide, photonic crystals can guide optical signals around the sharp bend from one optical waveguide to another optical waveguide.

FIG. 28A illustrates optical interconnections (in vertical configuration) for Super System on Chips 400A/400B, enabled by ultralow threshold lasers, high-bit rate modulators, two-dimensional photonic crystal wavelength multiplexers, optical switches (with nanoseconds switching time), two-dimensional photonic crystal wavelength demultiplexers and waveguide photodiodes.

Electronics scale in capacities with space division multiplexing, by adding parallel wires to a bus, while optical signal scale in capacities with wavelength division multiplexing, by adding parallel wavelengths to a single optical waveguide. Therefore, an array of microring resonator modulators (as translators) can be utilized to convert space division multiplexed electronic signals to wavelength division multiplexed optical signals.

Electrical signals of the Super System on Chip 400A/400B are then transferred to an array of ultralow threshold multi-wavelength lasers (e.g., a heater on a microscaled whispering gallery mode laser or a heater on a nanoscaled active area (FIGS. 28C-28D) can be an ultralow threshold multi-wavelength laser). High-bit rate optical signals from modulators on multiple wavelengths are multiplexed by a two-dimensional photonic crystal wavelength combiner/multiplexer, then switched by an N×M optical switch (FIGS. 28E-28F). Then the multiplexed optical signal of the N×M optical switch is presented to the photonic crystal wavelength demultiplexer, then demultiplexed (separated) high-bit rate optical signals to waveguide photodiodes. The outputs of the waveguide photodiodes are electrically connected through the metallized via holes to another Super System on Chip 400A/400B.

FIG. 28B is similar to FIG. 28A, except the N×M optical switch has a first all-optical random-access memory at each input and second all-optical random-access memory at each output of the N×M optical switch.

The high bit-rate modulator can be an electro-absorption or Mach-Zehnder (MZ) type modulator. Additionally, the high-bit rate modulator can be based on barium titanate material. The photodiodes can be based on photonic crystals. To reduce size, multi-mode interference Mach-Zehnder (MMI-MZ) wavelength multiplexers/demultiplexers can be utilized.

Optical components can be adhesively bonded onto silicon-on-insulator (SOI) substrate (with polymer waveguides) by DVS-bis-benzocyclybutene. Then the above silicon-on-insulator substrate can be flip-chip bonded onto an array of solder bumps forming connections between the optical components and an electronic circuit.

FIG. 28C illustrates a wavelength specific ultralow threshold laser, utilizing a heater directly on a buried heterostructured (BH) nanoscaled quantum well indium phosphide (InP) active region (about 3 microns×0.2 microns×0.2 microns in area and 300 nm in thickness) with its lateral P-i-N junction configuration. The front side can be coated with 2 microns thick spin-on-glass (SOG). The indium phosphide substrate can be removed and oxygen plasma can be utilized to bond and transfer the nanoscaled quantum well indium phosphide active region with its lateral P-i-N junction to a silicon substrate. After bonding to the silicon substrate, an air-bridge structure, current blocking trenches (of width 215 nanometers), an array of photonic crystals (air holes), n-metal contact and p-metal contact can be fabricated/constructed. The air bridge enables isolation for the nanoscaled quantum well indium phosphide active region. The carrier confinement of the nanoscaled active region is due to its buried heterostructure. The optical confinement of the nanoscaled active region is due to the array of photonic crystals (air holes). Light from the quantum well indium phosphide active region can be propagated horizontally, utilizing a grating coupler, then to a tapered silicon waveguide.

FIG. 28D illustrates the nanoscaled active region. Its wavelength can be tuned by changing current to the nanoscaled active region.

FIG. 28E illustrates a directional coupler vanadium dioxide thin-film (e.g., about 25 nm in thickness, 275 nm in width and 4,500 nm in length) based optical switch on a substrate (e.g, a silicon on insulator). To reduce filamentation related hot spots in vanadium dioxide thin-film, the length of vanadium dioxide thin-film can be segmented into a smaller (e.g., 200 nm) segment. When electrode 1 on vanadium dioxide thin-film is activated, the optical signal at the input port 1 can exit from the output port 2 rapidly. Similarly, when electrode 2 on vanadium dioxide thin-film is activated, the optical signal at the input port 2 can exit from the output port 1 rapidly.

A method of fabrication/construction of the directional coupler vanadium dioxide thin-film optical switch is summarized: RF magnetron deposition of vanadium dioxide thin-film on the silicon on insulator substrate, lithographic pattern of the directional coupler, reactive ion etching of the vanadium dioxide thin-film in CF4 and Ar gases, reactive ion etching of silicon ridge of about 220 nanometers in depth and lift off of Cr/Au metallization on vanadium dioxide thin-film without any misalignment.

A symmetrical on-off switching time can be obtained by planarization (e.g., utilizing aluminum oxide/hafnium silicate/zirconium silicate/hafnium dioxide/zirconium dioxide thin-film) of the area of the electrode 1 and electrode 2, to reduce resistance-capacitive electrical effects of metallization.

FIG. 28F illustrates tapering of the input port/output signal ports within a polymer core for efficient optical waveguide to optical fiber coupling.

The slow thermal recovery time can be reduced, if the active area of vanadium dioxide thin-film is nanoscaled and/or current through the material is limited and/or the heat dissipation is rapid.

FIG. 28G illustrates a precise electron pump. The precise electron pump utilizes a silicon quantum dot electrostatic trap to enable precise well-defined electrical current through a circuit. The shape of the quantum dot can be controlled by voltages applied to nearby electrodes. The quantum dot can be filled with electrons and then raised in energy by a process of back-tunneling. All but one of the electrons falling out of the quantum dot goes back into the source lead. Just one electron remains trapped in the quantum dot, which is then ejected into the output lead by tilting the trap. When this is repeated rapidly, it gives a precious current determined solely by the repetition rate and charge of the electron. Such an electron pump can be integrated with the directional coupler vanadium dioxide thin-film optical switch.

By fabricating/constructing a heat dissipation layer utilizing an ultra thin-film of synthetic diamond/boron arsenide/single walled carbon nanotube/graphene onto electrode 1 and electrode 2 (FIG. 28A) and then flip-chip mounting utilizing a nanoscaled heat spreader onto a highly thermally conducting substrate (e.g., diamond), the slow thermal recovery time can be reduced.

Figure 28H:
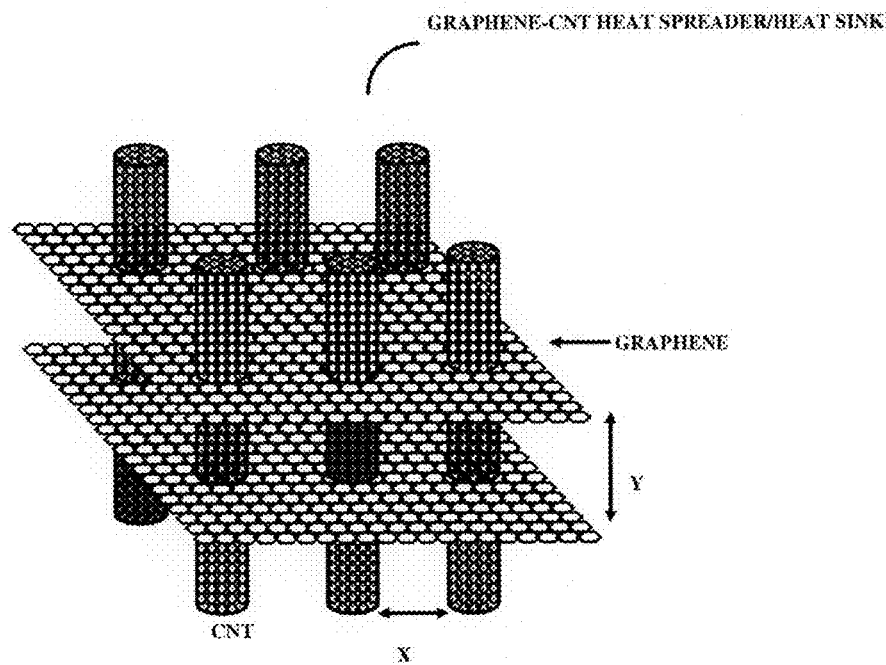

FIG. 28H illustrates a nanoscaled heat spreader, which is a three-dimensional configuration of carbon nanotube and graphene for rapid heat dissipation, wherein vertical heat conduction and/or horizontal heat conduction can be varied by changing the X dimension and Y dimension respectively.

Furthermore, a microscaled ion cloud cooling device/superlattice thermoelectric cooler can be utilized in conjunction with or without the heat dissipation layer and/or nanoscaled heat spreader.

Details of the microscaled ion cloud cooling device and superlattice thermoelectric cooler are described in U.S. Non-Provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 and the non-provisional patent application with its benefit patent applications are incorporated in its entirety herein with this application.

Faster optical switching time can be obtained by scaling/segmenting vanadium dioxide thin-film to a smaller area and/or optical activation rather than electrical activation.

Other chemical compositions of vanadium oxide (e.g., vanadium(III) oxide ($V_2O_3$)) and/or various configurations/combinations of graphene, vanadium oxide, graphene quantum dot and vanadium oxide quantum dots can be utilized to enable a higher performance optical switch.

The process of fabricating/constructing a graphene layer consists of dispersing a graphene oxide (GO) solution in a micropipette, depositing the solution locally and then reducing the graphene oxide to graphene by thermal or chemical treatment.

Furthermore, the optical switch can be integrated with a $log_2 N$ demultiplexer, which generally consists of rectangular shaped periodic frequency filters in series, wherein the rectangular shaped periodic frequency filters can be formed in a one-dimensional photonic crystal on a ridge waveguide.

FIG. 29A illustrates an ultrahigh density storage device, utilizing a phase transition/phase change material on a rotating nano positioning stage, wherein the phase transition/phase change material is excited by an optical filament with a device (FIG. 29D/29E) to focus below the Abbey's diffraction limit.

Figure 29B:
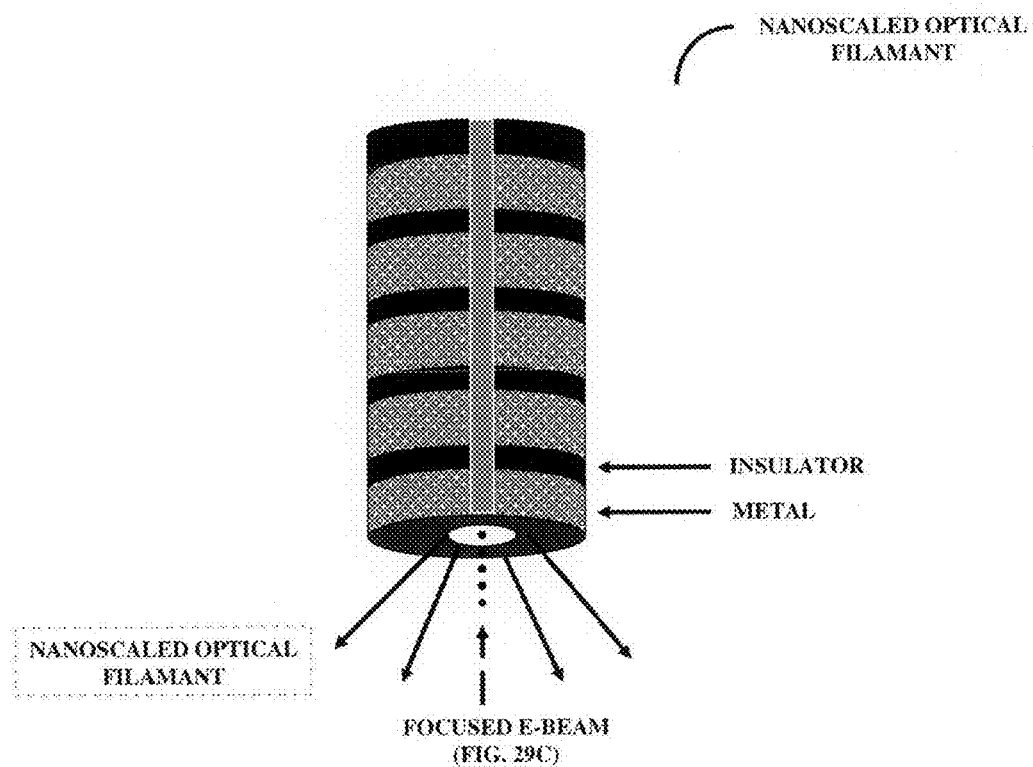
Figure 30A:
Figure 30B:
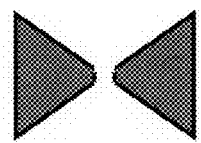
Figure 30C:
Figure 30D:
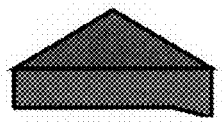
Figure 30E:

FIG. 29B illustrates a nanoscaled optical filament induced on an electronic beam in a metal-insulator configuration.

FIG. 29C illustrates an electron beam created from a focused electron beam emission tip.

FIG. 29D illustrates a tapered waveguide to focus the optical filament below the Abbey's diffraction limit. The waveguide comprises an ultrathin (about 100 nanometers) layer of silicon dioxide sandwiched between two ultrathin (about 30 nanometers) layers of gold. The waveguide can be tapered adiabatically (over 150 nanometers) in three dimensions to a singular point.

FIG. 29E illustrates a pattern of nanoscaled holes in ultrathin (100 nanometers) metal layer (supported by a transparent substrate) to focus the optical filament below the Abbey's diffraction limit. The pattern comprises about 20,000 nanoscaled holes, each hole having about 150 nanometers in diameter.

Alternatively, instead of scanning with a single (cw/pulsed) laser, two lasers can be utilized simultaneously. The first is the typical laser using an appropriate wavelength to excite a material. The second laser is the key component, this is focused so that it produces a donut of light overlapping the focal point of the first laser. This configuration can enable the laser to focus below the Abbey's diffraction limit for ultrahigh density storage Quantum dots (QDs) are tiny light sources with nanoscaled dimensions. They rely on internal electronic transitions which emit a stream of photons, with the color defined by the material, shape and size.

Graphene quantum dots can fluoresce brighter than conventional quantum dots. Graphene quantum dots or quantum dots of a two-dimensional material can be utilized instead of conventional quantum dots. Ultrasound can be utilized to chop up a graphene sheet into atomic scale dots. Then, potassium hydroxide can be utilized to enhance the surface area of these atomic scale dots.

FIGS. 30A-30E illustrate five different shapes of the metal (e.g., aluminum/gold/silver) nano optical antenna. The nano optical antenna can result in enhanced absorption and radiative emission rates, thus leading to higher intrinsic quantum efficiency of a quantum dot. The maximum dimension of the nano optical antenna can be less than 200 nanometers. The gap in FIGS. 30B, 30C and 30E can be less than 50 nanometers. The nano optical antenna can be enclosed within a nanoscaled box. The maximum dimension of the nanoscaled box can be less than 400 nanometers. The shape of the nanoscaled box can be arbitrary and/or closed and/or open.

Figure 31A:
Figure 31B:
Figure 31C:
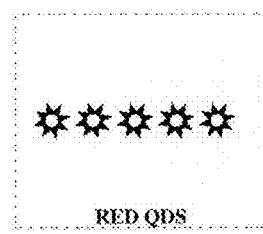

FIGS. 31A-31C illustrate blue quantum dots, green quantum dots and red quantum dots respectively.

Figure 31D:
Figure 31E:
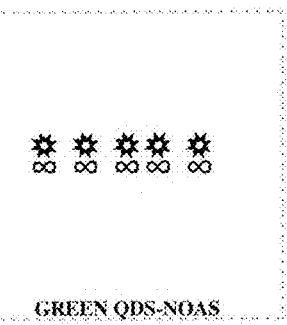
Figure 31F:
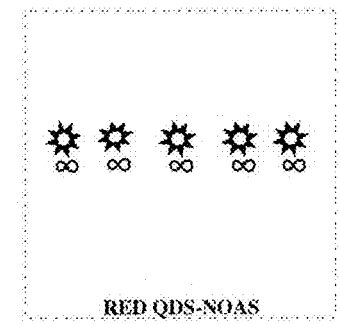

FIGS. 31D-31F illustrate blue quantum dots-nano optical antennas, green quantum dots-nano optical antennas and red quantum dots-nano optical antennas respectively.

Figure 31G:
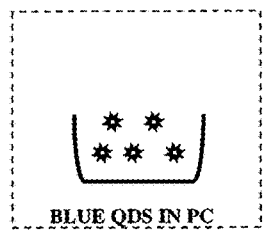
Figure 31H:
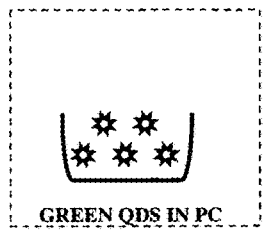
Figure 31I:
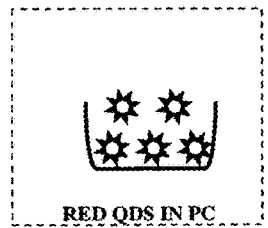

FIGS. 31G-31I illustrate blue quantum dots in a photonic crystal, green quantum dots in a photonic crystal and red quantum dots in a photonic crystal respectively. Photonic crystals can be one-dimensional/two-dimensional/three-dimensional.

An original silicon wafer master of a desired photonic crystal design can be fabricated/constructed by laser interference lithography and reactive ion etching. From the original silicon wafer master, many working stamps of a tri-layer material (thin polydimethylsiloxane with Young's modulus of 80 MPa+soft polydimethylsiloxane+thin glass substrate) can be created utilizing ultraviolet enhanced substrate conformal imprint lithography and inorganic silica sol-gel imprint photoresist. The working stamps of the tri-layer material with silica sol-gel is a suitable transfer mask for printing the desired photonic crystal onto a transparent substrate (to an incident light).

Inkjet printing can be utilized to print quantum dots (in a solution) onto the desired photonic crystal.

Similarly, a working stamp of the tri-layer material with silica sol-gel is a suitable transfer mask for printing the desired photonic crystal with the embedded nano optical antenna onto a substrate transparent (to an incident light).

Inkjet printing can be utilized to print quantum dots (from a solution) onto the desired photonic crystal with the embedded nano optical antenna.

Figure 31J:
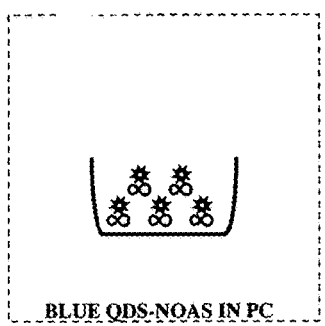
Figure 31K:
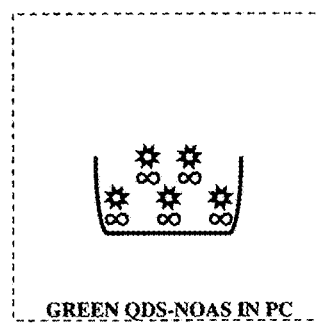
Figure 31L:

FIGS. 31J-31L illustrate blue quantum dots-nano optical antennas in a photonic crystal, green quantum dots-nano optical antennas in a photonic crystal and red quantum dots-nano optical antennas in a photonic crystal respectively.

FIGS. 32A-32G illustrate a light valve based on thin-film transistor enhanced liquid crystal light (TFT-LCD), microelectromechanical systems (MEMS), nanoelectromechanical systems (NEMS), piezo-microelectromechanical systems, piezo-nanoelectromechanical systems phase change material (e.g., germanium-antimony-tellurium $Ge_2Sb_2Ta_5$) and phase transition material (e.g., vanadium dioxide) respectively. The light valve can either allow or block light to propagate.

Details of the microelectromechanical systems light valve are described in U.S. Non-Provisional patent application Ser. No. 13/448,378 entitled "SYSTEM AND METHOD FOR INTELLIGENT SOCIAL COMMERCE", filed on Apr. 16, 2012 and the non-provisional patent application with its benefit patent applications are incorporated in its entirety herein with this application.

Phase change/phase transition materials switch rapidly between two distinct phases/states with the application of an electric field. Thus, electrically switchable light valves based on phase change/phase transition material (sandwiched between two transparent electrodes) can be faster. The transparent electrode can be indium tin oxide (ITO)/fluorine doped tin oxide (FTO)/graphene.

FIG. 33 illustrates a plasmonic transmission optical color filter based on gratings fabricated/constructed on a metal-insulator-metal structure by ion milling. Typically, the metal (e.g., aluminum) is about 20 nanometers in thickness and the insulator (e.g., zirconium oxide) is about 100 nanometers in thickness. By changing the grating pitch, duty cycle and depth, a blue/green/red specific transmission optical color filter can be realized.

However, a multi-layer thin-film transmission optical color filter can be utilized instead of a plasmonic transmission optical color filter.

FIGS. 34A-34C illustrate blue quantum dots in an electrically switchable liquid crystal gel, green quantum dots in an electrically switchable liquid crystal gel and red quantum dots in an electrically switchable liquid crystal gel respectively. The electrically switchable liquid crystal gel can lead to fluorescence emission of higher intensity, when the electric field is off and vice-a-versa.

The light emitting diode backlighting is usually composed of light emitting diodes, coated with a phosphor to give off a white light. In FIGS. 35A-35F, the backlighting is reflected by a substrate coated with high reflecting (HR) thin-film coatings.

FIG. 35A illustrates one pixel (with a blue subpixel, a green subpixel and a red subpixel), enabled by light emitting diode backlighting, light valves, blue quantum dots, green quantum dots and red quantum dots.

Figure 35B:
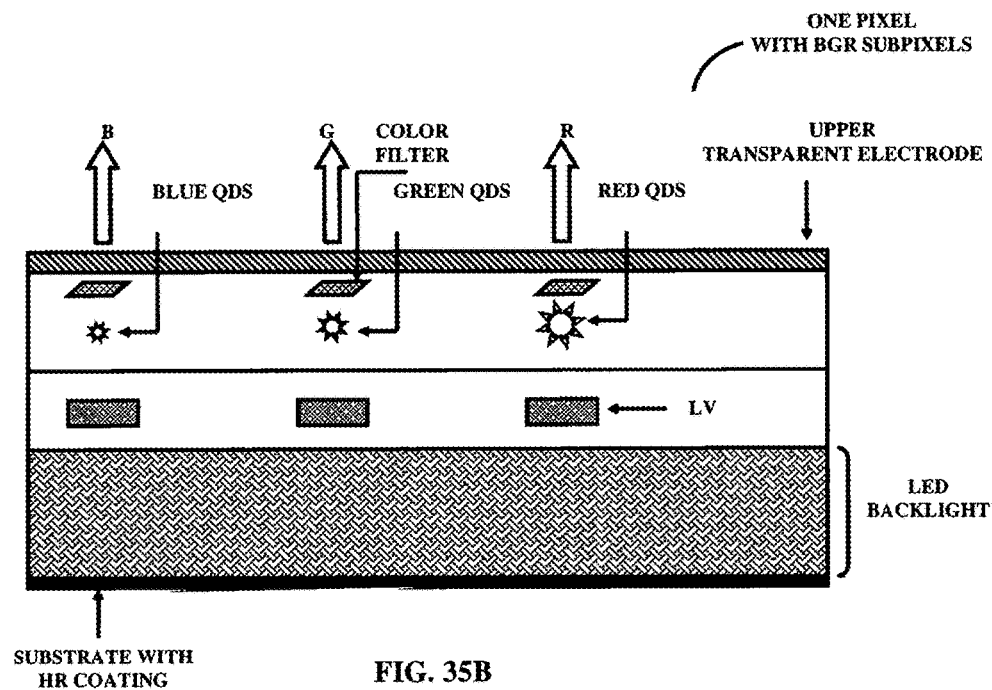

FIG. 35B illustrates one pixel (with a blue subpixel, a green subpixel and a red subpixel), enabled by light emitting diode backlighting, light valves, optical color filters and blue quantum dots, green quantum dots and red quantum dots.

Figure 35C:
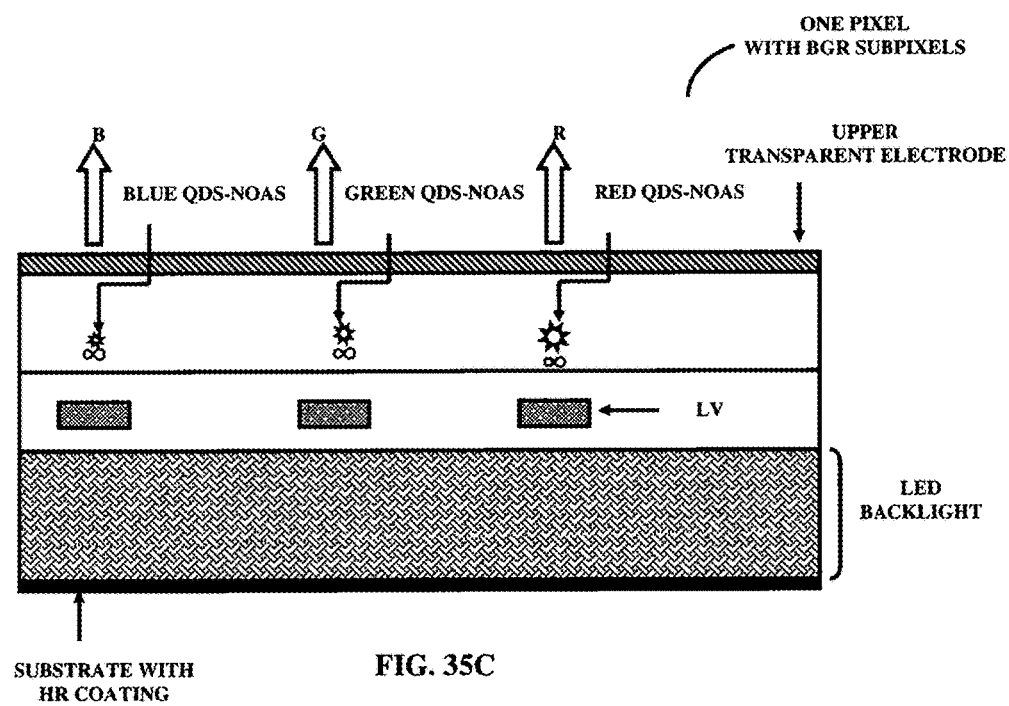

FIG. 35C illustrates one pixel (with a blue subpixel, a green subpixel and a red subpixel), enabled by light emitting diode backlighting, light valves, blue quantum dots-nano optical antennas, green quantum dots-nano optical antennas and red quantum dots-nano optical antennas. Each blue/green/red quantum dot is placed on/near the nano optical antenna in order to enable plasmonic coupling.

Figure 35D:
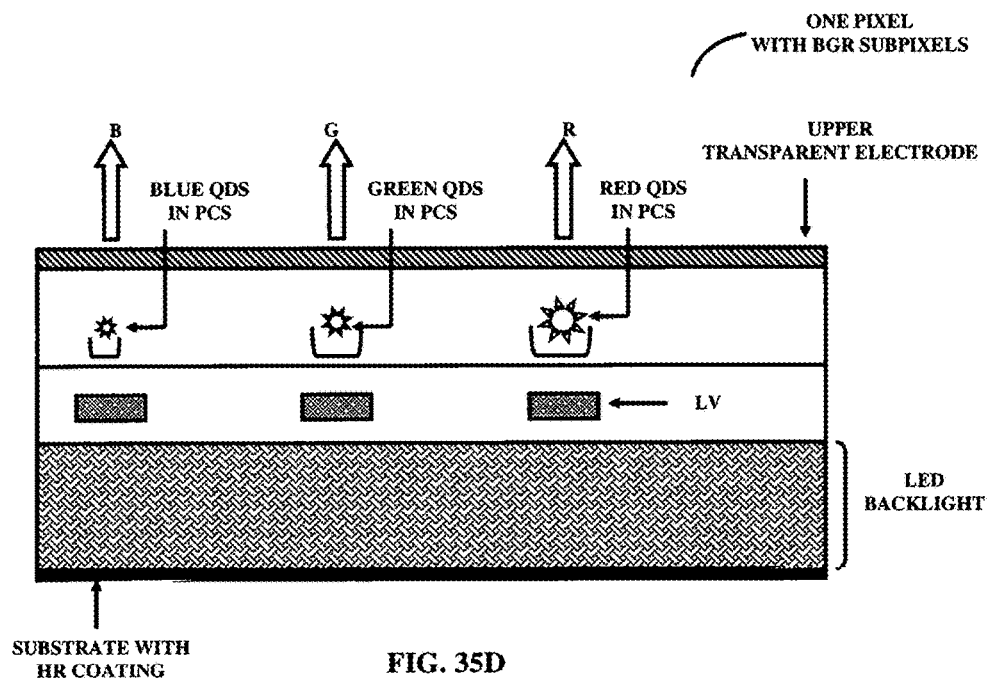

FIG. 35D illustrates one pixel (with a blue subpixel, a green subpixel and a red subpixel), enabled by light emitting diode backlighting, light valves, blue quantum dots in photonic crystals, green quantum dots in photonic crystals and red quantum dots in photonic crystals.

Figure 35E:
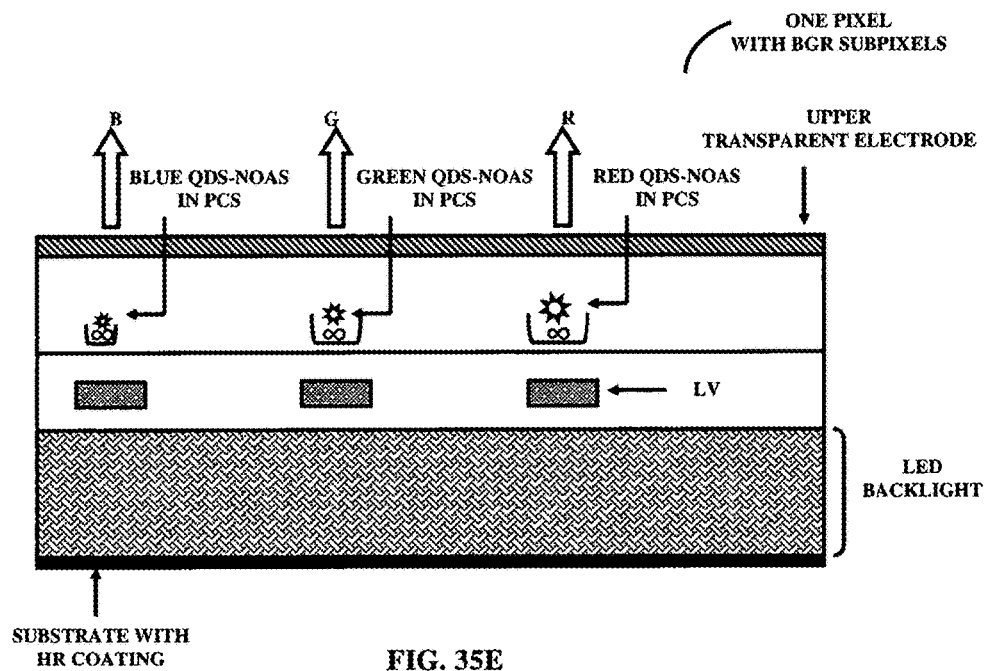

FIG. 35E illustrates one pixel (with a blue subpixel, a green subpixel and a red subpixel), enabled by light emitting diode backlighting, light valves, blue quantum dots-nano optical antennas in photonic crystals, green quantum dots-nano optical antennas in photonic crystals and red quantum dots-nano optical antennas in photonic crystals.

Figure 35F:
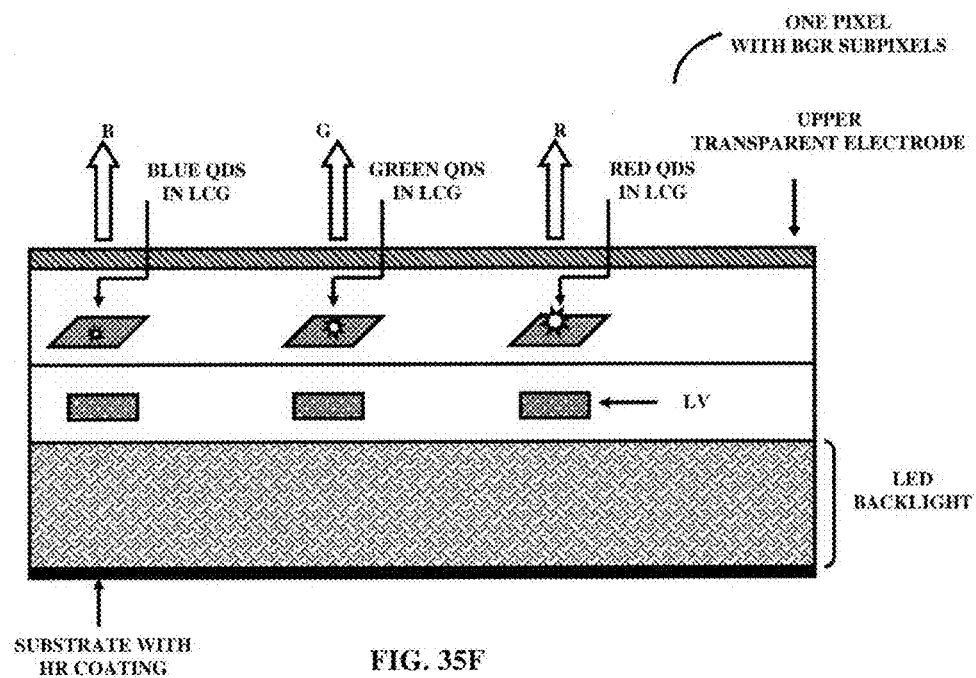

FIG. 35F illustrates one pixel (with a blue subpixel, a green subpixel and a red subpixel), enabled by light emitting diode backlighting, light valves, blue quantum dots in the electrically switchable liquid crystal gel, green quantum dots in the electrically switchable liquid crystal gel and red quantum dots in the electrically switchable liquid crystal gel.

Details of the quantum dots (nanocrystals) and light emitting diode backlighting enabled display are described in U.S. Non-Provisional patent application Ser. No. 13/448,378 entitled "SYSTEM AND METHOD FOR INTELLIGENT SOCIAL COMMERCE", filed on Apr. 16, 2012 and the non-provisional patent application with its benefit patent applications are incorporated in its entirety herein with this application.

Figure 36A:
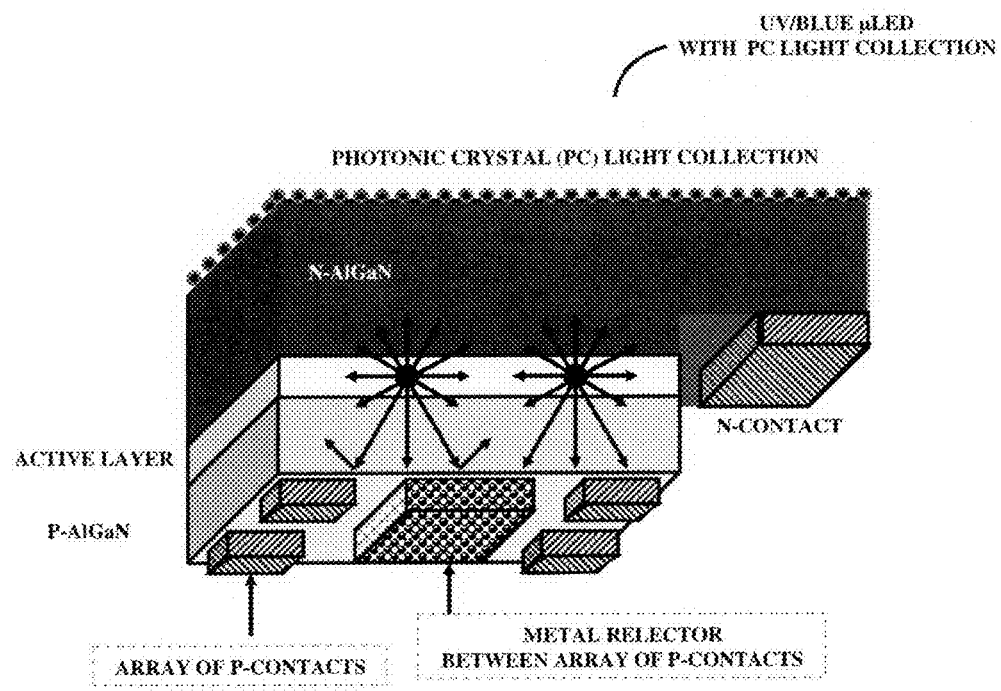

FIG. 36A illustrates a structure for an ultraviolet/blue microlight emitting diode, integrated with photonic crystals light collection optics. The structure has a typical PiN material structure and has an array of p-metal contacts, but the areas between the array of p-metal contacts comprise a metal (e.g., silver) reflector.

Figure 36B:
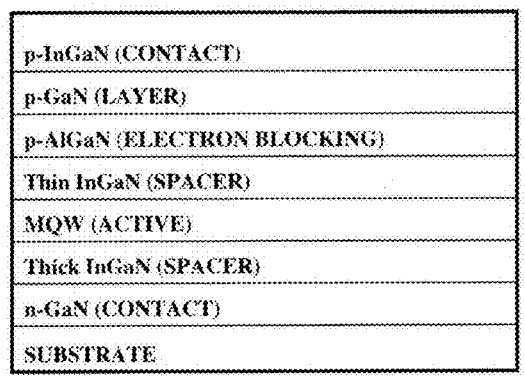
Figure 36C:
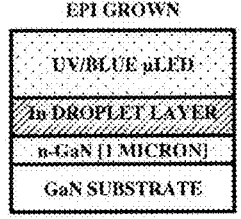
Figure 36D:
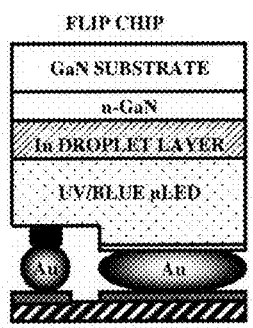
Figure 36E:
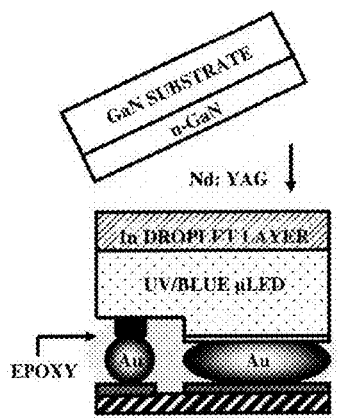
Figure 36F:
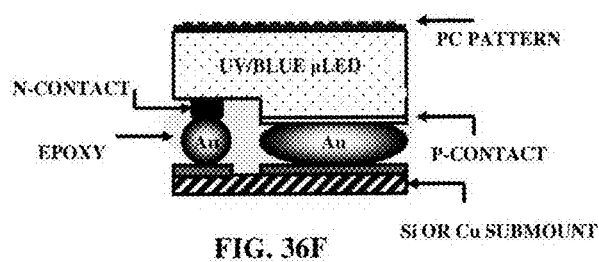

FIG. 36B illustrates typical layer material compositions of an ultraviolet/blue microlight emitting diode.

FIGS. 36C-36F illustrate sequential fabrication (utilizing a substrate lift-off process) for an ultraviolet/blue microlight emitting diode, integrated with the photonic crystals based light collection optics.

Figure 36G:
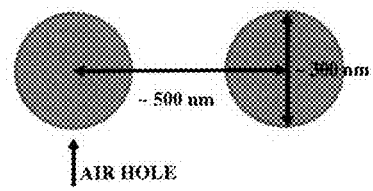

FIG. 36G illustrates typical dimensions of the photonic crystals based light collection optics, where the air hole diameter is about 300 nanometers and distance between the air holes is about 500 nanometers.

Figure 37A:
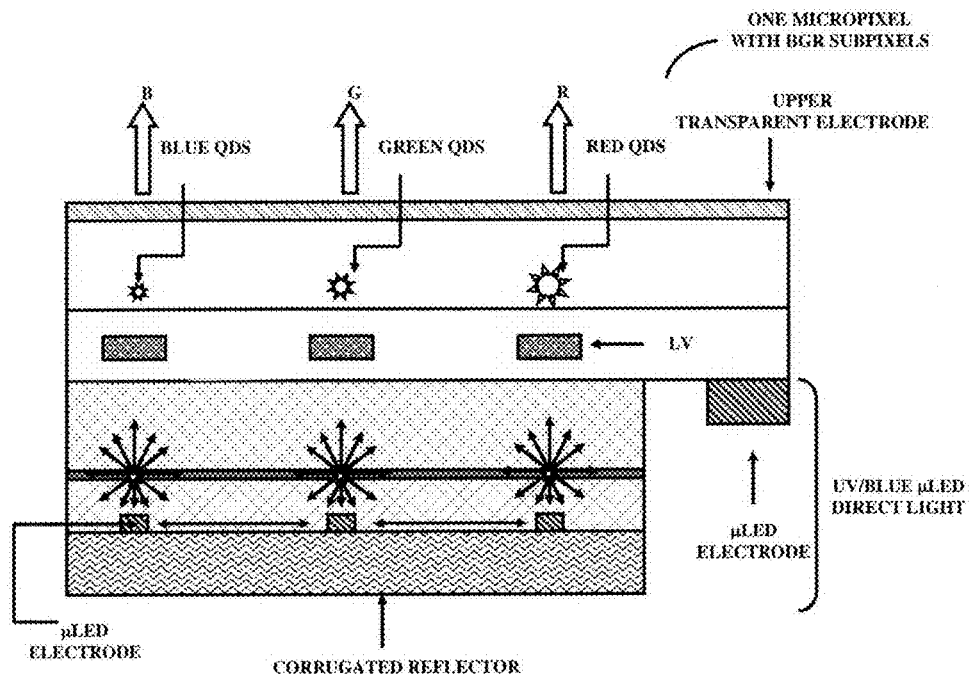

FIG. 37A illustrates one micropixel (with a blue submicropixel, a green submicropixel and a red submicropixel), enabled by ultraviolet/blue microlight emitting diodes, light valves, blue quantum dots, green quantum dots and red quantum dots.

Figure 37B:
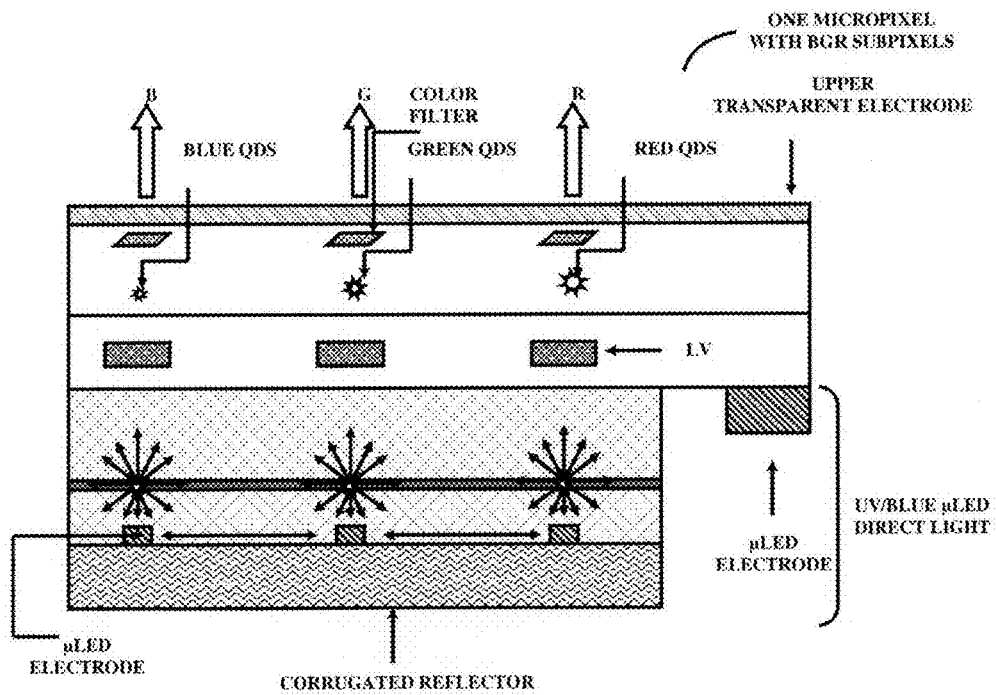

FIG. 37B illustrates one micropixel (with a blue submicropixel, a green submicropixel and a red submicropixel), enabled by ultraviolet/blue microlight emitting diodes, light valves, optical color filters, blue quantum dots, green quantum dots and red quantum dots.

Figure 37C:
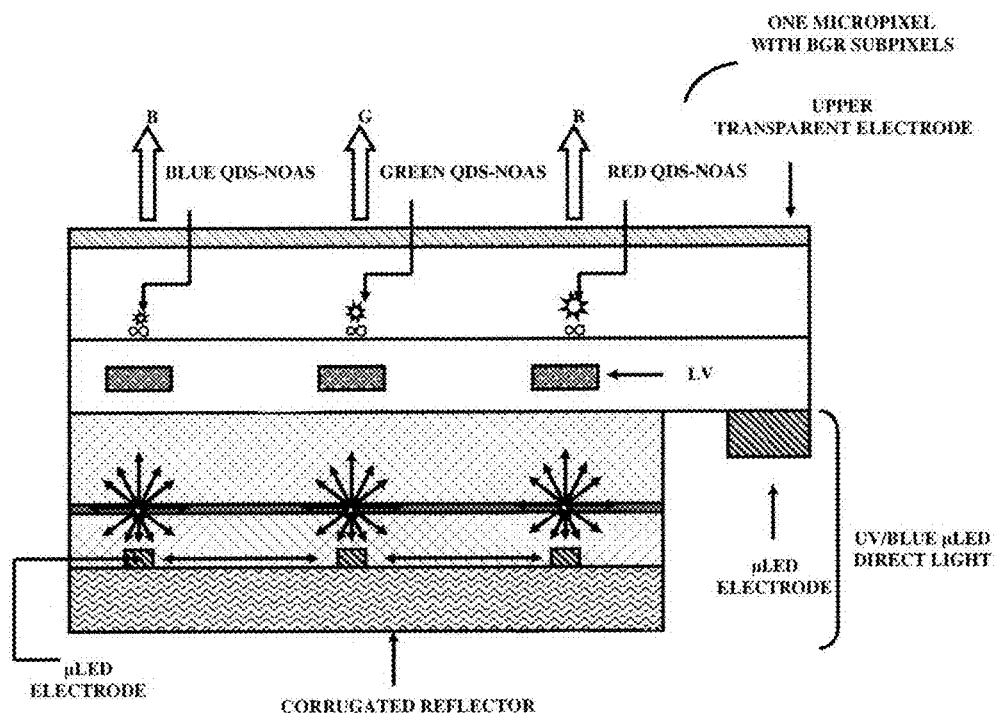

FIG. 37C illustrates one micropixel (with a blue submicropixel, a green submicropixel and a red submicropixel), enabled by ultraviolet/blue microlight emitting diodes, light valves, blue quantum dots-nano optical antennas, green quantum dots-nano optical antennas and red quantum dots-nano optical antennas. Each blue/green/red quantum dot is placed on/near the nano optical antenna in order to enable plasmonic coupling.

Figure 37D:
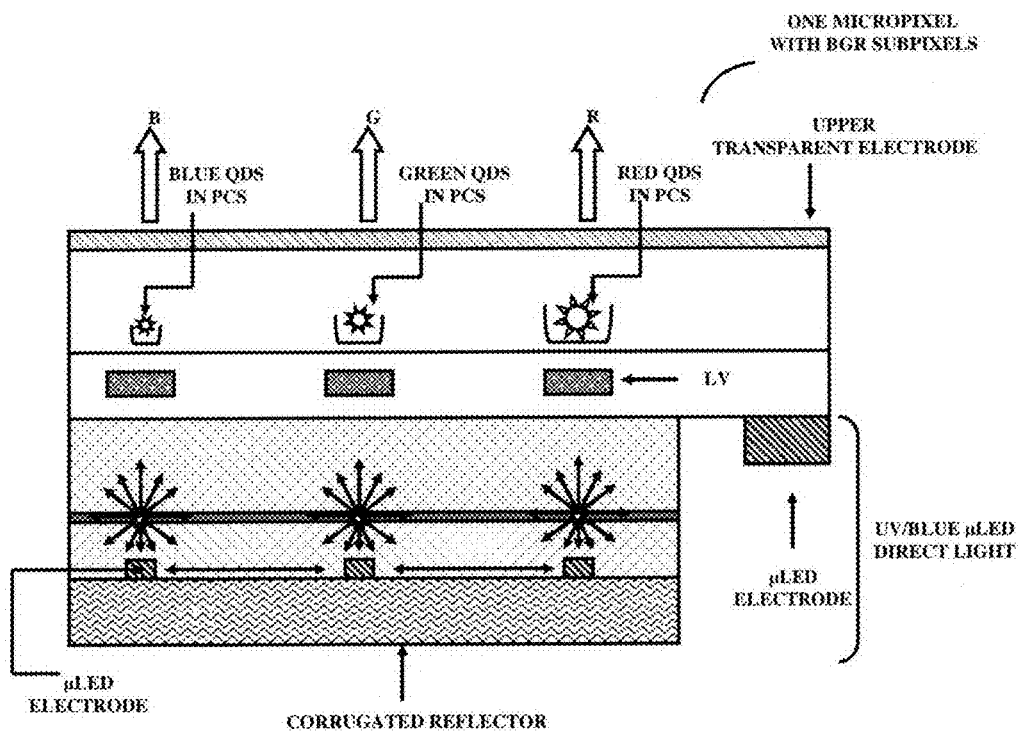

FIG. 37D illustrates one micropixel (with a blue submicropixel, a green submicropixel and a red submicropixel), enabled by ultraviolet/blue microlight emitting diodes, light valves, blue quantum dots in photonic crystals, green quantum dots in photonic crystals and red quantum dots in photonic crystals.

Figure 37E:
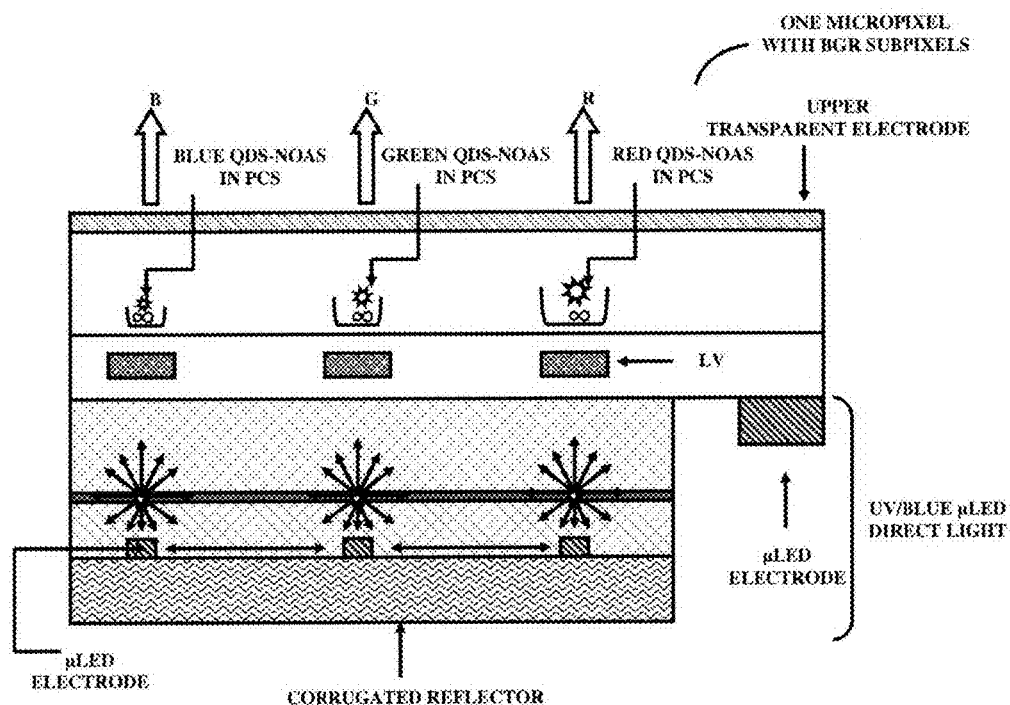

FIG. 37E illustrates one micropixel (with a blue submicropixel, a green submicropixel and a red submicropixel), enabled by ultraviolet/blue microlight emitting diodes, light valves, blue quantum dots-nano optical antennas in photonic crystals, green quantum dots-nano optical antennas in photonic crystals and red quantum dots-nano optical antennas in photonic crystals.

Figure 37F:
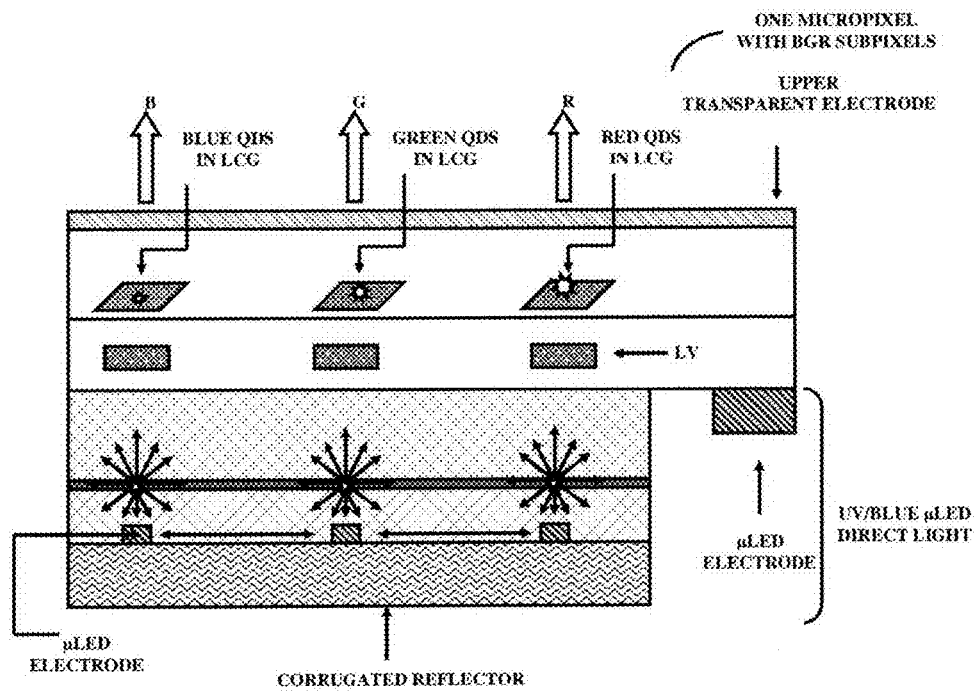

FIG. 37F illustrates one micropixel (with a blue submicropixel, a green submicropixel and a red submicropixel), enabled by ultraviolet/blue microlight emitting diodes, light valves, blue quantum dots in the electrically switchable liquid crystal gel, green quantum dots in the electrically switchable liquid crystal gel and red quantum dots in the electrically switchable liquid crystal gel.

FIG. 38 is a two-dimensional array of metal nanowires and this constitutes a plasmonic light guide (PLG). The plasmonic light guide can enable efficient light output from a light emitting diode.

FIGS. 39A-39F are identical to FIGS. 37A-37F, except the addition of a plasmonic light guide in FIGS. 37A, 37B, 37C, 37D, 37E and 37F.

It should be noted that ultraviolet/blue microlight emitting diodes (with photonic crystals light collection optics) can be utilized in FIGS. 37A-37F and FIGS. 39A-39F.

FIG. 40A illustrates vertically stacked blue, green and red organic light emitting diodes (with electrodes on a glass substrate) to act as a micropixel, utilizing a light valve on the upper transparent electrode (e.g., indium tin oxide/graphene). Backward transmitted light through the glass substrate can be collected by a solar cell (e.g., tungsten diselenide solar cell).

FIG. 40B is similar to 40A, except the vertically stacked blue, green and red organic light emitting diodes can be enhanced.

FIG. 40C illustrates an enhancement, where blue, green and red organic light emitting diode materials are mixed with specific sized quantum dots. For example, blue organic light emitting diode material is integrated with blue quantum dots, green light emitting diode material is integrated with green quantum dots and red light emitting diode material is integrated with red quantum dots.

FIG. 41A illustrates two-dimensional arrays of micropixels A, wherein one micropixel A has a blue subpixel, a green subpixel and a red subpixel. The micropixel A can be realized with quantum dots, photonic crystals/microlight emitting diodes/microlight emitting diodes (with photonic crystals based light collection optics)/vertically stacked organic light emitting diodes.

FIG. 41B illustrates drive electronics (in block diagram) of the microlight emitting diode for brightness control of a micropixel. Pulse width modulation (PWM) logic can read the ambient temperature and then compensates the intensities of blue, green and red microlight emitting diodes by changing the PWM duty cycle. Such compensation curves can be stored in EEPROM memory.

FIG. 42A illustrates a cross section of an integrated device, which comprises an array of micropixels A and cameras (e.g., CMOS sensor)/phototransistors—further co-packaged/monolithically integrated with the Super System on Chip 400A/400B. An array of microlenses is on the top of the array of micropixels and cameras/phototransistors.

The above integration is Super System on Chip 400C, which can enable the camera to see, store and process information simultaneously and it is capable of learning/relearning for self-intelligence, context-awareness and autonomous actions, remembering the patterns and movements.

FIG. 42B illustrates a front view of FIG. 42A.

Details of such integration of a camera with a Super System on Chip are described in U.S. Non-Provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and the non-provisional patent application with its benefit patent applications are incorporated in its entirety herein with this application.

FIG. 43A illustrates a frustrated vertical cavity surface emitting laser (F-VCSEL) A, which is similar to FIG. 22B, but the top mirror is metal with a nanohole. The diameter of the nanohole can be less than 5,000 nanometers. Laser light cannot escape easily, thus frustrated only to escape through the nanohole.

FIG. 43B is packaging of the frustrated vertical cavity surface emitting laser A.

FIG. 43C illustrates a frustrated vertical cavity surface emitting laser B, which is similar to FIG. 43A, except a nano optical antenna is fabricated/constructed near the nanohole.

FIG. 43D is packaging of the frustrated vertical cavity surface emitting laser B.

Figure 44A:
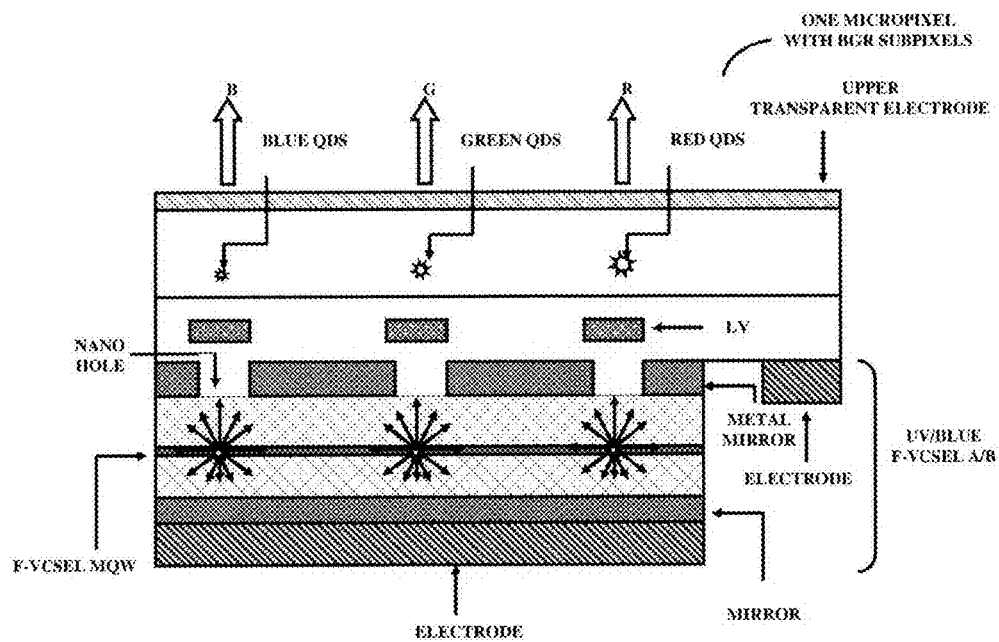

FIG. 44A illustrates one micropixel (with a blue submicropixel, a green submicropixel and a red submicropixel), enabled by frustrated vertical cavity surface emitting lasers A/B, light valves, blue quantum dots, green quantum dots and red quantum dots.

Figure 44B:
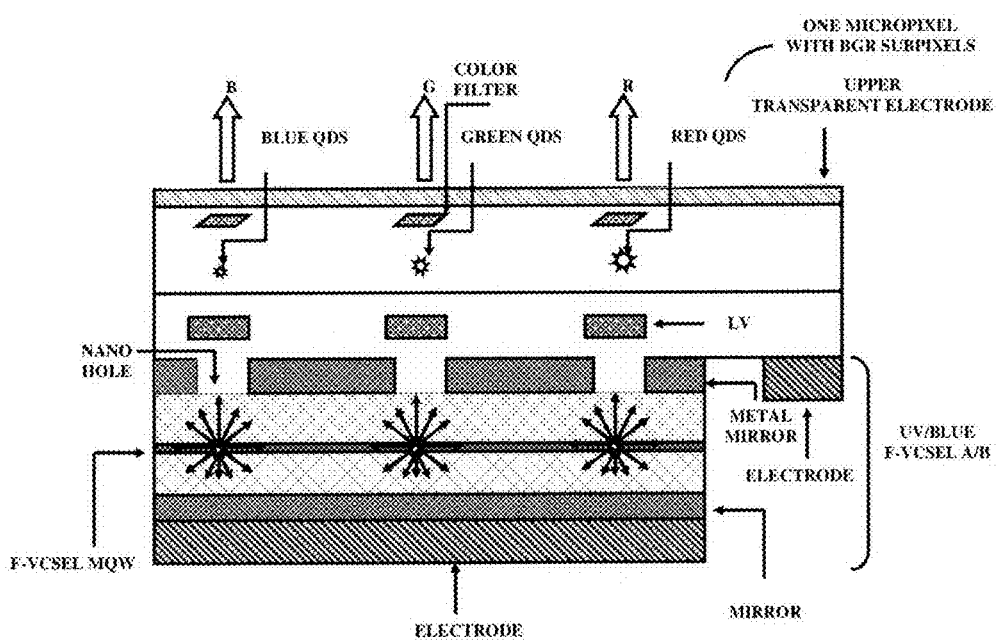

FIG. 44B illustrates one micropixel (with a blue submicropixel, a green submicropixel and a red submicropixel), enabled by frustrated vertical cavity surface emitting lasers A/B, light valves, optical color filters, blue quantum dots, green quantum dots and red quantum dots.

Figure 44C:
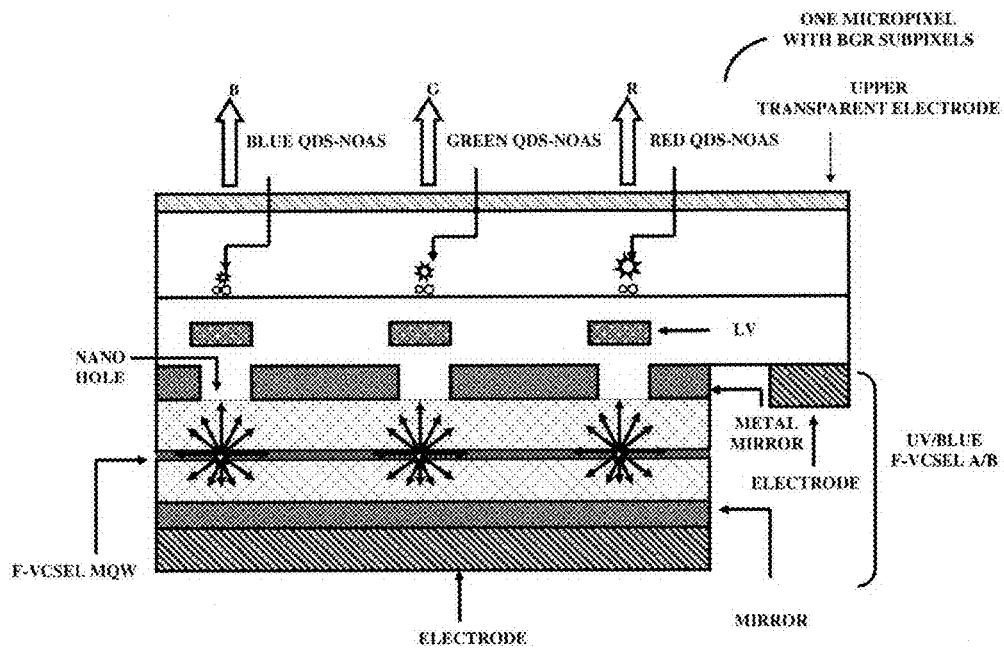

FIG. 44C illustrates one micropixel (with a blue submicropixel, a green submicropixel and a red submicropixel), enabled by frustrated vertical cavity surface emitting lasers A/B, light valves, blue quantum dots-nano optical antennas, green quantum dots-nano optical antennas and red quantum dots-nano optical antennas. Each blue/green/red quantum dot is placed on/near the nano optical antenna. Each blue/green/red quantum dot is placed on/near the nano optical antenna in order to enable plasmonic coupling.

Figure 44D:
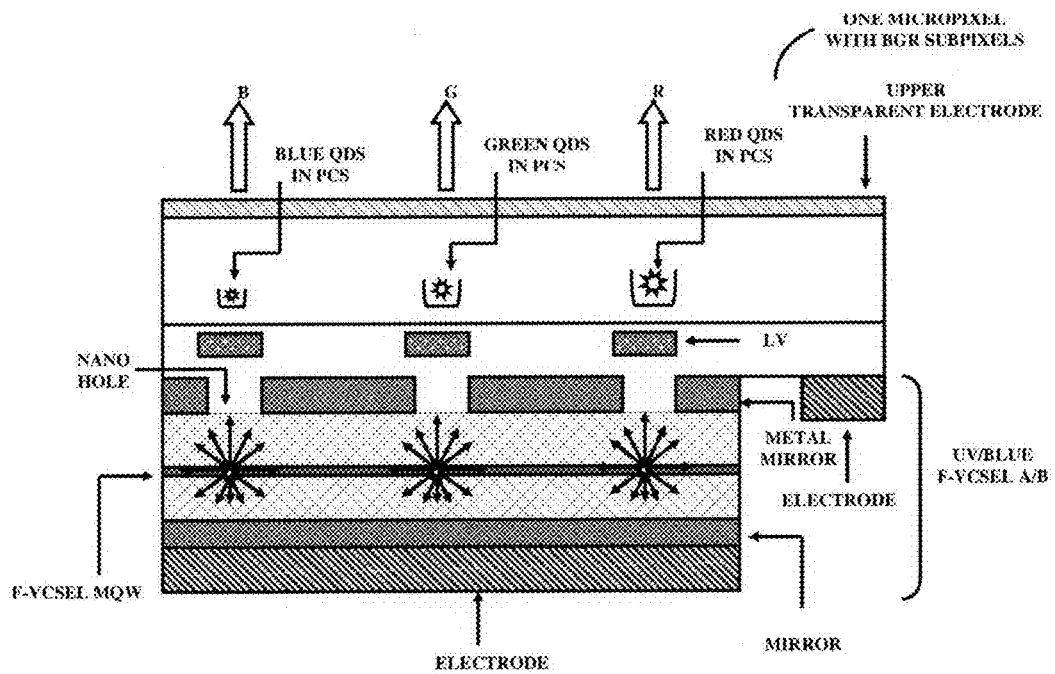

FIG. 44D illustrates one micropixel (with a blue submicropixel, a green submicropixel and a red submicropixel), enabled by frustrated vertical cavity surface emitting lasers A/B, light valves, blue quantum dots in photonic crystals, green quantum dots in photonic crystals and red quantum dots in photonic crystals.

Figure 44E:
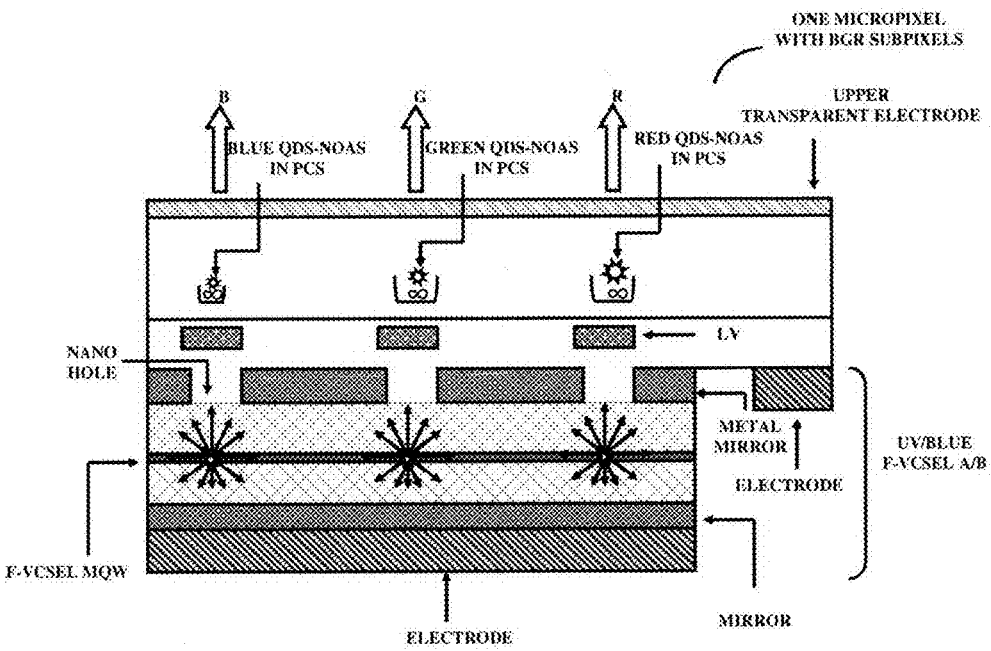

FIG. 44E illustrates one micropixel (with a blue submicropixel, a green submicropixel and a red submicropixel), enabled by frustrated vertical cavity surface emitting lasers A/B, light valves, blue quantum dots-nano optical antennas in photonic crystals, green quantum dots-nano optical antennas in photonic crystals and red quantum dots-nano optical antennas in photonic crystals.

Figure 44F:
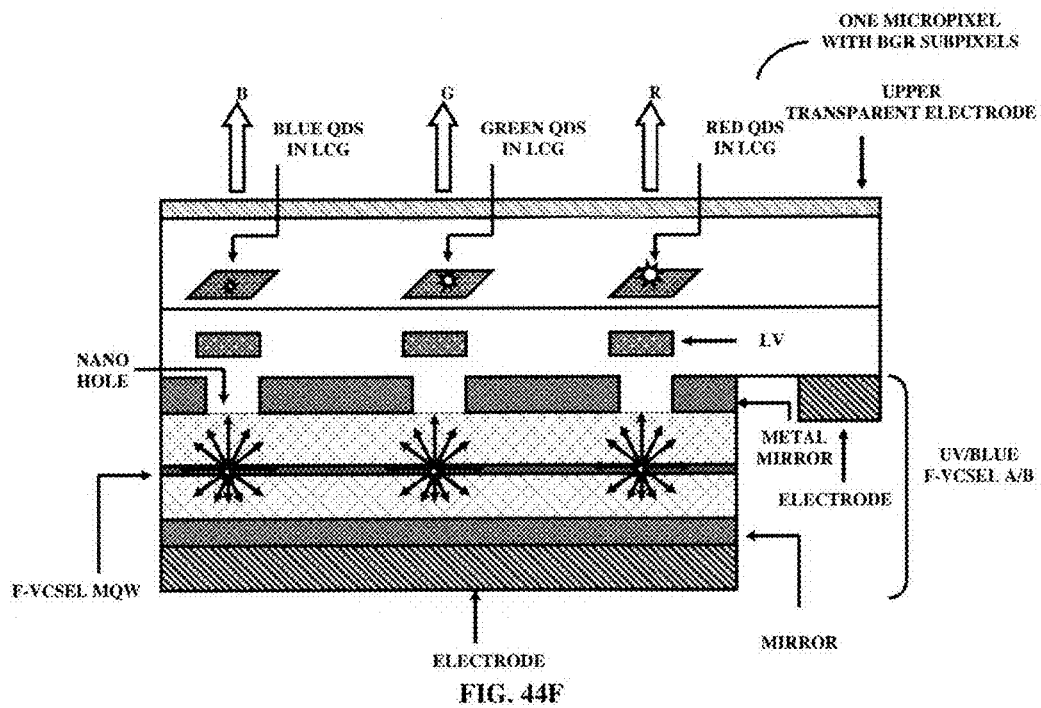

FIG. 44F illustrates one micropixel (with a blue submicropixel, a green submicropixel and a red submicropixel), enabled by frustrated vertical cavity surface emitting lasers A/B, light valves, blue quantum dots in the electrically switchable liquid crystal gel, green quantum dots in the electrically switchable liquid crystal gel and red quantum dots in the electrically switchable liquid crystal gel.

FIG. 45 illustrates two-dimensional arrays of micropixels B, wherein one micropixel B has a blue subpixel, a green subpixel and a red subpixel. The micropixel B can be realized with quantum dots and frustrated vertical cavity surface emitting lasers A/B.

FIG. 46A illustrates a micropixel. Blue quantum dots, green quantum dots and red quantum dots are excited by a stack of light emitting semiconductor layers (epitaxial lifted-off and bonded onto a thin glass substrate).

FIG. 46B is similar to 46A, except blue quantum dots are in a photonic crystal, green quantum dots are in a photonic crystal and red quantum dots are in a photonic crystal.

FIG. 47A illustrates a micropixel, utilizing electron emissions from selected (utilizing row and column electrodes) sharp microtips and phosphor layers. The emission from the phosphor layer is controlled by a light valve.

FIG. 47B is similar to 46A, except nanotubes replaces sharp microtips.

FIG. 48A illustrates a cross section of an integrated device, which comprises an array of micropixels B and cameras (e.g., CMOS sensor)/phototransistors—further co-packaged/monolithically integrated with the Super System on Chip 400A/400B. An array of microlenses is on top of the array of micropixels and cameras/phototransistors.

The above integration Super System on Chip is 400D, can enable the camera to store and process information simultaneously and it is capable of learning/relearning for self-intelligence, context-awareness and autonomous actions, remembering the patterns and movements.

FIG. 48B illustrates a front view of FIG. 48A.

FIG. 49 illustrates a three-dimensional/holographic display 340, utilizing a two-dimensional array of micropixels A/B and an array of microlenses. The three-dimensional/holographic display 340 can be fabricated/constructed in transparent synthetic spinel (magnesium aluminate) instead of glass.

Furthermore, the array of microlenses can be an array of ultrathin flat microlenses (e.g., graphene on glass). The ultrathin flat microlens can be distortion free.

FIG. 50A illustrates a microprojector, enabled by an electrically switchable light valve and a micro (nano) mechanical system based scanning mirror. Blue, green and red photonic crystals light collection optics vertical cavity surface emitting lasers (VCSEL-PCO) are flip-chip mounted within v-grooves in silica on silicon substrate.

The photonic crystals light collection optics vertical cavity surface emitting lasers are rapidly switched to mix a color spectrum by a phase change/phase transition material light valve. The outputs of the light valve are multiplexed by a focusing slab waveguide and then focused to a micro (nano) mechanical system based scanning mirror by a (about 45-degree angle) deflecting mirror to enable a microprojector.

Any light valve can be utilized instead of the phase change/phase transition material light valve.

FIG. 50B illustrates guiding of light output from the photonic crystals light collection optics vertical cavity surface emitting laser into a waveguide. Light from photonic crystals light collection optics vertical cavity surface emitting lasers is collimated by a microlens and then focused by an about 45-degree angle mirror.

FIG. 50C illustrates electronics (in block diagram) to drive the microprojector. Outputs of a video processor are inputs to laser driver(s) of the blue/green/red photonic crystals light collection optics based vertical cavity surface emitting lasers. Light from photonic crystals light collection optics based vertical cavity surface emitting lasers are collimated, transmitted through the phase change/phase transition material light valve (to control their respective intensities) and then multiplexed by an optical multiplexer. The multiplexed light is incident on the micro(nano)-electromechanical systems (M(N)EMS) scanning mirror, which is controlled by a driver. The driver receives input from the video processor.

Figure 51A:
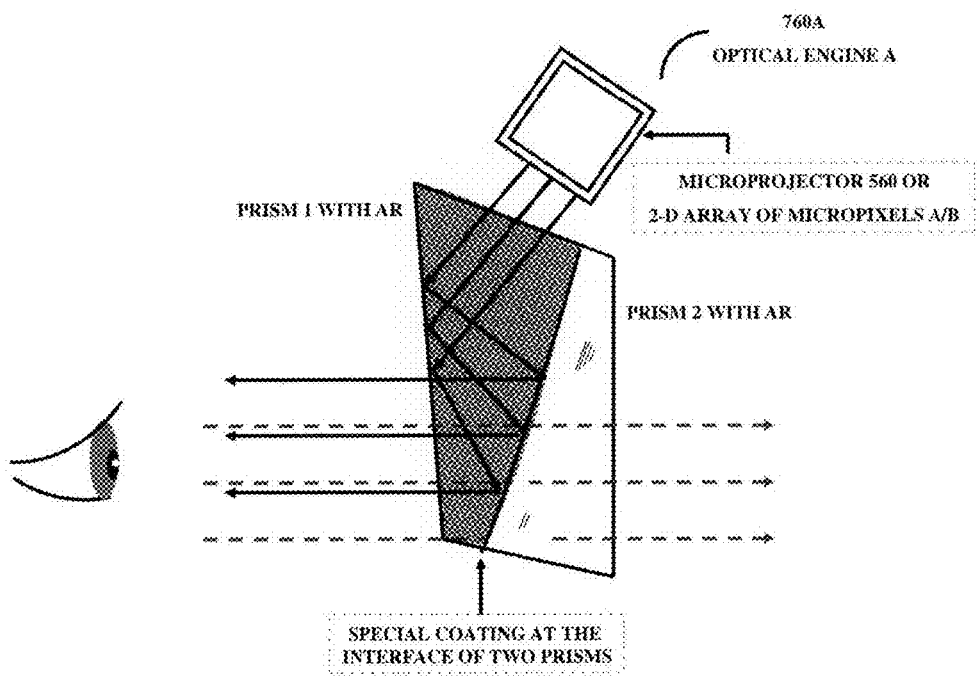

FIG. 51A illustrates an optical engine A, 760A receiving input from the microprojector 560/two-dimensional array of micropixels A/two-dimensional array of micropixels B. The optical engine A, 760A comprises two specially shaped prisms. The interface between the two prisms has a thin-film coating to enable reflection of a device/computer generated image and view real events through one eye. The front side of prism 1 and prism 2 can be antireflection (AR) coated.

Figure 51B:
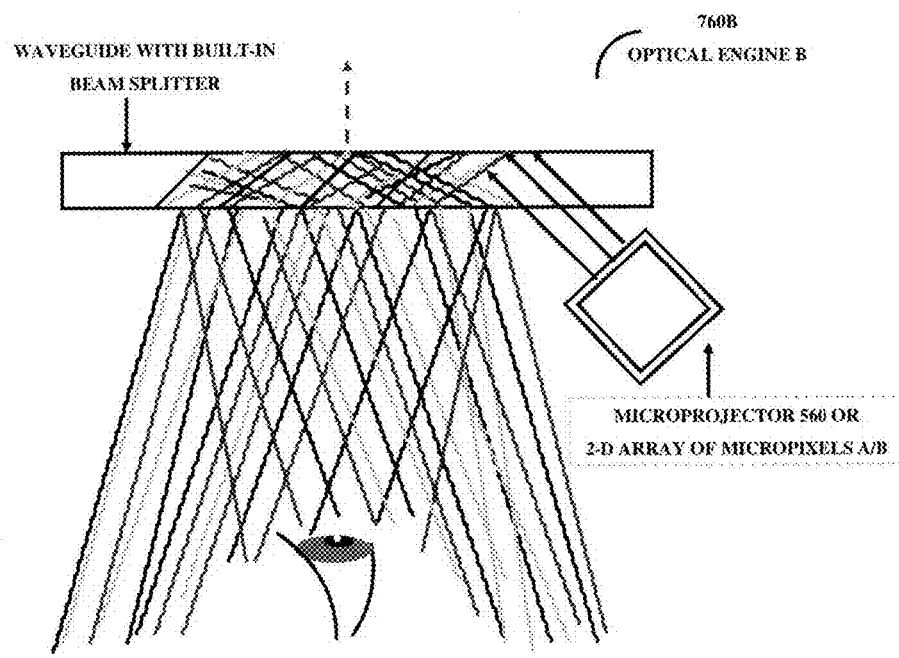

FIG. 51B illustrates another optical engine B, 760B receiving input from the microprojector 560/two-dimensional array of micropixels A/two-dimensional array of micropixels B. The optical engine B, 760B comprises a waveguide with built-in beam splitter.

Figure 51C:
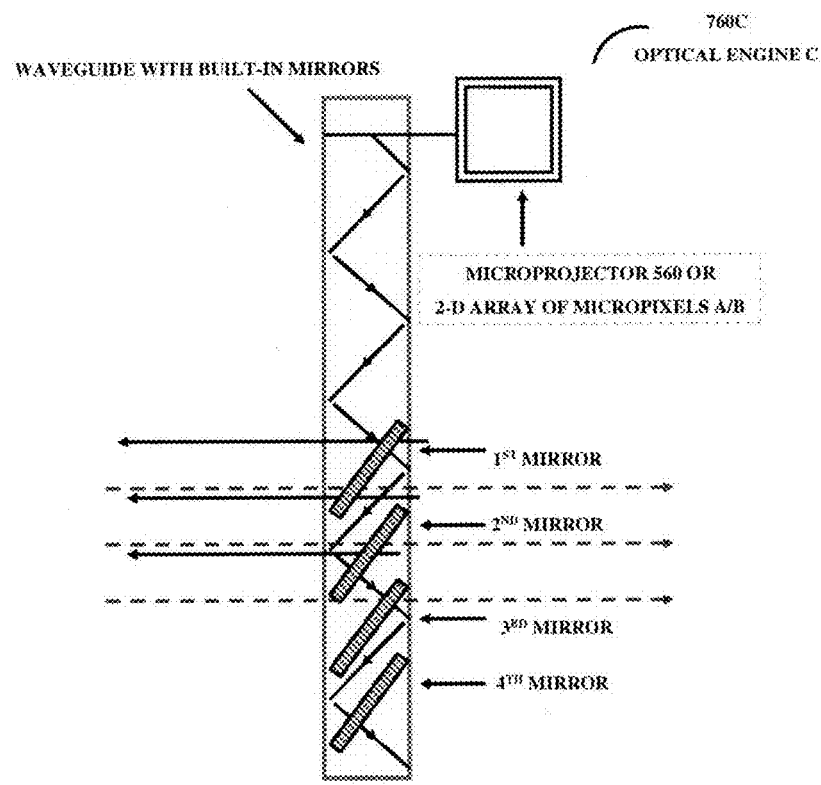

FIG. 51C illustrates another optical engine C, 760C receiving input from the microprojector 560/two-dimensional array of micropixels A/two-dimensional array of micropixels B. The optical engine C, 760C comprises a waveguide with built-in mirrors.

Figure 51D:
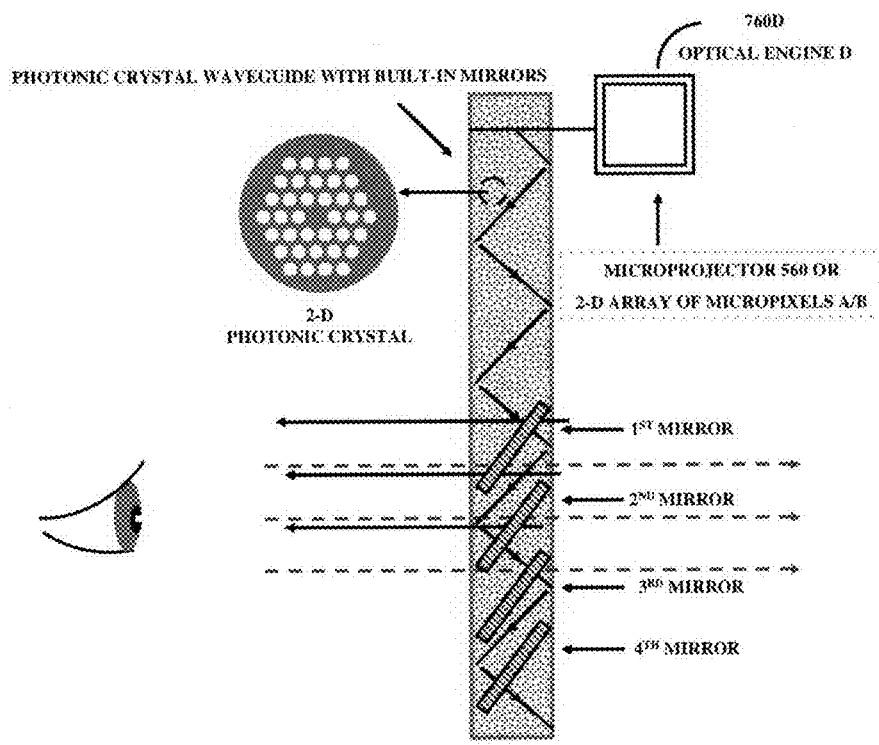

FIG. 51D illustrates another optical engine D, 760D receiving input from the microprojector 560/two-dimensional array of micropixels A/two-dimensional array of micropixels B. The optical engine D, 760D comprises a two-dimensional photonic crystal (can be fabricated/constructed by nanoimprint lithography) waveguide with built-in mirrors.

The grey area indicates waveguide material (e.g., glass) and the white circles are about 2 to 5 microns diameter air holes in the two-dimensional photonic crystal.

Figure 52A:
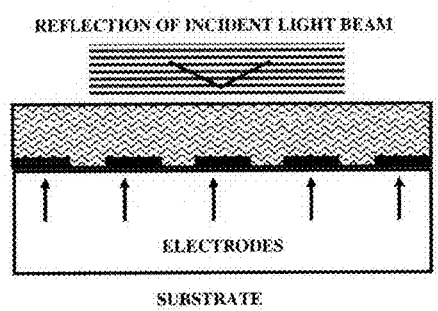
Figure 52B:
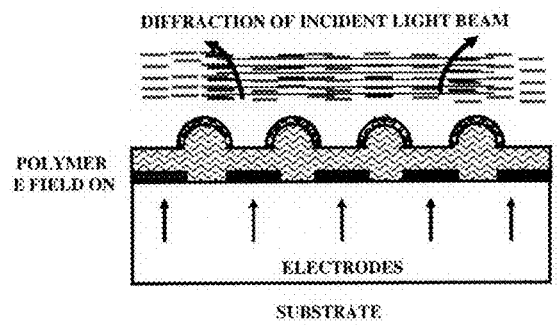

A spatial light modulator is a device that enables spatially varying modulation on a beam of light. FIGS. 52A-52B illustrate a high resolution electrically induced spatial light modulator (SLM) utilizing about 15 microns thick poly (vinylidene fluoride-trifluoroethylene-chlorofluoroethylene) terpolymer film on a transparent substrate.

FIG. 52A illustrates a flat mirror shape of the polymer film without the electric field.

FIG. 52B illustrates a grating(s) shape of the polymer film with the electric field (about 100 volts per micron thickness), as the polymer film shrinks.

Each electrode is about 5 microns in width. The gap between two electrodes is about 15 microns.

Another suitable electro-optic polymer can be utilized instead of poly(vinylidene fluoride-trifluoroethylene-chlorofluoroethylene) terpolymer.

Figure 52C:
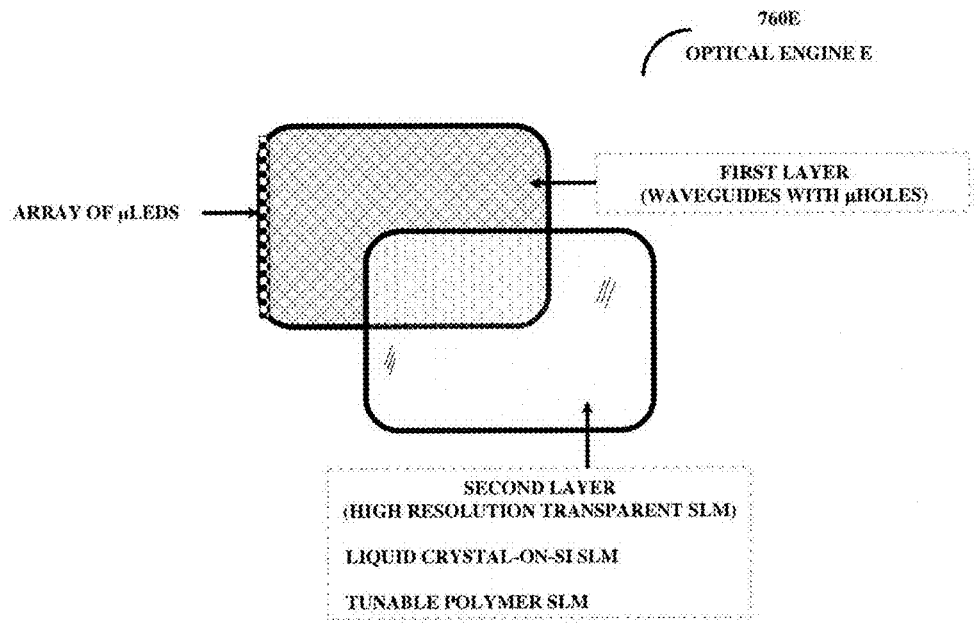

FIG. 52C illustrates another optical engine E, 760E. The optical engine E, 760E comprises a first layer with built-in waveguides with microholes and a second layer with a high resolution spatial light modulator (e.g., based on liquid crystal on silicon on insulator (LC-SOI)/electrically activated tunable polymer). The side edge of the first layer is illuminated by an array of microlight emitting diodes, as illustrated previously.

Figure 52D:
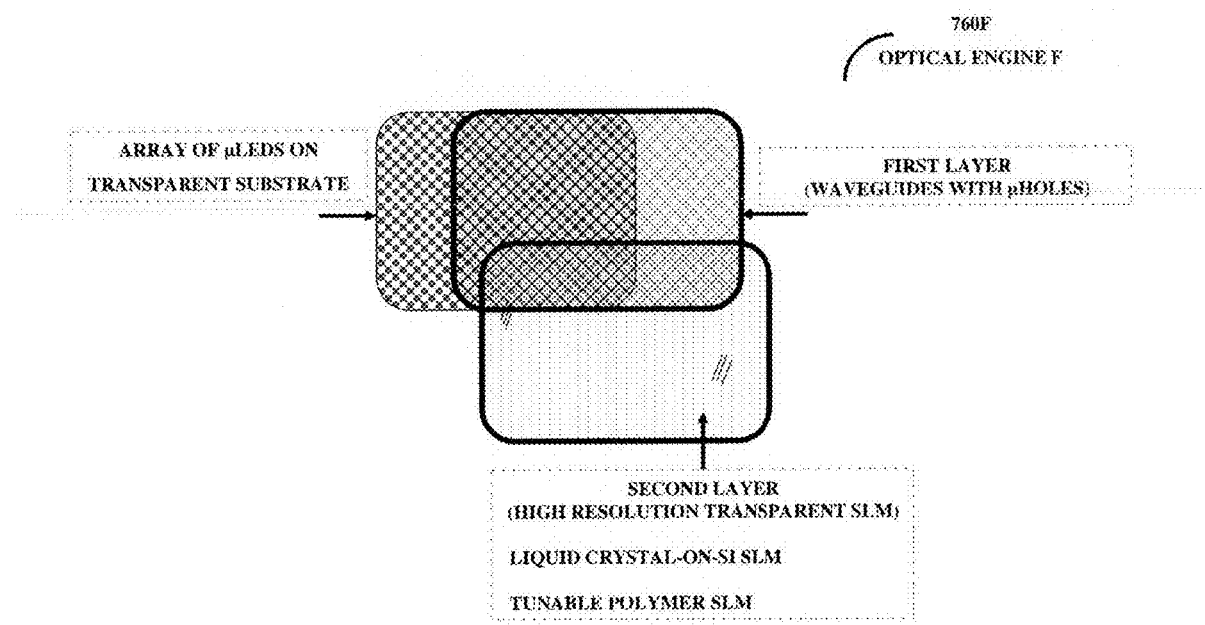

FIG. 52D illustrates another optical engine F, 760F. The optical engine F, 760F comprises a first layer with built-in waveguides with microholes and a second layer with a high resolution spatial light modulator. The first layer is directly illuminated by an array of microlight emitting diodes on a transparent substrate.

Augmented reality refers to what a user can perceive through his/her biological senses (e.g., viewing) and the user's perception can be enhanced with device/computer generated input data (e.g., images, sound and video). Augmented reality makes more information available to the user by combining device/computer generated input data to what the user experiences (or views). For example, the user can find a nearby café with the menu of the café translated from a local language to the user's own native language by augmented reality enabled enhancement.

FIG. 53 illustrates an intelligent wearable augmented reality personal assistant device 180, which comprises a multichip module (MCM) system 740, an optical engine 760A/B/C/D/E/F and an eye tracking sensor.

The eye tracking sensor comprises an infrared light source and two cameras. The infrared light reflects off the pupil and cornea and the reflections are captured by the two cameras and then processed by an image processing algorithm.

The key components of the multichip module system 740 (in block diagram) are listed below:

| Component | Description |
|---|---|
| 380 | Communication Radio* (WiMax/LTE) |
| 400A/B/C/D | Super System On Chip |
| 420 | Operating System Algorithm |
| 440 | Security & Authentication Algorithm |
| 480 | Surround Sound Microphone |
| 500 | Front Facing High Resolution Camera |
| 520 | Back Facing High Resolution Camera |
| 540 | High Resolution Camcorder |
| 580 | Proximity Radio* (Near Field Communication/Bluetooth LE) TxRx |
| 600 | Personal Area Networking Radio 1* (Bluetooth/Wi-Fi) TxRx |
| 620 | Personal Area Networking Radio 2* (Ultrawide Band/Millimeter-Wave) TxRx |
| 640 | Positioning System (Global Positioning System* & Indoor Positioning System) |

-continued

| Component | Description |
|---|---|
| 660 | Universal Communication Interface |
| 700 | Electrical Powering Device (Solar Cell + Battery + Ultracapacitor) |

[*With Radio Specific Antenna] [TxRx Means Transceiver]

A universal communication interface can integrate animation, animated GIF, drawings, emotions, gestures (hand/eye), location data, text, voices, voice snippets and videos.

The intelligent wearable augmented reality personal assistant device 180 can comprise a wearable electrical power providing patch.

Details of the wearable electrical power providing patch are described in U.S. Non-Provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and the non-provisional patent application with its benefit patent applications are incorporated in its entirety herein with this application.

The intelligent wearable augmented reality personal assistant device 180 is sensor-aware and context-aware, as it is wirelessly connected/sensor connected with objects 120A, object nodes 120, bioobjects 120B and bioobject nodes 140.

FIG. 54A represents a generic biomarker binder, which can be an antibody/aptamer/molecular beacon.

FIG. 54B represents a generic biomarker binder chemically coupled with a fluorophore (e.g., a quantum dot fluorophore).

FIG. 54C is similar to FIG. 54B, except the fluorophore (which is coupled with a biomarker binder) is near or within a nano optical antenna.

FIG. 55A illustrates a disposable diagnostic chip 1. This has an inlet for a drop of blood, an array of capillaries to separate and propagate serum from the blood toward the end of the disposable diagnostic chip 1, where disease specific biomarker binders coupled with fluorophores are embedded. When disease specific biomarkers from the serum chemically bind with biomarker binders, then the disposable diagnostic chip 1 can fluoresce.

FIG. 55B illustrates a disposable diagnostic chip 2. FIG. 55B is similar to FIG. 55A, except the fluorophore (coupled with a biomarker binder) is near or within the nano optical antenna to enhance fluorescence.

The disposable diagnostic chip 1/disposable diagnostic chip 2 can be fabricated/constructed on a polymer/paper substrate.

FIG. 55C illustrates a measurement system, which has an insertion socket (for the disposable diagnostic chip 1/disposable diagnostic chip 2). The measurement system can detect fluorescence by an ultrasensitive light detector (e.g., indium gallium arsenide avalanche photodiode/charge coupled device/complementary metal oxide semiconductor) when the biomarker binders-biomarkers section is excited by a light source (e.g., a light emitting diode/laser). The measurement system can connect (wired or wirelessly) with the intelligent portable internet appliance 160.

FIG. 56A illustrates an exterior view of a wearable personal health assistant device. This is a computing device with a micro-USB port, a microphone (for voice command) and a proximity radio transceiver and sensing device for continuous bio data (e.g., (a) body temperature, (b) pulse rate, (c) % oxygen saturation and (d) blood sugar level) recording and reminder. A two-wavelength reflection pulse oximetry can be utilized to measure % oxygen saturation.

The wearable personal health assistant device can be integrated with a pulse oximeter, an insertion socket (for the disposable diagnostic chip 1/disposable diagnostic chip 2), an ultrasensitive light detector (for fluorescence measurement), a wearable diagnostic device A and a wearable diagnostic device B. The wearable personal health assistant device can be electrically coupled with a patch with spiropyran, passive patch, active patch, sensor and LifeSoC. An alarm can remind the user about potential mistakes/conflicts.

The key components of the wearable personal health assistant device are listed below:

Low Power Processor
Digital Memory
Operating System Algorithm
Wrap-around Display
High Density Solid State Data Storage
Microphone
Proximity Radio * (Near Field Communication/Bluetooth LE) TxRx
Universal Communication Inter face
Electrical Powering Device (Solar Cell + Battery + Ultracapacitor)
Ultrasensitive Light Detector A universal communication interface can integrate animation, animated GIF, drawings, emotions, gestures (hand/eye), location data, text, voices, voice snippets and videos.

The micro-USB port can enable transfer of encrypted personal health records in the high density solid state storage device. The disposable diagnostic chip 1/disposable diagnostic chip 2 can be inserted into the insert socket for detection and analysis of fluorescence.

Figure 56B:
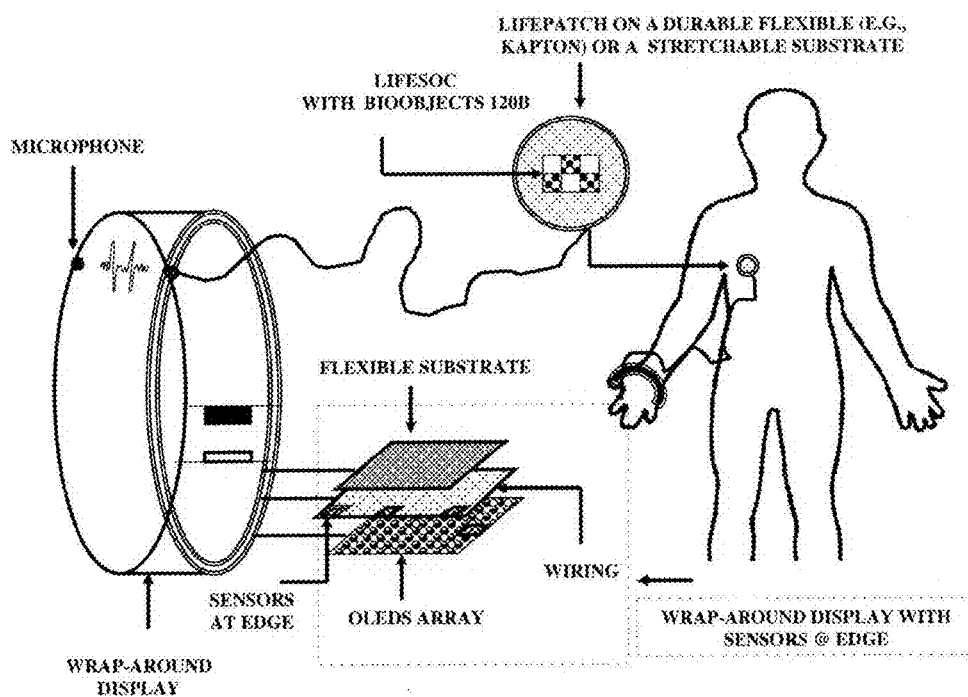

FIG. 56B illustrates an interior view of the device. A wrap-around display can be fabricated/constructed by utilizing organic light emitting diodes on a flexible substrate (e.g., DuPont Kapton) with wiring.

With wiring, a small electrical current can be applied to the skin, along with pilocarpine (drug) to induce the skin to sweat for analysis by a wearable diagnostic device A.

Details of a wearable diagnostic device A, wearable diagnostic device B, patch with spiropyran, passive patch and active patch will be described later.

An array of sensors can be fabricated/constructed at the edge of the flexible substrate. Bioobject(s) 120B can be integrated with a LifeSoC, multichip module electronics to collect reliable signals from the bioobject(s) 120B. Details of LifeSoC are illustrated in FIG. 56C.

Figure 56C:
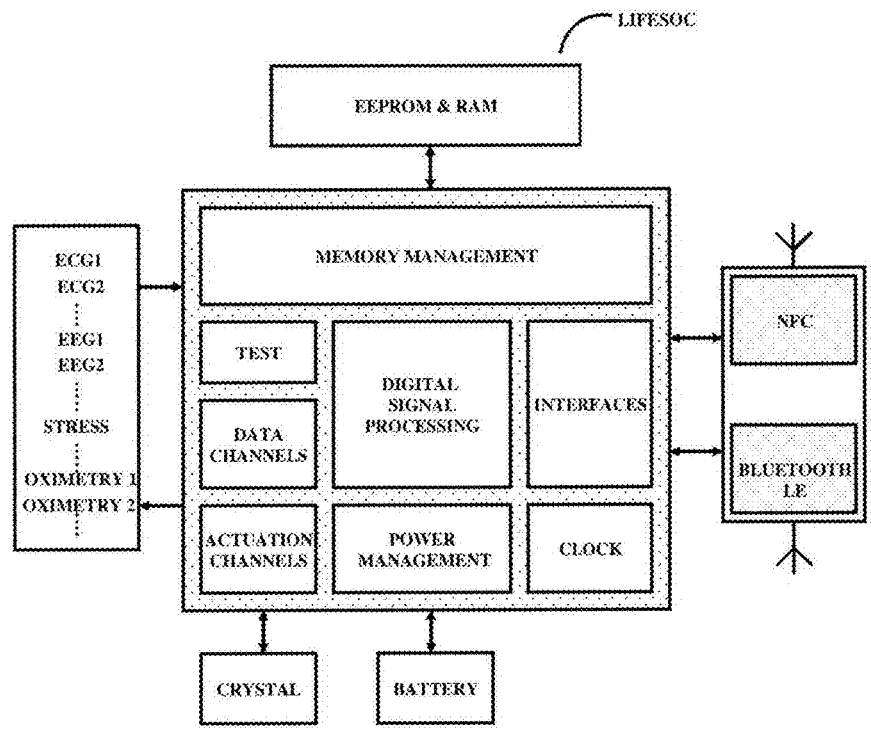

FIG. 56C illustrates a LifeSoC in block diagram. LifeSoC has digital signal processing, memory management and power management capabilities, as it is interfacing with various bio/health sensors (e.g., ECG, EEG, stress and oximetry), Bluetooth LE and near field communication. LifeSoC can be fabricated/constructed on a flexible/stretchable substrate.

Details of Life SoC are described in U.S. Non-Provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and the non-provisional patent application with its benefit patent applications are incorporated in its entirety herein with this application.

Biomarkers contained in sweat can give indications about the physical state of the body. They comprise electrolytes (e.g., calcium, chloride, potassium and sodium), metabolites (creatinine, glucose, lactate and uric acid), proteins (interleukins, neuropeptides and tumor necrosis factor) and small molecules (amino acids, cortisol and DHEA).

Figure 56D:
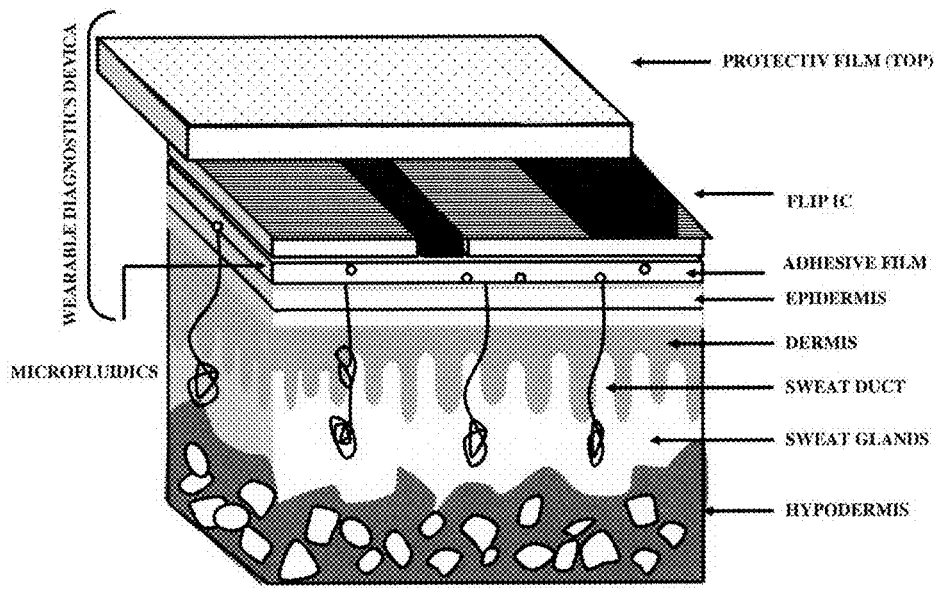

FIG. 56D illustrates a wearable diagnostic device A on sweat networks on skin.

Figure 56G:
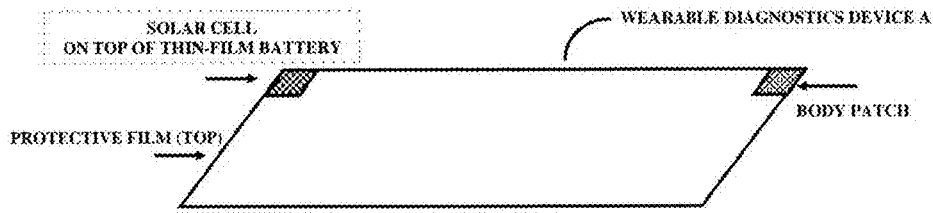
Figure 56F:
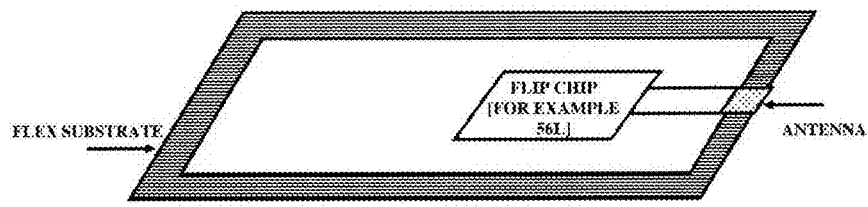
Figure 56E:
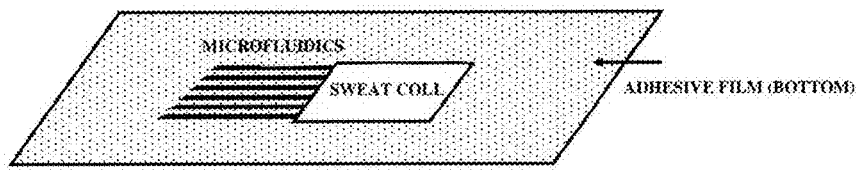

FIGS. 56E-56G illustrate details of the wearable diagnostic device A.

FIG. 56E illustrates a bottom adhesive film with microfluidic channels to wick sweat from human skin and the microfluidic channels are connected with an ultra absorbent sweat collector/reservoir. The ultra absorbent sweat collector/reservoir is electrically coupled with a flip-chip bonded chip to detect biomarkers in sweat.

Figure 56H:
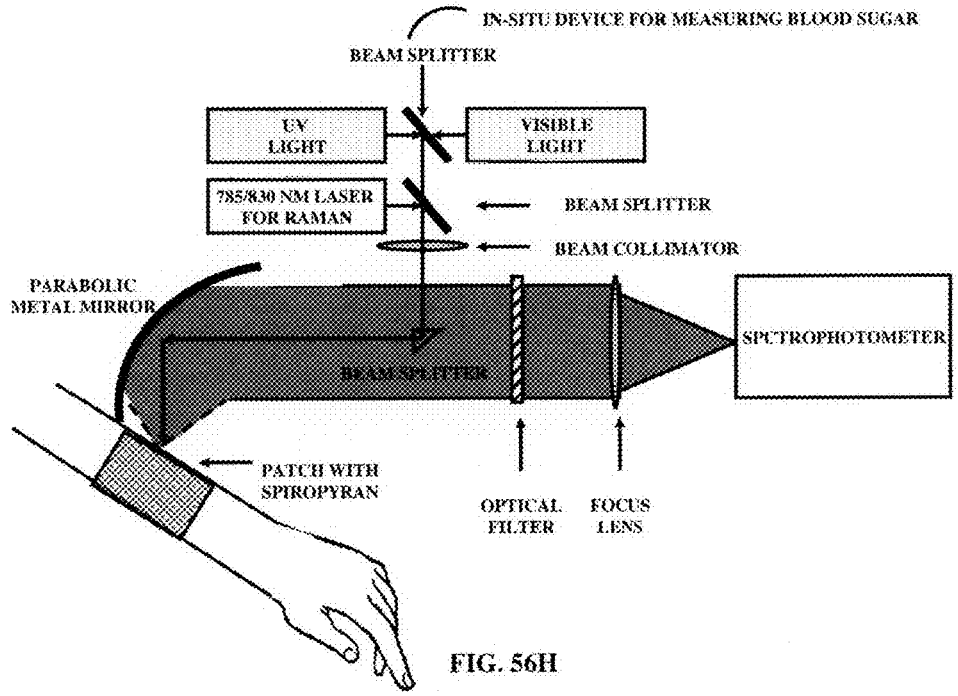
Figure 56I:
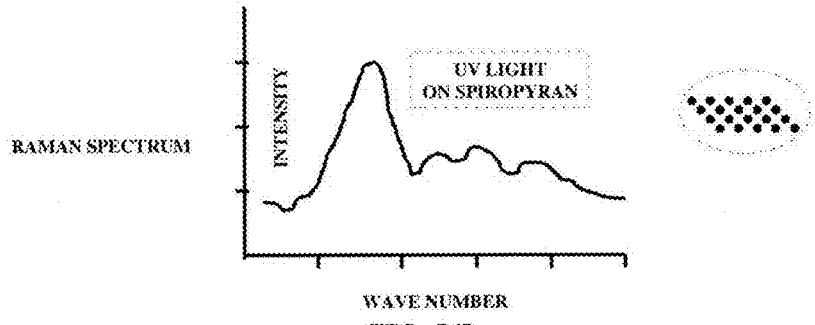
Figure 56J:
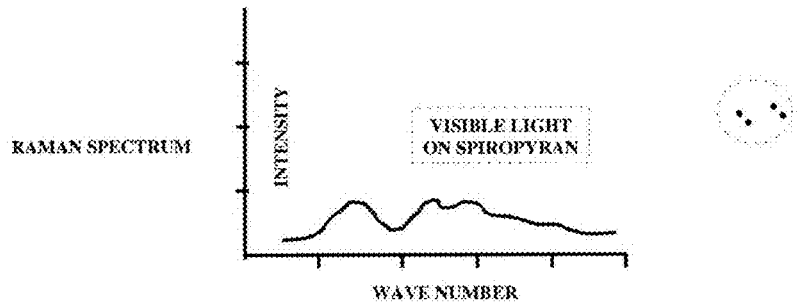
Figure 56K:
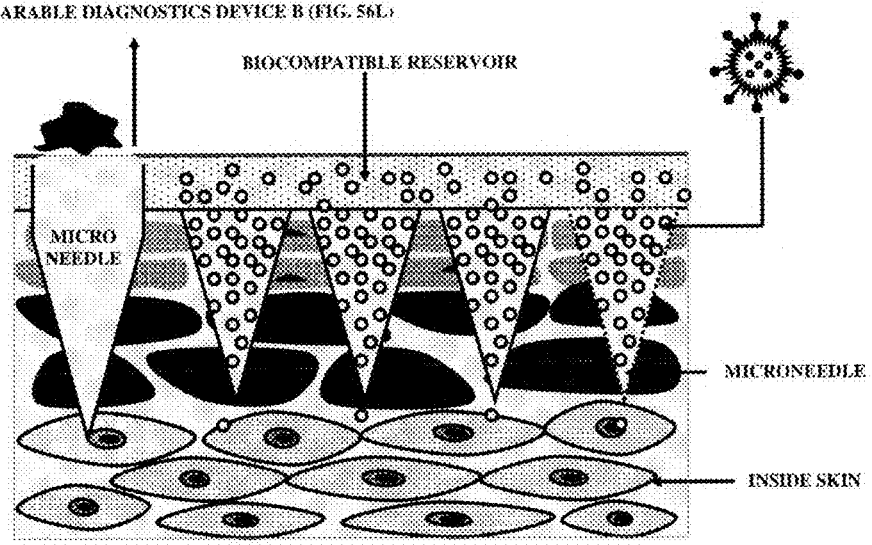
Figure 56L:
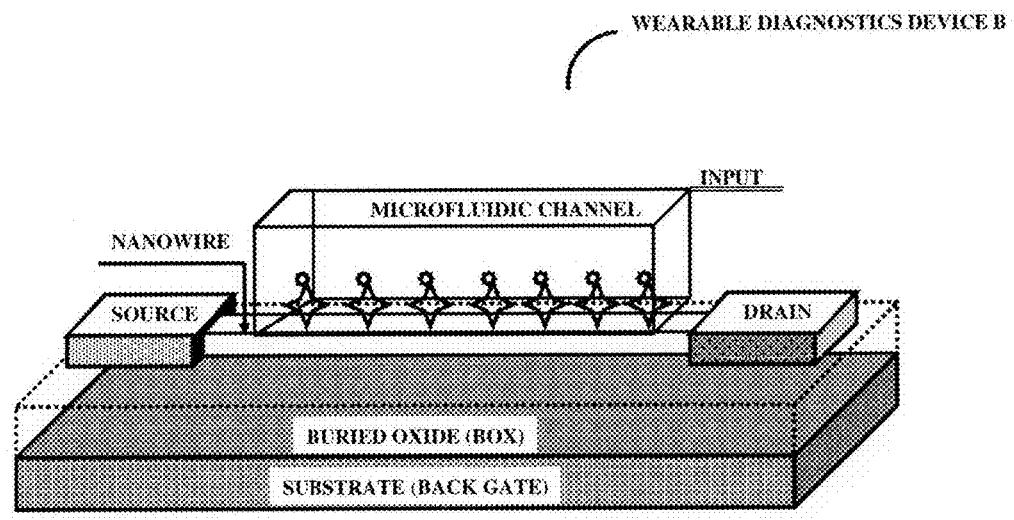

FIG. 56F illustrates the flip-chip bonded chip (on a flexible substrate), which can be as described in FIG. 56L (without the input channel for blood). The flip-chip bonded chip can comprise many circuits for real time detection of biomarkers in sweat and an antenna to transmit data.

FIG. 56G illustrates a top protective film, which comprises a solar cell on top of a battery and a body patch for providing electrical power.

Details of the body patch are described in U.S. Non-Provisional patent application Ser. No. 14/120,835 entitled "CHEMICAL COMPOSITION & ITS DELIVERY FOR LOWERING THE RISKS OF ALZHEIMER'S, CARDIO-VASCULAR AND TYPE-2 DIABETES DISEASES", filed on Jul. 1, 2014 and the non-provisional patent application with its benefit patent applications are incorporated in its entirety herein with this application.

The input of the microfluidic channels in FIG. 56E can be also connected to an ultrathin-hydrogel film-embedded with one specific type of biomarker binders (e.g., antibodies/aptamers/designer proteins/molecular beacons). The optical properties of ultrathin-hydrogel film can change, when the specific biomarker binders chemically couples with the biomarkers in sweat. This change can be detected by an optical detector/spectrophotometer.

FIG. 56H illustrates a two-layer patch to measure blood sugar in-situ. The first layer is a porous membrane with spiropyran and it is attached to human skin. The second layer (on top of the first layer) is hydrogels embedded with glucose sensors (e.g., boronic acid).

If UV light is beamed through spiropyran, the chemical structure of spiropyran is charged (polar) and open structure—enabling more glucose molecules to diffuse through the first layer from skin. If irradiated with visible light, the chemical structure of spiropyran reverts back to normal/closed structure—enabling fewer glucose molecules to diffuse to the first layer from skin. By comparing the optical spectrum taken under UV light against the optical spectrum taken under visible light, glucose in blood can be quantified. By embedding other molecular sensors in the second layer, other biomarkers/analytes (e.g., creatinine and electrolytes) in blood can also be quantified. This method to measure blood sugar in-situ can be integrated with the wearable diagnostic device A.

FIG. 56H illustrates a two-layer patch to measure blood sugar in-situ. The first layer is a porous membrane embedded with spiropyran and the first layer is attached to human skin.

Hydrogels embedded with glucose sensors (e.g., boronic acid) is a second layer. The second layer is attached onto the first layer.

If UV light is beamed through spiropyran, the chemical structure of spiropyran is charged (polar)/open structure—enabling more glucose to diffuse to the first layer from the outer most layer of skin/skin. If visible light is beamed through spiropyran, the chemical structure of spiropyran reverts back to normal/closed structure—enabling less glucose to diffuse to the first layer from the outer most layer of skin. By comparing optical spectra taken under UV and visible light, glucose in blood can be quantified. Additionally, by embedding suitable molecular sensors in the second layer, other analytes (e.g., creatinine and electrolytes) in blood can be quantified.

Alternatively, only the porous membrane spiropyran (the first layer) can be utilized. If UV light is beamed through spiropyran, the chemical structure of spiropyran is charged (polar)/open structure—enabling more glucose to diffuse to the first layer from the outer most layer of skin/skin and glucose can then be quantified by a Raman spectrophotometer. Raman spectra is induced by a laser and propagated through a beam splitter, collimating lens, hyperbolic metal concentrator, an optical filter and focusing lens to the Raman spectrophotometer. The hyperbolic metal concentrator can be utilized to collect scattered photons. Raman measurement can be calibrated with other direct blood sugar measurements. An algorithm can be utilized with the Raman spectrophotometer to correct for any concentration and time lag effects. Thus, a look up table and/or algorithm can enable continuous or quasi continuous in situ blood sugar measurement FIG. 56I illustrates Raman spectrum, under UV light, when more glucose can diffuse to the first layer from skin.

FIG. 56J Raman spectrum, under visible light, when few glucose molecules can diffuse to the first layer from skin.

Alternatively, a porous membrane with a biocompatible needle can be utilized to create a microscopic pore at the outermost layer (about 20 microns in depth) of skin for interstitial fluid to cross the outer skin barrier. Glucose in interstitial fluid can be converted into hydrogen peroxide by glucose oxidase. Hydrogen peroxide can chemically react with horseradish peroxidase to generate colored liquid resorufin, which absorbs/emits red light. The optical signature of resorufin is a measure of glucose in human blood and it can be quantified by Raman spectrophotometer/optical coherence tomography/plasmonic interferometer/spectrophotometer/(organic light emitting diode or ultrasensitive detector of the wearable personal health assistant device).

FIG. 56K illustrates an array of biocompatible microneedles (e.g., made from sugar/hyaluronic acid) with built-in nanoscaled (about 10 nm) roughness on them to reduce any bacterial infection. These microneedles can enable (a) the transport of blood to an input of the wearable diagnostic device B and (b) also deliver a bioactive compound(s)/a bioactive compound(s) encapsulated within a smart nanoshell in synchronization with in-situ measurements by the wearable diagnostic device B.

The smart nanoshell can be of any shape and build by DNA origami.

The bioactive compound can also mean RNA-i, engineered riboswitch and synthetic notch molecule.

Smart nanoshells can be stored in a biocompatible reservoir (e.g., a microelectromechanical system biocompatible reservoir) and their movement from the biocompatible reservoir can be controlled by a micropump. Smart nanoshells have to meet a suitable external condition(s) and/or couple with a specific receptor(s) to release a bioactive compound.

For example, the smart nanoshell can be made of water-fearing molecules (pointing inward) and water-loving molecules (pointing outward). The smart nanoshell can encapsulate insulin molecules/long acting insulin molecules/smart insulin molecules. The external surface of the smart nanoshell can be coupled with an enzyme to convert glucose into gluconic acid. In the presence of excess glucose, the enzyme (converting glucose into gluconic acid) creates a lack of oxygen and causes water-loving molecules (pointing outward) to collapse—enabling to the delivery of insulin/ long acting insulin/smart insulin at a suitable external condition.

In another example, a smart nanoshell (fabricated/constructed by DNA origami) can be decorated with an aptamer/ engineered riboswitch based (excess) glucose sensor. In the presence of excess glucose, the smart nanoshell can collapse—enabling the delivery of insulin/long acting insulin/ smart insulin at a suitable external condition.

Smart insulin can be Ins-PBA-F, which can consist of a long-acting insulin derivative that has a chemical moiety with phenylboronic acid added at one end. Under normal condition, smart insulin can bind with serum proteins (circulating in blood). In the presence of excess glucose, it can bind with phenylboronic acid to release Ins-PBA-F.

In another example, a smart nanoshell (fabricated/constructed by DNA origami) can be decorated with an aptamer/ engineered riboswitch to detect cancer cells. In the presence of cancer cells, the smart nanoshells can collapse—enabling the delivery of a synthetic notch molecule/engineered riboswitch to activate a T-cell.

FIG. 56L illustrates the wearable diagnostic device B, wherein a source electrode and a drain electrode are connected by a nanowire. The nanowire can be fabricated/ constructed in two-dimensional materials (e.g., molybdenum disulphide/graphene). The nanowire can be embedded with biomarker binders. The nanowire can be connected with a microfluidic channel, having an input microfluidic to separate serum from blood (propagated from the microneedles). Electrical parameters will change upon chemical coupling of the biomarker binders (on the nanowire) with biomarkers (in serum) and these changes can be quantified.

Details of the smart nanoshells and the wearable diagnostic device B are described in U.S. Non-Provisional patent application Ser. No. 13/663,376 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Oct. 29, 2012 and the non-provisional patent application with its benefit patent applications are incorporated in its entirety herein with this application.

FIG. 57A illustrates passive delivery of a bioactive compound(s) encapsulated within the smart nanoshell via a porous magnetic membrane patch. Smart nanoshells (encapsulating a bioactive compound(s)) can be stored in a microelectromechanical system reservoir.

Figure 57B:
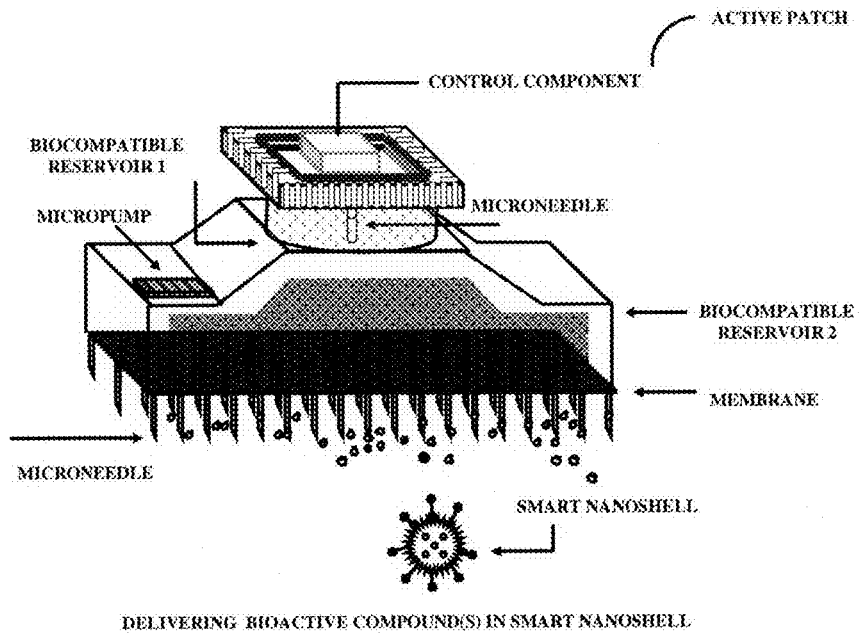

FIG. 57B illustrates active (utilizing a micropump-controlled by a control component) delivery of a bioactive compound(s) encapsulated within the smart nanoshell via a membrane patch integrated with microneedles. Smart nanoshells (encapsulating a bioactive compound(s)) can be stored in reservoir 2. Reservoir 2 is connected with reservoir 1 via a microneedle.

Figures 57C, 57D:
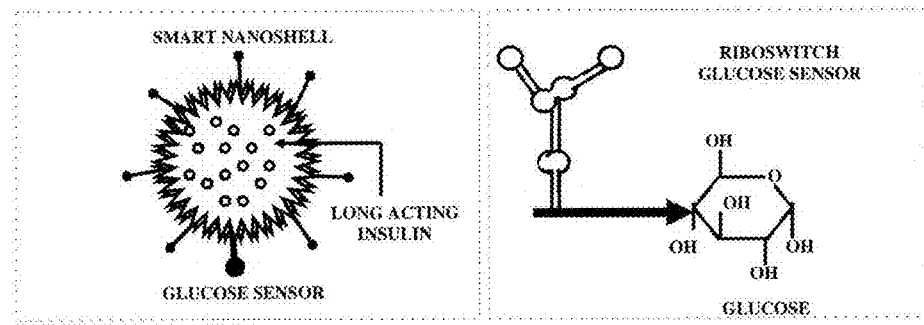

FIG. 57C illustrates a smart nanoshell (encapsulating insulin/long acting insulin/smart insulin) decorated with a glucose sensor.

Figure 57E:
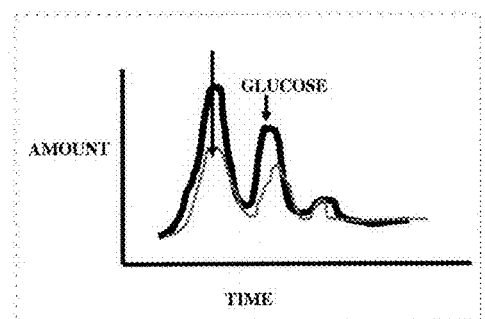

FIG. 57D illustrates an engineered riboswitch glucose sensor. FIG. 57E illustrates how the smart nanoshell manages excess glucose over time. FIG. 57F illustrates a molecular arrangement of a riboswitch.

FIG. 57G illustrates a smart nanoshell (encapsulating an engineered riboswitch/synthetic notch molecule). The smart nanoshell is decorated with a ligand(s) to bind with a specific cell receptor (s) to deliver the engineered riboswitch/synthetic notch signaling molecule or a bioactive compound. For example, the bioactive compound 2-(4-morpholinoanilino)-6-cyclohexylaminopurine can induce death of a cancer cell selectively. Similarly, the bioactive compound Lomaiviticin A, can induce cell death of a cancer cell selectively, by cleaving a cancer cell's DNA structure. The structure of Lomaiviticin A is given below.

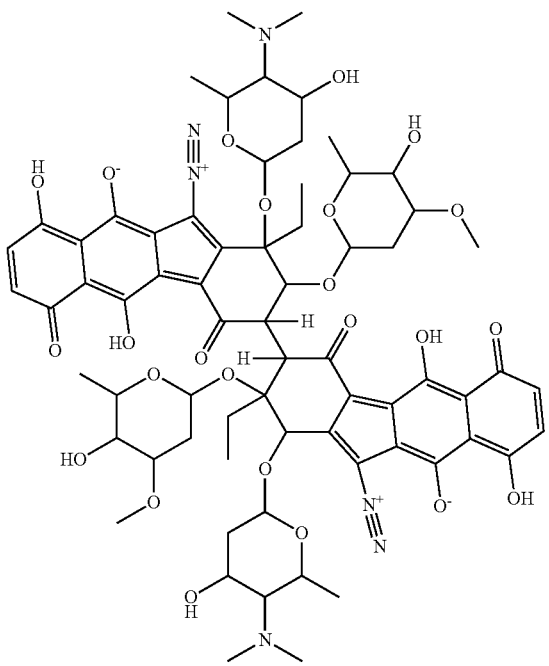 [SMILES: CCC1(OC2CC(O)C(N(C)C)C(C)O2)C2=C([N+]#N)c3c([O-])c4c(c(O)c3=C2C(=O)C(C2C(=O)C3=c5c(O)c6c(c([O-])c5C([N+]#N)=C3C(OC3CC(O)C(N(C)C)C(C)O3)C2(CC)OC2CC(OC)C(O)C(C)O2)=C(O)C=CC6=O)C1OC1CC(OC)C(O)C(C)O1)C(=O)C=CC=4O]

Structure of Lomaiviticin A

Figure 57H:
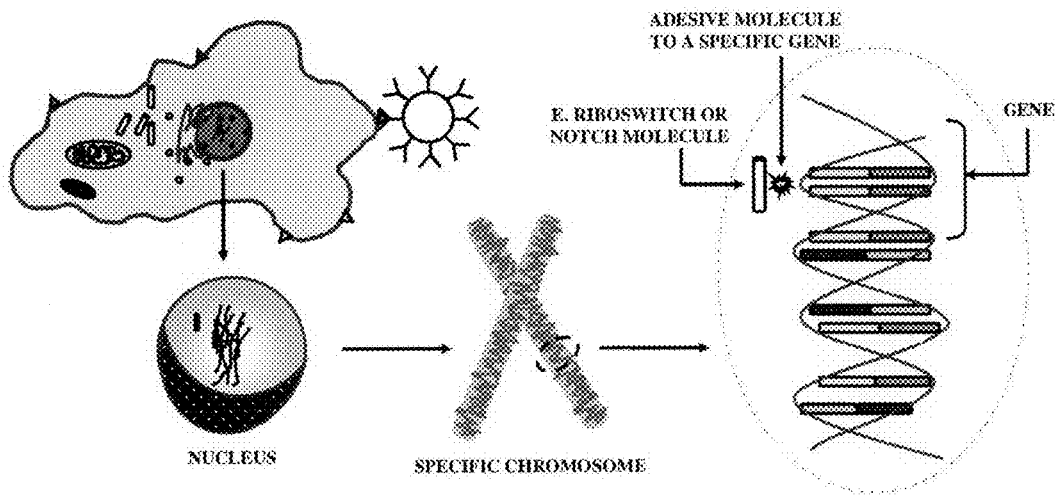

FIG. 57H illustrates implanting/coupling of engineered riboswitch/synthetic notch signaling molecule to a gene of (a specific chromosome) in the nucleus via the nuclear pore.

In the case of the engineered riboswitch, the gene can be turned on and off with a small inducer molecule. Thus, human cells can be programmed/reprogrammed with the engineered riboswitch to manufacture a specific protein only when a person takes a pill (containing the small inducer molecule), otherwise it is neutral or non-programmed.

In the case of the synthetic notch signaling molecule, the genome can be turned on and off. However, a gene can mean either natural or edited gene.

FIG. 58A illustrates an early diagnostic system A, which comprises a two-dimensional array of nanowaveguides on a transparent substrate (e.g., glass).

The two-dimensional array of nanowaveguides is within a flow cell. A nano optical antenna can be fabricated/ constructed at the bottom of each nanowaveguide. The height of each nanowaveguide can be less than 300 nanometers. The diameter of each nanowaveguide can be less than 400 nanometers. The maximum dimension of the nano optical antenna can be less than 200 nanometers.

The nano optical antenna is illustrated in FIGS. 30A-30E.

Incident light from only one laser of an array of lasers (e.g., emitting in the visible wavelength range—typically at 470/530/640 nanometers) via an optical column can excite a fluorophore (fluorescence can be due to chemical coupling/ interaction between a biomarker binder and a biomarker, wherein the biomarker is chemically coupled with the fluorophore). The optical column with an objective lens can be positioned by a precision positioning system from one nanowaveguide to the next, as the center to center distance between nanowaveguides can be larger than the diameter of the nanowaveguide. A dichroic mirror can separate the optical paths of the incident light and fluorescence light. Fluorescence light can be demultiplexed by a color splitter and then focused by a lens onto an ultrasensitive optical detector (e.g., electron multiplying charged coupled detector).

However, instead of scanning with a single (cw/pulsed) laser, two lasers can be utilized simultaneously. The first is the typical laser using an appropriate wavelength to excite a material. The second laser is the key component, this is focused so that it produces a donut of light overlapping the focal point of the first laser. This configuration can enable the laser to focus below the Abbey's diffraction limit.

The nanowaveguide with an integrated nano optical antenna can allow a single molecule to be isolated for enhanced fluorescence detection at a high concentration. The advantages of the early diagnostic system A are (a) ultimate sensitivity down to the single molecule level, (b) no amplification induced false positive data and (c) small sample volume.

Key fabrication/construction steps of the nanowaveguide with integrated nano optical antenna on a transparent substrate (e.g., 100 millimeters in diameter and 175 microns in thickness glass) are listed below: first electron beam lithography of the nano optical antenna, lift off of metal (e.g., aluminum/gold/silver) nano optical antenna, second electron beam lithography for protection of the nano optical antenna, third electron beam lithography of the nanowaveguide (utilizing a negative tone process), lift-off of metal (e.g., aluminum/gold or gold and aluminum) nanowaveguide, removal of all photoresists, passivation on the walls of the nanowaveguide by a biological material to increase single molecule occupancy level and dicing of the wafer into chip A.

Furthermore, the nanowaveguide can be scaled to a zero-mode waveguide.

FIG. 58B illustrates a nanofiber. The tip of the nanofiber can be fabricated/constructed with a flat mirror/spherical mirror/silicon waveguide for efficient optical coupling. Instead of bulk optics, an array of nanofibers can be utilized as a conduit for the incident and fluorescence light. Furthermore, the array of nanofibers can be connected to inputs of a N×1 optical switch and the output of the N×1 optical switch can be connected to the detector/spectrophotometer. This configuration can enable faster analysis.

Figure 59A:
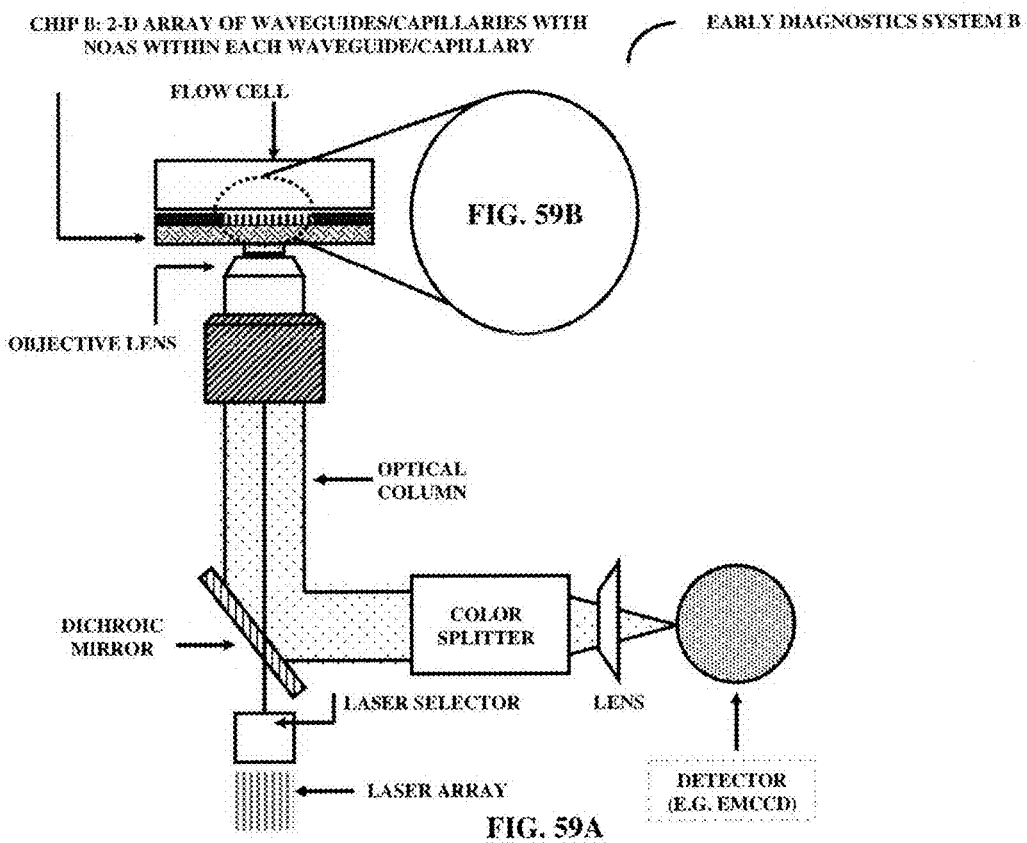

FIG. 59A illustrates an early diagnostic system B, which comprises a two-dimensional array of waveguides/capillaries on a transparent substrate. FIG. 59A is similar to FIG. 58, except the diameter of the waveguide/capillary is larger for integrating n (e.g., n=10 to 100) nano optical antennas at the bottom of each waveguide/capillary (FIG. 59B).

Figure 59B:
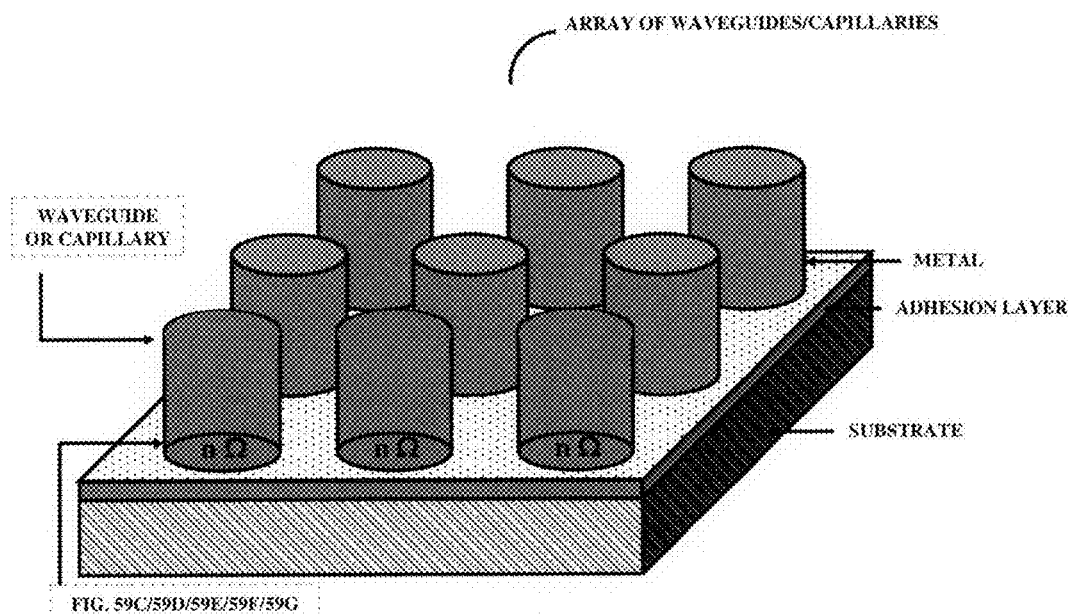

FIG. 59B illustrates the two-dimensional array of waveguides/capillaries of metal (e.g., aluminum/gold or gold and aluminum) on an adhesion layer (e.g., 10 nanometers chromium) with biomarker binder-biomarker coupling on a nano optical antenna (represented by a symbol Ω).

Figure 59C:
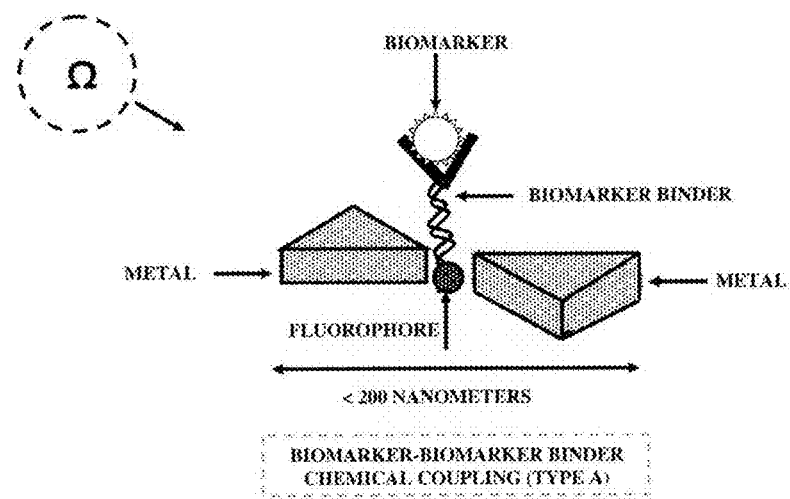

FIG. 59C represent type A biomarker binder-biomarker chemical coupling on a nano optical antenna (represented by a symbol Ω), wherein the nano optical antenna is like a bowtie of metal (e.g., aluminum/gold/silver), having a gap of less than 50 nanometers and a maximum dimension of less than 200 nanometers. The fluorophore of the biomarker binder is substantially within or near the gap to enable plasmonic coupling. But, the fluorophore can be chemically coupled with a biological material (e.g., DNA) for attaching it onto an electrically isolated nanospot within the gap. This can enable the positioning of fluorophore preciously within the gap of the nano optical antenna.

Figure 59D:
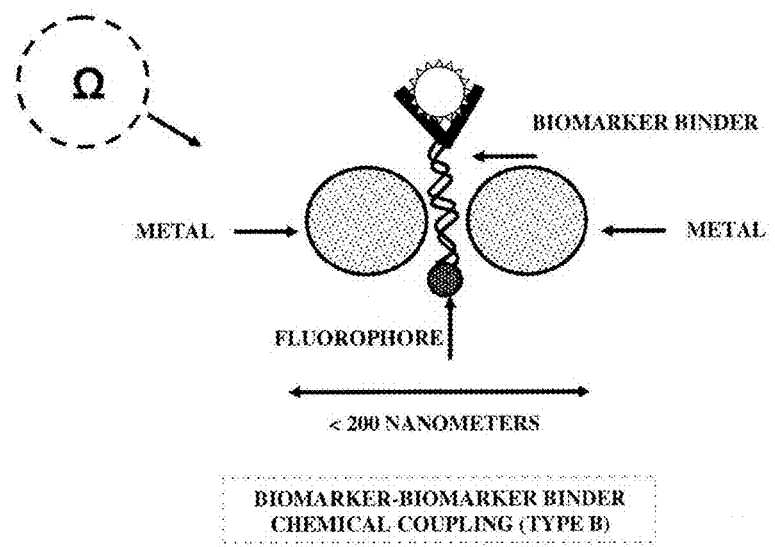
Figure 59E:
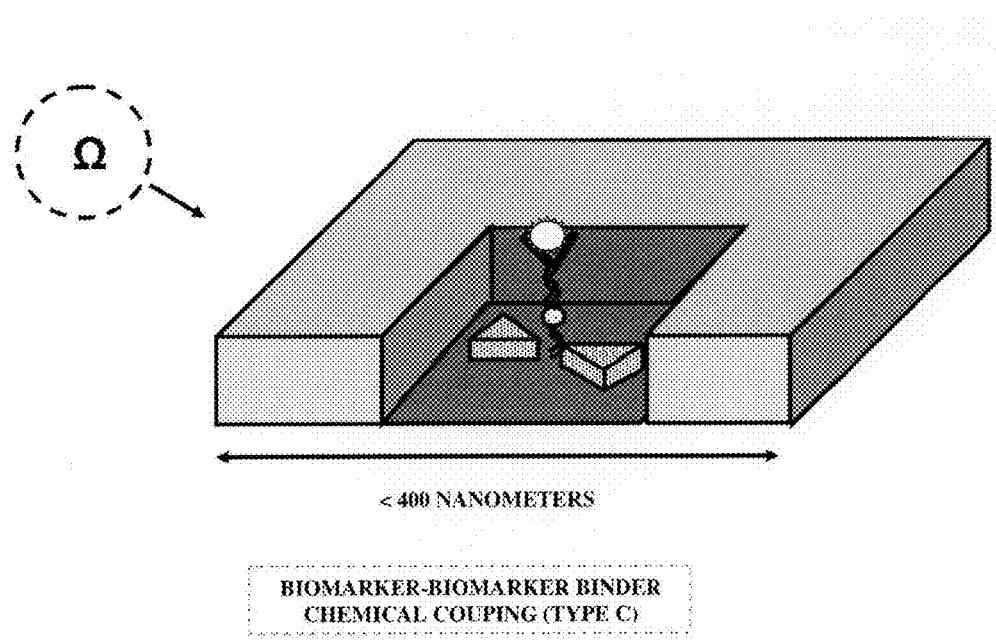
Figure 59F:
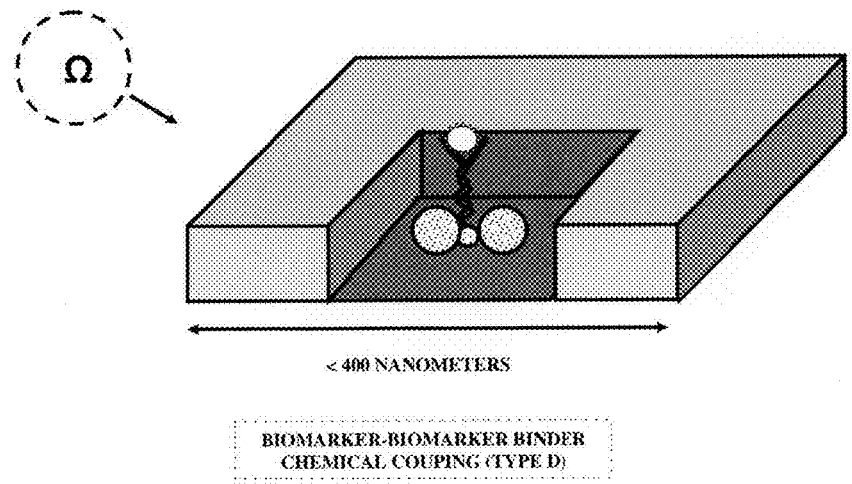

FIG. 59D represents type B biomarker binder-biomarker chemical coupling on a nano optical antenna (represented by a symbol Ω), wherein the nano optical antenna comprises two metal nanospheres, having a gap of less than 50 nanometers and a maximum dimension of less than 200 nanometers. The fluorophore of the biomarker binder is substantially within or near the gap to enable plasmonic coupling. But, the fluorophore can be chemically coupled with a biological material (e.g., DNA) for attaching it onto an electrically isolated nanospot within the gap. This can enable the positioning of fluorophore preciously within the gap of the nano optical antenna In FIG. 59E, previous type A biomarker binder-biomarker chemical coupling is enclosed within a nanoscaled box (represented as type C) to reduce background fluorescence. The maximum dimension of the nanoscaled box can be less than 400 nanometers In FIG. 59F, previous type B biomarker binder-biomarker chemical coupling is enclosed within a nanoscaled box (represented as type D) to reduce background fluorescence. The maximum dimension of the nanoscaled box can be less than 400 nanometers.

The shape of the nanoscaled box (represented as type and type D) can be arbitrary and/or closed and/or open.

Figure 59G:
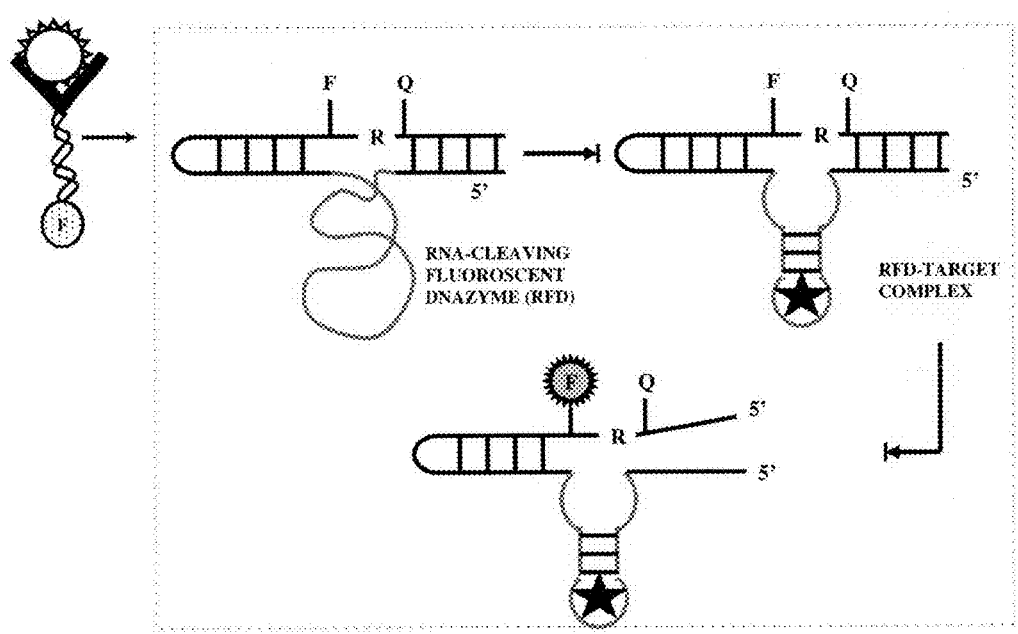

FIG. 59G represents a switch-on biomarker binder (e.g., a molecular beacon), which can be utilized to reduce background fluorescence.

Figure 60A:
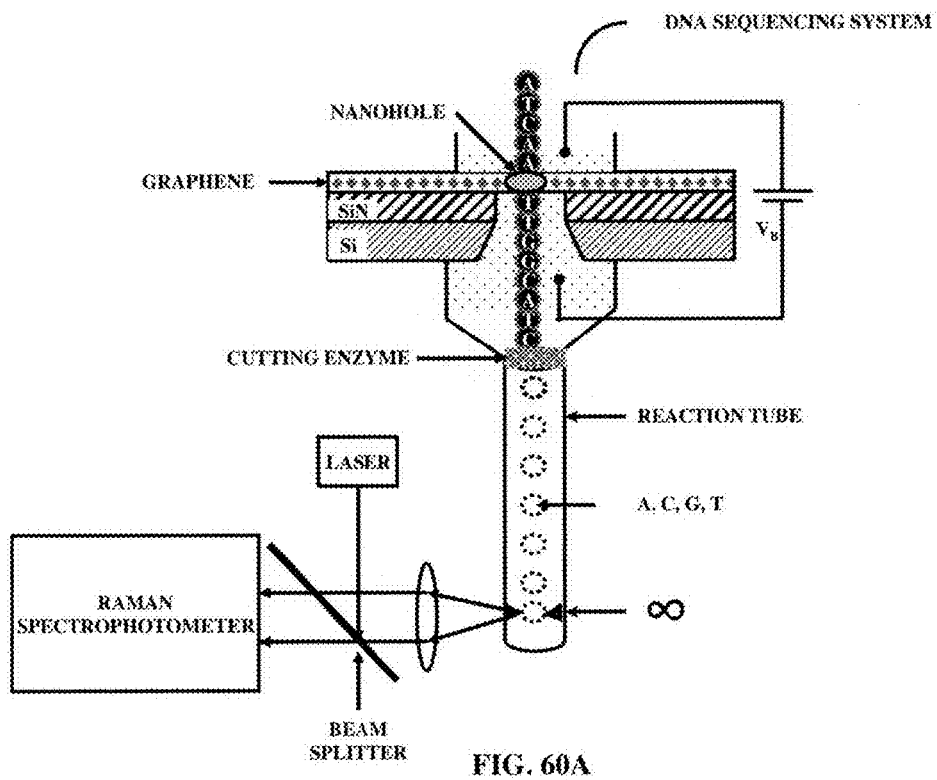
Figure 60B:
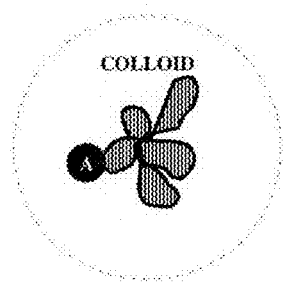
Figure 60C:
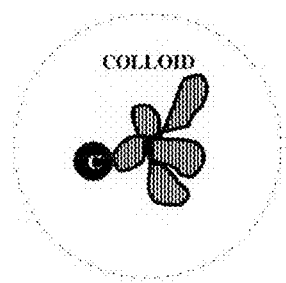
Figure 60D:
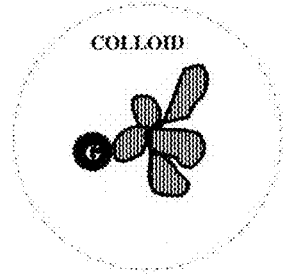
Figure 60E:
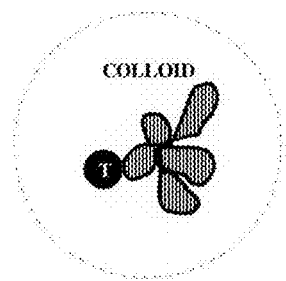

FIG. 60A illustrates a DNA sequencing system, wherein DNA can be pulled through a nanohole on an angstrom thin membrane (the angstrom thin membrane is mechanically supported by silicon nitride and/or silicon membrane) electrically. The angstrom thin membrane can be fabricated/constructed in a two-dimensional material. Upon passing through the nanohole, a cutting enzyme can cut nucleotides A, C, G and T of the DNA in a reaction tube. Then, each nucleotide A, C, G and T can be chemically coupled with a colloidal molecule in the reaction tube. As each nucleotide A, C, G and T chemically (coupled with colloidal molecule) passes through a specific zone of the reaction tube, it is identified by an ultrasensitive Raman spectrophotometer. At a zone of Raman measurement, a nano optical antenna can be fabricated/constructed to enhance the Raman signal.

Details of the nanohole based DNA sequencing system are described in U.S. Non-Provisional patent application Ser. No. 13/663,376 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Oct. 29, 2012 and the non-provisional patent application with its benefit patent applications are incorporated in its entirety herein with this application.

FIGS. 60B-60E illustrate chemically coupling of nucleotide A, C, G and T with a colloidal molecule respectively.

Figure 60F:
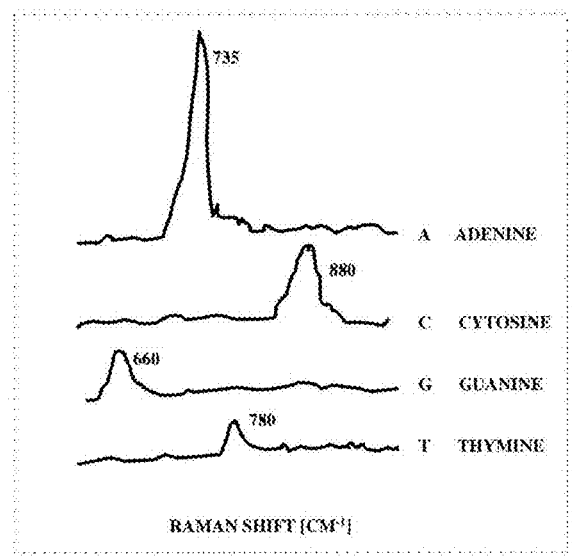

FIG. 60F illustrates the Raman shift spectrum of nucleotide A, C, G and T.

Exosome contains RNAs. Cells communicate each other by sending and receiving exosomes. Thus, an exosome can be viewed as cellular Twitter for cell-to-cell biological communication directly by surface expressed ligands or transferring molecules from the originating cells. For example, exosomes can carry material from an originating cancer cell to suppress the immune system and stimulate angiogenesis for the growth of cancer cells. Recipient cells act utilizing RNAs for protein manufacturing. Thus, exosomes can be utilized as a universal nanoshell to deliver RNA (e.g., a specific small interfering RNA (siRNA)) for therapeutic purposes.

FIGS. 61A-61C illustrates an exosome diagnostic system for early detection/prediction of a disease.

FIG. 61A illustrates a biochemical chamber to obtain RNAs/proteins caged within exosomes. The biochemical chamber can be a molded poly(dimethylsiloxane) (PDMS). The biochemical chamber is degassed via vacuum prior to its use. The absorption of gas by PDMS provides the mechanism for actuating and metering the flow of fluid in microfluidic channels and between various parts of the biochemical chamber. The biochemical chamber can take in blood at inlets. The biochemical chamber can use tiny microfluidic channels of about 30 microns in diameter underneath the inlets to separate serum from blood by utilizing laws of microscale physics. The serum moves through the biochemical chamber via a process called degas-driven flow.

Superparamagnetic nanoparticles iron oxide ($Fe_3O_4$) can be synthesized with positive electrical charges to bond onto the membrane surface of exosomes' negative electrical charge due to electrostatic interactions. The biochemical chamber can be integrated with a magnet. Exposure to a magnetic field can separate superparamagnetic nanoparticles iron oxide ($Fe_3O_4$) (once attached with exosomes) from exosomes. Capture of exosomes by superparamagnetic nanoparticles iron oxide ($Fe_3O_4$) is realized in Capture+Wash Microchamber.

Alternatively, a nanosieve/nanomembrane/nanofilter of about 100 nanometers pore diameter can filter exosomes. For example, a nanosieve/nanomembrane/nanofilter can be graphene based. Nanoholes in graphene (a hexagonal array of carbon atoms) can be fabricated/constructed in a two-stage process. First, a graphene sheet is bombarded with gallium/helium ions, which disrupt the carbon bonds. Second, the graphene sheet is wet etched in an oxidizing solution that reacts strongly with the disrupted carbon bonds, producing a nanohole at each spot, where the gallium/helium ions once bombarded/struck. By controlling how long the graphene sheet is left in the oxidizing solution, the average size of the nanoholes can be controlled.

FIG. 61B illustrates a removable Lysis+Probe Microchamber. A suitable chemical can be added in the removable Lysis+Probe Microchamber to break the membrane surface of exosomes to obtain caged RNAs and proteins within the exosomes. The removable Lysis+Probe Microchamber which has disease specific biomarker binders (e.g., an aptamer/molecular beacon binder) and can be chemically coupled with a fluorophore (e.g., fluorescent protein/quantum dot fluorophore) to bind with disease specific mRNAs, which were once caged within the exosomes.

The nano optical antenna can be integrated with the fluorophore to enhance fluorescence. Alternatively, the removable Lysis+Probe Microchamber can be configured with nano optical antennas on the floor of the Removable Lysis+Probe Microchamber to enhance fluorescence.

FIG. 61C illustrates another embodiment of the removable Lysis+Probe Microchamber. In this configuration, the disease specific biomarker binders are designer proteins with leave-one-out configuration (each designer protein has an omitted molecular segment to create a binding site to fit a disease specific protein) to bind with disease specific proteins which were once caged within the exosomes.

Above mRNAs and proteins can be analyzed utilizing the early diagnostic system A (FIGS. 58A-58B).

Details of exosome diagnostic system are described in U.S. Non-Provisional patent application Ser. No. 14/120,835 entitled "CHEMICAL COMPOSITION & ITS DELIVERY FOR LOWERING THE RISKS OF ALZHEIMER'S, CARDIOVASCULAR AND TYPE-2 DIABETES DISEASES", filed on Jul. 1, 2014 and the non-provisional patent application with its benefit patent applications are incorporated in its entirety herein with this application.

FIG. 62A illustrates a three-dimensional micro/nanoprinter. A short pulse laser beam is manipulated by an attenuator and/or a shutter. The laser beam can be divided by a beam splitter. The intensity of the laser beam can be measured by a detector. The laser beam (via an objective) can excite a material (in a material tray). The intensity and spatial movement of the laser beam can be manipulated by a three-axis scanning stage and a controller. The controller is connected with a cloud computer system. The three-dimensional printer can remain in locked configuration, unless the cloud computer system generally verifies a desired design against other publicly available designs. A three-dimensional imager scanner can consist of a very large-scale integration of coherent interferometers, which can measure the intensity, phase and frequency of the reflected laser light from different points on an object. The three-dimensional micro/nanoprinter can be integrated with the three-dimensional image scanner.

A waveguide device (FIG. 29D) can focus the incident laser beam below Abbey's diffraction limit for nanoprinting. A nanohole patterned circular disc (FIG. 29E) can focus the incident laser beam below Abbey's diffraction limit for nanoprinting.

FIG. 62B is similar to 62A, except this configuration utilizes two laser beams for printing, wherein the second laser beam is manipulated by an optical phase plate.

Additionally, two-photon polymerization can be utilized to fabricate/construct microstructures in biocompatible ormocers material. A printed micro/nano component can be attached to live/bioprinted biological materials. Alternatively, instead of scanning with a single (cw/pulsed) laser, two lasers can be utilized simultaneously. The first is the typical laser using an appropriate wavelength to excite a material. The second laser is the key component, this is focused so that it produces a donut of light overlapping the focal point of the first laser. This configuration can enable the laser to focus below the Abbey's diffraction limit for nanoprinting.

FIG. 63A illustrate the intelligent algorithm 100X, which is similar to FIG. 1B, except 100C is replaced by 100C1 (Human OS application) and 100N is bioinformatics knowledge base.

The connections between various algorithm submodules can be like synaptic networks topology to enable deep learning of the intelligent algorithm 100X.

FIG. 63B illustrates a configuration to determine a personalized Human Operating System (OS), a healthcare expert system with Super System on Chips 400A/400B/400C/400D, which comprises an intelligent algorithm 100X. The healthcare expert system connects (a) an exosome diagnostic system, (b) an early diagnostic system A/B, (c) a DNA diagnostic system, (d) the intelligent portable internet appliance 160 and healthcare/remote healthcare providers. The intelligent portable internet appliance 160 connects with a point-of-care diagnostic system and wearable personal health assistant device. The personalized Human OS can enable predictive disease disposition of the user.

In the above disclosed specifications "I" has been used to indicate an "or".

Any example in the above disclosed specifications is by way of an example only and not by way of any limitation.

Any dimension in the above disclosed specifications is by way of an approximation only and not by way of any limitation.

The above disclosed specifications are the preferred best mode embodiments of the present invention. However, they are not intended to limited only to the preferred best mode embodiments of the present invention. Numerous variations and/or modifications are possible within the scope of the present invention. Accordingly, the disclosed preferred best mode embodiments are to be construed as illustrative only. Those who are skilled in the art can make various variations and/or modifications without departing from the scope and spirit of this invention.

We claim:

1. A display device comprising:
   (a) a light source of emitting a first light of a first color;
   (b) a light emitting layer comprises quantum dots; and
      wherein the quantum dots are in or on a photonic crystal,
      wherein the light emitting layer absorbs a portion of the first light of the first color from the light source,
      wherein the light emitting layer emits a second light of a second color,
   (c) an electrically switchable light valve or an electrically switchable light shutter.

2. The display device according to claim 1, wherein the quantum dot comprises: a two-dimensional material.

3. The display device according to claim 1, wherein the quantum dot is electromagnetically coupled with a three-dimensional structure of dimension less than 400 nanometers.

4. The display device according to claim 1, wherein the light source is an organic light emitting diode, or an organic light emitting diode comprising quantum dots.

5. The display device according to claim 1, wherein the light source is a microlight emitting diode, or a microlight emitting diode with a light collection layer comprising photonic crystals.

6. The display device according to claim 1, wherein the light source is a vertical cavity surface emitting laser.

7. The display device according to claim 1, wherein the light source is a vertical cavity surface emitting laser, wherein the vertical cavity surface emitting laser comprises: two metallized Bragg mirrors, wherein one metallized Bragg mirror comprises: a hole.

8. The display device according to claim 1, wherein the electrically switchable light valve or the electrically switchable light shutter comprises: a phase change material, or a phase transition material.

9. The display device according to claim 1, further comprises: an optical filter, or a microlens.

10. The display device according to claim 1, further comprises: a camera sensor, wherein the camera sensor is in proximity to a display pixel.

11. A display device comprising:
    (a) a light source of emitting a first light of a first color;
       wherein the light source comprises: a microlight emitting diode, or an organic light emitting diode, or an organic light emitting diode comprising quantum dots,
    (b) a light emitting layer comprises quantum dots;
       wherein the quantum dots are in or on a photonic crystal,
       wherein the light emitting layer absorbs a portion of the first light of the first color from the light source,
       wherein the light emitting layer emits a second light of a second color,
    (c) an electrically switchable light valve or an electrically switchable light shutter; and
    (d) a microlens.

12. The display device according to claim 11, wherein the quantum dot comprises: a two-dimensional material.

13. The display device according to claim 11, wherein the quantum dot is electromagnetically coupled with a three-dimensional structure of dimension less than 400 nanometers.

14. The display device according to claim 11, wherein the electrically switchable light valve or the electrically switchable light shutter comprises: a phase change material, or a phase transition material.

15. The display device according to claim 11, further comprises: an optical filter, or a lens.

16. The display device according to claim 11, further comprises: a camera sensor, wherein the camera sensor is in proximity to a display pixel.

17. A display device comprising:
    (a) a light source of emitting a first light of a first color;
       wherein the light source comprises: a vertical cavity surface emitting laser,
       wherein the vertical cavity surface emitting laser comprises: two metallized mirrors,
       wherein one metallized mirror comprises: a hole,
    (b) a light emitting layer comprises quantum dots; and
       wherein the quantum dots are in or on a photonic crystal,
       wherein the light emitting layer absorbs a portion of the first light of the first color from the light source,
       wherein the light emitting layer emits a second light of a second color,
    (c) an electrically switchable light valve or an electrically switchable light shutter.

18. The display device according to claim 17, wherein the quantum dot comprises: a two-dimensional material.

19. The display device according to claim 17, wherein the quantum dot is electromagnetically coupled with a three-dimensional structure of dimension less than 400 nanometers.

20. The display device according to claim 17, further comprises: an optical filter, or a microlens.

* * * * *